United States Patent
Zhang et al.

(10) Patent No.: US 7,884,117 B2
(45) Date of Patent: Feb. 8, 2011

(54) CARBONYLAMINO PYRROLOPYRAZOLES, POTENT KINASE INHIBITORS

(75) Inventors: Junhun Zhang, San Diego, CA (US); Anle Yang, San Diego, CA (US); Susan Elizabeth Kephart, San Diego, CA (US); Liming Dong, Shanghai (CN); Chuangxing Guo, San Diego, CA (US); Yufeng Hong, San Diego, CA (US); Mary Catherine Johnson, San Diego, CA (US); Indrawan James McAlpine, San Diego, CA (US); Jayashree Tikhe, San Diego, CA (US); Haitao Li, Rockville, MD (US)

(73) Assignee: Pfizer Inc., New York, NY (US)

(*) Notice: Subject to any disclaimer, the term of this patent is extended or adjusted under 35 U.S.C. 154(b) by 190 days.

(21) Appl. No.: 12/158,241

(22) PCT Filed: Dec. 12, 2006

(86) PCT No.: PCT/IB2006/003646

§ 371 (c)(1),
(2), (4) Date: Sep. 12, 2008

(87) PCT Pub. No.: WO2007/072153

PCT Pub. Date: Jun. 28, 2007

(65) Prior Publication Data

US 2009/0318440 A1    Dec. 24, 2009

Related U.S. Application Data

(60) Provisional application No. 60/753,349, filed on Dec. 21, 2005, provisional application No. 60/864,932, filed on Nov. 8, 2006.

(51) Int. Cl.
*A61K 31/422* (2006.01)
*A61K 31/4162* (2006.01)
*C07D 261/06* (2006.01)
*C07D 231/54* (2006.01)

(52) U.S. Cl. .................. 514/378; 514/406; 548/248; 548/360.5

(58) Field of Classification Search .............. 514/378, 514/406; 548/248, 360.5
See application file for complete search history.

(56) References Cited

U.S. PATENT DOCUMENTS

2003/0171357 A1   9/2003   Fancelli

FOREIGN PATENT DOCUMENTS

| WO | WO02/12242 A | 2/2002 |
| WO | WO2004/013144 A | 2/2004 |
| WO | WO2004/056827 A | 7/2004 |
| WO | WO2005/030776 A | 4/2005 |
| WO | WO2006/072831 A1 | 7/2006 |

OTHER PUBLICATIONS

Bagodia, S et al., "Cdc42 and PAK-mediated Signaling Leads to Jun Kinase and p38 Mitogen-activated Protein Kinase Activation," *The Journal of Biological Chemistry*, 1995, 270:27995-27998.

Callow, M. et al., "Requirement for PAK4 in the Anchorage-independent Growth of Human Cancer Cell Lines," *The Journal of Biological Chemistry*, 2002, 277:550-558.

Chaudhary, A et al., "Phosphatidylinositol 3-kinase regulates Raf1 through Pak Phosphorylation of serine 338," Current Biology, 2000, 10:551-554.

Daniels, R. et al., "P21-Activated protein kinase: a crucial component of morphological signaling," *Trends Biochemical Science*, 1999, 24:350-355.

Frost, J. et al., "Cross-cascade activation of ERKs and ternary complex factors by Rho family proteins," *The EMBO Journal*, 1997, 16:6426-6438.

Gnesutta, N. et al., "The Serine/Threonine Kinase PAK4 Prevents Caspase Activation and Protects Cells from Apoptosis," The Journal of Biological Chemistry, 2001, 276:14414-14419.

King, A. et al., "The protein kinase Pak3 positively regulates Raf-1 activity through Phosphorylation of serine 338," *Nature*, 1998, 396:180-183.

Manser, E. et al., "A brain serine/Threonine protein kinase activated by Cdc42 and Rac1," *Nature*, 1994, 367:40-46.

Qu, J. et al., "Activated PAK4 Regulates Cell Adhesion and Anchorage-Independent Growth," *Molecular and Cellular Biology*, 2001, 21:3523-3533.

Roig, J et al., "p21-activated Protein Kinase y-PAK is activated by Ionizing Radiation and Other DNA-damaging Agents," *The Journal of Biological Chemistry*, 1999, 274:31119-31122.

(Continued)

*Primary Examiner*—Kamal A Saeed
*Assistant Examiner*—Samantha L Shterengarts
(74) *Attorney, Agent, or Firm*—Ye Hua; Jeffrey H. Tidwell

(57) ABSTRACT

Carbonylamino Pyrrolopyrazole compounds of formula I, compositions including these compounds and methods of their use are provided. Preferred compounds of formula I have activity as protein kinase inhibitors, including as inhibitors of PAK4.

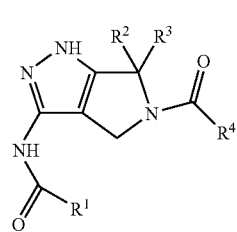

23 Claims, 1 Drawing Sheet

OTHER PUBLICATIONS

Rudel, T. et al., "Membrane and Morphological Changes in Apoptotic Cells Regulated by Caspase-Mediated Activation of PAK2," *Science*, 1997, 276:1571-1574.

Schumann, A et al., "p21-Activated Kinase 1 Phosphorylates the Death Agonist Bad and Protects Cells from Apoptosis," *Molecular and Cellular Biology*, 2000, 20:453-461.

Sells, M. et al., "Emerging from the Pak: the p21-activated protein kinase family," Trends in Cell Biology, 1997, 7:162-167.

Sun, H. et al., "Regulation of the protein kinase Raf-1 by oncogenic Ras through phosphatidylinositol 3-kinase, Cdc42/Rac and Pak," *Current Biology*, 2000, 10:281-284.

Yablonski, D. Et al., "A Nck-Pak1 signaling module is required for T-cell receptor-mediated activation of NFAT, but not of JNK," *The EMBO Journal*, 1998, 17:5647-5657.

CARBONYLAMINO PYRROLOPYRAZOLES, POTENT KINASE INHIBITORS

This application is the national stage filing under 35 U.S.C. 371, of Patent Cooperation Treaty Patent Application No. PCT/IB2006/003646, filed Dec. 12, 2006, which claims the benefit of U.S. Provisional Patent Application Nos. 60/753,349 filed Dec. 21, 2005 and 60/864,932 filed Nov. 8, 2006, the disclosures of which are incorporated herein by reference in their entireties.

FIELD OF THE INVENTION

The present invention relates generally to novel chemical compounds and methods. More particularly, the invention provides novel carbonylamino pyrrolopyrazole compounds and their analogs, having protein kinase activity, and methods of synthesizing and using such compounds.

BACKGROUND

Protein kinases are a family of enzymes that catalyze phosphorylation of the hydroxyl groups of specific tyrosine, serine, or threonine residues in proteins. Typically, such phosphorylation can dramatically change the function of the protein and thus protein kinases can be pivotal in the regulation of a wide variety of cellular process, including metabolism, cell proliferation, cell differentiation, and cell survival. The mechanism of these cellular processes provides a basis for targeting protein kinases to treat disease conditions resulting from or involving disorder of these cellular processes. Examples of such diseases include, but are not limited to, cancer and diabetes.

Protein kinases can be broken into two types, protein tyrosine kinases (PTKs) and serine-threonine kinases (STKs). Both PTKs and STKs can be receptor protein kinases or non-receptor protein kinases. PAK is a family of non-receptor STKs. The p21-activated protein kinase (PAK) family of serine/threonine protein kinases plays important roles in cytoskeletal organization and cellular morphogenesis (Daniels et al., *Trends Biochem. Sci.* 24: 350-355 (1999); Sells et al., *Trends Cell. Biol.* 7: 162-167 (1997)). PAK proteins were initially identified by their interaction with the active small GTPases, Cdc42, and Rac, and their homology to yeast kinase Step 20 (Manser et al., *Nature* 367: 40-46 (1994)). In addition to mediating the regulation of actin cytoskeleton and cell adhesion by Cdc42 and Rac (Daniels et al., *Trends Biochem. Sci.* 24: 350-355 (1999)), it was determined that some PAK proteins protect cells from apoptosis (Gnesutta et al., *J. Biol. Chem.* 276: 14414-14419 (2001); Rudel et al., Science 276: 1571-1574 (1997); Schurmann et al., *Mol. Cell. Biol.* 20: 453-461 (2000)); modulate mitogen activated protein (MAP) kinase pathways (Bagrodia et al., *J. Biol. Chem.* 270: 27995-27998 (1995); Brown et al., *Curr. Biol.* 6: 598-605 (1996); Chaudhary et al., *Curr. Biol.* 10: 551-554 (2000); Frost et al., *EMBO J.* 16: 6426-6438 (1997); King et al., *Nature* 396: 180-183 (1998); Sun et al., *Curr. Biol.* 10: 281-284 (2000)); mediate T-cell antigen receptor (TCR) signaling (Yablonski et al., *EMBO J.* 17: 5647-5657 (1998)); and respond to DNA damage (Roig et al., *J. Biol. Chem.* 274: 31119-31122 (1999)). Through these diverse functions, PAK proteins regulate cell proliferation and migration.

The full-length PAK4 nucleic acid and amino acid sequences are disclosed in U.S. Pat. No. 6,013,500 and have been deposited in GenBank under accession numbers AF005046 (mRNA) and AAD01210 (amino acid). Modulation of human PAK4 activity is reported to result in alterations in cellular processes affecting cell growth and adhesion. For example, overexpression of PAK4 in fibroblasts leads to morphological changes that are characteristic of oncogenic transformation through induction of anchorage-independent growth and inhibition of apoptosis (Gnesutta et al., *J. Biol. Chem.* 276:14414-14419 (2001); Qu et al., *Mol. Cell. Biol.* 21: 3523-2533 (2001)). More recently, it was also shown that: PAK4 is frequently overexpressed in human tumor cell lines of various tissue origins; expression of an active PAK4 mutant has transforming potential, leading to anchorage-independent growth of NIH3T3 cell line; and a kinase-inactive PAK4 efficiently blocks transformation by activated Ras and inhibits anchorage-independent growth of HCT116 colon cancer cells. These data strongly implicate PAK4 in oncogenic transformation and suggest that PAK4 activation is required for Ras-driven, anchorage-independent growth of human cancer cells. (Smeal, et al, *J. Biol. Chem.* 277, 550-558 (2002)) In vivo efficacy in mice with implanted tumor of a compound that inhibits the PAK4 kinase domain is shown in the current application.

PAK4 therefore appears to us to be an attractive target for developing therapeutic agents effective for treating disorders involving abnormal cell growth, especially cancer.

For other background references, see U.S. Patent Application Publication No. 2003/0171357 and PCT Publication WO02/12242.

SUMMARY

In one embodiment, the current invention provides a compound of formula I,

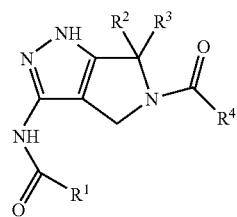

I wherein:

$R^1$ is ethyl, t-butyl, R, -L-($C_3$-$C_{12}$ cycloalkyl), -L-phenyl, -L-(5-12 member heteroaryl), -L-(3-12 member heterocyclyl) and -L-($C_3$-$C_{12}$ unsaturated nonaromatic carbocyclyl);

each $R^2$ and $R^3$ is independently H, $C_1$-$C_8$ alkyl, $C_2$-$C_8$ alkenyl, $C_2$-$C_8$ alkynyl, —($C_1$-$C_3$ alkylene)$_m$-($C_3$-$C_{12}$ cycloalkyl) or —($C_1$-$C_6$ perfluoroalkyl), and each $R^2$ and $R^3$ is optionally further substituted by 1-3 groups selected from halide, —CN, oxo, —OH, —$NH_2$, $C_1$-$C_6$ monoalkylamino and $C_2$-$C_8$ dialkylamino; or $R^2$ and $R^3$, together with the carbon atom that $R^2$ and $R^3$ attach to, form a ring selected from 3-5 member nonaromatic carbocyclylene and 3-5 member heterocyclylene, and the said ring is optionally further substituted by 1-3 groups selected from $C_1$-$C_3$ alkyl, $C_1$-$C_3$ perfluoroalkyl, oxo, —($C_1$-$C_3$ alkylene)$_m$-halide, —($C_1$-$C_3$ alkylene)$_m$-CN, —($C_1$-$C_3$ alkylene)$_m$-OH, —($C_1$-$C_3$ alkylene)$_m$-$NH_2$, —($C_1$-$C_3$ alkylene)$_m$-($C_1$-$C_6$ monoalkylamino) and —($C_1$-$C_3$ alkylene)$_m$-($C_2$-$C_8$ dialkylamino);

$R^4$ is selected from —$OR^5$, —O—$R^6$—$R^7$, —O—CH($R^8$)$R^9$, —N(R')—$R^6$—$R^7$, —N(R')CH($R^8$)$R^9$, —CH(R')—$R^6$—$R^7$, —CH(R')—CH($R^8$)—$R^9$, —B—($C_1$-$C_3$ alkylene)-CH($R^8$)$R^9$ and —B—($C_1$-$C_3$ alkylene)$_m$-CH($R^{10}$)$R^9$, and B is —O—, —N(R')— or —CH(R')—;

$R^5$ is R;

$R^6$ is a divalent radical selected from —($C_3$-$C_7$ cycloalkylene)-, -(3 to 7 member heterocyclylene)- and -(5 to 7 member heteroarylene)-, provided when $R^4$ is —$CH_2$—$R^6$—$R^7$ and $R^7$ is unsubstituted phenyl, $R^6$ is not unsubstituted thiazolylene; $R^6$ is optionally further substituted by 1-4 groups selected from $C_1$-$C_3$ alkyl, oxo, $C_1$-$C_3$ perfluoroalkyl, —($C_1$-$C_3$ alkylene)$_m$-halide, —($C_1$-$C_3$ alkylene)$_m$-($C_1$-$C_3$ alkylamino), —($C_1$-$C_3$ alkylene)$_m$-$NH_2$, —($C_1$-$C_3$ alkylene)$_m$-OH and —($C_1$-$C_3$ alkylene)$_m$-($C_1$-$C_3$ alkoxy);

$R^7$ is selected from phenyl, $C_{10}$-$C_{12}$ aryl, $C_3$-$C_{12}$ cycloalkyl, $C_4$-$C_{12}$ unsaturated nonaromatic carbocyclyl, 3-12 member heterocyclyl and 5-12 member heteroaryl;

$R^8$ is —($C_1$-$C_6$ alkylene)$_m$-$NR^pR^q$, wherein each $R^p$ and $R^q$ is independently H or $C_1$-$C_6$ alkyl, or $R^p$ and $R^q$, together with the nitrogen atom which $R^p$ and $R^q$ attach to, form a ring selected from 3-7 member heterocyclyl and 5-7 member heteroaryl, and the said ring is optionally further substituted by 1-6 groups selected from halide, $C_1$-$C_3$ alkyl, oxo and $C_1$-$C_3$ perfluoroalkyl;

$R^9$ is selected from $C_1$-$C_6$ alkyl, $C_2$-$C_6$ alkenyl, $C_2$-$C_6$ alkynyl, $C_1$-$C_6$ alkoxyl, $C_1$-$C_6$ perfluoroalkyl, phenyl, -($L^1$)-phenyl, $C_{10}$-$C_{12}$ aryl, -($L^1$)—($C_{10}$-$C_{12}$ aryl), $C_3$-$C_{12}$ cycloalkyl, -($L^1$)—($C_3$-$C_{12}$ cycloalkyl), $C_4$-$C_{12}$ unsaturated nonaromatic carbocyclyl, -($L^1$)—($C_4$-$C_{12}$ unsaturated nonaromatic carbocyclyl), 3-12 member heterocyclyl, -($L^1$)-(3-12 member heterocyclyl), 5-12 member heteroaryl and -($L^1$)-(5-12 member heteroaryl);

$R^{10}$ is selected from $C_1$-$C_6$ alkyl, $C_1$-$C_6$ perfluoroalkyl, —($C_1$-$C_6$ alkylene)$_m$-($C_1$-$C_6$ alkoxyl), —($C_1$-$C_6$ alkylene)$_m$-(CONR$^j$R$^k$) wherein each $R^j$ and $R^k$ is independently H or $C_1$-$C_3$ alkyl, —($C_1$-$C_3$ alkylene)$_m$-($C_3$-$C_6$ cycloalkyl) and —($C_1$-$C_3$ alkylene)$_m$-(3 to 6 member heterocyclyl), and $R^{10}$ is optionally further substituted by 1-3 groups selected from halide, —OH, oxo and $C_1$-$C_3$ alkyl, provided that when $R^4$ is —B—CH($R^{10}$)$R^9$, B is NH or $CH_2$ and $R^9$ is unsubstituted —$CH_3$ or unsubstituted phenyl, $R^{10}$ is not unsubstituted $CH_3$;

each R is independently selected from the group consisting of methyl, n-propyl, isopropyl, n-butyl, sec-butyl, isobutyl, $C_5$-$C_8$ alkyl, $C_2$-$C_8$ alkenyl, $C_2$-$C_8$ alkynyl, —($C_1$-$C_3$ alkylene)$_m$-($C_3$-$C_{12}$ cycloalkyl), —($C_1$-$C_3$ alkylene)$_m$-phenyl, —($C_1$-$C_3$ alkylene)$_m$-(5-12 member heteroaryl), —($C_1$-$C_3$ alkylene)$_m$-(3-12 member heterocyclyl), —($C_1$-$C_3$ alkylene)$_m$-($C_3$-$C_{12}$ unsaturated non-aromatic carbocyclyl), —($C_1$-$C_6$ perfluoroalkyl), —($C_1$-$C_3$ alkylene)$_m$-halide, —($C_1$-$C_3$ alkylene)$_m$-CN, —($C_1$-$C_3$ alkylene)$_m$-C(O)R$^a$, —($C_1$-$C_3$ alkylene)$_m$-C(O)OR$^a$, —($C_1$-$C_3$ alkylene)$_m$-C(O)NR$^a$R$^b$—($C_1$-$C_3$ alkylene)$_m$-OR$^b$, —($C_1$-$C_3$ alkylene)$_m$-OC(O)R$^a$, —($C_1$-$C_3$ alkylene)$_m$-OC(O)NR$^a$R$^b$—($C_1$-$C_3$ alkylene)$_m$-O—S(O)R$^a$, —($C_1$-$C_3$ alkylene)$_m$-OS(O)$_2$R$^a$, —($C_1$-$C_3$ alkylene)$_m$-OS(O)$_2$NR$^a$R$^b$, —($C_1$-$C_3$ alkylene)$_m$-OS(O)NR$^a$R$^b$, —($C_1$-$C_3$ alkylene)$_m$-$NO_2$, —($C_1$-$C_3$ alkylene)$_m$-NR$^a$R$^b$, —($C_1$-$C_3$ alkylene)$_m$-N(R$^a$)C(O)R$^b$, —($C_1$-$C_3$ alkylene)$_m$-N(R$^a$)C(O)OR$^b$, —($C_1$-$C_3$ alkylene)$_m$-N(R$^c$)C(O)NR$^a$R$^b$, —($C_1$-$C_3$ alkylene)$_m$-N(R$^a$)S(O)$_2$R$^b$, ($C_1$-$C_3$ alkylene)$_m$-N(R$^a$)S(O)R$^b$, —($C_1$-$C_3$ alkylene)$_m$-SR$^a$, —($C_1$-$C_3$ alkylene)$_m$-S(O)R$^a$, —($C_1$-$C_3$ alkylene)$_m$-S(O)$_2$R$^a$, —($C_1$-$C_3$ alkylene)$_m$-S(O)NR$^a$R$^b$, —($C_1$-$C_3$ alkylene)$_m$-S(O)$_2$NR$^a$—($C_1$-$C_3$ alkylene)$_m$-O—($C_1$-$C_3$ alkylene)$_m$-NR$^a$R$^b$ and —($C_1$-$C_3$ alkylene)$_m$-NR$^a$($C_1$-$C_3$ alkylene)-OR$^b$; the said $C_3$-$C_{12}$ cycloalkyl, the said phenyl, the said 3-12 member heterocyclyl and the said 5-12 member heteroaryl are independently optionally further substituted by 1-3 groups selected from —F, $C_1$-$C_3$ alkyl, $C_1$-$C_3$ perfluoroalkyl and oxo;

each $R^a$, $R^b$ and $R^c$ is independently H, $C_1$-$C_8$ alkyl, $C_2$-$C_8$ alkenyl, —($C_1$-$C_3$ alkylene)$_m$-($C_3$-$C_8$ cycloalkyl), —($C_1$-$C_3$ alkylene)$_m$-($C_3$-$C_8$ cycloalkenyl), $C_2$-$C_8$ alkynyl, —($C_1$-$C_3$ alkylene)$_m$-phenyl, —($C_1$-$C_3$ alkylene)$_m$-(5-7 member heteroaryl) or —($C_1$-$C_3$ alkylene)$_m$-(3-8 member heterocyclyl), and each $R^a$, $R^b$ and $R^c$ is independently optionally further substituted by 1-3 groups selected from halide, hydroxyl, —CN, $C_1$-$C_6$ alkyl, $C_1$-$C_6$ perfluoroalkyl, $C_1$-$C_6$ alkoxyl and $C_1$-$C_6$ alkylamino; or, when connected to the same nitrogen, $R^a$ and $R^b$ may optionally form a ring selected from -(5-7 member heteroaryl) and -(3-8 member heterocyclyl), and the said ring is optionally further substituted by 1-3 groups selected from halide, hydroxyl, —CN, $C_1$-$C_6$ alkyl, $C_1$-$C_6$ perfluoroalkyl, $C_1$-$C_6$ alkoxyl and $C_1$-$C_6$ alkylamino;

each $R^t$ is independently H or $C_1$-$C_3$ alkyl;

each $R^1$, $R^5$, $R^7$ and $R^9$ is independently optionally further substituted by 1-6 groups selected from oxo and $R^x$;

each $R^x$ is independently ethyl, t-butyl or R;

each L is independently a divalent radical selected from —($C_1$-$C_3$ alkylene)$_m$-($C_3$-$C_7$ cycloalkylene)-, —($C_2$-$C_8$ alkenylene)-, —($C_2$-$C_8$ alkynylene)-, —O—($C_1$-$C_3$ alkylene)$_m$-, —NH—($C_1$-$C_3$ alkylene)$_m$-;

each $L^1$ is independently a divalent radical selected from —($C_1$-$C_3$ alkylene)-, —O—, —($C_1$-$C_3$ alkylene)-O—, —N(R$^t$)— and —($C_1$-$C_3$ alkylene)-N(R$^t$)—; and each m is independently 0 or 1;

or a pharmaceutically acceptable salt, solvate or hydrate thereof.

In the 1$^{st}$ particular aspect of this embodiment, and in combination with any other particular aspects not inconsistent, each $R^2$ and $R^3$ is independently H, $C_1$-$C_6$ alkyl and $C_3$-$C_5$ cycloalkyl, and each $R^2$ and $R^3$ is independently optionally further substituted. More particularly, each $R^2$ and $R^3$ is independently optionally further substituted by 1-3 groups selected from —F, oxo, $C_1$-$C_3$ alkyl and $C_1$-$C_3$ perfluoroalkyl. Even more particularly, each $R^2$ and $R^3$ is independently H, unsubstituted $C_1$-$C_3$ alkyl and unsubstituted $C_3$-$C_5$ cycloalkyl. Even further more particularly, $R^2$ is unsubstituted methyl, and $R^3$ is unsubstituted methyl.

In the 2$^{nd}$ particular aspect of the embodiment, and in combination with any other particular aspects not inconsistent, $R^2$ and $R^3$, together with the carbon atom that $R^2$ and $R^3$ attach to, form a ring selected from $C_3$-$C_5$ cycloalkylene and 3-5 member heterocyclylene, and the said ring is optionally further substituted. More particularly, the said ring is optionally further substituted by 1-3 groups selected from —F, oxo, $C_1$-$C_3$ alkyl and $C_1$-$C_3$ perfluoroalkyl. Even more particularly, the said ring is selected from cyclopropylene, cyclobutylene and cyclopentylene. Even further more particularly, the said ring is cyclopropylene. More preferably, the said ring is unsubstituted cyclopropylene.

In the 3$^{rd}$ particular aspect of the embodiment, and in combination with any other particular aspects not inconsistent, especially particular aspect one or two, $R^1$ is selected from —($C_1$-$C_3$ alkylene)$_m$-phenyl and -L-phenyl, and $R^1$ is optionally further substituted by 1-6 groups selected from oxo and $R^x$. More particularly, $R^1$ is phenyl optionally substituted by 1-6 groups selected from oxo and $R^x$.

In the 4$^{th}$ particular aspect of the embodiment, and in combination with any other particular aspects not inconsistent, especially particular aspect one or two, $R^1$ is selected from —($C_1$-$C_3$ alkylene)$_m$-($C_3$-$C_{12}$ cycloalkyl) and -L-($C_3$-$C_{12}$ cycloalkyl), and $R^1$ is optionally further substituted by 1-6 groups selected from oxo and $R^x$. More particularly, $R^1$ is $C_3$-$C_{12}$ cycloalkyl optionally further substituted by 1-6 groups selected from oxo and $R^x$. Even more particularly, $R^1$ is selected from cyclopropyl, cyclobutyl, cyclopentyl and cyclohexyl, and $R^1$ is optionally further substituted by 1-6 groups selected from oxo and $R^x$.

In the 5th particular aspect of the embodiment, and in combination with any other particular aspects not inconsistent, especially particular aspect one or two, $R^1$ is selected from —$(C_1-C_3$ alkylene$)_m$-(5-10 member heteroaryl) and -L-(5-10 member heteroaryl), and $R^1$ is optionally further substituted by 1-6 groups selected from oxo and $R^x$. More particularly, $R^1$ is selected from 5-10 member heteroaryl optionally further substituted by 1-6 groups selected from oxo and $R^x$. Even more particularly, $R^1$ is selected from pyridinyl, thiophenyl, thiazolyl and imidazolyl, and $R^1$ is optionally further substituted by 1-6 groups selected from oxo and $R^x$.

In the 6th particular aspect of the embodiment, and in combination with any other particular aspects not inconsistent, especially particular aspect one or two, $R^1$ is selected from —$(C_1-C_3$ alkylene$)_m$-(3-10 member heterocyclyl) and -L-(3-10 member heterocyclyl), and $R^1$ is optionally further substituted by 1-6 groups selected from oxo and $R^x$. More particularly, $R^1$ is 3-10 member heterocyclyl optionally further substituted by 1-6 groups selected from oxo and $R^x$. Even more particularly, $R^1$ is selected from tetrohydrofuranyl, tetrahydropyranyl and morpholinyl, and $R^1$ is optionally further substituted by 1-6 groups selected from oxo and $R^x$.

In the 7th particular aspect of the embodiment, and in combination with any other particular aspects not inconsistent, especially particular aspect one or two, $R^1$ is selected from —$(C_1-C_3$ alkylene$)_m$-$(C_3-C_{12}$ unsaturated nonaromatic carbocyclyl) and -L-$(C_3-C_{12}$ unsaturated nonaromatic carbocyclyl), and $R^1$ is optionally further substituted by 1-6 groups selected from oxo and $R^x$. More particularly, $R^1$ is $C_3-C_{12}$ unsaturated nonaromatic carbocyclyl optionally further substituted by 1-6 groups selected from oxo and $R^x$.

In the 8th particular aspect of the embodiment, and in combination with any other particular aspects not inconsistent, especially particular aspect one or two, $R^1$ is selected from $C_1-C_8$ alkyl, $C_2-C_8$ alkenyl and $C_2-C_8$ alkynyl, and $R^1$ is optionally further substituted by 1-6 groups selected from oxo and $R^x$.

In the 9th particular aspect of the embodiment, and in combination with any other particular aspects not inconsistent, especially particular aspect one or two, $R^1$ is selected from -L-$(C_1-C_8$ alkyl), -L-$(C_2-C_8$ alkenyl) and -L-$(C_2-C_8$ alkynyl), and $R^1$ is optionally further substituted by 1-6 groups selected from oxo and $R^x$.

In the 10th particular aspect of the embodiment, and in combination with any other particular aspects not inconsistent, especially particular aspect one or two, $R^1$ is selected from $C_1-C_8$ alkyl, —$(C_1-C_3$ alkylene$)_m$-phenyl, —$(C_3-C_5$ cycloalkylene)-phenyl, —$(C_1-C_3$ alkylene$)_m$-(5-6 member heteroaryl), —$(C_3-C_5$ cycloalkylene)-(5-6 member heteroaryl), —$(C_1-C_3$ alkylene$)_m$-$(C_3-C_{10}$ cycloalkyl), —$(C_1-C_3$ alkylene$)_m$-$(C_5-C_{10}$ cycloalkenyl), —$(C_1-C_3$ alkylene$)_m$-(3-8 member heterocyclyl) and —$(C_3-C_5$ cycloalkylene)-(3-8 member heterocyclyl), and $R^1$ is optionally further substituted by 1-6 groups selected from oxo and $R^x$.

In the 11th particular aspect of the embodiment, and in combination with any other particular aspects not inconsistent, especially particular aspect one or two, $R^1$ is selected from $C_1-C_8$ alkyl, phenyl, —$(C_1-C_3$ alkylene)-phenyl, -(cyclopropylene)-phenyl, pyridinyl, —$(C_1-C_3$ alkylene)-pyridinyl, -(cyclopropylene)-pyridinyl, thiophenyl, thiazolyl, imidazolyl, -cyclopropyl, cyclopentyl, cyclohexyl, tetrohydrofuranyl, tetrahydropyranyl, morpholinyl, and $R^1$ is optionally further substituted by 1-6 groups selected from oxo and $R^x$.

In the 12th particular aspect of the embodiment, and in combination with any other particular aspects not inconsistent, especially particular aspects two to eleven, $R^1$ is optionally further substituted with 1-6 groups selected from $C_1-C_3$ alkyl, $C_1-C_3$ perfluoroalkyl, oxo, —$(C_1-C_3$ alkylene$)_m$-halide, —$(C_1-C_3$ alkylene$)_m$-CN, —$(C_1-C_3$ alkylene$)_m$-OH, —$(C_1-C_3$ alkylene$)_m$-OR$^d$, —$(C_1-C_3$ alkylene$)_m$-NH$_2$, —$(C_1-C_3$ alkylene$)_m$-$(C_1-C_6$ monoalkylamino), —$(C_1-C_3$ alkylene$)_m$-$(C_2-C_8$ dialkylamino), —$(C_1-C_3$ alkylene$)_m$-CONR$^d$R$^e$, wherein each R$^d$ and R$^e$ is independently H or $C_1-C_3$ alkyl. More particularly, $R^1$ is optionally further substituted by 1-3 groups selected from —F, $C_1-C_3$ alkyl, $C_1-C_3$ alkoxyl and $C_1-C_3$ perfluoroalkyl.

In the 13th particular aspect of the embodiment, and in combination with any other particular aspects not inconsistent, especially particular aspects two to twelve, $R^4$ is —OR$^6$—R$^7$.

In the 14th particular aspect of the embodiment, and in combination with any other particular aspects not inconsistent, especially particular aspects 2 to 12, $R^4$ is —N(R$^t$)R$^6$—R$^7$ wherein R$^t$ is H or $C_1-C_3$ alkyl. More preferably, $R^4$ is —NH—R$^6$—R$^7$.

In the 15th particular aspect of the embodiment, and in combination with any other particular aspects not inconsistent, especially particular aspects 2 to 12, $R^4$ is —CH(R$^t$)—R$^6$—R$^7$ wherein R$^t$ is H or $C_1-C_3$ alkyl. More preferably, $R^4$ is —CH$_2$—R$^6$—R$^7$.

In the 16th particular aspect of the embodiment, and in combination with any other particular aspects not inconsistent, especially particular aspect 13 to 15, $R^6$ is -(3-7 member heterocyclylene)-, and $R^6$ is optionally substituted. More preferably, $R^6$ is selected from aziridinyl, azitidinyl, pyrrolidinyl and piperidinyl, and $R^6$ is optionally further substituted. Even more preferably, $R^6$ is optionally further substituted by 1-4 groups selected from —F, $C_1-C_3$ alkyl, $C_1-C_3$ perfluoroalkyl and oxo. Even further more preferably, $R^6$ is selected from unsubstituted aziridinyl, unsubstituted azitidinyl, unsubstituted pyrrolidinyl and unsubstituted piperidinyl.

In the 17th particular aspect of the embodiment, and in combination with any other particular aspects not inconsistent, especially particular aspects 13 to 15, $R^6$ is selected from -cyclopropylene-, -cyclobutylene- and -cyclopentylene-, $R^6$ is optionally further substituted. More particularly, $R^6$ is -cyclopropylene- optionally further substituted by 1-4 groups selected from oxo, —F, $C_1-C_3$ alkyl and $C_1-C_3$ perfluoroalkyl. Even more particularly, $R^6$ is unsubstituted cyclopropylene.

In the 18th particular aspect of the embodiment, and in combination with any other particular aspects not inconsistent, especially particular aspects thirteen to seventeen, $R^7$ is phenyl, and $R^7$ is optionally further substituted.

In the 19th particular aspect of the embodiment, and in combination with any other particular aspects not inconsistent, especially particular aspects 13 to 17, $R^7$ is 5 member heteroaryl containing 1-3 heteroatoms selected from N, S and O, and $R^7$ is optionally further substituted. More particularly, $R^7$ is 5 member heteroaryl containing 1-2 N heteroatoms, and $R^7$ is optionally further substituted.

In the 20th particular aspect of the embodiment, and in combination with any other particular aspects not inconsistent, especially particular aspects 13 to 17, $R^7$ is 6 member heteroaryl containing 1-3 heteroatoms selected from N, S and O, and $R^7$ is optionally further substituted. More particularly, $R^7$ is 6 member heteroaryl containing 1-2 N heteroatoms, and $R^7$ is optionally further substituted.

In the 21st particular aspect of the embodiment, and in combination with any other particular aspects not inconsistent, especially particular aspects 18 to 20, $R^7$ is optionally further substituted by 1-6 groups selected from —F, $C_1-C_3$ alkyl, $C_1$-$C_3$ perfluoroalkyl. More preferably, $R^7$ is optionally further substituted by 1-6 groups selected from halide and $C_1$-$C_3$ alkyl.

In the 22$^{nd}$ particular aspect of the embodiment, and in combination with any other particular aspects not inconsistent, especially particular aspects 2 to 12, $R^4$ is selected from —O—CH($R^8$)—$R^9$.

In the 23$^{rd}$ particular aspect of the embodiment, and in combination with any other particular aspects not inconsistent, especially particular aspects 2 to 12, $R^4$ is —B—($C_1$-$C_3$ alkylene)-CH($R^8$)—$R^9$, wherein B is —O—, —$NR^t$— or —CH($R^t$)— and $R^t$ is H or $C_1$-$C_3$ alkyl. More preferably, $R^t$ is H.

In the 24$^{th}$ particular aspect of the embodiment, and in combination with any other particular aspects not inconsistent, especially particular aspects 2 to 12, $R^4$ is selected from —N($R^t$)CH($R^8$)$R^9$ and wherein $R^t$ is H or $C_1$-$C_3$ alkyl.

In the 25$^{th}$ particular aspect of the embodiment, and in combination with any other particular aspects not inconsistent, especially particular aspects 2 to 12, $R^4$ is selected from —CH($R^t$)—CH($R^8$)—$R^9$, and wherein $R^t$ is H or $C_1$-$C_3$ alkyl.

In the 26$^{th}$ particular aspect of the embodiment, and in combination with any other particular aspects not inconsistent, especially particular aspect 23, 24 or 25, $R^t$ is H.

In the 27$^{th}$ particular aspect of the embodiment, and in combination with any other particular aspects not inconsistent, especially particular aspects 22 to 26, $R^8$ is —($C_1$-$C_6$ alkylene)$_m$-$NR^pR^q$, wherein each $R^p$ and $R^q$ is independently H or $C_1$-$C_3$ alkyl. More particularly, $R^8$ is selected from —$CH_2$—N—$(CH_3)_2$, —$CH_2$—NH—$CH_3$ and —$CH_2$—$NH_2$.

In the 28$^{th}$ particular aspect of the embodiment, and in combination with any other particular aspects not inconsistent, especially particular aspects 22 to 26, $R^8$ is —($C_1$-$C_6$ alkylene)$_m$-$NR^pR^q$, and wherein $R^p$ and $R^q$, together with the nitrogen atom they attach to, form a ring selected from 3-7 member heterocyclyl and 5-7 member heteroaryl, the said ring is optionally further substituted by 1-6 groups selected from halide, $C_1$-$C_3$ alkyl and $C_1$-$C_3$ perfluoroalkyl.

In the 29$^{th}$ particular aspect of the embodiment, and in combination with any other particular aspects not inconsistent, especially particular aspects 22 to 28, $R^9$ is phenyl, and $R^9$ is optionally further substituted.

In the 30$^{th}$ particular aspect of the embodiment, and in combination with any other particular aspects not inconsistent, especially particular aspects 22 to 28, $R^9$ is 6 member heteroaryl containing 1-2 N heteroatoms, $R^9$ is optionally further substituted. More preferably, $R^9$ is pyridinyl, and $R^9$ is optionally further substituted.

In the 31$^{st}$ particular aspect of the embodiment, and in combination with any other particular aspects not inconsistent, especially particular aspects 22 to 28, $R^9$ is 5 member heteroaryl containing 1-2 N heteroatoms, and $R^9$ is optionally further substituted.

In the 32$^{nd}$ particular aspect of the embodiment, and in combination with any other particular aspects not inconsistent, especially particular aspects 22 to 28, $R^9$ is $C_5$-$C_7$ cycloalkyl, and $R^9$ is optionally further substituted.

In the 33$^{rd}$ particular aspect of the embodiment, and in combination with any other particular aspects not inconsistent, especially particular aspects 22 to 28, $R^9$ is 5-7 member heterocyclyl containing 1-2 heteroatoms selected from N, S and O, $R^9$ is optionally further substituted.

In the 34$^{th}$ particular aspect of the embodiment, and in combination with any other particular aspects not inconsistent, especially particular aspects 22 to 33, $R^9$ is optionally further substituted by 1-6 groups selected from —($C_1$-$C_3$ alkylene)$_m$-halide, —($C_1$-$C_3$ alkylene)$_m$-hydroxyl, —($C_1$-$C_3$ alkylene)$_m$-CN, $C_1$-$C_6$ alkyl, $C_1$-$C_6$ perfluoroalkyl, —($C_1$-$C_3$ alkylene)$_m$-($C_1$-$C_6$ alkoxyl), —($C_1$-$C_3$ alkylene)$_m$-$NH_2$, and —($C_1$-$C_3$ alkylene)$_m$-($C_1$-$C_6$ alkylamino). More particularly, $R^9$ is optionally further substituted by 1-6 groups selected from —F, $C_1$-$C_3$ alkyl, $C_1$-$C_3$ perfluoroalkyl, $C_1$-$C_3$ alkoxyl and oxo.

In the 35$^{th}$ particular aspect of the embodiment, and in combination with any other particular aspects not inconsistent, especially particular aspects 1 to 12 and particular aspects 29 to 34, $R^4$ is —O—($C_1$-$C_3$ alkylene)$_m$-CH($R^{10}$)$R^9$. More particularly, $R^4$ is —O—CH($R^{10}$)$R^9$. Even more particularly, $R^{10}$ is selected from $C_1$-$C_6$ alkyl, —($C_1$-$C_6$ alkylene)$_m$—($C_1$-$C_6$ alkoxyl) and —($C_1$-$C_3$ alkylene)$_m$-(3-6 member heterocyclyl), and $R^{10}$ is optionally further substituted.

In the 36$^{th}$ particular aspect of the embodiment, and in combination with any other particular aspects not inconsistent, especially particular aspects 1 to 12 and particular aspects 29 to 34, $R^4$ is —$NR^t$—($C_1$-$C_3$ alkylene)$_m$-CH($R^{10}$)$R^9$. More particularly, $R^4$ is —$NR^t$—CH($R^{10}$)$R^9$. Even more particularly, $R^t$ is H. Even further more particularly, $R^{10}$ is selected from $C_1$-$C_6$ alkyl, —($C_1$-$C_6$ alkylene)$_m$-($C_1$-$C_6$ alkoxyl) and —($C_1$-$C_3$ alkylene)$_m$-(3-6 member heterocyclyl), and $R^{10}$ is optionally further substituted.

In the 37$^{th}$ particular aspect of the embodiment, and in combination with any other particular aspects not inconsistent, especially particular aspects 1 to 12 and particular aspects 29 to 34, $R^4$ is —$CHR^t$—($C_1$-$C_3$ alkylene)$_m$-CH($R^{10}$)$R^9$. More particularly, $R^4$ is —$CHR^t$—CH($R^{10}$)$R^9$. Even more particularly, $R^t$ is H. Even further more particularly, $R^{10}$ is selected from $C_1$-$C_6$ alkyl, —($C_1$-$C_6$ alkylene)$_m$-($C_1$-$C_6$ alkoxyl) and —($C_1$-$C_3$ alkylene)$_m$-(3-6 member heterocyclyl), and $R^{10}$ is optionally further substituted.

In the 38$^{th}$ particular aspect of the embodiment, and in combination with any other particular aspects not inconsistent, $R^2$ is unsubstituted methyl; $R^3$ is unsubstituted methyl; $R^1$ is selected from the group consisting of $C_1$-$C_8$ alkyl, —($C_1$-$C_3$ alkylene)$_m$-phenyl, —($C_3$-$C_7$ cycloalkylene)-phenyl, —($C_1$-$C_3$ alkylene)$_m$-($C_3$-$C_{12}$ cycloalkyl), —($C_3$-$C_7$ cycloalkylene)-($C_3$-$C_{12}$ cycloalkyl), —($C_1$-$C_3$ alkylene)$_m$-($C_3$-$C_{12}$ unsaturated nonaromatic carbocyclyl), —($C_3$-$C_7$ cycloalkylene)-($C_3$-$C_{12}$ unsaturated nonaromatic carbocyclyl)-($C_1$-$C_3$ alkylene)$_m$-(5-10 member heteroaryl), —($C_3$-$C_7$ cycloalkylene)-(5-10 member heteroaryl), —($C_1$-$C_3$ alkylene)$_m$-(3-10 member heterocyclyl) and —($C_3$-$C_7$ cycloalkylene)-(3-10 member heterocyclyl), and $R^1$ is optionally further substituted by 1-6 groups selected from the group consisting of $C_1$-$C_3$ alkyl, —($C_1$-$C_3$ alkylene)$_m$-($C_3$-$C_5$ cycloalkyl), —($C_1$-$C_3$ alkylene)$_m$-(3-6 member heterocyclyl optionally further substituted by 1-2 methyl), F, Cl, —CN, $C_1$-$C_3$ perfluoroalkyl, —($C_1$-$C_3$ alkylene)$_m$-$NH_2$, —($C_1$-$C_3$ alkylene)$_m$-NH($C_1$-$C_4$ alkyl), —($C_1$-$C_3$ alkylene)$_m$-N($C_1$-$C_4$ alkyl)($C_1$-$C_4$ alkyl), —($C_1$-$C_3$ alkylene)$_m$-NH—($C_3$-$C_5$ cycloalkyl)-($C_1$-$C_3$ alkylene)$_m$-OH, —($C_1$-$C_3$ alkylene)$_m$-O—($C_1$-$C_4$ alkyl), —($C_1$-$C_3$ alkylene)$_m$-O—($C_3$-$C_5$ cycloalkyl), —($C_1$-$C_3$ alkylene)$_m$-C(O)—$NH_2$, —($C_1$-$C_3$ alkylene)$_m$-C(O)—NH—($C_1$-$C_4$ alkyl) and —($C_1$-$C_3$ alkylene)$_m$-C(O)—N($C_1$-$C_4$ alkyl)($C_1$-$C_4$ alkyl).

In the 39$^{th}$ particular aspect of the embodiment, and in combination with any other particular aspects not inconsistent, $R^2$ is unsubstituted methyl; $R^3$ is unsubstituted methyl; $R^1$ is selected from the group consisting of $C_1$-$C_8$ alkyl, $C_3$-$C_8$ cycloalkyl, phenyl, —($C_1$-$C_3$ alkylene)-phenyl, -(cyclopropylene)-phenyl, -pyridinyl, —($C_1$-$C_3$ alkylene)-pyridinyl, -(cyclopropylene)-pyridinyl, -pyrimidinyl, —($C_1$-$C_3$ alkylene)-pyrimidinyl, -(cyclopropylene)-pyrimidinyl, thiophenyl, —($C_1$-$C_3$ alkylene)-thiophenyl, -(cyclopropylene)-thiophenyl, pyrazolyl, —($C_1$-$C_3$ alkylene)-pyrazolyl, -(cyclopropylene)-pyrazolyl, tetrahydrofuranyl, —($C_1$-$C_3$ alkylene)-tetrahydrofuranyl, —($C_1$-$C_3$ cyclopropylene)-tetrahydrofuranyl, tetrahydropyranyl, —($C_1$-$C_3$ alkylene)-tetrahydropyranyl, —($C_1$-$C_3$ cyclopropylene)-tetrahydropyranyl, morpholinyl, —($C_1$-$C_3$ alkylene)-morpholinyl, -(cyclopropylene)-morpholinyl, imidazolyl, —($C_1$-$C_3$ alkylene)-imidazolyl, -(cyclopropylene)-imidazolyl, thiazolyl, —($C_1$-$C_3$ alkylene)-thiazolyl, -(cyclopropylene)-thiazolyl, isothiazolyl, —($C_1$-$C_3$ alkylene)-isothiazolyl, -(cyclopropylene)-isothiazolyl, oxazolyl, —($C_1$-$C_3$ alkylene)-oxazolyl, -(cyclopropylene)-oxazolyl, isoxazolyl, —($C_1$-$C_3$ alkylene)-isoxazolyl, -(cyclopropylene)-isoxazolyl, benzothiophenyl, —($C_1$-$C_3$ alkylene)-benzothiophenyl, -(cyclopropylene)-benzothiophenyl, benzothiazolyl, —($C_1$-$C_3$ alkylene)-benzothiazolyl, -(cyclopropylene)-benzothiazolyl, dihydrobenzofuranyl, —($C_1$-$C_3$ alkylene)-dihydrobenzofuranyl, -(cyclopropylene)-dihydrobenzofuranyl, pyrazinyl, —($C_1$-$C_3$ alkylene)-pyrazinyl and -(cyclopropylene)-pyrazinyl, wherein $R^1$ is optionally further substituted by 1-3 groups selected from F, Cl, $C_1$-$C_3$ alkyl, $C_1$-$C_3$ perfluoroalkyl and $C_1$-$C_3$ alkoxyl.

In the $40^{th}$ particular aspect of this embodiment, and in combination of any other particular aspects not inconsistent, $R^2$ and $R^3$ forms a unsubstituted cyclopropylene group.

In another embodiment, the current invention provides a compound of formula II,

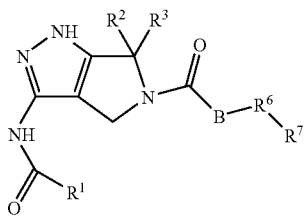

II wherein:

B is —O—, —$NR^t$— or —$CHR^t$—, wherein $R^t$ is H or $C_1$-$C_3$ alkyl;

$R^1$ is selected from $C_1$-$C_8$ alkyl, —($C_1$-$C_3$ alkylene)$_m$-phenyl, —($C_3$-$C_5$ cycloalkylene)-phenyl, —($C_1$-$C_3$ alkylene)$_m$-($C_3$-$C_{10}$ cycloalkyl), —($C_1$-$C_3$ alkylene)$_m$-($C_5$-$C_{10}$ cycloalkenyl), —($C_1$-$C_3$ alkylene)$_m$-(3-10 member heterocyclyl), —($C_3$-$C_5$ cycloalkylene)-(3-10 member heterocyclyl), —($C_1$-$C_3$ alkylene)$_m$-(5-12 member heteroaryl) and —($C_3$-$C_5$ cycloalkylene)-(5-12 member heteroaryl), and $R^1$ is optionally further substituted by 1-6 groups selected from —($C_1$-$C_3$ alkylene)$_m$-halide, —($C_1$-$C_3$ alkylene)$_m$-hydroxyl, —($C_1$-$C_3$ alkylene)$_m$-CN, $C_1$-$C_6$ alkyl, $C_1$-$C_6$ perfluoroalkyl, —($C_1$-$C_3$ alkylene)$_m$-($C_1$-$C_6$ alkoxyl), —($C_1$-$C_3$ alkylene)$_m$-$NH_2$, —($C_1$-$C_3$ alkylene)$_m$-($C_1$-$C_6$ alkylamino), —($C_1$-$C_3$ alkylene)$_m$-($C_3$-$C_5$ cycloalkyl) and —($C_1$-$C_3$ alkylene)$_m$-(3-5 member heterocyclyl), and the said $C_3$-$C_5$ cycloalkyl and the said 3-5 member heterocyclyl is optionally further substituted by 1-3 group selected from —F, $C_1$-$C_3$ alkyl, $C_1$-$C_3$ perfluoroalkyl and oxo;

each $R^2$ and $R^3$ is independently $C_1$-$C_3$ alkyl, or $R^2$ and $R^3$, together with the carbon atom that $R^2$ and $R^3$ attach to, form a $C_3$-$C_4$ cycloalkylene;

$R^6$ is a divalent radical selected from cyclopropylene, cyclobutylene, cyclopentylene and -(3-6 member heterocylene)-, $R^6$ is optionally further substituted by 1-6 groups selected from halide, $C_1$-$C_3$ alkyl, oxo and $C_1$-$C_3$ perfluoroalkyl;

$R^7$ is selected from phenyl, 5 member heteroaryl, pyridinyl, 6 member heteroaryl containing 2-3 heteroatoms selected from N, S and O, 7-10 member heteroaryl and 3-12 member heterocyclyl, $R^7$ is optionally further substituted by 1-6 groups selected from halide, —$C_1$-$C_3$ perfluoroalkyl, $C_1$-$C_3$ alkyl, $C_1$-$C_3$ alkoxy, $C_1$-$C_3$ alkylamino, —OH, —$NH_2$ and —CN;

each m is independently 0 or 1; or a pharmaceutically acceptable salt, solvate or hydrate thereof.

In the $1^{st}$ particular aspect of the embodiment, and in combination with any other particular aspects not inconsistent, B is —O—.

In the $2^{nd}$ particular aspect of the embodiment, and in combination with any other particular aspects not inconsistent, B is —$NR^t$—. More particularly, $R^t$ is H. Also more particularly, $R^t$ is $C_1$-$C_3$ alkyl.

In the $3^{rd}$ particular aspect of the embodiment, and in combination with any other particular aspects not inconsistent, B is —$CHR^t$—. More particularly, $R^t$ is H. Also more particularly, $R^t$ is $C_1$-$C_3$ alkyl.

In the $4^{th}$ particular aspect of the embodiment, and in combination with any other particular aspects not inconsistent, especially particular aspects 2 to 3, $R^2$ is methyl, and $R^3$ is methyl.

In the $5^{th}$ particular aspect of the embodiment, and in combination with any other particular aspects not inconsistent, especially particular aspects 2 to 4, $R^1$ is $C_1$-$C_8$ alkyl, and $R^1$ is optionally further substituted.

In the $6^{th}$ particular aspect of the embodiment, and in combination with any other particular aspects not inconsistent, especially particular aspects 2 to 4, $R^1$ is phenyl, and $R^1$ is optionally further substituted.

In the $7^{th}$ particular aspect of the embodiment, and in combination with any other particular aspects not inconsistent, especially particular aspects 2 to 4, $R^1$ is —($C_1$-$C_3$ alkylene)-phenyl, and $R^1$ is optionally further substituted.

In the $8^{th}$ particular aspect of the embodiment, and in combination with any other particular aspects not inconsistent, especially particular aspects 2 to 4, wherein $R^1$ is —($C_3$-$C_5$ cycloalkylene)-phenyl, and $R^1$ is optionally further substituted.

In the $9^{th}$ particular aspect of the embodiment, and in combination with any other particular aspects not inconsistent, especially particular aspects 2 to 4, $R^1$ is 5-10 member heteroaryl, and $R^1$ is optionally further substituted. More particularly, the 5-10 member heteroaryl is selected from pyridinyl, thiophenyl, thiazolyl and imidazolyl, and $R^1$ is optionally further substituted.

In the $10^{th}$ particular aspect of the embodiment, and in combination with any other particular aspects not inconsistent, especially particular aspects 2 to 4, $R^1$ is —($C_1$-$C_3$ alkylene)-(5-10 member heteroaryl), and $R^1$ is optionally further substituted. More particularly, the 5-10 member heteroaryl is selected from pyridinyl, thiophenyl, thiazolyl and imidazolyl, and $R^1$ is optionally further substituted.

In the $11^{th}$ particular aspect of the embodiment, and in combination with any other particular aspects not inconsistent, especially particular aspects 2 to 4, $R^1$ is —($C_3$-$C_5$ cycloalkylene)-(5-10 member heteroaryl), and $R^1$ is optionally further substituted. More particularly, the 5-10 member heteroaryl is selected from pyridinyl, thiophenyl, thiazolyl and imidazolyl, and $R^1$ is optionally further substituted.

In the 12$^{th}$ particular aspect of the embodiment, and in combination with any other particular aspects not inconsistent, especially particular aspects 2 to 4, $R^1$ is —($C_1$-$C_3$ alkylene)-($C_3$-$C_{10}$ cycloalkyl), and $R^1$ is optionally further substituted. More particularly, the $C_3$-$C_{10}$ cycloalkyl is selected from cyclopropyl, cyclobutyl, cyclopentyl and cyclohexyl, and $R^1$ is optionally further substituted.

In the 13$^{th}$ particular aspect of the embodiment, and in combination with any other particular aspects not inconsistent, especially particular aspects 2 to 4, $R^1$ is $C_3$-$C_{10}$ cycloalkyl, and $R^1$ is optionally further substituted. More particularly, the $C_3$-$C_{10}$ cycloalkyl is selected from cyclopropyl, cyclobutyl, cyclopentyl and cyclohexyl, and $R^1$ is optionally further substituted.

In the 14$^{th}$ particular aspect of the embodiment, and in combination with any other particular aspects not inconsistent, especially particular aspects 2 to 4, $R^1$ is —($C_1$-$C_3$ alkylene)-($C_5$-$C_{10}$ cycloalkenyl), and $R^1$ is optionally further substituted.

In the 15$^{th}$ particular aspect of the embodiment, and in combination with any other particular aspects not inconsistent, especially particular aspects 2 to 4, $R^1$ is $C_5$-$C_{10}$ cycloalkenyl, and $R^1$ is optionally further substituted.

In the 16$^{th}$ particular aspect of the embodiment, and in combination with any other particular aspects not inconsistent, especially particular aspects 2 to 4, $R^1$ is —($C_1$-$C_3$ alkylene)-(3-10 member heterocyclyl), and $R^1$ is optionally further substituted. More particularly, the 3-10 member heterocyclyl is selected from tetrohydrofuranyl, tetrahydropyranyl and morpholinyl, and $R^1$ is optionally further substituted.

In the 17$^{th}$ particular aspect of the embodiment, and in combination with any other particular aspects not inconsistent, especially particular aspects 2 to 4, $R^1$ is —($C_3$-$C_5$ cycloalkylene)-(3-10 member heterocyclyl), and $R^1$ is optionally further substituted. More particularly, the 3-10 member heterocyclyl is selected from tetrohydrofuranyl, tetrahydropyranyl and morpholinyl, and $R^1$ is optionally further substituted.

In the 18$^{th}$ particular aspect of the embodiment, and in combination with any other particular aspects not inconsistent, especially particular aspects 2 to 4, $R^1$ is 3-10 member heterocyclyl, and $R^1$ is optionally further substituted. More particularly, the 3-10 member heterocyclyl is selected from tetrohydrofuranyl, tetrahydropyranyl and morpholinyl, and $R^1$ is optionally further substituted.

In the 19$^{th}$ particular aspect of the embodiment, and in combination with any other particular aspects not inconsistent, especially particular aspects 2 to 18, $R^1$ is optionally further substituted by 1-6 groups selected from halide, $C_1$-$C_3$ alkyl, $C_1$-$C_3$ perfluoroalkyl, —OH, $C_1$-$C_3$ alkoxy, —NH$_2$, $C_1$-$C_3$ alkylamino and CN.

In the 20$^{th}$ particular aspect of the embodiment, and in combination with any other particular aspects not inconsistent, especially particular aspects 2 to 19, $R^6$ is cyclopropylene optionally further substituted. More preferably, $R^6$ is unsubstituted cyclopropylene.

In the 21$^{st}$ particular aspect of the embodiment, and in combination with any other particular aspects not inconsistent, especially particular aspects 2 to 19, $R^6$ is cyclobutylene optionally substituted. More preferably, $R^6$ is unsubstituted cyclobutylene.

In the 22$^{nd}$ particular aspect of the embodiment, and in combination with any other particular aspects not inconsistent, especially particular aspects 2 to 19, $R^6$ is -(3-6 member heterocyclylene)-, and $R^6$ is optionally substituted. More preferably, $R^6$ is selected from aziridinyl, azitidinyl, pyrrolidinyl and piperidinyl, and $R^6$ is optionally further substituted. Even more preferably, $R^6$ is optionally further substituted by 1-4 groups selected from —F, $C_1$-$C_3$ alkyl and oxo. Even further more preferably, $R^6$ is selected from unsubstituted aziridinyl, unsubstituted azitidinyl, unsubstituted pyrrolidinyl and unsubstituted piperidinyl.

In the 23$^{rd}$ particular aspect of the embodiment, and in combination with any other particular aspects not inconsistent, especially particular aspects 2 to 19, $R^6$ is cyclopentylene, and $R^6$ is optionally substituted. More preferably, $R^6$ is unsubstituted cyclopentylene.

In the 24$^{th}$ particular aspect of the embodiment, and in combination with any other particular aspects not inconsistent, especially particular aspects 2 to 23, $R^7$ is phenyl, and $R^7$ is optionally substituted. More particularly, $R^7$ is optionally further substituted by 1-6 groups selected from halide, $C_1$-$C_3$ alkyl and $C_1$-$C_3$ perfluoroalkyl.

In the 25$^{th}$ particular aspect of the embodiment, and in combination with any other particular aspects not inconsistent, especially particular aspects 2 to 23, $R^7$ is pyridinyl, and $R^7$ is optionally substituted. More particularly, $R^7$ is optionally further substituted by 1-6 groups selected from halide, $C_1$-$C_3$ alkyl and $C_1$-$C_3$ perfluoroalkyl.

In the 26$^{th}$ particular aspect of the embodiment, and in combination with any other particular aspects not inconsistent, especially particular aspects 2 to 23, $R^7$ is 5 member heteroaryl, and $R^7$ is optionally further substituted. More particularly, $R^7$ is optionally further substituted by 1-6 groups selected from halide, $C_1$-$C_3$ alkyl and $C_1$-$C_3$ perfluoroalkyl.

In the 27$^{th}$ particular aspect of the embodiment, and in combination with any other particular aspects not inconsistent, especially particular aspects 2 to 23, $R^7$ is 6 member heteroaryl containing 2-3 heteroatoms selected from N, S and O, and $R^7$ is optionally further substituted. More particularly, $R^7$ is optionally further substituted by 1-6 groups selected from halide, $C_1$-$C_3$ alkyl and $C_1$-$C_3$ perfluoroalkyl.

In the 28$^{th}$ particular aspect of the embodiment, and in combination with any other particular aspects not inconsistent, especially particular aspects 2 to 23, $R^7$ is 7-10 member heteroaryl, and $R^7$ is optionally further substituted. More particularly, $R^7$ is optionally further substituted by 1-6 groups selected from halide, $C_1$-$C_3$ alkyl and $C_1$-$C_3$ perfluoroalkyl In the 29$^{th}$ particular aspect of the embodiment, and in combination with any other particular aspects not inconsistent, especially particular aspects 2 to 23, $R^7$ is 3-12 member heterocyclyl, and $R^7$ is optionally further substituted. More particularly, $R^7$ is optionally further substituted by 1-6 groups selected from halide, $C_1$-$C_3$ alkyl and $C_1$-$C_3$ perfluoroalkyl.

In the 30$^{th}$ particular aspect of the embodiment, and in combination with any other particular aspects not inconsistent, $R^2$ is methyl; $R^3$ is methyl; B is —O—, —NH— or —CH$_2$—; $R^1$ is selected from the group consisting of $C_1$-$C_8$ alkyl, phenyl, —($C_1$-$C_3$ alkylene)-phenyl, -(cyclopropylene)-phenyl, $C_3$-$C_{10}$ cycloalkyl, —($C_1$-$C_3$ alkylene)-($C_3$-$C_{10}$ cycloalkyl), 3-10 member heterocyclyl, —($C_1$-$C_3$ alkylene)-(3-10 member heterocyclyl), -(cyclopropylene)-(3-10 member heterocyclyl), 5-12 member heteroaryl, —($C_1$-$C_3$ alkylene)-(5-12 member heteroaryl) and -(cyclopropylene)-(5-12 member heteroaryl), and $R^1$ is optionally further substituted by 1-6 groups selected from F, Cl, hydroxyl, CN, $C_1$-$C_6$ alkyl, $C_1$-$C_6$ perfluoroalkyl and —($C_1$-$C_3$ alkylene)$_m$-($C_1$-$C_6$ alkoxyl). Preferably, $R^6$ is unsubstituted cyclopropylene or cyclopropylene substituted by 1-3 groups selected from F, Cl, $C_1$-$C_3$ alkyl and $C_1$-$C_3$ perfluoalkyl. Also preferably, $R^7$ is selected from the group consisting of phenyl, 5-6 member heteroaryl and 4-7 member heterocyclyl, and $R^7$ is optionally further substituted by 1-3 groups selected from F, Cl, $C_1$-$C_3$ alkyl, $C_1$-$C_3$ perfluoalkyl and $C_1$-$C_3$ alkoxyl.

In the 31$^{st}$ particular aspect of this embodiment, and in combination of any other particular aspects not inconsistent, $R^2$ and $R^3$ forms a unsubstituted cyclopropylene group.

In another embodiment, the currently invention provides a compound of formula III,

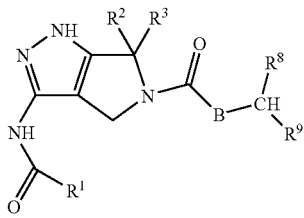

III wherein:

B is —O—, —NR$^t$— or —CHR$^t$—, wherein R$^t$ is H or $C_1$-$C_3$ alkyl;

$R^1$ is selected from $C_1$-$C_8$ alkyl, —($C_1$-$C_3$ alkylene)$_m$-phenyl, —($C_3$-$C_5$ cycloalkylene)-phenyl, —($C_1$-$C_3$ alkylene)$_m$-($C_3$-$C_{10}$ cycloalkyl), —($C_1$-$C_3$ alkylene)$_m$-($C_5$-$C_{10}$ cycloalkenyl), —($C_1$-$C_3$ alkylene)$_m$-(3-10 member heterocyclyl), —($C_3$-$C_5$ cycloalkylene)-(3-10 member heterocyclyl), —($C_1$-$C_3$ alkylene)$_m$-(5-12 member heteroaryl) and —($C_3$-$C_5$ cycloalkylene)-(5-12 member heteroaryl), and $R^1$ is optionally further substituted by 1-6 groups selected from —($C_1$-$C_3$ alkylene)$_m$-halide, —($C_1$-$C_3$ alkylene)$_m$-hydroxyl, —($C_1$-$C_3$ alkylene)$_m$-CN, $C_1$-$C_6$ alkyl, $C_1$-$C_6$ perfluoroalkyl, —($C_1$-$C_3$ alkylene)$_m$-($C_1$-$C_6$ alkoxyl), —($C_1$-$C_3$ alkylene)$_m$-NH$_2$, —($C_1$-$C_3$ alkylene)$_m$-($C_1$-$C_6$ alkylamino), —($C_1$-$C_3$ alkylene)$_m$-($C_3$-$C_5$ cycloalkyl) and —($C_1$-$C_3$ alkylene)$_m$-(3-5 member heterocyclyl), and the said $C_3$-$C_5$ cycloalkyl and the said 3-5 member heterocyclyl is optionally further substituted by 1-3 group selected from —F, $C_1$-$C_3$ alkyl, $C_1$-$C_3$ perfluoroalkyl and oxo;

each $R^2$ and $R^3$ is independently $C_1$-$C_3$ alkyl, or $R^2$ and $R^3$, together with the carbon atom that $R^2$ and $R^3$ attach to, form a $C_3$-$C_4$ cycloalkylene;

$R^8$ is —($C_1$-$C_6$ alkylene)$_m$-NR$^p$R$^q$, wherein each R$^p$ and R$^q$ is independently H, $C_1$-$C_3$ alkyl, or R$^p$ and R$^q$, together with the nitrogen atom they attach to, form a ring selected from 3-7 member heterocyclyl and 5-7 member heteroaryl, the said ring is optionally further substituted by 1-6 groups selected from halide, $C_1$-$C_3$ alkyl and $C_1$-$C_3$ perfluoroalkyl;

$R^9$ is selected from $C_1$-$C_6$ alkyl, $C_1$-$C_6$ perfluoroalkyl, phenyl, —($C_1$-$C_3$ alkylene)-phenyl, $C_{10}$-$C_{12}$ aryl, $C_3$-$C_{12}$ cycloalkyl, —($C_1$-$C_3$ alkylene)-($C_3$-$C_{12}$ cycloalkyl), $C_4$-$C_{12}$ unsaturated nonaromatic carbocyclyl, —($C_1$-$C_3$ alkylene)-($C_4$-$C_{12}$ unsaturated nonaromatic carbocyclyl), 3-12 member heterocyclyl, —($C_1$-$C_3$ alkylene)-(3-12 member heterocyclyl), 5-12 member heteroaryl and —($C_1$-$C_3$ alkylene)-(5 to 12 member heteroaryl), and each $R^9$ is independently optionally further substituted by 1-6 groups selected from halide, $C_1$-$C_6$ alkyl, $C_1$-$C_6$ perfluoroalkyl, —OH, $C_1$-$C_6$ alkoxy, —($C_1$-$C_6$ alkylene)-($C_1$-$C_6$ alkoxy)-NH$_2$, —($C_1$-$C_6$ alkylene)-NH$_2$, —($C_1$-$C_6$ alkylene)-($C_1$-$C_6$ alkylamino) and $C_1$-$C_6$ alkylamino and CN; and each m is independently 0 or 1;

or a pharmaceutically acceptable salt, solvate or hydrate thereof.

In the 1$^{st}$ particular aspect of this embodiment, and in combination with any other particular aspects not inconsistent, B is —O—.

In the 2$^{nd}$ particular aspect of this embodiment, and in combination with any other particular aspects not inconsistent, B is —NR$^t$—. More particularly, R$^t$ is H. Also more particularly, R$^t$ is $C_1$-$C_3$ alkyl.

In the 3$^{rd}$ particular aspect of this embodiment, and in combination with any other particular aspects not inconsistent, B is —CHR$^t$—. More particularly, R$^t$ is H. Also more particularly, R$^t$ is $C_1$-$C_3$ alkyl.

In the 4$^{th}$ particular aspect of this embodiment, and in combination with any other particular aspects not inconsistent, especially particular aspects 1 to 3, $R^2$ is methyl, and $R^3$ is methyl.

In the 5$^{th}$ particular aspect of this embodiment, and in combination with any other particular aspects not inconsistent, especially particular aspects 1 to 4, $R^1$ is $C_1$-$C_8$ alkyl, and $R^1$ is optionally further substituted.

In the 6$^{th}$ particular aspect of this embodiment, and in combination with any other particular aspects not inconsistent, especially particular aspects 1 to 4, $R^1$ is phenyl, and $R^1$ is optionally further substituted.

In the 7$^{th}$ particular aspect of this embodiment, and in combination with any other particular aspects not inconsistent, especially particular aspects 1 to 4, $R^1$ is —($C_1$-$C_3$ alkylene)-phenyl, and $R^1$ is optionally further substituted.

In the 8$^{th}$ particular aspect of this embodiment, and in combination with any other particular aspects not inconsistent, especially particular aspects 1 to 4, $R^1$ is —($C_3$-$C_5$ cycloalkylene)-phenyl, and $R^1$ is optionally further substituted.

In the 9$^{th}$ particular aspect of this embodiment, and in combination with any other particular aspects not inconsistent, especially particular aspects 1 to 4, $R^1$ is 5-10 member heteroaryl, and $R^1$ is optionally further substituted. More particularly, the 5-10 member heteroaryl is selected from pyridinyl, thiophenyl, thiazolyl and imidazolyl, and $R^1$ is optionally further substituted.

In the 10$^{th}$ particular aspect of this embodiment, and in combination with any other particular aspects not inconsistent, especially particular aspects 1 to 4, $R^1$ is —($C_1$-$C_3$ alkylene)-(5-10 member heteroaryl), and $R^1$ is optionally further substituted. More particularly, the 5-10 member heteroaryl is selected from pyridinyl, thiophenyl, thiazolyl and imidazolyl, and $R^1$ is optionally further substituted.

In the 11$^{th}$ particular aspect of this embodiment, and in combination with any other particular aspects not inconsistent, especially particular aspects 1 to 4, $R^1$ is —($C_3$-$C_5$ cycloalkylene)-(5-10 member heteroaryl), and $R^1$ is optionally further substituted. More particularly, the 5-10 member heteroaryl is selected from pyridinyl, thiophenyl, thiazolyl and imidazolyl, and $R^1$ is optionally further substituted.

In the 12$^{th}$ particular aspect of this embodiment, and in combination with any other particular aspects not inconsistent, especially particular aspects 1 to 4, $R^1$ is —($C_1$-$C_3$ alkylene)-($C_3$-$C_{10}$ cycloalkyl), and $R^1$ is optionally further substituted. More particularly, the $C_3$-$C_{10}$ cycloalkyl is selected from cyclopropyl, cyclobutyl, cyclopentyl and cyclohexyl, and $R^1$ is optionally further substituted.

In the 13$^{th}$ particular aspect of this embodiment, and in combination with any other particular aspects not inconsistent, especially particular aspects 1 to 4, $R^1$ is $C_3$-$C_{10}$ cycloalkyl, and $R^1$ is optionally further substituted. More particularly, the $C_3$-$C_{10}$ cycloalkyl is selected from cyclopropyl, cyclobutyl, cyclopentyl and cyclohexyl, and $R^1$ is optionally further substituted.

In the 14th particular aspect of this embodiment, and in combination with any other particular aspects not inconsistent, especially particular aspects 1 to 4, $R^1$ is —($C_1$-$C_3$ alkylene)-($C_5$-$C_{10}$ cycloalkenyl), and $R^1$ is optionally further substituted.

In the 15th particular aspect of this embodiment, and in combination with any other particular aspects not inconsistent, especially particular aspects 1 to 4, $R^1$ is $C_5$-$C_{10}$ cycloalkenyl, and $R^1$ is optionally further substituted.

In the 16th particular aspect of this embodiment, and in combination with any other particular aspects not inconsistent, especially particular aspects 1 to 4, $R^1$ is —($C_1$-$C_3$ alkylene)-(3-10 member heterocyclyl), and $R^1$ is optionally further substituted. More particularly, the 3-10 member heterocyclyl is selected from tetrohydrofuranyl, tetrahydropyranyl and morpholinyl, and $R^1$ is optionally further substituted.

In the 17th particular aspect of this embodiment, and in combination with any other particular aspects not inconsistent, especially particular aspects 1 to 4, $R^1$ is —($C_3$-$C_5$ cycloalkylene)-(3-10 member heterocyclyl), and $R^1$ is optionally further substituted. More particularly, the 3-10 member heterocyclyl is selected from tetrohydrofuranyl, tetrahydropyranyl and morpholinyl, and $R^1$ is optionally further substituted.

In the 18th particular aspect of this embodiment, and in combination with any other particular aspects not inconsistent, especially particular aspects 1 to 4, $R^1$ is 3-10 member heterocyclyl, and $R^1$ is optionally further substituted. More particularly, the 3-10 member heterocyclyl is selected from tetrohydrofuranyl, tetrahydropyranyl and morpholinyl, and $R^1$ is optionally further substituted.

In the 19th particular aspect of this embodiment, and in combination with any other particular aspects not inconsistent, especially particular aspects 5 to 18, $R^1$ is optionally further substituted by 1-6 groups selected from halide, $C_1$-$C_3$ alkyl, $C_1$-$C_3$ perfluoroalkyl, —OH, $C_1$-$C_3$ alkoxy, —$NH_2$, $C_1$-$C_3$ alkylamino and CN.

In the 20th particular aspect of this embodiment, and in combination with any other particular aspects not inconsistent, especially particular aspects 1 to 19, $R^8$ is —($C_1$-$C_6$ alkylene)$_m$-$NR^pR^q$, wherein each $R^p$ and $R^q$ is independently H, $C_1$-$C_3$ alkyl. More particularly, $R^8$ is selected from —$CH_2$—N—$(CH_3)_2$, —$CH_2$—NH—$CH_3$ and —$CH_2$—$NH_2$.

In the 21st particular aspect of this embodiment, and in combination with any other particular aspects not inconsistent, especially particular aspects 1 to 19, $R^8$ is —($C_1$-$C_6$ alkylene)$_m$-$NR^pR^q$, and $R^p$ and $R^q$, together with the nitrogen atom they attach to, form a 3-7 member heterocyclyl, the said 3-7 member heterocyclyl is optionally further substituted by 1-6 groups selected from halide, $C_1$-$C_3$ alkyl and $C_1$-$C_3$ perfluoroalkyl.

In the 22nd particular aspect of this embodiment, and in combination with any other particular aspects not inconsistent, especially particular aspects 1 to 19, $R^8$ is —($C_1$-$C_6$ alkylene)$_m$-$NR^pR^q$, and $R^p$ and $R^q$, together with the nitrogen atom they attach to, form a 5-7 member heteroaryl, the said 5-7 member heteroaryl is optionally further substituted by 1-6 groups selected from halide, $C_1$-$C_3$ alkyl and $C_1$-$C_3$ perfluoroalkyl.

In the 23rd particular aspect of this embodiment, and in combination with any other particular aspects not inconsistent, especially particular aspects 1 to 22, $R^9$ is phenyl, and $R^9$ is optionally further substituted.

In the 24th particular aspect of this embodiment, and in combination with any other particular aspects not inconsistent, especially particular aspects 1 to 22, $R^9$ is 6 member heteroaryl containing 1-2 N heteroatoms, and $R^9$ is optionally further substituted. More preferably, $R^9$ is pyridinyl, and $R^9$ is optionally further substituted.

In the 25th particular aspect of this embodiment, and in combination with any other particular aspects not inconsistent, especially particular aspects 1 to 22, $R^9$ is 5 member heteroaryl containing 1-2 N heteroatoms, and $R^9$ is optionally further substituted.

In the 26th particular aspect of this embodiment, and in combination with any other particular aspects not inconsistent, especially particular aspects 1 to 22, $R^9$ is $C_5$-$C_7$ cycloalkyl, $R^9$ is optionally further substituted. More preferably, $R^9$ is cyclohexyl, and $R^9$ is optionally further substituted.

In the 27th particular aspect of this embodiment, and in combination with any other particular aspects not inconsistent, especially particular aspects 1 to 22, $R^9$ is 5-7 member heterocyclyl containing 1-2 heteroatoms selected from N, S and O, $R^9$ is optionally further substituted.

In the 28th particular aspect of this embodiment, and in combination with any other particular aspects not inconsistent, especially particular aspects 1 to 22, $R^9$ is —($C_1$-$C_3$ alkylene)-phenyl, and $R^9$ is optionally further substituted. More preferably, $R^9$ is —$CH_2$-phenyl, and $R^9$ is optionally further substituted.

In the 29th particular aspect of this embodiment, and in combination with any other particular aspects not inconsistent, especially particular aspects 1 to 22, $R^9$ is —($C_1$-$C_3$ alkylene)-(5 to 12 member heteroaryl), and $R^9$ is optionally further substituted.

In the 30th particular aspect of this embodiment, and in combination with any other particular aspects not inconsistent, especially particular aspects 1 to 22, $R^9$ is —($C_1$-$C_3$ alkylene)-($C_3$-$C_{12}$ cycloalkyl), and $R^9$ is optionally further substituted.

In the 31st particular aspect of this embodiment, and in combination with any other particular aspects not inconsistent, especially particular aspects 1 to 22, $R^9$ is selected from $C_1$-$C_6$ alkyl, $C_1$-$C_6$ perfluoroalkyl and $C_1$-$C_6$ alkoxyl, and $R^9$ is optionally further substituted.

In the 32nd particular aspect of this embodiment, and in combination with any other particular aspects not inconsistent, especially particular aspects 1 to 22, $R^9$ is —($C_1$-$C_3$ alkylene)-(3 to 12 member heterocyclyl), and $R^9$ is optionally further substituted.

In the 33rd particular aspect of this embodiment, and in combination with any other particular aspects not inconsistent, especially particular aspects 23 to 32, $R^9$ is optionally further substituted by 1-6 groups selected from halide, hydroxyl, —CN, $C_1$-$C_6$ alkyl, $C_1$-$C_6$ perfluoroalkyl, $C_1$-$C_6$ alkoxyl and $C_1$-$C_6$ alkylamino.

In the 34th particular aspect of this embodiment, and in combination with any other particular aspects not inconsistent, especially particular aspects 1 to 33, the compound is of the stereochemistry of the compound for formula IIIa:

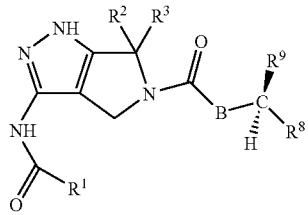

IIIa

The In the 35$^{th}$ particular aspect of this embodiment, and in combination with any other particular aspects not inconsistent, especially particular aspects 1 to 33, the compound has an enantiomeric enrichment of the enantiomeric isomer of formula IIIa of higher than 80%. Preferably, the compound has an enantiomeric enrichment of the enantiomeric isomer of formula IIIa of higher than 90%. Even more preferably, the compound has an enantiomeric enrichment of the enantiomeric isomer of formula IIIa of higher than 95%.

The In the 36$^{th}$ particular aspect of this embodiment, and in combination with any other particular aspects not inconsistent, $R^2$ is methyl; $R^3$ is methyl; B is —O—, —NH— or —CH$_2$—; $R^1$ is selected from the group consisting of $C_1$-$C_8$ alkyl, phenyl, —($C_1$-$C_3$ alkylene)-phenyl, -(cyclopropylene)-phenyl, $C_3$-$C_{10}$ cycloalkyl, —($C_1$-$C_3$ alkylene)-($C_3$-$C_{10}$ cycloalkyl), 3-10 member heterocyclyl, —($C_1$-$C_3$ alkylene)-(3-10 member heterocyclyl), -(cyclopropylene)-(3-10 member heterocyclyl), 5-12 member heteroaryl, —($C_1$-$C_3$ alkylene)-(5-12 member heteroaryl) and -(cyclopropylene)-(5-12 member heteroaryl), and $R^1$ is optionally further substituted by 1-6 groups selected from F, Cl, hydroxyl, CN, $C_1$-$C_6$ alkyl, $C_1$-$C_6$ perfluoroalkyl and —($C_1$-$C_3$ alkylene)$_m$-($C_1$-$C_6$ alkoxyl). Preferably, $R^8$ is —($C_1$-$C_6$ alkylene)$_m$-NR$^p$R$^q$, wherein each R$^p$ and R$^q$ is independently H or $C_1$-$C_3$ alkyl. Ever more preferably, $R^8$ is selected from —CH$_2$—N—(CH$_3$)$_2$, —CH$_2$—NH—CH$_3$ and —CH$_2$—NH$_2$. Also preferably, $R^8$ is —($C_1$-$C_6$ alkylene)$_m$-NR$^p$R$^q$, and R$^p$ and R$^q$, together with the nitrogen atom they attach to, form a 3-7 member heterocyclyl, the said 3-7 member heterocyclyl is optionally further substituted by 1-6 groups selected from halide, $C_1$-$C_3$ alkyl and $C_1$-$C_3$ perfluoroalkyl. Also preferably, $R^9$ is selected from the group consisting of $C_1$-$C_8$ alkyl, phenyl, —($C_1$-$C_3$ alkylene)-phenyl, 5-6 member heteroaryl and 3-7 member cycloalkyl, and $R^9$ is optionally further substituted with 1-6 groups selected from F, Cl, $C_1$-$C_6$ alkyl, $C_1$-$C_6$ perfluoroalkyl, —OH, $C_1$-$C_6$ alkoxy, —($C_1$-$C_6$ alkylene)-($C_1$-$C_6$ alkoxy) and CN.

In the 37$^{th}$ particular aspect of this embodiment, and in combination of any other particular aspects not inconsistent, $R^2$ and $R^3$ forms a unsubstituted cyclopropylene group.

In another embodiment, the current invention provides a compound selected from the group consisting of

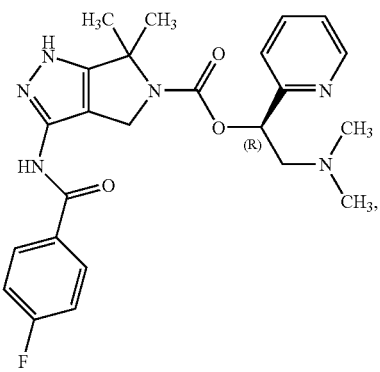

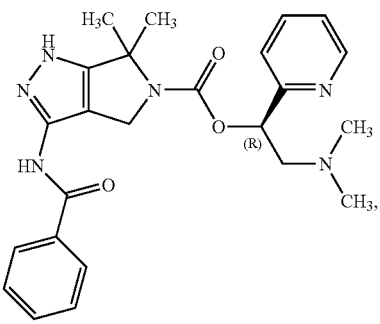

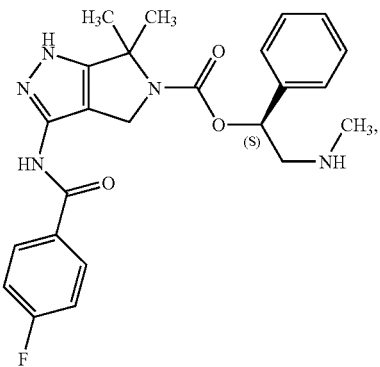

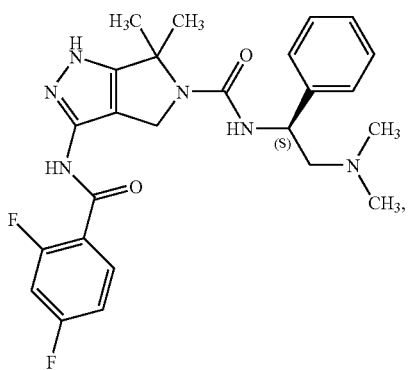

-continued
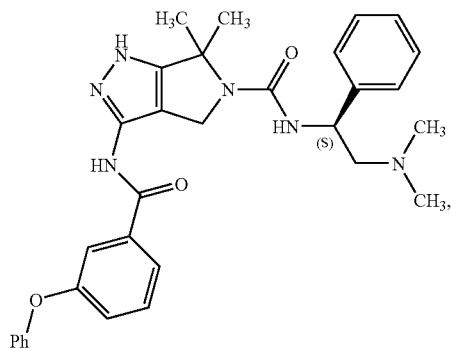
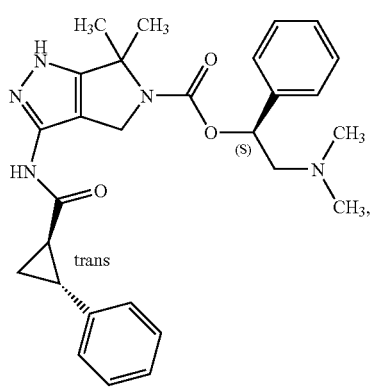
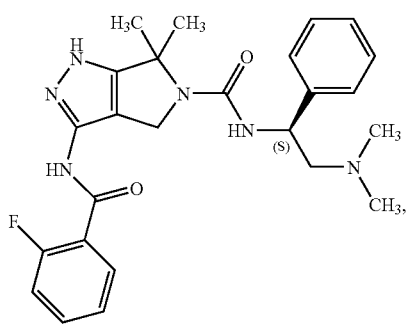
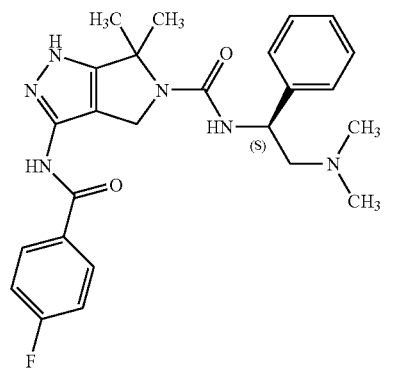
-continued
or a pharmaceutically acceptable salt thereof.
In another embodiment, the current invention provides a compound selected from the group consisting of

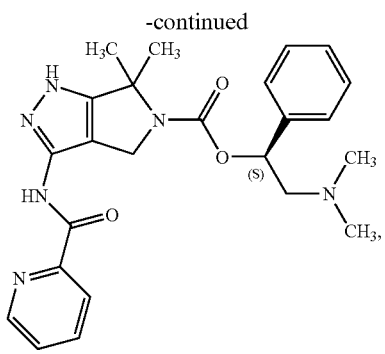
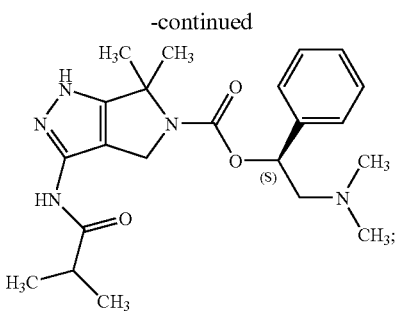
or a pharmaceutically acceptable salt thereof.
In another embodiment, the current invention provides a compound selected from the group consisting of

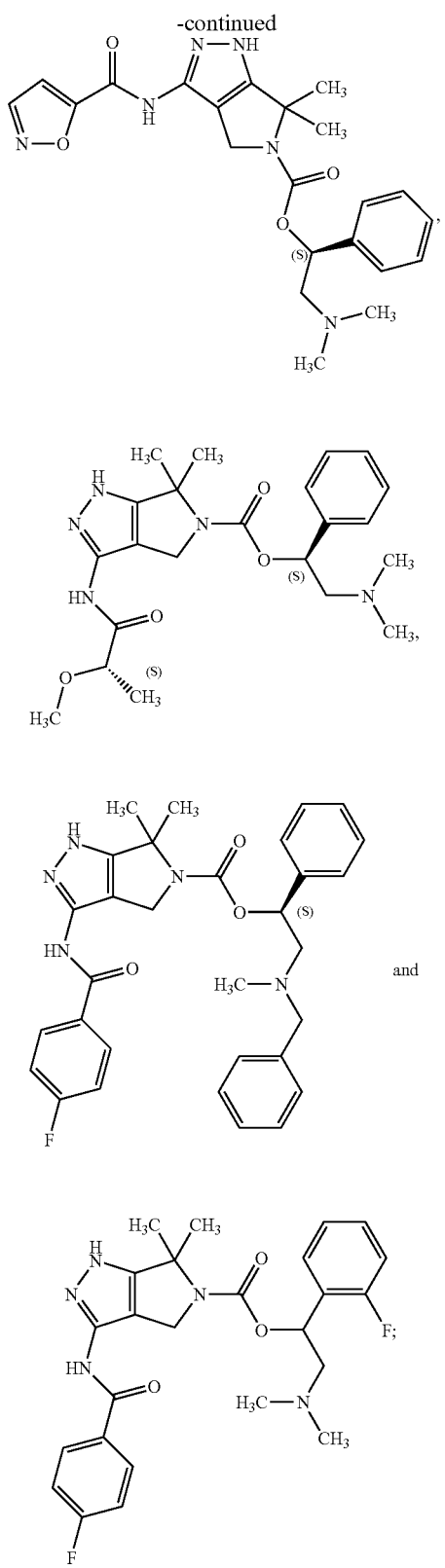

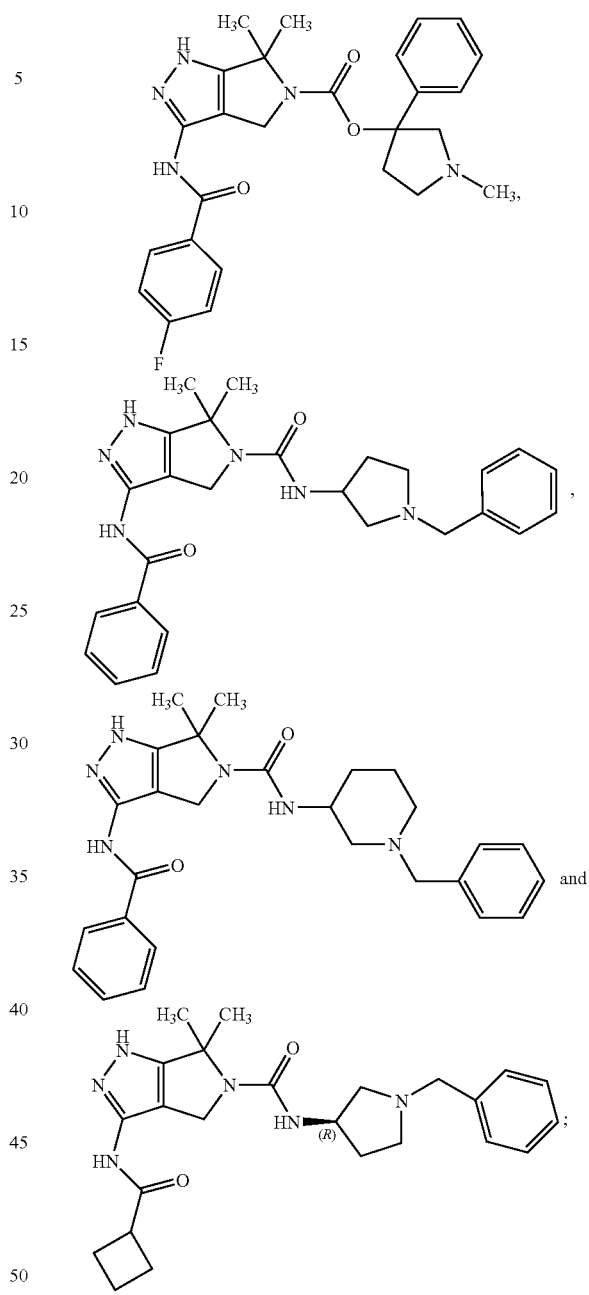

or a pharmaceutically acceptable salt thereof.

In another embodiment, the current invention provides a compound selected from the group consisting of or a pharmaceutically acceptable salt thereof.

In another embodiment, the current invention provides a method to treat abnormal cell growth in a mammal, comprising administering to the mammal the compound the current invention. More particularly, the abnormal cell growth is cancer.

In yet another embodiment, the current invention provides a pharmaceutical composition comprising a compound of the invention.

In yet another embodiment, the current invention provides a pharmaceutical composition comprising a compound of the invention and a pharmaceutically acceptable carrier.

In yet another embodiment, the current invention provides a method of treating a mammalian disease condition mediated by protein kinase activity, comprising administering to a mammal a therapeutically acceptable amount of a compound, salt, hydrate or solvate of the invention. In one aspect of this embodiment, mammalian disease condition is tumor growth or abnormal cell proliferation.

In yet another embodiment, the current invention provides a method of modulating the activity of a protein kinase, comprising contacting the protein kinase with an effective amount of a compound, or pharmaceutically acceptable salt, solvate of any of the invention. In one aspect of this embodiment, the protein kinase is a PAK4 protein kinase.

In some embodiments, the present teachings provide pharmaceutical compositions comprising any of the compounds described herein and a pharmaceutically acceptable carrier. Examples of such compositions are described below.

In some embodiments, the present teachings provide a method of treating abnormal cell growth in a mammal, including a human, the method comprising administering to the mammal any of compound or pharmaceutical composition of the present teachings.

In some embodiments, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In some embodiments, said abnormal cell growth is a benign proliferative disease, including, but not limited to, psoriasis, benign prostatic hypertrophy or restinosis.

In some embodiments, the method further comprises administering to the mammal an amount of one or more substances selected from anti-tumor agents, anti-angiogenesis agents, signal transduction inhibitors, and antiproliferative agents, which amounts are together effective in treating said abnormal cell growth. Such substances include those disclosed in PCT Publication Nos. WO 00/38715, WO 00/38716, WO 00/38717, WO 00/38718, WO 00/38719, WO 00/38730, WO 00/38665, WO 00/37107 and WO 00/38786, the disclosures of which are incorporated herein by reference in their entireties.

Examples of anti-tumor agents include mitotic inhibitors, for example vinca alkaloid derivatives such as vinblastine vinorelbine, vindescine and vincristine; colchines allochochine, halichondrine, N-benzoyltrimethyl-methyl ether colchicinic acid, dolastatin 10, maystansine, rhizoxine, taxanes such as taxol (paclitaxel), docetaxel (Taxotere), 2'-N-[3-(dimethylamino)propyl]glutaramate (taxol derivative), thiocholchicine, trityl cysteine, teniposide, methotrexate, azathioprine, fluorouricil, cytocine arabinoside, 2'2'-difluorodeoxycytidine (gemcitabine), adriamycin and mitamycin. Alkylating agents, for example cis-platin, carboplatin oxiplatin, iproplatin, Ethyl ester of N-acetyl-DL-sarcosyl-L-leucine (Asaley or Asalex), 1,4-cyclohexadiene-1,4-dicarbamic acid, 2,5-bis(1-azirdinyl)-3,6-dioxo-, diethyl ester (diazi- quone), 1,4-bis(methanesulfonyloxy)butane (bisulfan or leucosulfan) chlorozotocin, clomesone, cyanomorpholinodoxorubicin, cyclodisone, dianhydroglactitol, fluorodopan, hepsulfam, mitomycin C, hycantheonemitomycin C, mitozolamide, 1-(2-chloroethyl)-4-(3-chloropropyl)-piperazine dihydrochloride, piperazinedione, pipobroman, porfiromycin, spirohydantoin mustard, teroxirone, tetraplatin, thiotepa, triethylenemelamine, uracil nitrogen mustard, bis(3-mesyloxypropyl)amine hydrochloride, mitomycin, nitrosoureas agents such as cyclohexyl-chloroethylnitrosourea, methylcyclohexyl-chloroethylnitrosourea 1-(2-chloroethyl)-3-(2,6-dioxo-3-piperidyl)-1-nitroso-urea, bis(2-chloroethyl)nitrosourea, procarbazine, dacarbazine, nitrogen mustard-related compounds such as mechloroethamine, cyclophosphamide, ifosamide, melphalan, chlorambucil, estramustine sodium phosphate, strptozoin, and temozolamide. DNA anti-metabolites, for example 5-fluorouracil, cytosine arabinoside, hydroxyurea, 2-[(3hydroxy-2-pyrinodinyl)methylene]-hydrazinecarbothioamide, deoxyfluorouridine, 5-hydroxy-2-formylpyridine thiosemicarbazone, alpha-2'-deoxy-6-thioguanosine, aphidicolin glycinate, 5-azadeoxycytidine, beta-thioguanine deoxyriboside, cyclocytidine, guanazole, inosine glycodialdehyde, macbecin II, pyrazolimidazole, cladribine, pentostatin, thioguanine, mercaptopurine, bleomycin, 2-chlorodeoxyadenosine, inhibitors of thymidylate synthase such as raltitrexed and pemetrexed disodium, clofarabine, floxuridine and fludarabine. DNA/RNA antimetabolites, for example, L-alanosine, 5-azacytidine, acivicin, aminopterin and derivatives thereof such as N-[2-chloro-5-[[(2,4-diamino-5-methyl-6-quinazolinyl)-methyl]amino]benzoyl]-L-aspartic acid, N-[4-[[(2,4-diamino-5-ethyl-6-quinazolinyl)methyl]amino]-benzoyl]-L-aspartic acid, N-[2-chloro-4-[[(2,4-diaminopteridinyl)methyl]amino]benzoyl]-L-aspartic acid, soluble Baker's antifol, dichloroallyl lawsone, brequinar, ftoraf, dihydro-5-azacytidine, methotrexate, N-(phosphonoacetyl)-L-aspartic acid tetrasodium salt, pyrazofuran, trimetrexate, plicamycin, actinomycin D, cryptophycin, and analogs such as cryptophycin-52 or, for example, one of the preferred anti-metabolites disclosed in European Patent Application No. 239362 such as N-(5-[N-(3,4-dihydro- 2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; proteins, for example interferon; and anti-hormones, for example antiestrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

Anti-angiogenesis agents include MMP-2 (matrix-metalloprotienase 2) inhibitors, MMP-9 (matrix-metalloprotienase 9) inhibitors, and COX-II (cyclooxygenase II) inhibitors. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Examples of MMP inhibitors include AG-3340, RO 32-3555, RS 13-0830, and the following compounds: 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; 3-[4-(4-chloro-phenoxy)-benzenesulfonylamino]-tetrahydro-pyran-3-carboxylic acid hydroxyamide; (2R,3R) 1-[4-(4-fluoro-2-methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxy-carbamoyltetrahydro-pyran-4-yl)-amino]-propionic acid; 3-exo-3-[4-(4-chloro-phenoxy)benzene-sulfonylamino]-8-oxa-bicyclo[3.2.1]octane-3-carboxylic acid hydroxyamide; 3-endo-3-[4-(4-fluoro-phenoxy)-benzenesulfonylamino]-8-oxa-bicyclo[3.2.1]octane-3-carboxylic acid hydroxyamide; 3-[4-(4-fluoro-phenoxy)-benzenesulfonylamino]-tetrahydro-furan-3-carboxylic acid hydroxyamide; and pharmaceutically acceptable salts, solvates and hydrates thereof.

Examples of signal transduction inhibitors include agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998). EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.).

VEGF inhibitors, for example SU-5416 and SU-6668 (Sugen Inc. of South San Francisco, Calif., USA), can also be combined or co-administered with the composition. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); anti-VEGF monoclonal antibody bevacizumab (Genentech, Inc. of South San Francisco, Calif.); and angiozyme, a synthetic ribozyme from Ribozyme (Boulder, Colo.) and Chiron (Emeryville, Calif.).

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), may be administered in combination with the composition. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are herein incorporated by reference in their entirety.

Other antiproliferative agents that may be used include inhibitors of the enzyme farnesyl protein transferase and inhibitors of the receptor tyrosine kinase PDGFr, including the compounds disclosed and claimed in the following U.S. patent application Ser. Nos. 09/221,946 (filed Dec. 28, 1998); 09/454,058 (filed Dec. 2, 1999); 09/501,163 (filed Feb. 9, 2000); 09/539,930 (filed Mar. 31, 2000); 09/202,796 (filed May 22, 1997); 09/384,339 (filed Aug. 26, 1999); and 09/383,755 (filed Aug. 26, 1999); and the compounds disclosed and claimed in the following U.S. provisional patent applications 60/168,207 (filed Nov. 30, 1999); 60/170,119 (filed Dec. 10, 1999); 60/177,718 (filed Jan. 21, 2000); 60/168,217 (filed Nov. 30, 1999), and 60/200,834 (filed May 1, 2000). Each of the foregoing patent applications and provisional patent applications is herein incorporated by reference in their entirety.

Compositions of the invention can also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors. Specific CTLA4 antibodies that can be used in the present invention include those described in U.S. Provisional Application 60/113,647 (filed Dec. 23, 1998) which is herein incorporated by reference in its entirety.

Unless otherwise stated, the following terms used in the specification and claims have the meanings discussed below. Variables defined in this section, such as R, X, n and the like, are for reference within this section only, and are not meant to have the save meaning as may be used outside of this definitions section. Further, many of the groups defined herein can be optionally substituted. The listing in this definitions section of typical substituents is exemplary and is not intended to limit the substituents defined elsewhere within this specification and claims.

As used herein, the symbol [------] when incorporated into the chemical structure of a substituent means that the atom to which [------] is attached is the point of attachment of that substitutent to some position on another molecule. For example, X in the hypothetical molecule $CH_3CH_2$—X might be defined as X is

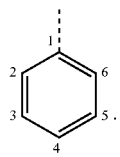

In which case, the placement of [------] attached to the arbitrarily numbered position C-1, means that C-1 of the phenyl ring is attached to the methylene carbon.

The symbols "..⟨⟨⟨" and "⟨⟨" when used together in a single molecule without further indication otherwise, for example, chemical name or accompanying description, merely indicate relative stereochemistry of trans or cis where applicable. The symbol "..⟨⟨⟨" and the symbol "⟨⟨" used together or separately, in combination with an indication of them representing the absolute stereochemistry, for example, an indication of "S" or "R" in the corresponding chemical structure or the accompanying chemical name, indicate the absolute stereochemistry of the corresponding chiral center.

When a diradical is referred as, for example, —O—$CH_2$— or —($C_1$-$C_3$ alkylene)-NH—, it is understood that each end of the diradical can equally connect to another moiety. For example, if K is defined as A-L-B, and L is a diradical selected from —O—$CH_2$— and —($C_1$-$C_3$ alkylene)-, it is understood that K is therefore selected from A-O—$CH_2$—B, A-$CH_2$—O—B, and A-($C_1$-$C_3$ alkylene)-B. A and B herein refer to different organic moieties.

"Aliphatic" refers to straight-chain, branched or cyclic $C_1$-$C_{12}$ hydrocarbons which are completely saturated or which contains one or more units of unsaturation but which are not aromatic. Examples of aliphatic groups include linear, branched or cyclic alkyl, alkenyl, alkynyl groups and hybrids thereof such as (cycloalkyl)alkyl, (cycloalkenyl)alkyl, etc. An aliphatic group may be optionally substituted by 1-6 substituents. Suitable substituents on an aliphatic group include: 3-12 member heterocyclyl, $C_6$-$C_{10}$ aryl, 5-12 member heteroaryl, halide, —$NO_2$, $NH_2$, $NR_2$, —CN, —COR, —COOR, —$CONR_2$, —OH, —OR, —OCOR, —SR, —SOR, —$SO_2$R, —$SONR_2$, —$SO_2NR_2$, wherein R is H, $C_1$-$C_{10}$ alkyl, 3-10 member heterocyclyl, $C_6$-$C_{10}$ aryl, 5-12 member heteroaryl.

"$C_1$-$C_{12}$ alkyl" refers to a straight chain or branched saturated hydrocarbon radical having from 1 to 12 carbon atoms. A $C_1$-$C_{12}$ alkyl group may be optionally substituted by at least one substituent. Suitable substituents on a $C_1$-$C_{12}$ alkyl group include, but are not limited to, 3-12 member heterocyclyl, $C_6$-$C_{10}$ aryl, 5-12 member heteroaryl, halide, —$NO_2$, —$NR_2$, —CN, —COR, —COOR, —$CONR_2$, —OH, —OR, —OCOR, —SR, —SOR, —$SO_2$R, —$SONR_2$, —$SO_2NR_2$, wherein each R is independently —H, $C_1$-$C_{10}$ alkyl, 3-12 member heterocyclyl, $C_6$-$C_{10}$ aryl, 5-12 member heteroaryl. Examples of $C_1$-$C_{12}$ alkyl groups include, but are not limited to methyl, ethyl, propyl, isopropyl, butyl, sec-butyl, iso-butyl, tert-butyl, pentyl, neo-pentyl, sec-pentyl, hexyl, heptyl, octyl, and the like, including substituted forms thereof. Further, the term "alkyl" refers to a straight chain or branched saturated hydrocarbon radical of 1 to 20 carbon atoms, or 1 to 12 carbon atoms, or 1 to 8 carbon atoms, or 1 to 6 carbon atoms, or 1 to 4 carbon atoms. "Lower alkyl" refers specifically to an alkyl group having 1 to 4 carbon atoms. Alkyl may be substituted or unsubstituted. Suitable substituents on an alkyl group are the same as those described for a $C_1$-$C_{12}$ alkyl group.

"Cycloalkyl" refers to a cyclic saturated hydrocarbon radical having from 3 to 20 carbon atoms. A cycloalkyl group may be monocyclic and where permissible may be bicyclic or polycyclic. A cycloalkyl group may be optionally substituted by at least one substituent. Suitable substituents on a cycloalkyl group are the same as those described for an alkyl group. Examples of cycloalkyl groups include, but are not limited to cyclopropyl, cyclobutyl, cyclopentyl, cyclohexyl, cycloheptyl, cyclooctyl, nobornyl, adamantyl, and the like, including substituted forms thereof.

"Nonaromatic carbocyclyl" refers to a 3 to 12 member all-carbon monocyclic ring group, all-carbon bicyclic or multicyclic ring system group wherein one or more of the rings may contain one or more double bonds but none of the rings has a completely conjugated pi-electron system. Examples, without limitation, of nonaromatic carbocyclyl are cyclopropyl, cyclobutyl, cyclopentyl, cyclopentenyl, cyclohexyl, cyclohexadienyl, adamantanyl, cycloheptyl, cycloheptatrienyl, and the like. A nonaromatic carbocyclyl may be substituted or unsubstituted. Typical substituent groups are the same with those of alkyl group, as defined herein. Illustrative examples of nonaromatic carbocyclyl are derived from, but not limited to, the following:

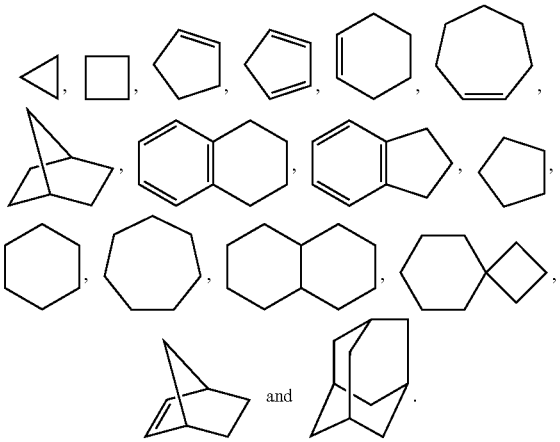

"Unsaturated nonaromatic carbocyclyl" or "nonaromatic unsaturated carbocyclyl" both refer to a nonaromatic carbocyclyl, as defined herein, that contains at least one carbon carbon double bond or one carbon carbon triple bond.

"$C_2$-$C_{12}$ alkenyl" refers to a straight chain or branched unsaturated hydrocarbon radical having from 2 to 12 carbon atoms. A $C_2$-$C_{12}$ alkenyl group may have one or more points of unsaturation (i.e.—one or more carbon-carbon double bonds). In the case where $C_2$-$C_{12}$ alkenyl has more than one carbon-carbon double bond, the carbon-carbon double bonds can be conjugated or unconjugated. A $C_2$-$C_{12}$ alkenyl group may be optionally substituted by at least one substituent. Suitable substituents on a $C_2$-$C_{12}$ alkenyl group are the same as those described for a $C_1$-$C_{12}$ alkyl group. Examples of $C_2$-$C_{12}$ alkenyl include, but are not limited to, ethenyl, 1-propenyl, 2-propenyl, 1-butenyl, 2-butenyl, iso-butenyl, and the like, including substituted forms thereof. Further, the term "alkenyl" refers to a straight chain or branched unsaturated hydrocarbon radical having from 2 to 20 carbon atoms, or 2 to 12 carbon atoms, or 2 to 8 carbon atoms, or 2 to 6 carbon atoms, or 2 to 4 carbon atoms. An alkenyl group may have one or more points of unsaturation (i.e.—one or more carbon-carbon double bonds). In the case where an alkenyl group has more than one carbon-carbon double bond, the carbon-carbon double bonds can be conjugated or unconjugated. An alkenyl group may be substituted or unsubstituted. Suitable substituents on an alkenyl group are the same as those described for a $C_1$-$C_{12}$ alkyl group.

"Alkoxy" or "alkoxyl" refers to —$OR^c$ wherein $R^c$ is $C_1$-$C_{12}$ alkyl, $C_2$-$C_{12}$ alkenyl, $C_2$-$C_{12}$ alkynyl, $C_3$-$C_{12}$ cycloalkyl or ($C_1$-$C_6$ alkylene)-($C_3$-$C_{12}$ cycloalkyl). A "$C_1$-$C_{12}$ alkoxy" or "$C_1$-$C_{12}$ alkoxyl" refers to an alkoxy group, as defined herein, wherein $R^cC$ has 1 to 12 total carbon atoms.

"Alkoxyalkyl" refers to an alkyl, as defined herein, that is substituted by at least one alkoxy group as defined herein. A "$C_2$-$C_6$ alkylalkoxy" refers an alkylalkoxy wherein the total carbon number of the alkyl and its alkoxy substituents are from 2 to 6.

"Alkylamino" refers to —$NR^pR^q$ wherein each $R^p$ and $R^q$ is independently H, $C_1$-$C_{12}$ alkyl, $C_2$-$C_{12}$ alkenyl, $C_2$-$C_{12}$ alkynyl, $C_3$-$C_{12}$ cycloalkyl, ($C_1$-$C_6$ alkylene)-($C_3$-$C_{12}$ cycloalkyl) provided $R^p$ and $R^q$ are not both H. A "monoalkylamino" refers to an alkylamino group, as defined herein, wherein one of $R^p$ and $R^q$ is H. A "dialkylamino" refers to an alkylamino group, as defined herein, wherein none of $R^p$ and $R^q$ is H. A "$C_{1-12}$ alkylamino" refers to an alkylamino group that contains 1 to 10 carbon atoms.

"$C_2$-$C_{12}$ alkynyl" refers to a straight chain or branched hydrocarbon radical having from 2-12 carbon atoms and at least one carbon-carbon triple bond. In the case where $C_2$-$C_{12}$ alkynyl has more than one carbon-carbon double bond, the carbon-carbon double bonds can be conjugated or unconjugated. A $C_2$-$C_{12}$ alkynyl group may be optionally substituted by at least one substituent. Suitable substituents on a $C_2$-$C_{12}$ alkynyl group are the same as those described for a $C_1$-$C_{12}$ alkyl group. Examples of $C_2$-$C_{12}$ alkynyl include, but are not limited to, ethynyl, 1-propynyl, 2-propynyl, 1-butynyl, 2-butynyl, and the like, including substituted forms thereof. Further, the term "alkynyl" refers to a straight chain or branched hydrocarbon radical of 2 to 20 carbon atoms, or 2 to 12 carbon atoms, or 2 to 8 carbon atoms, or 2 to 6 carbon atoms, or 2 to 4 carbon atoms, and having at least one carbon-carbon triple bond. Alkynyl may be substituted or unsubstituted. Suitable substituents on an alkynyl group are the same as those described for a $C_1$-$C_{12}$ alkyl group.

"Amino" refers to —$NH_2$.

"$C_6$-$C_{10}$ aryl" refers to an all-carbon monocyclic ring or polycyclic ring of 6 to 10 carbon atoms having a completely conjugated pi-electron system. A $C_6$-$C_{10}$ aryl group may be optionally substituted by at least one substituent. Suitable substituents on a $C_6$-$C_{10}$ aryl group are the same as those described for a $C_1$-$C_{12}$ alkyl group. Examples of $C_6$-$C_{10}$ aryl include, but are not limited to, phenyl and naphthyl. Further, the term "aryl" refers to an all-carbon monocyclic ring or polycyclic ring of 6 to 20 carbon atoms having a completely conjugated pi-electron system. The aryl group may be substituted or unsubstituted. Examples of aryl include, but are not limited to, anthracenyl, phenanthreneyl and perylenyl.

"Aralkyl" refers to alkyl, as defined herein, that is substituted with an $C_{6-10}$ aryl group as defined above; e.g., —$CH_2$-phenyl, —$(CH_2)_2$phenyl, —$(CH_2)_3$phenyl, $CH_3CH(CH_3)$$CH_2$phenyl, and the like and derivatives thereof. A $C_1$-$C_6$ aralkyl refers to a $C_1$-$C_6$ alkyl that is substituted with a $C_6$-$C_{10}$ aryl group.

"Heteroaralkyl" group means alkyl, as defined herein, that is substituted with a 5-12 member heteroaryl group; e.g., —$CH_2$pyridinyl, —$(CH_2)_2$pyrimidinyl, —$(CH_2)_3$imidazolyl, and the like, and derivatives thereof. A $C_1$-$C_6$ heteroaralkyl refers to a $C_1$-$C_6$ alkyl that is substituted with an 5-12 member heteroaryl group.

"Heteroaryl" refers to a monocyclic or fused ring group of 5 to 12 ring atoms containing one, two, three or four ring heteroatoms selected from N, O, and S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine, tetrazole, triazine, and carbazole. The heteroaryl group may be substituted or unsubstituted. Typical substituents include $C_{1-12}$ aliphatic, 3-10 member heterocyclyl, 6-10 member aryl, halide, —$NO_2$, $NH_2$, $NR_2$, —CN, —COR, —COOR, —$CONR_2$, —OH, —OR, —OCOR, —SR, —SOR, —$SO_2R$, —$SONR_2$, —$SO_2NR_2$, wherein R is a $C_{1-10}$ aliphatic, 3-10 member heterocyclyl, $C_{6-10}$aryl, 5-10 member heteroaryl.

A "pharmaceutically acceptable heteroaryl" is one that is sufficiently stable to be attached to a compound of the invention, formulated into a pharmaceutical composition and subsequently administered to a patient in need thereof.

Examples of typical monocyclic heteroaryl groups include, but are not limited to:

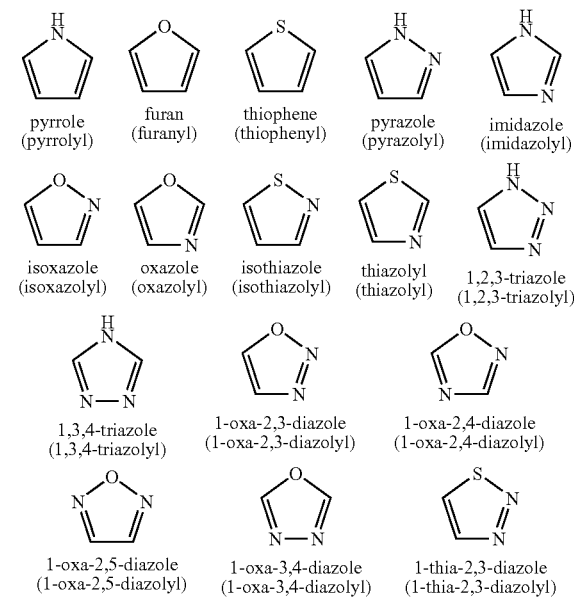

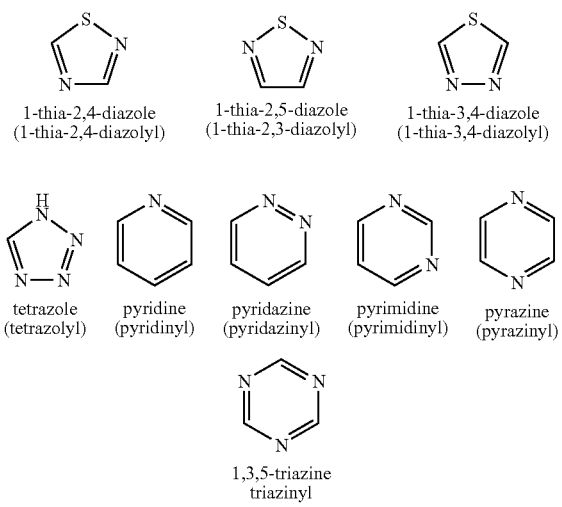
Examples of bicyclic heteroaryl groups include, but are not limited to:
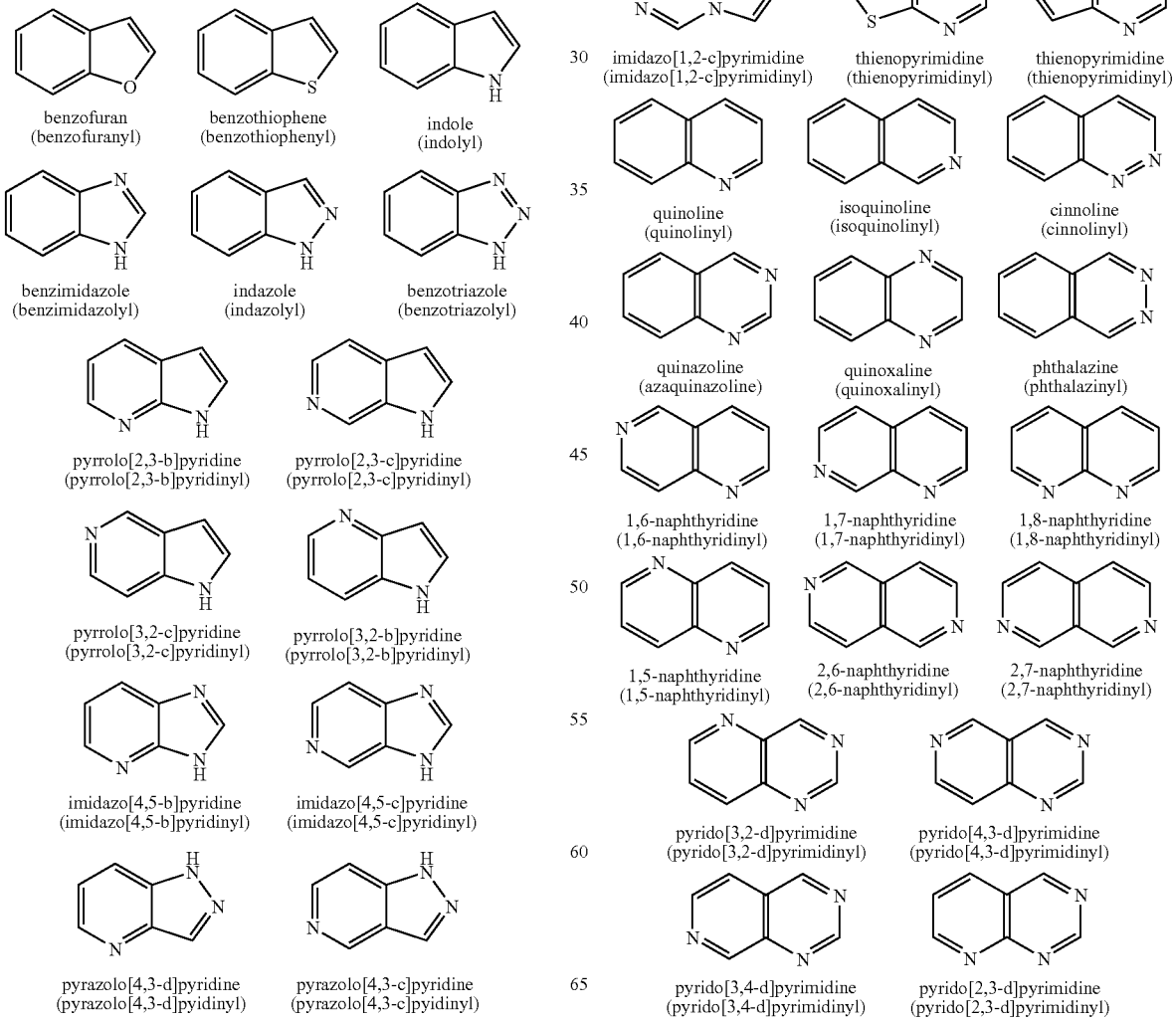

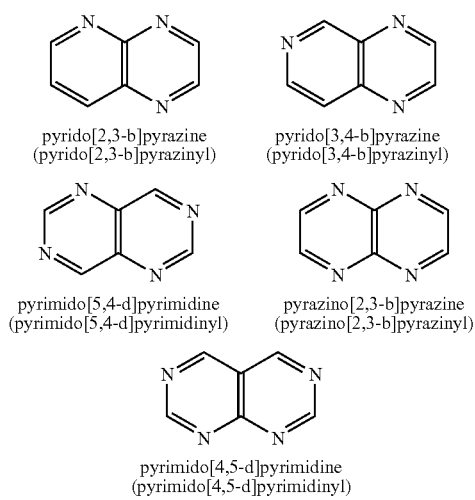

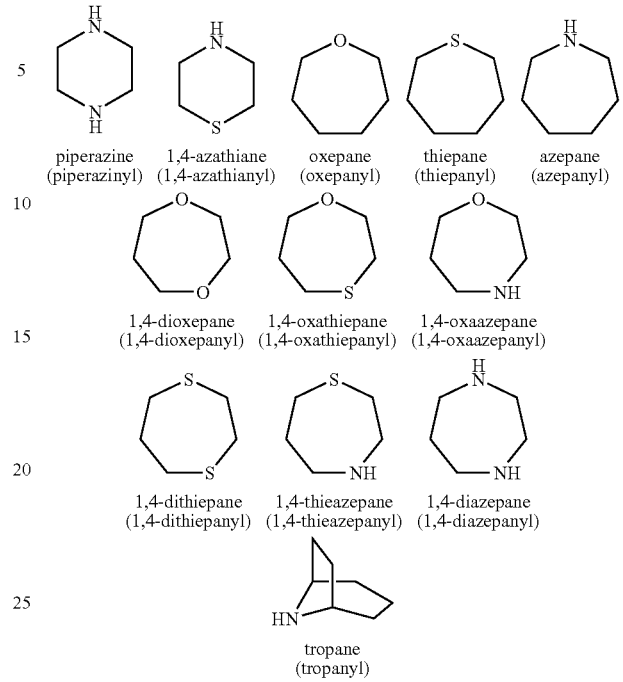

"Heteroalicyclic" or "heterocyclyl" refers to a monocyclic or polycyclic group having from 3 to 12 ring atoms, wherein from 1 to 4 ring atoms are heteroatoms selected from N, O, and S. "Heteroalicyclic" or "heterocyclyl" may also have one or more double bonds. However, "Heteroalicyclic" or "heterocyclyl" do not have a completely conjugated pi-electron system. "Heteroalicyclic" or "heterocyclyl" can be substituted or unsubstituted. Typical substituents include, but are not limited to, $C_1$-$C_{12}$ aliphatic, 6-10 member aryl, 6-10 member aryl, halide, —$NO_2$, $NH_2$, $NR_2$, —CN, —COR, —COOR, —$CONR_2$, —OH, —OR, —OCOR, —SR, —SOR, —$SO_2R$, wherein R is a $C_1$-$C_{10}$ alkyl, 3-10 member heterocyclyl, $C_6$-$C_{10}$ aryl, 5-10 member heteroaryl.

Examples of saturated heterocyclyl groups include, but are not limited to:

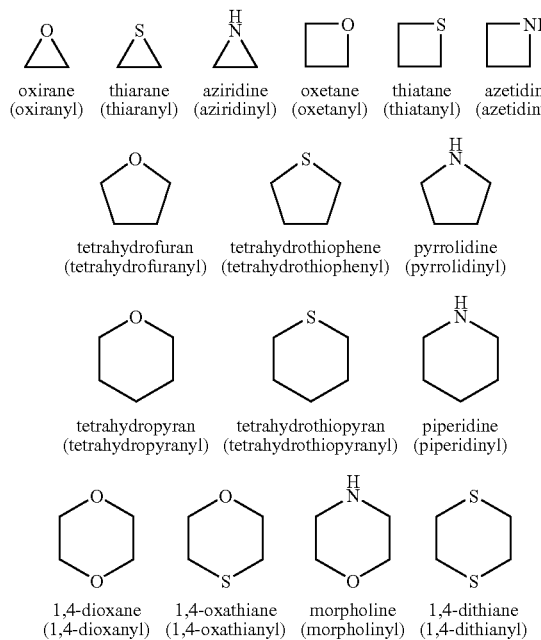

Examples of partially unsaturated heterocyclyl groups include, but are not limited to:

A "diradical" refers to a group that has two open valences and is further connected to two other groups. Examples of diradicals are, but are not limited to —$CH_2$—, —O—.

When "ene" is added after the "yl" at the end of any of the previously defined terms to form a new term, the new term refers to a diradical formed by removing one hydrogen atom from the original term of which the new term derived from. For example, an alkylene refers to a diradical group formed by removing one hydrogen atom from an alkyl group and that a "methylene" refers to a divalent radical —$CH_2$— derived from removing one hydrogen atom from methyl. More examples of such diradicals include, but are not limited to: alkenylene, alkynylene, cycloalkylene, phenylene, heterocyclylene, heteroarylene and (nonaromatic unsaturated carbocyclylene), which are derived from alkenyl, alkynyl, cycloalkyl, phenyl, heterocyclyl, heteroaryl and (nonaromatic unsaturated carbocyclyl), respectively. For example, "cyclopropylene" refers to both

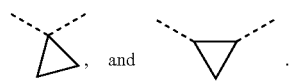

For example, "$C_1$-$C_2$ alkylene" refers to all of the following: —$CH_2$—, —$CH(CH_3)$— and —$CH_2$—$CH_2$—.

"oxo" refers to an oxygen double bond "═O" substitution.

"Hydroxy" or "hydroxyl" both refer to —OH.

"Perfluoroalkyl" refers to an alkyl group in which all of its hydrogen atoms are replaced by fluorine atoms.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with the alkyl group.

When a group is "optionally substituted" or "optionally further substituted" by some substituents, it means the hydrogen atoms of this group, except when the group itself is a hydrogen, where permissible, is substituted by some substituents. For example, such definition of a group "R is H, $C_1$-$C_3$ alkyl and phenyl, and R is optionally further substituted by 1-3 groups selected from —F, oxo and $C_1$-$C_3$ perfluoroalkyl", it is intended that R is 1) H (when R is H, R cannot be further substituted); 2) $C_1$-$C_3$ alkyl optionally further substituted by 1-3 groups selected from —F, oxo and $C_1$-$C_3$ perfluoroalkyl; and 3) phenyl optionally further substituted by 1-3 groups selected from —F and $C_1$-$C_3$ perfluoroalkyl. Optional substitution of oxo does not apply when R is phenyl because no single atom of the phenyl group possess two hydrogen atoms to be substituted by oxo, i.e. ═O bond.

A "pharmaceutical composition" refers to a mixture of one or more of the compounds described herein, or physiologically/pharmaceutically acceptable salts, solvates, hydrates or prodrugs thereof, with other chemical components, such as physiologically/pharmaceutically acceptable carriers and excipients. The purpose of a pharmaceutical composition is to facilitate administration of a compound to an organism.

As used herein, a "physiologically/pharmaceutically acceptable carrier" refers to a carrier or diluent that does not cause significant irritation to an organism and does not abrogate the biological activity and properties of the administered compound.

A "pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

As used herein, the term "pharmaceutically acceptable salt" refers to those salts that retain the biological effectiveness and properties of the parent compound. Such salts include:

(1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"PK" refers to receptor protein tyrosine kinase (RTKs), non-receptor or "cellular" tyrosine kinase (CTKs) and serine-threonine kinases (STKs).

"Modulation" or "modulating" refers to the alteration of the catalytic activity of RTKs, CTKs and STKs. In particular, modulating refers to the activation of the catalytic activity of RTKs, CTKs and STKs, preferably the activation or inhibition of the catalytic activity of RTKs, CTKs and STKs, depending on the concentration of the compound or salt to which the RTK, CTK or STK is exposed or, more preferably, the inhibition of the catalytic activity of RTKs, CTKs and STKs.

"Catalytic activity" refers to the rate of phosphorylation of tyrosine under the influence, direct or indirect, of RTKs and/or CTKs or the phosphorylation of serine and threonine under the influence, direct or indirect, of STKs.

"Contacting" refers to bringing a compound of the present teachings and a target PK together in such a manner that the compound can affect the catalytic activity of the PK, either directly, i.e., by interacting with the kinase itself, or indirectly, i.e., by interacting with another molecule on which the catalytic activity of the kinase is dependent. Such "contacting" can be accomplished "in vitro," i.e., in a test tube, a petri dish or the like. In a test tube, contacting may involve only a compound and a PK of interest or it may involve whole cells. Cells may also be maintained or grown in cell culture dishes and contacted with a compound in that environment. In this context, the ability of a particular compound to affect a PK related disorder, i.e., the $IC_{50}$ of the compound, can be determined before use of compounds in vivo with more complex living organisms is attempted. For cells outside the organism, multiple methods exist, and are well-known to those skilled in the art, to get the PKs in contact with the compounds including, but not limited to, direct cell microinjection and numerous transmembrane carrier techniques.

"in vitro" refers to procedures performed in an artificial environment such as, e.g., without limitation, in a test tube or culture medium.

"in vivo" refers to procedures performed within a living organism such as, without limitation, a mouse, rat or rabbit.

"PK related disorder," "PK driven disorder," and "abnormal PK activity" all refer to a condition characterized by inappropriate, i.e., under or, more commonly, over, PK catalytic activity, where the particular PK can be an RTK, a CTK or an STK. Inappropriate catalytic activity can arise as the result of either: (1) PK expression in cells which normally do not express PKs, (2) increased PK expression leading to unwanted cell proliferation, differentiation and/or growth, or, (3) decreased PK expression leading to unwanted reductions in cell proliferation, differentiation and/or growth. Over-activity of a PK refers to either amplification of the gene encoding a particular PK or production of a level of PK activity which can correlate with a cell proliferation, differentiation and/or growth disorder (that is, as the level of the PK increases, the severity of one or more of the symptoms of the cellular disorder increases). Under-activity is, of course, the converse, wherein the severity of one or more symptoms of a cellular disorder increase as the level of the PK activity decreases.

"Treat", "treating" and "treatment" refer to a method of alleviating or abrogating a PK mediated cellular disorder and/or its attendant symptoms. With regard particularly to cancer, these terms simply mean that the life expectancy of an individual affected with a cancer will be increased or that one or more of the symptoms of the disease will be reduced.

"Organism" refers to any living entity comprised of at least one cell. A living organism can be as simple as, for example, a single eukariotic cell or as complex as a mammal, including a human being.

"Therapeutically effective amount" refers to that amount of the compound being administered which will relieve to some extent one or more of the symptoms of the disorder being treated. In reference to the treatment of cancer, a therapeutically effective amount refers to that amount which has at least one of the following effects:
(1) reducing the size of the tumor;
(2) inhibiting (that is, slowing to some extent, preferably stopping) tumor metastasis;
(3) inhibiting to some extent (that is, slowing to some extent, preferably stopping) tumor growth, and
(4) relieving to some extent (or, preferably, eliminating) one or more symptoms associated with the cancer.

"Monitoring" means observing or detecting the effect of contacting a compound with a cell expressing a particular PK. The observed or detected effect can be a change in cell phenotype, in the catalytic activity of a PK or a change in the interaction of a PK with a natural binding partner. Techniques for observing or detecting such effects are well-known in the art. The effect is selected from a change or an absence of change in a cell phenotype, a change or absence of change in the catalytic activity of said protein kinase or a change or absence of change in the interaction of said protein kinase with a natural binding partner in a final aspect of this invention.

"Cell phenotype" refers to the outward appearance of a cell or tissue or the biological function of the cell or tissue. Examples, without limitation, of a cell phenotype are cell size, cell growth, cell proliferation, cell differentiation, cell survival, apoptosis, and nutrient uptake and use. Such phenotypic characteristics are measurable by techniques well-known in the art.

"Natural binding partner" refers to a polypeptide that binds to a particular PK in a cell. Natural binding partners can play a role in propagating a signal in a PK-mediated signal transduction process. A change in the interaction of the natural binding partner with the PK can manifest itself as an increased or decreased concentration of the PK/natural binding partner complex and, as a result, in an observable change in the ability of the PK to mediate signal transduction.

DETAILED DESCRIPTION

Figure 1:
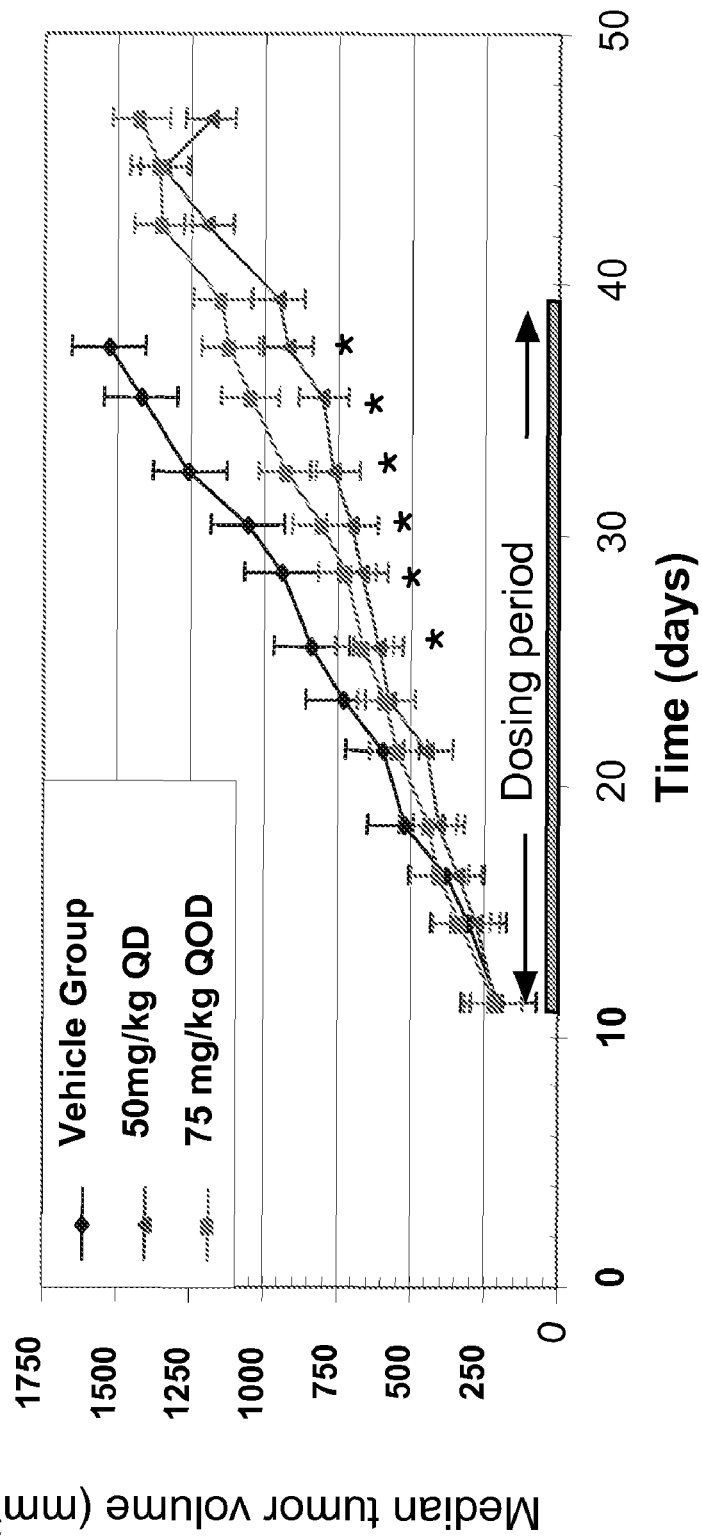
FIG. 1 shows that a compound of the current invention showed in vivo tumor growth inhibition and tumor growth delay of HCT116 human colorectal carcinoma xenografts in athymic mice.

Compounds of formulas I, II, III and IIIa can be made following the synthetic routes in Scheme 1 and Scheme 2. In Scheme 1 and Scheme 2 and the descriptions following, "BOC", "Boc" or "boc" means N-tert-butoxycarbonyl, DCM means $CH_2Cl_2$, DIPEA (also known as Hunig's base) means diisopropyl ethyl amine, DMA means dimethyl amine, "DMF" means dimethyl formamide, "DMSO" means dimethylsulfoxide, Et means —$CH_2CH_3$, "MTBE" means methyl t-butyl ether, NMP means 1-methyl-2-pyrrolidinone, TEA means triethyl amine, TFA means trifluoro acetic acid, THF means tetrahydrofuran. While schemes 1 and 2 and the description refer to compound 1, schemes 1 and 2 and the description are equally applicable to compounds II, III and IIIa.

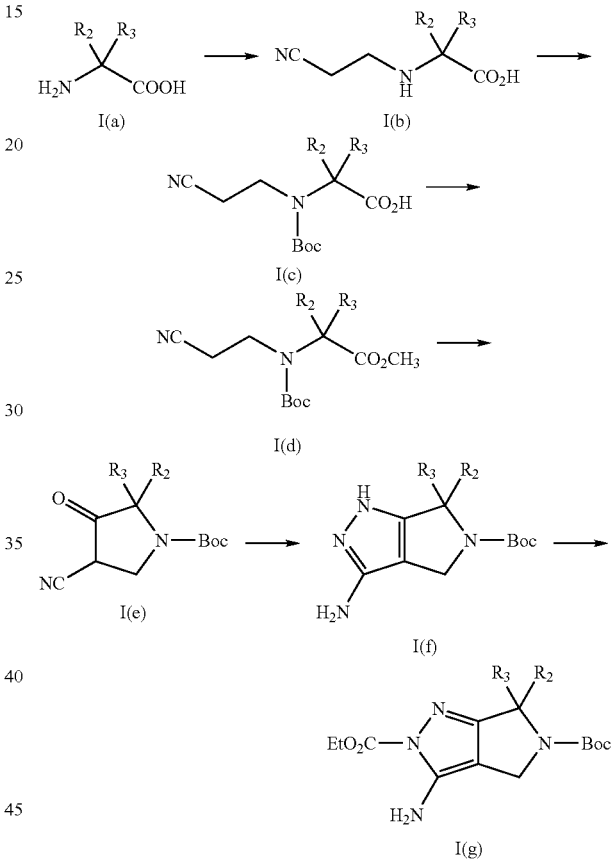

Scheme 1 illustrates the synthesis of the intermediate I(a) used to make compounds of formula I. The amino group of the substituted amino acid I(a) is alkylated to give compound I(b). This can typically be done by treating compound I(a) with an alkylating agent in the presence of a base. An activated electrophilic double bond moiety is a commonly used alkylating reagent. A typical reaction condition of alkylating I(a) with an activated electrophilic double bond moiety is to treat I(a) with the activated double bond moiety in the presence of a strong base. Subsequent aqueous work up affords compound I(b). The amino group of compound I(b) is then protected with a boc group to give compound I(c). This can typically be done by treating compound I(b) with Boc agent in the presence of a base. A typical condition is to treat compound I(b) with (Boc)$_2$O in the presence of Me$_4$NOH in MeCN as a solvent. The carboxylic acid group of compound I(c) is then converted into a methyl ester of compound I(d). A typical condition of converting the carboxylic acid group into the methyl ester group is to treat I(c) with methyl iodide in DMF in the presence of a base. Compound I(d) then undergoes an intramolecular aldol condensation to give compound I(e). This can typically be done by treating compound I(d) with a strong base in an aprotic solvent. A typical condition is to treat compound I(d) with t-BuOK in toluene. Subsequent aqueous workup gives compound I(e). Compound I(e) then undergoes a 2+3 cyclization with a hydrazine moiety to form compound I(f). A typical condition of the cyclization is to reflux compound I(e) with hydrazine and acetic acid in EtOH.

The free base pyrazole nitrogen of compound I(f) is then acylated to give compound I(g). A typical condition of the acylation is to treat compound I(f) with chloro ethyl carbonate in THF.

More detailed synthetic conditions to compound I(g) of Scheme 1 can be found in U.S. Patent Application Publication No. 2003/0171357 and PCT Publication WO 02/12242, the disclosure of which are incorporated herein by reference.

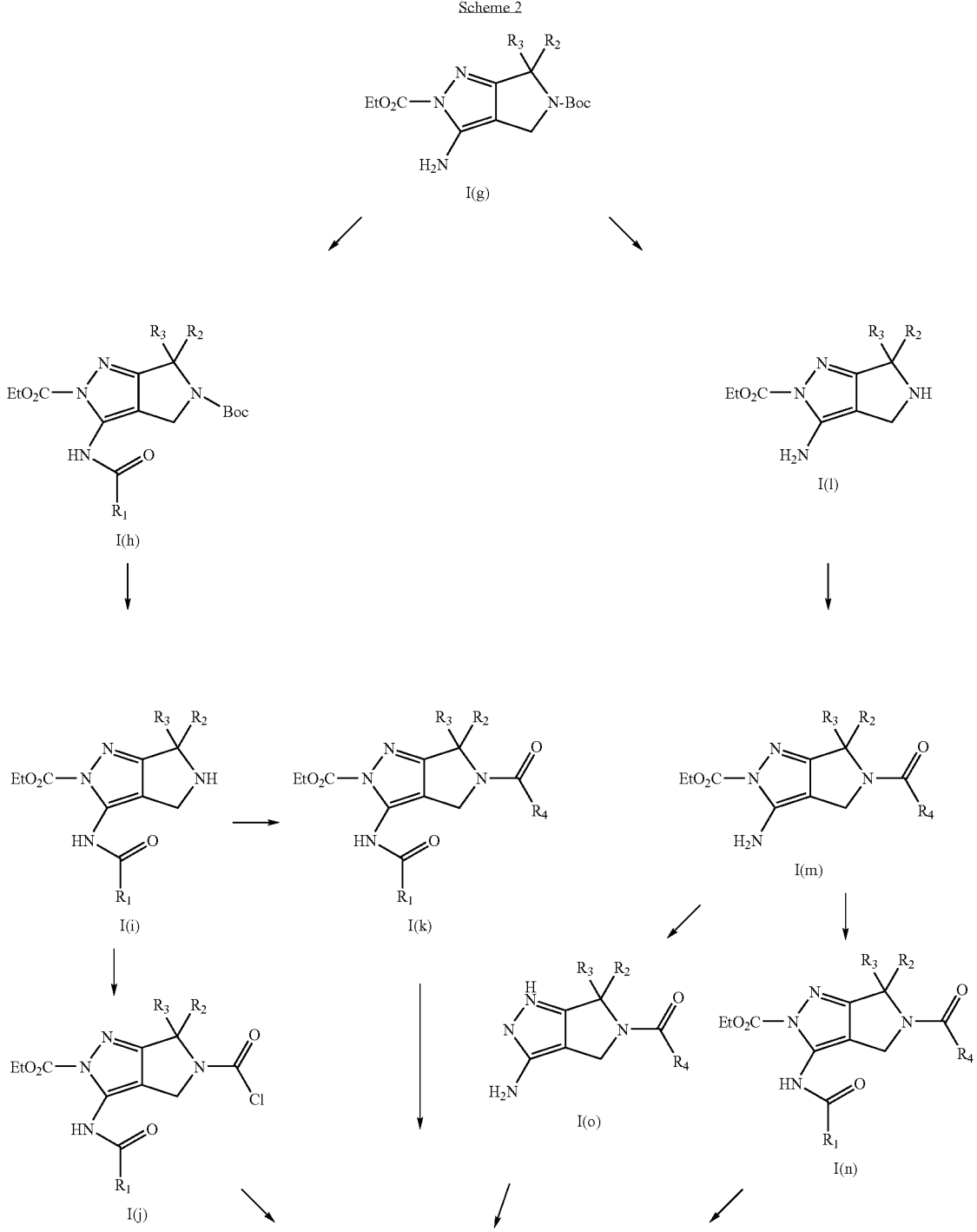

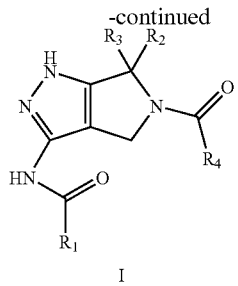

I

Scheme 2 illustrates two routes through which compounds of formula I can be made from intermediate I(g). In the first route of Scheme 2, compound I(g) undergoes a nucleophilic reaction with an $R^1$ electrophile moiety. This nucleophilic reaction can be an acylation, alkylation, sulfonylation, reductive amination or one of many other reactions that an amine functionality carries out. A typical acylation reaction condition is to treat compound I(g) with an acylating agent such as $R^1$—COCl, in the presence of a base such as 2 equivalents of DIPEA, in a solvent such as dichloromethane. The reaction mixture is stirred at between 0° C. and room temperature for 12 hours. Subsequent aqueous workup gives compound I(h). The Boc group on the pyrrole nitrogen of compound I(h) is then removed to give compound I(l). This can typically be done by treating I(h) with a strong acid. A typical reaction condition is to treat compound I(h) with 4N HCl in dioxane and DCM. Subsequent aqueous workup affords compound I(i). The pyrrole NH of compound I(i) is then acylated to give chloroformate I(j). This can typically be done using phosgene, triphosgene, or some equivalent. A typical reaction condition is to treat I(i) with 2 equivalents of triphosgene in DCM at 0° C. for four hours. Subsequent mild basic workup with saturated NaHCO$_3$ and purification gives compound I(j). Compound I(j) is then treated with an $R^1$ nucleophile moiety. The nucleophile can be an alcohol, amine or one of many other functionalities that can react with the chloroformate I(j). A typical reaction involves treating I(j) with a nucleophile such as 1.5 equivalents of an alcohol in the presence of 2 equivalents of base such as K$_2$CO$_3$ in a solvent such as DME. The reaction is heated to 80° C. for eight hours and the solvent removed. Alternatively, I(j) can be treated with 1.5 equivalents of an amine in the presence of 1 equivalent of base such as DIPEA in a solvent such as THF. Subsequent work up in a protic solvent such as methanol in the presence of base such as TEA followed by purification give compound of formula I.

Alternatively, compound I(i) can then undergoes a nucleophilic reaction with an $R^4$ electrophile give compound I(k). The nucleophilic reaction carried out for this transformation can be an alkylation, acylation, sulfonylation, reductive amination. An acylation reaction of I(i) to give I(k) is carried out by treating compound I(i) with an acylating reagent in the presence of base. A typical reaction condition is to mix compound I(i) with excess of base, such as DIPEA in DCM and adding the resulting solution to an isocyanate at 0° C. The reaction is stirred for 2 hours and subsequent aqueous workup gives compound I(k). The ethyl ester protecting group on the pyrazole nitrogen of compound I(k) is removed to give compound of formula I. This can typically be done by treating compound I(k) with a base. A typical reaction condition is to reflux compound I(k) in dioxane and DCM in the presence of 2-3 equivalents of LiOH. Subsequent aqueous workup affords compound of formula I.

In the second route of Scheme 2, the Boc group on the pyrrole nitrogen is removed to give compound I(l). The can typically be carried out by treating compound I(g) with a strong acid. A typical reaction condition is to treat compound I(g) with 4N HCl in dioxane and DCM. Subsequent aqueous workup affords compound I(l). Compound I(l) can then undergoes a nucleophilic reaction with an $R^4$ electrophile give compound I(m). Because the —NH$_2$ group attached to the pyrazole in compound I(l) is less reactive than the pyrrole nitrogen of I(l), the transformation of I(l) to I(m) can be carried out without protecting the pyrazole —NH$_2$ group of compound I(l). The nucleophilic reaction carried out for this transformation can be an alkylation, acylation, sulfonylation, reductive amination. Relative mild reaction conditions are preferred to achieve the reaction selectivity. An acylation reaction of I(l) to give I(m) is carried out by treating compound I(l) with an acylating reagent in the presence of base. A typical reaction condition is to mix compound I(l) with excess of base, such as DIPEA in DCM and adding the resulting solution to an isocyanate at 0° C. The reaction mixture is held at 0° C. for about two hours and subsequent aqueous workup gives compound I(m).

Compound I(m) then undergoes a nucleophilic reaction with an $R^1$ electrophile moiety. This nucleophilic reaction can be an acylation, alkylation, sulfonylation, reductive amination or one of many other reactions that an amine functionality carries out. A typical acylation reaction condition is to treat compound I(m) with an acylating agent such as $R^1$—NCO in the presence of a base such as 2 equivalents of DIPEA in a solvent such as dichloromethane for 2 hours. Alternatively, I(m) can be treated with an acylating agent such as $R^1$—COOR, where R is an activating group such as p-nitrophenyl, in the presence of a base such as 2 equivalents of DIPEA, in a solvent such as 1,2-dichloroethane. Subsequent aqueous workup gives compound I(n). The ethyl ester protecting group on the pyrazole nitrogen of compound I(n) is removed typically with a base to give the free base compound I. A typical reaction condition is to mix compound I(n) with TEA in a protic solvent such as methanol followed by purification to give compound of formula I.

Alternatively, the ethyl ester protecting group on the pyrazole nitrogen of compound I(m) is removed to give the free base compound I(o). This can typically be done by treating compound I(m) with a base. A typical reaction condition is to reflux compound I(m) in dioxane and DCM in the presence of 2-3 equivalents of LiOH. Subsequent aqueous workup affords compound I(o). Compound I(o) then undergoes a nucleophilic reaction with an $R^1$ electrophile moiety. This nucleophilic reaction can be an acylation, alkylation, sulfonylation, reductive amination or one of many other reactions that amine functionality carries out. A typical acylation reaction condition is to treat compound I(o) with an acylating agent such as R¹—COCl, in the presence of a base such as 2 equivalents of DIPEA in a solvent such as dichloromethane. The reaction mixture is stirred for four hours and subsequent aqueous workup and purification gives compound of formula I.

Unless indicated otherwise, all references herein to the inventive compounds include references to salts, solvates, hydrates and complexes thereof, and to solvates, hydrates and complexes of salts thereof, including polymorphs, stereoisomers, and isotopically labeled versions thereof.

Pharmaceutically acceptable salts include acid addition and base salts (including disalts).

Suitable acid addition salts are formed from acids which form non-toxic salts. Examples include the acetate, aspartate, benzoate, besylate, bicarbonate/carbonate, bisulphate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

It is understood when a particular salt of a free base compound B or a particular salt of an free acid compound A is disclosed in the current invention, the corresponding free base compound B or free acid compound A is also within the contemplation of the current invention. Treating the salt of free base compound B with small amount of aqueous $K_2CO_3$ followed by extraction of the aqueous solution with large amount of organic solvent usually affords free base compound B in good yield. If the free base compound B is extremely water soluble, it is recommended appropriate organic solvent be used to dissolve the salt followed by adding solid $K_2CO_3$. Subsequent filtration or chromatography usually affords free base compound B. Free acid compound A can be obtained from its salt following similar methods.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002), the disclosure of which is incorporated herein by reference in its entirety.

A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, $d_6$-acetone, $d_6$-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975), the disclosure of which is incorporated herein by reference in its entirety.

Also within the scope of the invention are polymorphs, prodrugs, and isomers (including optical, geometric and tautomeric isomers) of the inventive compounds Derivatives of compounds of the invention which may have little or no pharmacological activity themselves but can, when administered to a patient, be converted into the inventive compounds, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association), the disclosures of which are incorporated herein by reference in their entireties.

Prodrugs in accordance with the invention can, for example, be produced by replacing appropriate functionalities present in the inventive compounds with certain moieties known to those skilled in the art as 'pro-moieties' as described, for example, in "Design of Prodrugs" by H Bundgaard (Elsevier, 1985), the disclosure of which is incorporated herein by reference in its entirety.

Some examples of prodrugs in accordance with the invention include:

(i) where the compound contains a carboxylic acid functionality (—COOH), an ester thereof, for example, replacement of the hydrogen with $(C_1-C_8)$alkyl;

(ii) where the compound contains an alcohol functionality (—OH), an ether thereof, for example, replacement of the hydrogen with $(C_1-C_6)$alkanoyloxymethyl; and (iii) where the compound contains a primary or secondary amino functionality (—NH$_2$ or —NHR where R≠H), an amide thereof, for example, replacement of one or both hydrogens with $(C_1-C_{10})$alkanoyl.

Further examples of replacement groups in accordance with the foregoing examples and examples of other prodrug types may be found in the aforementioned references.

Finally, certain inventive compounds may themselves act as prodrugs of other of the inventive compounds.

Compounds of the invention containing one or more asymmetric carbon atoms can exist as two or more stereoisomers. Where a compound of the invention contains an alkenyl or alkenylene group, geometric cis/trans (or Z/E) isomers are possible. Where the compound contains, for example, a keto or oxime group or an aromatic moiety, tautomeric isomerism ('tautomerism') can occur. A single compound may exhibit more than one type of isomerism.

Included within the scope of the invention are all stereoisomers, geometric isomers and tautomeric forms of the inventive compounds, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art; see, for example, "Stereochemistry of Organic Compounds" by E L Eliel (Wiley, New York, 1994), the disclosure of which is incorporated herein by reference in its entirety.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labeled compounds of the invention, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, 2H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

The compounds can be administered alone or in combination with one or more other compounds of the invention, or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the invention and methods for their preparation will be readily apparent to those skilled in the art. Such compositions and methods for their preparation can be found, for example, in 'Remington's Pharmaceutical Sciences', 19th Edition (Mack Publishing Company, 1995), the disclosure of which is incorporated herein by reference in its entirety.

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety.

Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and microneedle or needle-free (e.g. Powderject™, Bioject™, etc.) injection. The disclosures of these references are incorporated herein by reference in their entireties.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may include a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as I-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 μg to 20 mg of the compound of the invention per actuation and the actuation volume may vary from 1 μL to 100 μL. A typical formulation includes a compound of the invention, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing a desired mount of the compound of the invention. The overall daily dose may be administered in a single dose or, more usually, as divided doses throughout the day.

Rectal/Intravaginal Administration

Compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

Ocular Administration

Compounds of the invention may also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

Dosage

The amount of the active compound administered will be dependent on the subject being treated, the severity of the disorder or condition, the rate of administration, the disposition of the compound and the discretion of the prescribing physician. However, an effective dosage is typically in the range of about 0.001 to about 100 mg per kg body weight per day, preferably about 0.01 to about 35 mg/kg/day, in single or divided doses. For a 70 kg human, this would amount to about 0.07 to about 7000 mg/day, preferably about 0.7 to about 2500 mg/day. In some instances, dosage levels below the lower limit of the aforesaid range may be more than adequate, while in other cases still larger doses may be used without causing any harmful side effect, with such larger doses typically divided into several smaller doses for administration throughout the day.

Kit-Of-Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

EXAMPLES

In the following examples and preparations, "BOC", "Boc" or "boc" refers to N-tert-butoxycarbonyl, "CBZ" refers to carbobenzyloxy, "DCE" refers to dichloroethane, "DCM" refers to dichloromethane, "DIC" refers to diisopropylcarbodiimide, "DIPEA" or "DIEA" refers to diisopropyl ethyl amine, DMA refers to N,N-dimethylacetamide, "DME"

refers to 1,2-dimethoxyethane, "DMF" refers to dimethyl formamide, "DMSO" refers to dimethylsulfoxide, "DPPP" refers to 1,3-bis(diphenylphosphino)propane, "HATU" refers to O-(7-azabenzotriazol-1-yl)-N,N,N',N'-tetramethyluronium hexafluorophosphate, "HBTU" refers to O-benzotriazol-1-yl-N,N,N',N'-tetramethyluronium hexafluorophosphate, "HOAc" refers to acetic acid, "HOBt" refers to 1-hydroxybenzotriazole hydrate, "IPA" refers to isopropyl alcohol, "LAH" refers to lithium aluminum hydride, "LiHMDS" refers to lithium bis(trimethylsilyl)amide, "MTBE" refers to methyl t-butyl ether, "NMP" refers to 1-methyl 2-pyrrolidinone, "TEA" refers to triethyl amine, "TFA" refers to trifluoro acetic acid, "TIPS" refers to triisopropylsilyl- and "Trt" refers to triphenylmethyl-.

SPECIFIC EXAMPLES

Route II

Tail-First

Example 1

(1S)-2-(dimethylamino)-1-phenylethyl 3-(benzoylamino)-6,6-dimethyl-4,6-dihydropyrrolo[3,4-c]pyrazole-5(1H)-carboxylate

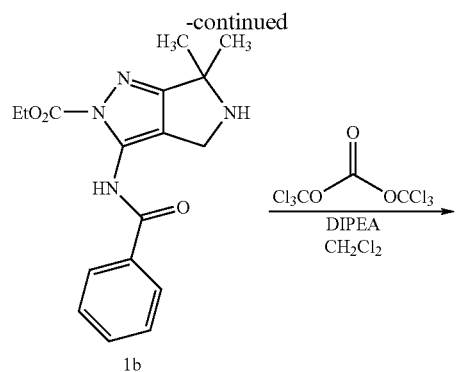

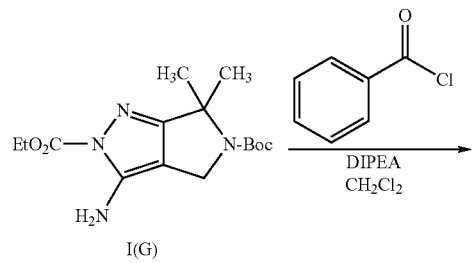

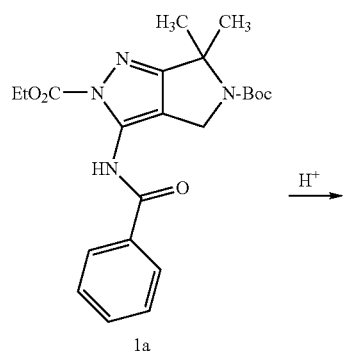

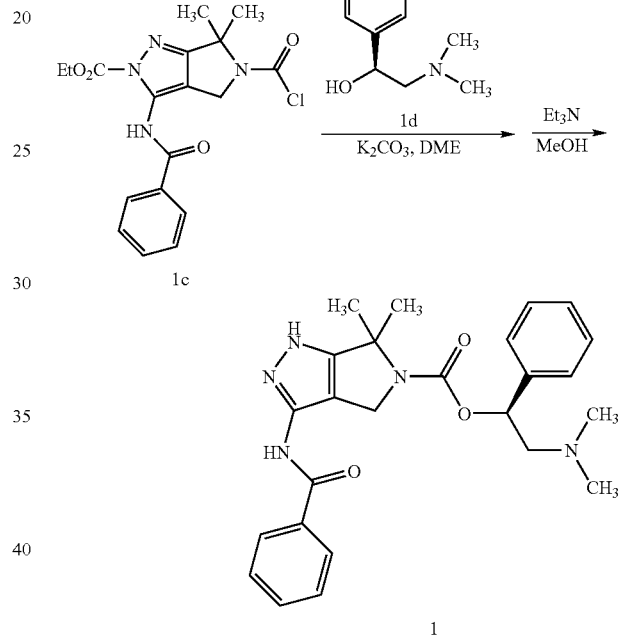

Preparation of Compound 1a: 5-tert-butyl 2-ethyl 3-(benzoylamino)-6,6-dimethylpyrrolo[3,4-c]pyrazole-2,5(4H,6H)-dicarboxylate To a cooled (0° C.) and stirred solution of I(g) (12.0 g, 37.0 mmol) and DIPEA (13.0 mL, 74.0 mmol) in dichloromethane (100 mL) was drop wise added a solution of benzoyl chloride (5.75 g, 40.7 mmol) in dichloromethane (50 mL). The resulting clear solution was stirred at room temperature for 12 h. The reaction mixture was washed with water (2×75 mL), dried over $Na_2SO_4$, filtered and concentrated. The residue was purified on silica gel column chromatography (40% ethyl acetate in hexane) to give amide 1a (15.0 g, 95.0%) as an off-white solid. $^1$H NMR (300 MHz, $CDCl_3$) δ: 1.44-1.56 (m, 12H) 1.69 (s, 3H) 1.75 (s, 3H) 4.58 (q, J=7.10 Hz, 2H) 4.74 (s, 1H) 4.79 (s, 1H) 7.44-7.64 (m, 3H) 7.87-7.96 (m, 2H) 10.97-11.11 (m, 1H).

| Structure and Example # | Chemical name, Analytical data and comments |
|---|---|
| 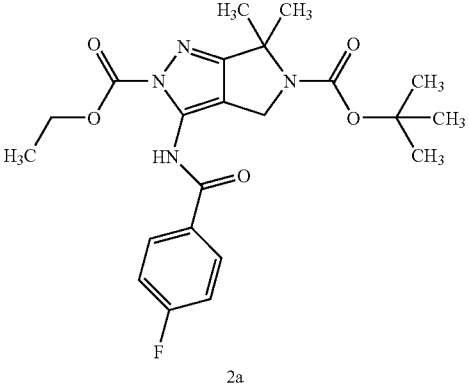<br>2a | 5-tert-butyl 2-ethyl 3-[(4-fluorobenzoyl)amino]-6,6-dimethylpyrrolo[3,4-c]pyrazole-2,5(4H,6H)-dicarboxylate.<br>1H NMR (300 MHz, CHLOROFORM-d) δ ppm 1.44-1.58 (m, 12 H) 1.68 (s, 3H) 1.75 (s, 3H) 4.58 (q, J = 7.16 Hz, 2H) 4.72 (s, 1H) 4.77 (s, 1H) 7.13-7.24 (m, 2H) 7.89-7.99 (m, 2H) 11.01 (d, J = 24.68 Hz, 1H). LCMS (APCI, M + H$^+$): 447.5.<br>Method of 1a: Made in 94% yield from I(g) and 4-fluoro benzoyl chloride. Recystallized from ethyl acetate and hexane. |
| 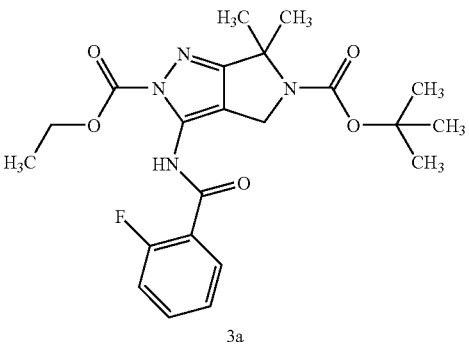<br>3a | 5-tert-butyl 2-ethyl 3-[(2-fluorobenzoyl)amino]-6,6-dimethylpyrrolopyrrolo[3,4-c]pyrazole-2,5(4H,6H)-dicarboxylate.<br>1H NMR (300 MHz, CHLOROFORM-d) δ ppm 1.43-1.57 (m, 12 H) 1.69 (s, 3H) 1.75 (s, 3H) 4.59 (q, J = 7.03 Hz, 2H) 4.73 (s, 1H) 4.79 (s, 1H) 7.20 (dd, J = 7.54, 4.52 Hz, 1H) 7.27-7.37 (m, 1H) 7.50-7.61 (m, 1H) 8.08-8.20 (m, 1H) 11.34 (dd, J = 17.71, 13.19 Hz, 1H). LCMS (APCI, M +H$^+$): 447.6.<br>Method of 1a: Made in 91% yield from I(g) and 2-fluoro benzoyl chloride. |
| 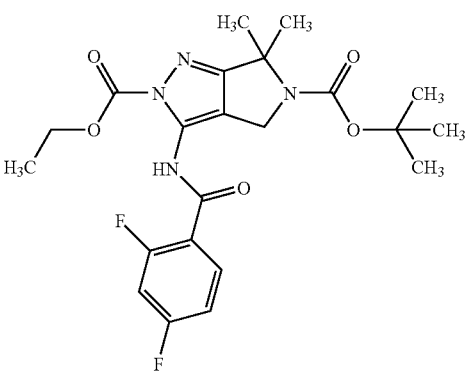<br>4a | 5-tert-butyl 2-ethyl 3-[(2,4-difluorobenzoyl) amino]-6,6-dimethyl pyrrolo [3,4-c]pyrazole-2,5(4H,6H)-dicarboxylate.<br>1H NMR (300 MHz, CHLOROFORM-d) δ ppm 1.44-1.57 (m, 12 H) 1.69 (s, 3H) 1.75 (s, 3H) 4.58 (q, J = 7.10 Hz, 2H) 4.72 (s, 1H) 4.77 (s, 1H) 6.89-7.00 (m, 1H) 7.04 (t, J = 8.19 Hz, 1H) 8.12-8.25 (m, 1H) 11.29 (dd, J = 18.46, 13.00 Hz, 1H). LCMS (APCI, M + H$^+$): 465.4.<br>Method of Ia: Made in 91% yield from I(g) and 2,4-difluoro benzoyl chloride. Recystallized from hexane. |
| 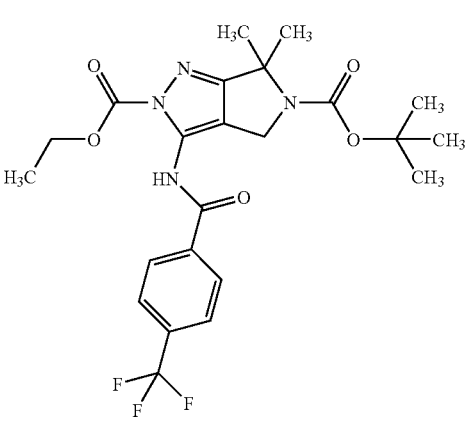<br>5a | 5-tert-butyl 2-ethyl 6,6-dimethyl-3-{[4-(trifluoromethyl) benzoyl]amino}pyrrolo[3,4-c]pyrazole-2,5(4H,6H)-dicarboxylate.<br>1H NMR (300 MHz, CHLOROFORM-d) δ ppm 1.45-1.60 (m, 12 H) 1.71 (s, 3H) 1.77 (s, 3H) 4.61 (q, J = 7.10 Hz, 2H) 4.75 (s, 1H) 4.81 (s, 1H) 7.74-7.87 (m, 2H) 8.00-8.10 (m, 2H) 11.15 (d, J = 25.06 Hz, 1H). LCMS (APCI, M + H$^+$): 497.5.<br>Method of 1a: Made in 72% yield from I(g) and 4-trifluoromethyl benzoyl chloride. |

| Structure and Example # | Chemical name, Analytical data and comments |
|---|---|
| 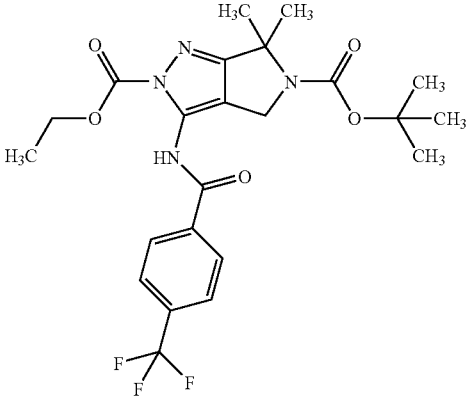<br>6a | 5-tert-butyl 2-ethyl 6,6-dimethyl-3-[(pyridin-2-ylcarbonyl)amino]pyrrolo[3,4-c]pyrazole-2,5(4H,6H)-dicarboxylate.<br>1H NMR (300 MHz, DMSO-$d_6$) d ppm 1.38 (t, J = 7.06 Hz, 3H) 1.46 (d, J = 5.46 Hz, 9H) 1.60 (d, J = 4.90 Hz, 6H) 4.47 (q, J = 7.03 Hz, 2 H) 4.61 (d, J = 8.48 Hz, 2H) 7.69-7.77 (m, 1H) 8.09 (t, J = 7.72 Hz, 1H) 8.15-8.22 (m, 1H) 8.75 (d, J = 4.52 Hz, 1H) 12.10 (d, J = 5.84 Hz, 1H). ). LCMS (APCI, M + H$^+$): 430.5.<br>Method of 1a: Made in 93% yield from I(g) and 2-pyridyl carbonyl chloride. |
| 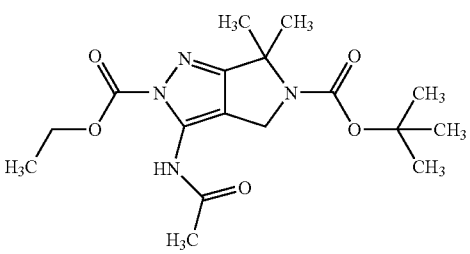<br>7a | 5-tert-butyl 2-ethyl 3-(acetylamino)-6,6-dimethylpyrrolo[3,4-c]pyrazole-2,5(4H,6H)-dicarboxylate.<br>1H NMR (dmso-$d_6$) δ: 1.34 (t, J = 8.0 Hz, 3H), 1.42-1.45 (m, 9H), 1.56 (s, 3H), 1.57 (s, 3H), 2.12-2.13 (d, J = 4.0 Hz, 3H), 4.36-4.43 (m, 4H), 10.15 (s, 1H). LCMS [M +H]$^+$ 367.<br>Method of 1a: Made in 54% yield from I(g) and acetyl chloride |
| 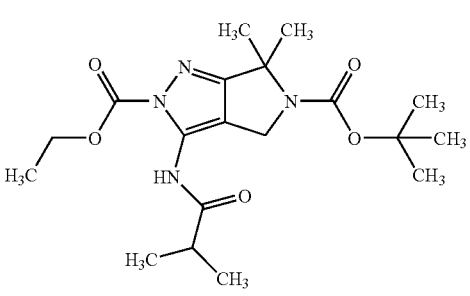<br>8a | 5-tert-butyl 2-ethyl 3-(isobutyrylamino)-6,6-dimethylpyrrolo[3,4-c]pyrazole-2,5(4H,6H)-dicarboxylate.<br>$^1$H NMR (dmso-$d_6$) δ: 1.11 (d, J = 7.1 Hz, 6H), 1.34 (t, J = 7.1 Hz, 3H), [1.43 (s), 1.46 (s) 9H together], [1.57 (s), 1.58 (s) 6H together], 2.70 (quint of d, $J_{quint}$ = 6.8 Hz, $J_d$ = 3.5 Hz, 1H), [4.48 (s), 4.43 (s) 2H together], 4.42 (q, J = 7.1 Hz, 2H), 10.12 (s, 1H). Anal. ($C_{19}H_{30}N_4O_5$) C, H, N. LCMS (APCI, M + H$^+$): 395.4.<br>Method of 1a: Made in 94% yield from I(g) and isobutyryl chloride. |
| 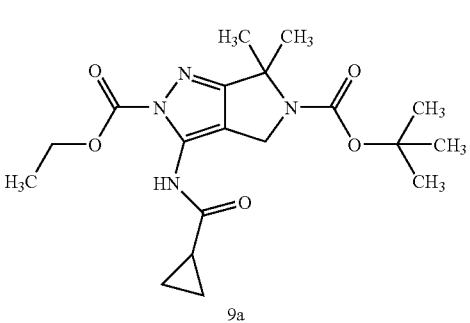<br>9a | 5-tert-butyl 2-ethyl 3-[(cyclopropylcarbonyl)amino]-6,6-dimethyl pyrrolo [3,4-c]pyrazole-2,5(4H,6H)-dicarboxylate.<br>$^1$H NMR (dmso-$d_6$) δ: 0.85 (m, 4H), 1.35 (t, J = 7.1 Hz, 3H), [1.42 (s), 1.45 (s) 9H together], [1.55 (s), 1.57 (s) 6H together], 1.99 (m, 1H), [4.32 (s), 4.36 (s) 2H together], 4.42 (q, J = 7.1 Hz, 2H), 10.41 (s, 1H). Anal. ($C_{19}H_{28}N_4O_5$) C, H, N. LCMS (APCI, M + H$^+$): 393.4.<br>Method of 1a: Made in 95% yield from I(g) and cyclopropane carbonyl chloride. |

-continued

| Structure and Example # | Chemical name, Analytical data and comments |
|---|---|
| 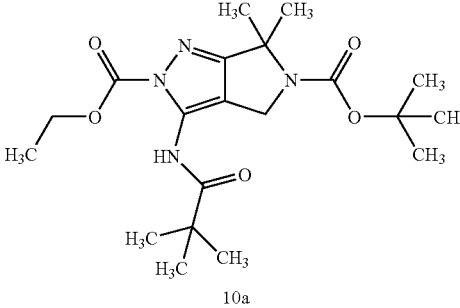<br>10a | 5-tert-butyl 2-ethyl 3-[(2,2-dimethylpropanoyl) amino]-6,6-dimethyl pyrrolo[3,4-c]pyrazole-2,5(4H,6H)-dicarboxylate.<br>$^1$H NMR (dmso-d$_6$) δ: 1.21 (s, 9H), 1.34 (t, J = 7.1 Hz, 3H), [1.43 (s), 1.46 (s) 9H together], [1.56 (s), 1.58 (s) 6H together], [4.43 (s), 4.47 (s) 2H together], 4.43 (q, J = 7.1 Hz, 2H), [10.21 (s), 10.25 (s) 1H together]. Anal. (C$_{20}$H$_{32}$N$_4$O$_5$) C, H, N. LCMS (APCI, M + H$^+$): 353.2.<br>Method of 1a: Made in 95% yield from I(g) and trimethylacetyl chloride. |
| 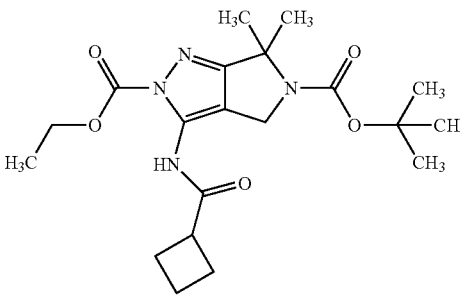<br>11a | 5-tert-butyl 2-ethyl 3-[(cyclobutylcarbonyl)amino]-6,6-dimethyl pyrrolo [3,4-c]pyrazole-2,5(4H,6H)-dicarboxylate.<br>$^1$H NMR (DMSO-d$_6$) 1.34 (t, J = 8.0 Hz, 3H), 1.43-1.46 (m, 9H), 1.56 (s, 3H), 1.58 (s, 3H), 1.75-1.84 (m, 1H), 1.90-1.99 (m, 1H), 2.13-2.21 (m, 4H), 3.29-3.37 (m, 1H), 4.38-4.44 (m, 4H), 9.98 (s, 1H). LCMS [M +H]$^+$ 407.<br>Method of 1a: Made in 70% yield from I(g) and cyclobutanecarbonyl chloride. |
| 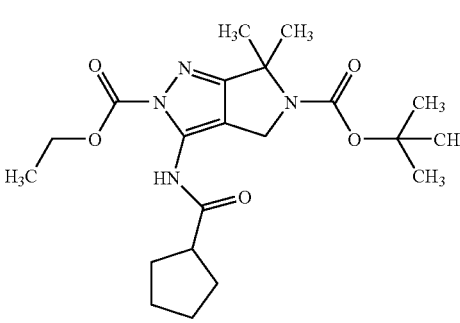<br>12a | 5-tert-butyl 2-ethyl 3-[(cyclopentylcarbonyl)amino]-6,6-dimethyl pyrrolo [3,4-c]pyrazole-2,5(4H,6H)-dicarboxylate.<br>$^1$H NMR (dmso-d$_6$) δ: 1.34 (t, J = 7.1 Hz, 3H), [1.43 (s), 1.45 (s) 9H together], 1.53 (m, 1H), [1.56 (s), 1.57 (s) 6H together], 1.65 (m, 5H), 1.85 (m, 2H), 2.90 (m, 1H), [4.38 (s), 4.42 (s) 2H together], 4.41 (q, J = 7.1 Hz, 2H), 10.11 (s, 1H). Anal. (C$_{21}$H$_{32}$N$_4$O$_5$) C, H, N. LCMS (APCI, M + H$^+$): 421.4.<br>Method of 1a: Made in 98% yield from I(g) and cyclopentanecarbonyl chloride. |
| 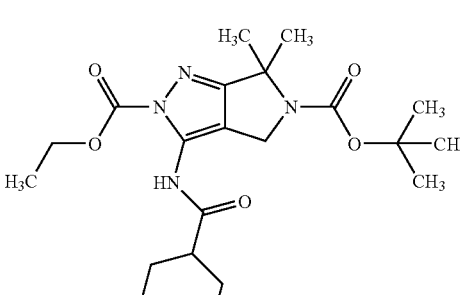<br>13a | 5-tert-butyl 2-ethyl 3-[(cyclohexylcarbonyl)amino]-6,6-dimethylpyrrolo[3,4-c]pyrazole-2,5(4H,6H)-dicarboxylate.<br>$^1$H NMR (dmso-d$_6$) δ: 1.21-1.39 (m, 5H), 1.34 (t, J = 7.1 Hz, 3H), [1.43 (s), 1.45 (s) 9H together], [1.55 (s), 1.57 (s) 6H together], 1.61 (m, 1H), 1.71 (m, 2H), 1.82 (m, 2H), 2.43 (m, 1H), 4.42 (m, 4H), 10.11 (s, 1H). Anal. (C$_{22}$H$_{34}$N$_4$O$_5$) C, H, N. LCMS (APCI, M + H$^+$): 435.4.<br>Method of 1a: Made in 94% yield from I(g) and cyclohexanecarbonyl chloride. |

| Structure and Example # | Chemical name, Analytical data and comments |
|---|---|
| 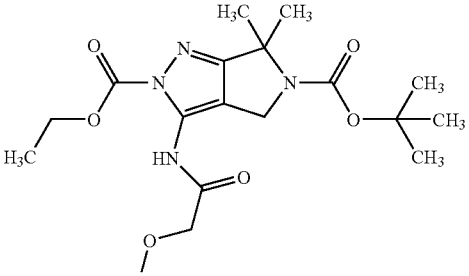<br>14a | 5-tert-butyl 2-ethyl 3-[(methoxyacetyl)amino]-6,6-dimethyl pyrrolo [3,4-c]pyrazole-2,5(4H,6H)-dicarboxylate.<br>$^1$H NMR (dmso-d$_6$) δ: 1.34 (t, J = 7.1 Hz, 3H), [1.42 (s), 1.46 (s) 9H together], [1.57 (s), 1.58 (s) 6H together], 3.41 (s, 3H), [4.06 (s), 4.07 (s) 2H together], 4.42 (q, J = 7.1 Hz, 2H), [4.46 (s), 4.49 (s) 2H together], [10.65 (s), 10.67 (s) 1H together]. Anal. (C$_{18}$H$_{28}$N$_4$O$_6$) C, H, N. LCMS (APCI, M + H$^+$): 397.4.<br>Method of 1a: Made in 84% yield from I(g) and methoxyacetyl chloride. |
| 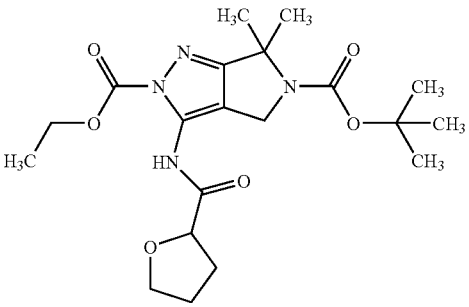<br>15a | 5-tert-butyl 2-ethyl 6,6-dimethyl-3-[(tetrahydrofuran-2-ylcarbonyl)amino]pyrrolo[3,4-c]pyrazole-2,5(4H,6H)-dicarboxylate.<br>$^1$H NMR (dmso-d$_6$) δ: 1.35 (t, J = 7.1 Hz, 3H), [1.43 (s), 1.45 (s) 9H together], 1.58 (dd, J = 2.8, 6.6 Hz, 6H), 1.86 (m, 2H), 1.98 (m, 1H), 2.23 (m, 1H), 3.91 (m, 2H), 4.45 (m, 5H), 10.80 (d, J = 2.0 Hz, 1H). Anal. (C$_{20}$H$_{30}$N$_4$O$_6$) C, H, N. LCMS (APCI, M + H$^+$): 423.4.<br>Method of 1a: Made in 82% yield from I(g) and tetrahydro-furan-2-carbonyl chloride. |
| 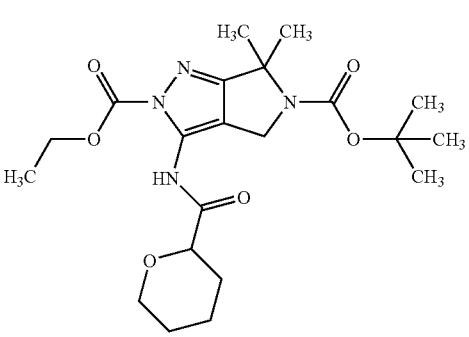<br>16a | 5-tert-butyl 2-ethyl 6,6-dimethyl-3-[(tetrahydro-2H-pyran-2-yl carbonyl) amino] pyrrolo[3,4-c]pyrazole-2,5(4H,6H)-dicarboxylate.<br>$^1$H NMR (dmso-d$_6$) δ: 1.34 (t, J = 7.1 Hz, 3H), 1.37 (m, 1H), [1.42 (s), 1.45 (s) 9H together], 1.52 (m, 3H), 1.57 (d, J = 6.8 Hz, 6H), 1.80 (m, 1H), 1.97 (m, 1H), 3.54 (t of d, J$_t$ = 10.8, J$_d$ = 3.3 Hz, 1H), 4.02 (m, 2H), 4.42 (q, J = 7.1 Hz, 2H), 4.46 (m, 2H), 10.71 (d, J = 6.8 Hz, 1H). Anal. (C$_{21}$H$_{32}$N$_4$O$_6$•0.1EtOAc) C, H, N. LCMS (APCI, M + H$^+$): 437.4.<br>Method of 1a: Made in 100% yield from I(g) and tetrahydro-pyran-2-carbonyl chloride. |
| 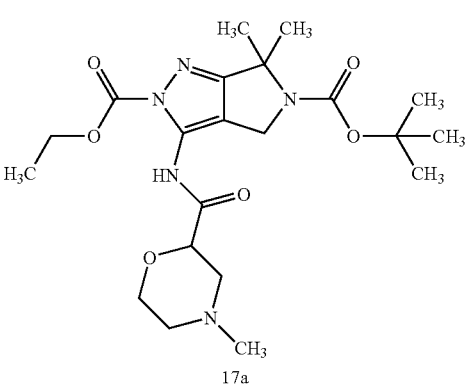<br>17a | 5-tert-butyl 2-ethyl 6,6-dimethyl-3-{[(4-methylmorpholin-2-yl)carbonyl]amino}pyrrolo[3,4-c]pyrazole-2,5(4H,6H)-dicarboxylate.<br>$^1$H NMR (dmso-d$_6$) δ: 1.34 (t, J = 7.1 Hz, 3H), [1.43 (s), 1.45 (s) 9H together], 1.57 (d, J = 6.6 Hz, 6H), 1.96 (t, J = 10.6 Hz, 1H), 2.05 (t of d, J$_t$ = 11.4, J$_d$ = 3.0 Hz, 1H), 2.21 (s, 3H), 2.60 (d, J = 11.6 Hz, 1H), 2.95 (d, J = 10.6 Hz, 1H), 3.97 (t of d, J$_t$ = 10.9, J$_d$ = 2.0 Hz, 1H), 3.96 (d, J = 11.4 Hz, 1H), 4.19 (d, J = 9.9 Hz, 1H), 4.42 (q, J = 7.1 Hz, 2H), 4.48 (d, J = 13.9 Hz, 2H), 10.75 (s, 1H). Anal. (C$_{21}$H$_{33}$N$_5$O$_6$) C, H, N. LCMS (APCI, M + H$^+$): 452.1.<br>Method of 1a: Made in 29% yield from I(g) and 4-methyl-morpholine-2-carbonyl chloride. |

| Structure and Example # | Chemical name, Analytical data and comments |
|---|---|
| 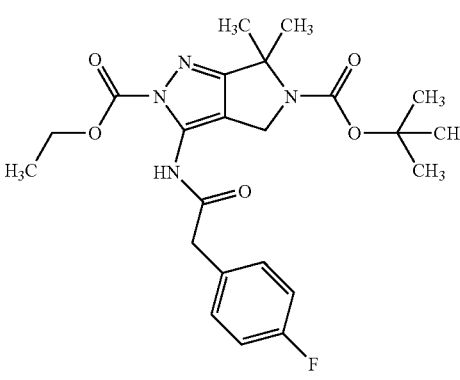<br>18a | 5-tert-butyl 2-ethyl 3-{[(4-fluorophenyl)acetyl]amino}-6,6-dimethyl pyrrolo [3,4-c]pyrazole-2,5(4H,6H)-dicarboxylate.<br>$^1$H NMR (CDCl$_3$) δ: [1.41 (t, J = 7.1 Hz), 1.42 (t, J = 7.1 Hz) 3H together], [1.47 (s), 1.51 (s) 9H together], [1.63 (s), 1.69 (s) 6H together], [3.69 (s), 3.70 (s) 2H together], [4.46 (q, J = 7.1 Hz), 4.47 (q, J = 7.1 Hz), 2H together], [4.61 (s), 4.65 (s) 2H together], 7.08 (m, 2H), 7.28 (m, 2H), [9.98 (s), 10.11 (s) 1H together]. Anal. (C$_{23}$H$_{29}$FN$_4$O$_5$•0.15H$_2$O) C, H, N, F. LCMS (APCI, M + H$^+$): 461.4.<br>Method of 1a: Made in 88% yield from I(g) and (4-fluoro-phenyl)-acetyl chloride. |
| 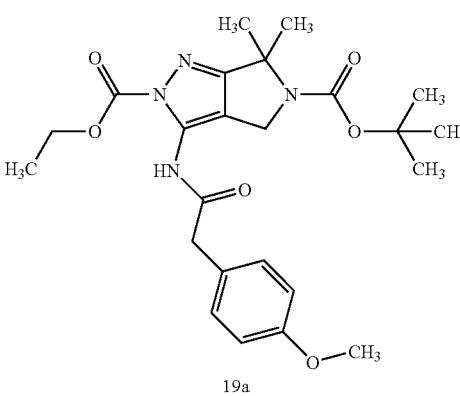<br>19a | 5-tert-butyl 2-ethyl 3-{[(4-methoxyphenyl)acetyl]amino}-6,6-dimethyl pyrrolo[3,4-c]pyrazole-2,5(4H,6H)-dicarboxylate.<br>$^1$H NMR (CDCl$_3$) δ: [1.40 (t, J = 6.8 Hz), 1.41 (t, J = 7.1 Hz) 3H together], [1.47 (s), 1.51 (s) 9H together], [1.63 (s), 1.69 (s) 6H together], [3.65 (s), 3.67 (s) 2H together], 3.81 (s, 3H), [4.45 (q, J = 7.1 Hz), 4.46 (q, J = 7.1 Hz), 2H together], [4.61 (s), 4.65 (s) 2H together], 6.91 (m, 2H), 7.22 (m, 2H), [9.94 (s), 10.07 (s) 1H together]. Anal. (C$_{24}$H$_{32}$N$_4$O$_6$) C, H, N. LCMS (APCI, M + H$^+$): 473.4.<br>Method of 1a: Made in 81% yield from I(g) and (4-methoxy-phenyl)-acetyl chloride. |
| 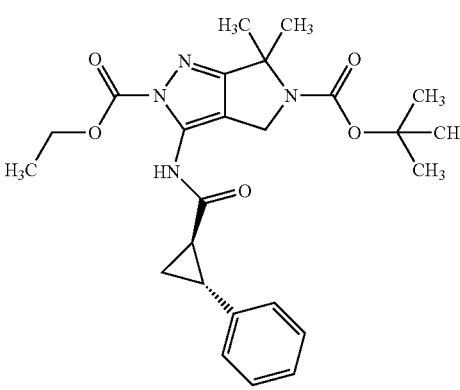<br>20a | 5-tert-butyl 2-ethyl 6,6-dimethyl-3-({[trans-2-phenyl cyclopropyl]carbonyl}amino)pyrrolo[3,4-c]pyrazole-2,5(4H,6H)-dicarboxylate.<br>$^1$H NMR (dmso-d$_6$) δ: 1.32 (t, J = 7.1 Hz, 3H), 1.38 (m, 1H), [1.43 (s), 1.46 (s) 9H together], 1.50 (m, 1H), 1.57 (dd, J = 10.0, 6.6 Hz, 6H), 2.44 (m, 2H), [4.37 (s), 4.41 (s) 2H together], 4.39 (q, J = 6.8 Hz, 2H), 7.19 (m, 2H), 7.28 (t, J = 7.3 Hz, 3H), 10.50 (s, 1H). Anal. (C$_{25}$H$_{32}$N$_4$O$_5$) C, H, N. LCMS (APCI, M + H$^+$): 469.4.<br>Method of 1a: Made in 91% yield from I(g) and trans-2-phenyl-1-cyclopropane carbonyl chloride. |
| 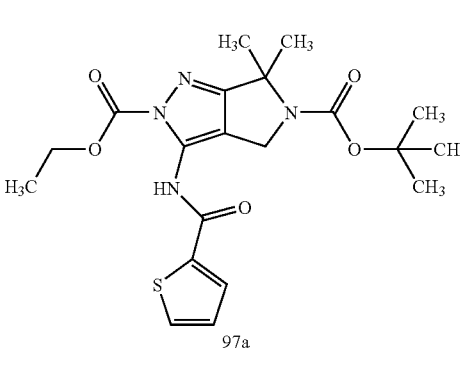<br>97a | 5-tert-butyl 2-ethyl 6,6-dimethyl-3-[(2-thienylcarbonyl)amino]pyrrolo[3,4-c]pyrazole-2,5(4H,6H)-dicarboxylate<br>$^1$H NMR (400 MHz, CHLOROFORM-d) δ ppm: 1.45 (t, 12H), 1.67 (d, 6H), 4.53 (q, J = 7.16 Hz, 2H), 4.67 (d, 2H), 7.05-7.17 (m, 1H), 7.51-7.67 (m, 2H), 10.87 (d, 1H)<br>Method of 1a. |

| Structure and Example # | Chemical name, Analytical data and comments |
|---|---|
| 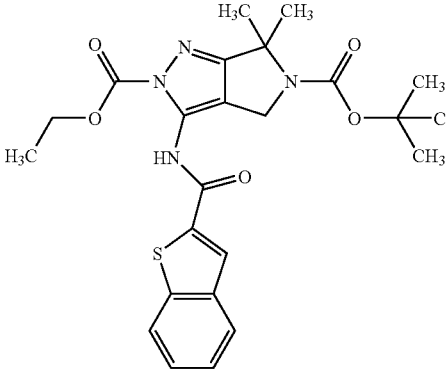<br>99a | 5-tert-butyl 2-ethyl 3-[(1-benzothien-2-ylcarbonyl)amino]-6,6-dimethylpyrrolo[3,4-c]pyrazole-2,5(4H,6H)-dicarboxylate<br>$^1$H NMR (400 MHz, CHLOROFORM-d) δ ppm: 1.46-1.55 (m, 12H) 1.72 (d, 6H) 4.61 (q, J = 7.07 Hz, 2H) 4.75 (d, 2H) 7.39-7.53 (m, 2H) 7.83-7.97 (m, 3H) 11.08 (d, 1H).<br>Method of 1a. |

Preparation of Compound 1b: ethyl 3-(benzoylamino)-6,6-dimethyl-5,6-dihydropyrrolo[3,4-c]pyrazole-2(4H)-carboxylate To a stirred slurry of intermediate 1a (15.0 g, 35.0 mmol) in ethanol (150 mL) was drop wise added HCl 4 M solution in hexanes (44 mL). The resulting clear solution was stirred at room temperature for 12 h. The reaction mixture was concentrated under vacuum to a residue and stirred with hexane (250 mL) for 10 min. The solid product was collected by filtration, washed with hexane (100 mL) and dried under vacuum at 40° C. for 15 h to give the dihydrochloride salt of amine 1b (13.5 g, 96.4%), an off-white solid. $^1$H NMR (300 MHz, DMSO-d$_6$) δ ppm 1.36 (t, J=6.97 Hz, 3H) 1.67 (s, 6H) 4.47 (q, J=7.16 Hz, 2H) 4.59 (s, 2H) 7.55-7.74 (m, 3H) 7.92 (d, J=7.54 Hz, 2H) 10.23 (s, 2H) 10.93 (s, 1H)

In the following table, compound 2b to 17b in the following table were made as HCl salts, and compound 18b, 19b and 20b were made as free base.

| Structure and Example # | Chemical name, Analytical data and comments |
|---|---|
| 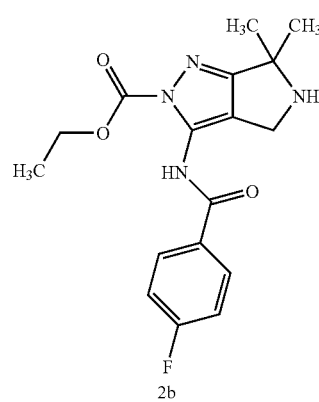<br>2b | ethyl 3-[(4-fluorobenzoyl)amino]-6,6-dimethyl-5,6-dihydropyrrolo[3,4-c]pyrazole-2(4H)-carboxylate.<br>1H NMR (300 MHz, CHLOROFORM-d) δ ppm 1.48 (t, 9H) 2.47 (s, 1H) 4.30 (s, 2H) 4.56 (q, J = 7.16 Hz, 2H) 7.18 (t, J = 8.38 Hz, 2H) 7.92 (dd, J = 8.48, 5.27 Hz, 2H) 10.86 (none, 1H) 11.01 (s, 1H). ).<br>LCMS (APCI, M + H$^+$): 347.<br>Method of 1b: Made in 96% yield from 2a. |
| 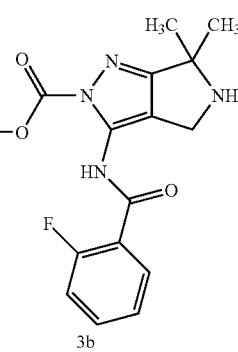<br>3b | ethyl 3-[(2-fluorobenzoyl)amino]-6,6-dimethyl-5,6-dihydropyrrolo[3,4-c]pyrazole-2(4H)-carboxylate.<br>1H NMR (300 MHz, DMSO-d$_6$) δ ppm 1.36 (t, J = 7.06 Hz, 3H) 1.66 (s, 6H) 4.47 (q, J = 7.16 Hz, 2H) 4.63 (s, 2H) 7.35-7.55 (m, 2H) 7.70-7.81 (m, 1H) 7.95-8.09 (m, 1H) 10.04 (s, 2H) 11.23 (d, J = 10.74 Hz, 1H). ). LCMS (APCI, M + H$^+$): 347.3.<br>Method of 1b: Made in 96% yield from 3a. |

| Structure and Example # | Chemical name, Analytical data and comments |
|---|---|
| 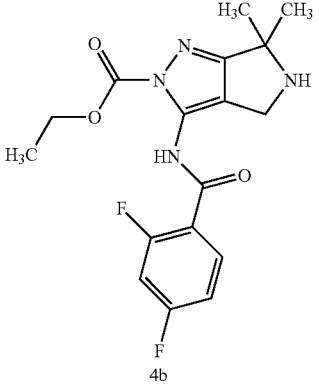<br>4b | ethyl 3-[(2,4-difluorobenzoyl)amino]-6,6-dimethyl-5,6-dihydropyrrolo [3,4-c]pyrazole-2(4H)-carboxylate.<br>1H NMR (300 MHz, CHLOROFORM-d) δ ppm 1.41-1.54 (m, 9H) 2.05 (s, 2H) 4.26-4.37 (m, 2H) 4.49-4.63 (m, 2H) 6.88-7.00 (m, 1H) 7.00-7.09 (m, 1H) 8.10-8.24 (m, 1H) 11.29 (d, J = 12.43 Hz, 1H). ). LCMS (APCI, M + H$^+$): 365.4.<br>Method of 1b: Made in 98% yield from 4a. |
| 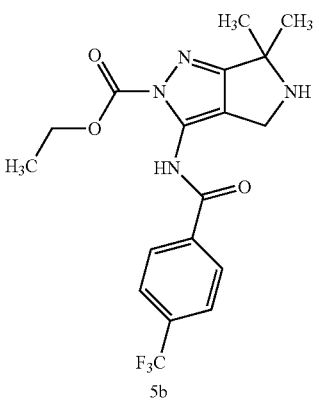<br>5b | ethyl 6,6-dimethyl-3-{[4-(trifluoromethyl)benzoyl]amino}-5,6-dihydro pyrrolo [3,4-c]pyrazole-2(4H)-carboxylate.<br>1H NMR (300 MHz, CHLOROFORM-d) δ ppm 1.40-1.55 (m, 9H) 2.72 (s, 1H) 4.34 (s, 2H) 4.57 (q, J = 7.16 Hz, 2H) 7.77 (d, J = 8.29 Hz, 2H) 8.02 (d, J = 8.10 Hz, 2H) 11.14 (s, 1H). ). LCMS (APCI, M + H$^+$): 397.5.<br>Method of 1b: Made in 95% yield from 5a. |
| 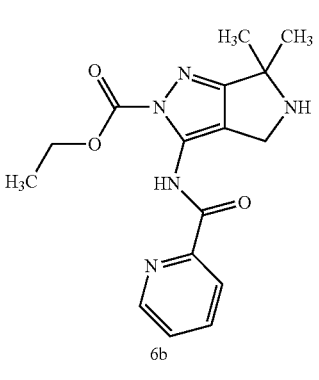<br>6b | ethyl 6,6-dimethyl-3-[(pyridin-2-ylcarbonyl)amino]-5,6-dihydro pyrrolo [3,4-c]pyrazole-2(4H)-carboxylate.<br>1H NMR (300 MHz, DMSO-d$_6$) δ ppm 1.39 (t, J = 7.16 Hz, 3H) 1.62 (s, 6H) 4.49 (q, J = 7.16 Hz, 2H) 4.64 (s, 2H) 7.68-7.82 (m, 1H) 8.05-8.25 (m, 2H) 8.78 (d, J = 4.71 Hz, 1H) 12.16 (s, 1H). ). LCMS (APCI, M + H$^+$): 330.4.<br>Method of 1b: Made in 97% yield from 6a. |
| 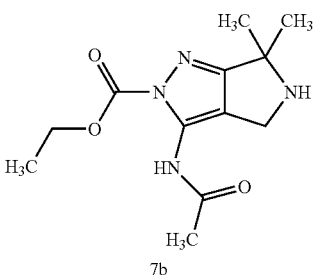<br>7b | ethyl 3-(acetylamino)-6,6-dimethyl-5,6-dihydro pyrrolo[3,4-c]pyrazole-2(4H)-carboxylate.<br>$^1$H NMR (dmso-d$_6$) δ 1.34 (t, J = 8.0 Hz, 3H), 1.63 (s, 6H), 2.16 (s, 3H), 4.45-4.40 (m, 4H), 10.31 (s, 1H); LCMS [M + H]$^+$ 267.<br>Method of 8b: 99% yield from 7a. |

| Structure and Example # | Chemical name, Analytical data and comments |
|---|---|
| 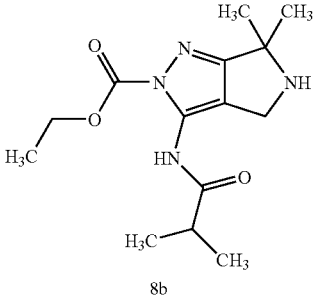 8b | ethyl 3-(isobutyrylamino)-6,6-dimethyl-5,6-dihydropyrrolo[3,4-c]pyrazole-2(4H)-carboxylate.<br>$^1$H NMR (dmso-d$_6$) δ: 1.12 (d, J = 6.8 Hz, 6H), 1.35 (t, J = 7.1 Hz, 3H), 1.62 (s, 6H), 2.75 (quint, J = 6.8 Hz, 1H), 4.43 (q, J = 7.1 Hz, 2H), 4.45 (s, 2H), 9.99 (br s, 2H), 10.26 (s, 1H). Anal. (C$_{14}$H$_{22}$N$_4$O$_3$•1.0HCl) C, H, N, Cl. LCMS (APCI, M + H$^+$): 295.4.<br>Modified method: Intermediate 8a was stirred in 4M HCl-dioxane (no co-solvent) for 2.5 hr at room temperature. Evaporation and trituration from acetonitrile afforded the monohydrochloride salt in 95% yield. |
| 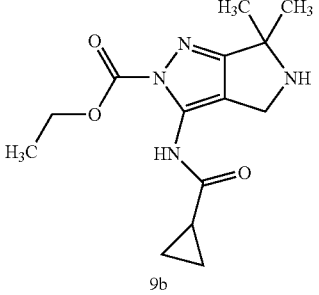 9b | ethyl 3-[(cyclopropylcarbonyl)amino]-6,6-dimethyl-5,6-dihydro pyrrolo [3,4-c]pyrazole-2(4H)-carboxylate.<br>$^1$H NMR (dmso-d$_6$) δ: 0.89 (m, 4H), 1.35 (t, J = 7.1 Hz, 3H), 1.61 (s, 6H), 2.07 (m, 1H), 4.38 (s, 2H), 4.44 (q, J = 7.2 Hz, 2H), 9.96 (br s, 2H), 10.57 (s, 1H). Anal. (C$_{14}$H$_{20}$N$_4$O$_3$•1.0HCl) C, H, N, Cl. LCMS (APCI, M + H$^+$): 293.4.<br>Method of 8b: 90% yield from 9a. |
| 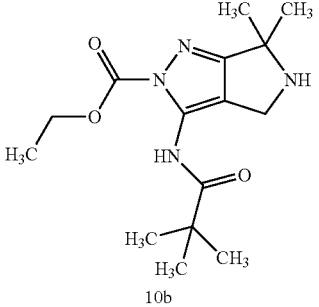 10b | ethyl 3-[(2,2-dimethylpropanoyl)amino]-6,6-dimethyl-5,6-dihydro pyrrolo [3,4-c]pyrazole-2(4H)-carboxylate.<br>$^1$H NMR (dmso-d$_6$) δ: 1.22 (s, 9H), 1.35 (t, J = 7.1 Hz, 3H), 1.63 (s, 6H), 4.45 (q, J = 7.2 Hz, 2H), 4.50 (s, 2H), 10.09 (br s, 2H), 10.30 (s, 1H). Anal. (C$_{15}$H$_{24}$N$_4$O$_3$•1.0HCl) C, H, N, Cl. LCMS (APCI, M + H$^+$): 309.4.<br>Method of 8b: 96% yield from 10a. |
| 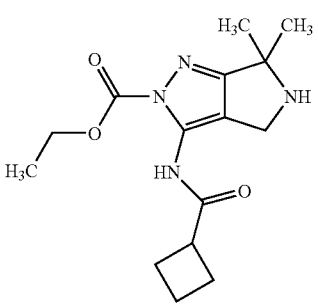 11b | ethyl 3-[(cyclobutylcarbonyl)amino]-6,6-dimethyl-5,6-dihydropyrrolo [3,4-c]pyrazole-2(4H)-carboxylate.<br>$^1$H NMR (DMSO-d$_6$) 1.34 (t,, J = 8.0 Hz, 3H), 1.63 (s, 6H), 1.68-1.85 (m, 1H), 1.89-2.01 (m, 1H), 2.14-2.24 (m, 4H), 3.36-3.45 (m, 1H), 4.39-4.48 (m, 4H), 10.12 (s, 1H). LCMS [M + H]$^+$ 307.<br>Method of 8b: 99% yield from 11a. |
| 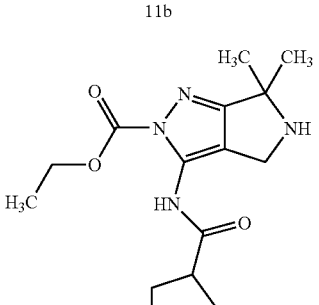 12b | ethyl 3-[(cyclopentylcarbonyl)amino]-6,6-dimethyl-5,6-dihydro pyrrolo [3,4-c]pyrazole-2(4H)-carboxylate.<br>$^1$H NMR (dmso-d$_6$) δ: 1.34 (t, J = 7.1 Hz, 3H), 1.62 (s, 6H), 1.64 (m, 6H), 1.86 (m, 2H), 2.96 (quint, J = 7.7 Hz, 1H), 4.43 (q, J = 7.1 Hz, 2H), 4.44 (s, 2H), 9.98 (br s, 2H), 10.24 (s, 1H). Anal. (C$_{16}$H$_{24}$N$_4$O$_3$•1.0HCl) C, H, N, Cl. LCMS (APCI, M + H$^+$): 321.4.<br>Method of 8b: 92% yield from 12a. |

| Structure and Example # | Chemical name, Analytical data and comments |
|---|---|
| 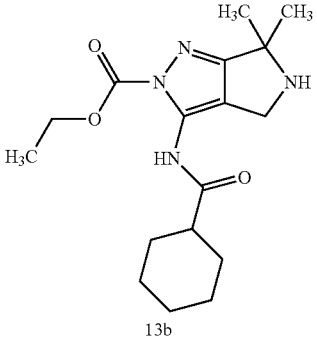<br>13b | ethyl 3-[(cyclohexylcarbonyl)amino]-6,6-dimethyl-5,6-dihydropyrrolo[3,4-c]pyrazole-2(4H)-carboxylate.<br>$^1$H NMR (dmso-d$_6$) δ: 1.15-1.40 (m, 5H), 1.34 (t, J = 7.1 Hz, 3H), 1.62 (m, 1H), 1.62 (s, 6H), 1.73 (m, 2H), 1.83 (m, 2H), 2.53 (m, 1H), 4.43 (q, J = 7.1 Hz, 2H), 4.45 (s, 2H), 10.12 (br s, 2H), 10.25 (s, 1H). Anal. (C$_{17}$H$_{26}$N$_4$O$_3$•1.0HCl) C, H, N, Cl. LCMS (APCI, M + H$^+$): 335.4.<br>Method of 8b: 96% yield from 13a. |
| 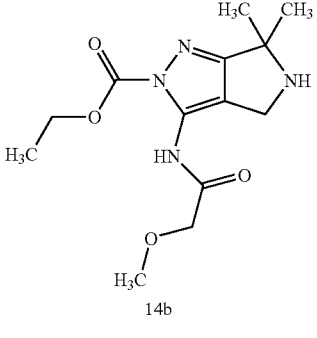<br>14b | ethyl 3-[(methoxyacetyl)amino]-6,6-dimethyl-5,6-dihydropyrrolo[3,4-c]pyrazole-2(4H)-carboxylate.<br>$^1$H NMR (dmso-d$_6$) δ: 1.34 (t, J = 7.1 Hz, 3H), 1.64 (s, 6H), 3.42 (s, 3H), 4.10 (s, 2H), 4.44 (q, J = 7.1 Hz, 2H), 4.50 (s, 2H), 10.30 (br s, 2H), 10.73 (s, 1H). Anal. (C$_{13}$H$_{20}$N$_4$O$_4$•1.0HCl) C, H, N, Cl. LCMS (APCI, M + H$^+$): 297.4.<br>Method of 8b: 90% yield from 14a. |
| 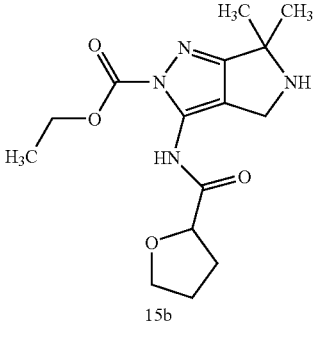<br>15b | ethyl 6,6-dimethyl-3-[(tetrahydrofuran-2-ylcarbonyl)amino]-5,6-dihydro pyrrolo [3,4-c]pyrazole-2(4H)-carboxylate<br>$^1$H NMR (dmso-d$_6$) δ: 1.35 (t, J = 7.1 Hz, 3H), 1.63 (s, 6H), 1.86 (m, 2H), 1.98 (m, 1H), 2.24 (m, 1H), 3.91 (m, 2H), 4.44 (q, J = 7.1 Hz, 2H), 4.51 (m, 3H), 10.07 (br s, 2H), 10.87 (s, 1H). Anal. (C$_{15}$H$_{22}$N$_4$O$_4$•1.0HCl) C, H, N, Cl.<br>LCMS (APCI, M + H$^+$): 323.4.<br>Method of 8b: 94% yield from 15a. |
| 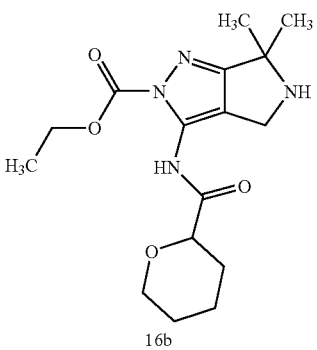<br>16b | ethyl 6,6-dimethyl-3-[(tetrahydro-2H-pyran-2-ylcarbonyl)amino]-5,6-dihydropyrrolo[3,4-c]pyrazole-2(4H)-carboxylate<br>$^1$H NMR (dmso-d$_6$) δ: 1.34 (t, J = 7.2 Hz, 3H), 1.39 (m, 1H), 1.53 (m, 3H), 1.63 (s, 6H), 1.82 (d, J = 11.6 Hz, 1H), 1.97 (d, J = 12.9 Hz, 1H), 3.55 (t of d, J$_t$ = 11.0 Hz, J$_d$ = 3.3 Hz, 1H), 4.05 (dd, J = 11.1, 2.3 Hz, 2H), 4.44 (q, J = 7.1 Hz, 2H), 4.52 (m, 2H), 10.07 (br s, 2H), 10.78 (s, 1H). Anal. (C$_{16}$H$_{24}$N$_4$O$_4$• 1.0HCl) C, H, N, Cl. LCMS (APCI, M + H$^+$): 337.4.<br>Method of 8b: 83% yield from 16a. |

| Structure and Example # | Chemical name, Analytical data and comments |
|---|---|
| 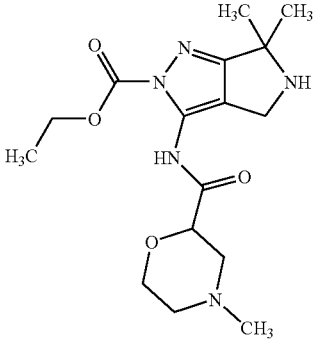<br>17b | ethyl 6,6-dimethyl-3-{[(4-methylmorpholin-2-yl)carbonyl]amino}-5,6-dihydropyrrolo[3,4-c]pyrazole-2(4H)-carboxylate<br>$^1$H NMR (dmso-d$_6$) δ: 1.34 (t, J = 7.2 Hz, 3H), 1.65 (s, 6H), 2.80 (s, 3H), 3.08 (br s, 2H), 3.42 (m, 1H), 3.73 (d, J = 11.9 Hz, 1H), 4.03 (t, J = 12.2 Hz, 1H), 4.25 (d, J = 11.6 Hz, 1H), 4.44 (q, J = 7.1 Hz, 2H), 4.49 (br s, 2H), 4.74 (d, J = 10.6 Hz, 1H), 10.34 (br s, 1H), 10.43 (br s, 1H), 10.80 (s, 1H), 11.82 (br s, 1H). Anal. (C$_{16}$H$_{25}$N$_5$O$_4$•2.0HCl•1.05H$_2$O) C, H, N, Cl. LCMS (APCI, M + H$^+$): 352.2.<br>Method of 8b: 90% yield from 17a. |
| 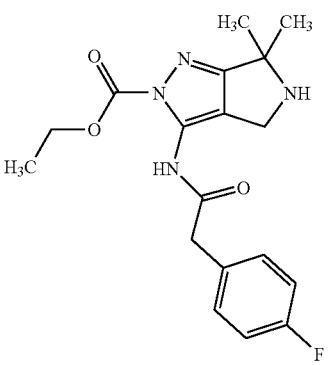<br>18b | ethyl 3-{[(4-fluorophenyl)acetyl]amino}-6,6-dimethyl-5,6-dihydro pyrrolo [3,4-c]pyrazole-2(4H)-carboxylate<br>1H NMR (dmso-d$_6$) δ: 1.26 (s, 6H), 1.31 (t, J = 7.0 Hz, 3H), 3.76 (s, 2H), 3.83 (s, 2H), 4.35 (q, J = 7.2 Hz, 2H), 7.16 (t, J = 8.9 Hz, 2H), 7.34 (dd, J = 5.7, 8.7 Hz, 2H), 10.10 (s, 1H). Anal. (C$_{18}$H$_{21}$FN$_4$O$_3$•0.1EtOAc) C, H, N, F. LCMS (APCI, M + H$^+$): 361.2.<br>Modified method: Intermediate 18a was treated with HCl/dioxane at room temperature for 3 hours, then evaporated to dryness, neutralized with 1M NaOH, and extracted with ethyl acetate. The organic extracts were concentrated to give the free base in 90% yield. |
| 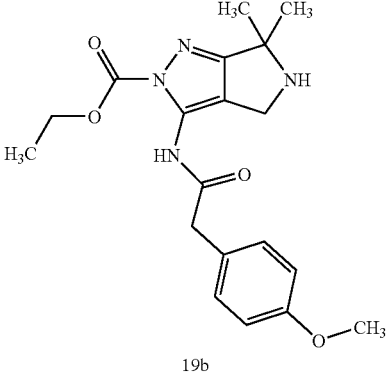<br>19b | ethyl 3-{[(4-methoxyphenyl)acetyl]amino}-6,6-dimethyl-5,6-dihydro pyrrolo [3,4-c]pyrazole-2(4H)-carboxylate<br>$^1$H NMR (dmso-d$_6$) δ: 1.26 (s, 6H), 1.30 (t, J = 7.1 Hz, 3H), 3.19 (br s, 1H), 3.67 (s, 2H), 3.72 (s, 3H), 3.83 (s, 2H), 4.34 (q, J = 7.2 Hz, 2H), 6.89 (d, J = 8.6 Hz, 2H), 7.22 (d, J = 8.67 Hz, 2H), 10.04 (s, 1H). Anal. (C$_{19}$H$_{24}$N$_4$O$_4$•0.5HCl•0.15EtOAc) C, H, N, Cl. LCMS (APCI, M + H$^+$): 373.2.<br>Method of 18b: Neutralized and isolated as free base in 90% yield from 19a. |
| 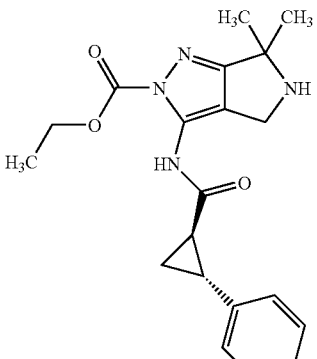<br>20b | ethyl 6,6-dimethyl-3-({[trans-2-phenylcyclopropyl]carbonyl}amino)-5,6-dihydropyrrolo[3,4-c]pyrazole-2(4H)-carboxylate<br>$^1$H NMR (dmso-d$_6$) δ: 1.28 (s, 6H), 1.31 (t, J = 7.1 Hz, 3H), 1.35 (m, 1H), 1.47 (m, 1H), 2.38 (t, J = 7.3 Hz, 2H), 3.14 (br s, 1H), 3.84 (s, 2H), 4.36 (q, J = 7.1 Hz, 2H), 7.18 (m, 3H), 7.28 (t, J = 7.3 Hz, 2H), 10.35 (s, 1H). Anal. (C$_{20}$H$_{24}$N$_4$O$_3$•0.25H2O•0.05dioxane) C, H, N. . LCMS (APCI, M + H$^+$): 369.4.<br>Method of 18b: Neutralized and isolated as free base in 90% yield from 19a |

| Structure and Example # | Chemical name, Analytical data and comments |
|---|---|
| 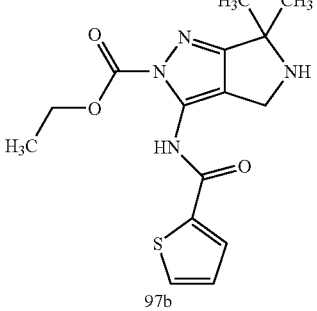<br>97b | Ethyl 6,6-dimethyl-3-[(2-thienylcarbonyl)amino]-5,6-dihydropyrrolo[3,4-c]pyrazole-2(4H)-carboxylate<br>$^1$H NMR (400 MHz, CHLOROFORM-d) δ ppm: 1.42-1.53 (m, 9H) 4.29 (s, 2H) 4.57 (q, J = 7.07 Hz, 2H) 7.15 (dd, J = 5.05, 3.79 Hz, 1H) 7.60 (dd, J = 4.93, 1.14 Hz, 1H) 7.66 (dd, J = 3.79, 1.01 Hz, 1H) 10.92 (br. s., 1H).<br>Method of 1b. |

Preparation of Compound 1c: ethyl 3-(benzoylamino)-5-(chlorocarbonyl)-6,6-dimethyl-5,6-dihydropyrrolo[3,4-c]pyrazole-2(4H)-carboxylate To a cooled (−10° C.) and stirred mixture of triphosgene (7.2 g, 24.3 mmol) and dihydrochloride salt 1b (13.0 g, 32.5 mmol) in DCM (150 mL) was drop wise added a solution of diisopropylethyl amine (28.4 mL, 162.5 mmol) in DCM (50 mL) over a period of 15 min. The resulting reaction mixture was stirred at 0° C. for 30 min. The reaction mixture was washed with water (2×100 mL), dried over Na$_2$SO$_4$, filtered and concentrated to give crude product. The crude product was stirred with 25% ethyl acetate in hexane. The resulting precipitate was collected by filtration and dried under vacuum at 40° C. to give 1c (12 g, 95%) as white solid. $^1$H NMR (300 MHz, CDCl$_3$) d ppm 1.51 (t, J=7.06 Hz, 3H) 1.75-1.84 (m, 6H) 4.60 (q, J=7.03 Hz, 2H) 5.08 (s, 2H) 7.46-7.69 (m, 3H) 7.85-7.98 (m, 2H) 11.10 (s, 1H)

| Structure and Example # | Chemical name, Analytical data and comments |
|---|---|
| 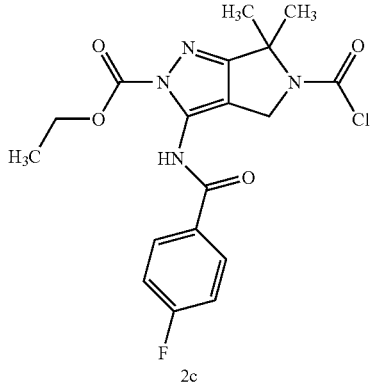<br>2c | ethyl 5-(chlorocarbonyl)-3-[(4-fluorobenzoyl)amino]-6,6-dimethyl-5,6-dihydropyrrolo [3,4-c]pyrazole-2(4H)-carboxylate.<br>1H NMR (300 MHz, CHLOROFORM-d) δ ppm 1.50 (t, J = 7.16 Hz, 3H) 1.79 (s, 6H) 4.60 (q, J = 7.10 Hz, 2H) 5.06 (s, 2H) 7.16-7.24 (m, 2H) 7.89-7.98 (m, 2H) 11.07 (s, 1H). ). LCMS (APCI, M + H$^+$): 409.3.<br>Method of 1c: Made in 89% yield from 2b. |
| 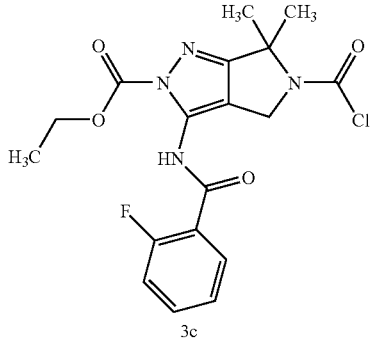<br>3c | ethyl 5-(chlorocarbonyl)-3-[(2-fluorobenzoyl)amino]-6,6-dimethyl-5,6-dihydro pyrrolo [3,4-c]pyrazole-2(4H)-carboxylate.<br>1H NMR (300 MHz, CHLOROFORM-d) δ ppm 1.49 (t, J = 7.06 Hz, 3H) 1.72-1.85 (m, 6H) 4.60 (q, J = 7.10 Hz, 2H) 5.07 (s, 2H) 7.17-7.24 (m, 1H) 7.28-7.38 (m, 1H) 7.52-7.64 (m, 1H) 8.08-8.19 (m, 1H) 11.42 (d, J = 13.19 Hz, 1H). LCMS (APCI, M + H$^+$): 409.3.<br>Method of 1c: Made in 87% yield from 3b. |

| Structure and Example # | Chemical name, Analytical data and comments |
|---|---|
| 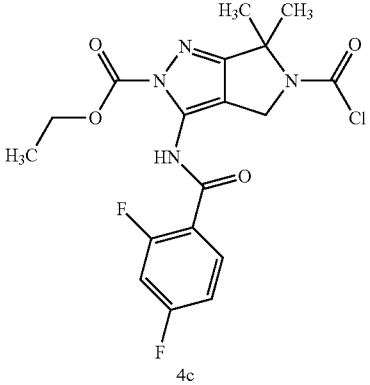<br>4c | ethyl 5-(chlorocarbonyl)-3-[(2,4-difluorobenzoyl)amino]-6,6-dimethyl-5,6-dihydropyrrolo[3,4-c]pyrazole-2(4H)-carboxylate.<br>1H NMR (300 MHz, CHLOROFORM-d) δ ppm 1.44-1.56 (m, 3H) 1.74-1.84 (m, 6H) 4.60 (q, J = 7.16 Hz, 2H) 5.06 (s, 2H) 6.89-7.14 (m, 2H) 8.09-8.28 (m, 1H) 11.37 (d, J = 13.00 Hz, 1H). LCMS (APCI, M + H$^+$): 427.<br>Method of 1c: Made in 87% yield from 4b. |
| 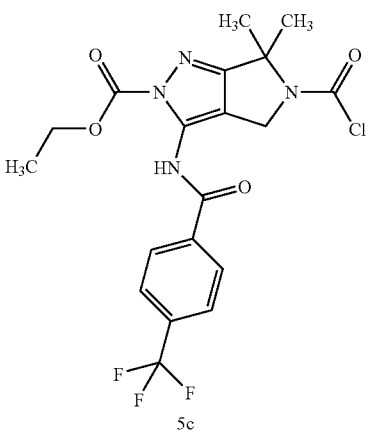<br>5c | ethyl 5-(chlorocarbonyl)-6,6-dimethyl-3-{[4-(trifluoromethyl)benzoyl]amino}-5,6-dihydro pyrrolo[3,4-c]pyrazole-2(4H)-carboxylate.<br>1H NMR (300 MHz, CHLOROFORM-d) δ ppm 1.51 (t, J = 7.16 Hz, 3H) 1.80 (s, 6H) 4.61 (q, J = 7.16 Hz, 2H) 5.08 (s, 2H) 7.80 (d, J = 8.29 Hz, 2H) 8.04 (d, J = 8.10 Hz, 2H) 11.20 (s, 1H). LCMS (APCI, M + H$^+$): 459.<br>Method of 1c: Made in 56% yield from 5b. |
| 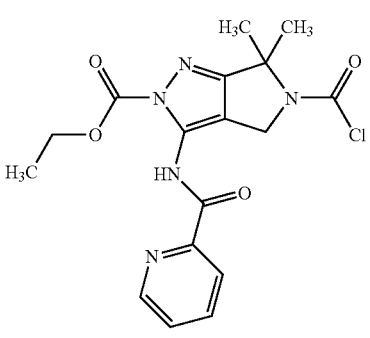<br>6c | ethyl 5-(chlorocarbonyl)-6,6-dimethyl-3-[(pyridin-2-ylcarbonyl)amino]-5,6-dihydropyrrolo[3,4-c]pyrazole-2(4H)-carboxylate.<br>1H NMR (300 MHz, CHLOROFORM-d) δ ppm 1.52 (t, J = 7.16 Hz, 3H) 1.77-1.83 (m, 6H) 4.63 (q, J = 7.03 Hz, 2H) 4.93-5.22 (m, 2H) 7.49-7.58 (m, 1H) 7.88-7.99 (m, 1H) 8.23 (d, J = 7.91 Hz, 1H) 8.73 (d, J = 4.71 Hz, 1H) 12.30 (s, 1H). LCMS (APCI, M + H$^+$): 392.3.<br>Method of 1c: Made in 90% yield from 6b. |
| 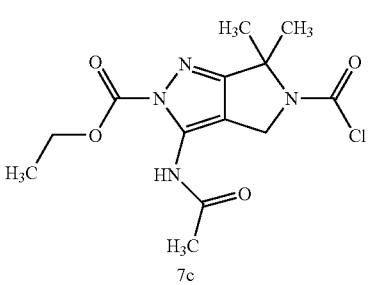<br>7c | ethyl 3-(acetylamino)-5-(chlorocarbonyl)-6,6-dimethyl-5,6-dihydro pyrrolo [3,4-c]pyrazole-2(4H)-carboxylate.<br>$^1$H NMR (dmso-d$_6$) δ 1.69 (t, J = 8.0 Hz, 3H), 1.98 (s, 6H), 2.83 (s, 3H), 4.78 (q, J = 8.0 Hz, 2H), 5.10 (s, 2H), 10.60 (s, 1H); LCMS [M + H]$^+$ 329.<br>Method of 1c: Made in 89% yield from intermediate 7b. |

| Structure and Example # | Chemical name, Analytical data and comments |
|---|---|
| 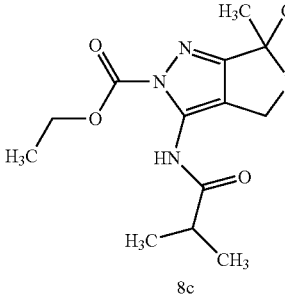<br>8c | ethyl 5-(chlorocarbonyl)-3-(isobutyrylamino)-6,6-dimethyl-5,6-dihydropyrrolo [3,4-c]pyrazole-2(4H)-carboxylate.<br>$^1$H NMR (dmso-d$_6$) δ: 1.12 (d, J = 6.8 Hz, 6H), 1.35 (t, J = 7.1 Hz, 3H), 1.64 (s, 6H), 2.73 (quint, J = 7.0 Hz, 1H), 4.43 (q, J = 7.1 Hz, 2H), 4.80 (s, 2H), 10.20 (s, 1H). Anal. (C$_{15}$H$_{21}$ClN$_4$O$_4$) C, H, N, Cl. LCMS (APCI, M + H$^+$): 357.2/359.2.<br>Method of 1c: Made in 84% yield from intermediate 8b. |
| 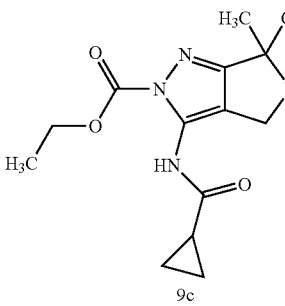<br>9c | ethyl 5-(chlorocarbonyl)-3-[(cyclopropylcarbonyl)amino]-6,6-dimethyl-5,6-dihydropyrrolo[3,4-c]pyrazole-2(4H)-carboxylate.<br>$^1$H NMR (dmso-d$_6$) δ: 0.87 (m, 4H), 1.36 (t, J = 7.1 Hz, 3H), 1.63 (s, 6H), 2.04 (m, 1H), 4.44 (q, J = 7.2 Hz, 2H), 4.74 (s, 2H), 10.50 (s, 1H). Anal. (C$_{15}$H$_{19}$ClN$_4$O$_4$) C, H, N, Cl. LCMS (APCI, M + H$^+$): 355.2/357.2.<br>Method of 1c: Made in 81% yield from intermediate 9b. |
| 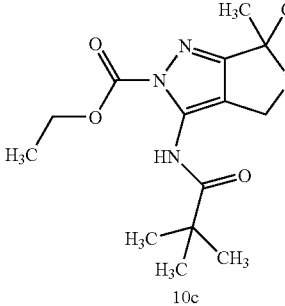<br>10c | ethyl 5-(chlorocarbonyl)-3-[(2,2-dimethylpropanoyl)amino]-6,6-dimethyl-5,6-dihydropyrrolo [3,4-c]pyrazole-2(4H)-carboxylate.<br>$^1$H NMR (dmso-d$_6$) δ: 1.22 (s, 9H), 1.35 (t, J = 7.1 Hz, 3H), 1.64 (s, 6H), 4.45 (q, J = 7.1 Hz, 2H), 4.85 (s, 2H), 10.28 (s, 1H). Anal. (C$_{16}$H$_{23}$ClN$_4$O$_4$) C, H, N, Cl. LCMS (APCI, M + H$^+$): 371.2/373.2.<br>Method of 1c: Made in 85% yield from intermediate 10b. |
| 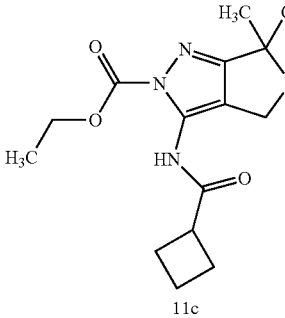<br>11c | ethyl 5-(chlorocarbonyl)-3-[(cyclobutylcarbonyl)amino]-6,6-dimethyl-5,6-dihydro pyrrolo[3,4-c]pyrazole-2(4H)-carboxylate.<br>$^1$H NMR (DMSO-d$_6$) 1.34 (t, J = 8.0 Hz, 3H), 1.64 (s, 6H), 1.76-1.85 (m, 1H), 1.91-2.14 (m, 1H), 2.14-2.24 (m, 4H), 3.34-3.42 (m, 1H), 4.42 (q, J = 8.0 Hz, 2H), 4.82 (s, 2H), 10.06 (s, 1H). LCMS [M +H]$^+$ 369.<br>Method of 1c: Made in 84% yield from intermediate 11b. |
| 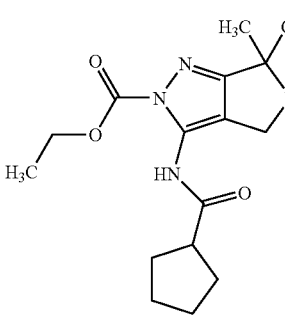<br>12c | ethyl 5-(chlorocarbonyl)-3-[(cyclopentylcarbonyl)amino]-6,6-dimethyl-5,6-dihydropyrrolo[3,4-c]pyrazole-2(4H)-carboxylate.<br>$^1$H NMR (dmso-d$_6$) δ: 1.35 (t, J = 7.1 Hz, 3H), 1.57 (m, 3H), 1.64 (s, 6H), 1.68 (m, 3H), 1.86 (m, 2H), 2.94 (quint, J = 7.8 Hz, 1H), 4.43 (q, J = 7.1 Hz, 2H), 4.80 (s, 2H), 10.18 (s, 1H). Anal. (C$_{17}$H$_{23}$ClN$_4$O$_4$•0.06EtOAc•0.02HCl) C, H, N, Cl. LCMS (APCI, M + H$^+$): 383.2/385.2.<br>Method of 1c: Made in 86% yield from intermediate 12b. |

| Structure and Example # | Chemical name, Analytical data and comments |
|---|---|
| 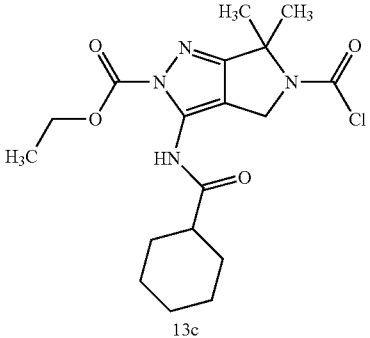<br>13c | ethyl 5-(chlorocarbonyl)-3-[(cyclohexylcarbonyl)amino]-6,6-dimethyl-5,6-dihydropyrrolo[3,4-c]pyrazole-2(4H)-carboxylate.<br>$^1$H NMR (dmso-d$_6$) δ: 1.29 (m, 6H), 1.35 (t, J = 7.1 Hz, 3H), 1.62 (m, 1H), 1.63 (s, 6H), 1.72 (d, J = 12.1 Hz, 2H), 1.84 (d, J = 11.9 Hz, 2H), 4.43 (q, J = 7.1 Hz, 2H), 4.80 (s, 2H), 10.19 (s, 1H). Anal. (C$_{18}$H$_{25}$ClN$_4$O$_4$) C, H, N, Cl. LCMS (APCI, M + H$^+$): 397.2/399.2.<br>Method of 1c: Made in 71% yield from intermediate 13b. |
| 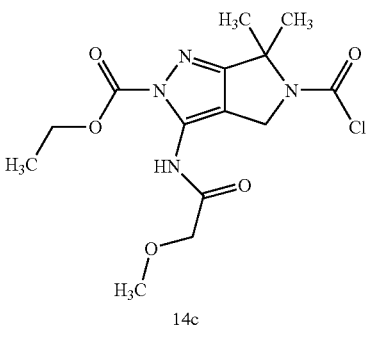<br>14c | ethyl 5-(chlorocarbonyl)-3-[(methoxyacetyl)amino]-6,6-dimethyl-5,6-dihydropyrrolo[3,4-c]pyrazole-2(4H)-carboxylate.<br>$^1$H NMR (dmso-d$_6$) δ: 1.35 (t, J = 7.1 Hz, 3H), 1.65 (s, 6H), 3.42 (s, 3H), 4.08 (s, 2H), 4.44 (q, J = 7.2 Hz, 2H), 4.86 (s, 2H), 10.70 (s, 1H). Anal. (C$_{14}$H$_{19}$ClN$_4$O$_5$•0.3H$_2$O) C, H, N, Cl. LCMS (APCI, M + H$^+$): 359.2/361.2.<br>Method of 1c: Made in 84% yield from intermediate 14b. |
| 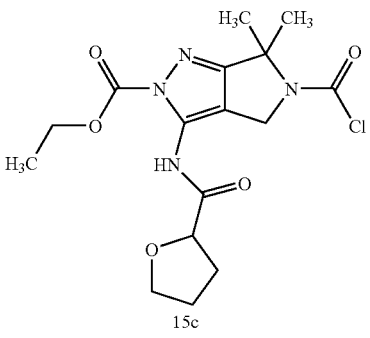<br>15c | ethyl 5-(chlorocarbonyl)-6,6-dimethyl-3-[(tetrahydrofuran-2-ylcarbonyl)amino]-5,6-dihydropyrrolo[3,4-c]pyrazole-2(4H)-carboxylate.<br>$^1$H NMR (dmso-d$_6$) δ: 1.35 (t, J = 7.1 Hz, 3H), 1.64 (d, J = 2.3 Hz, 6H), 1.86 (m, 2H), 1.98 (m, 1H), 2.23 (m, 1H), 3.91 (m, 2H), 4.45 (m, 3H), 4.87 (s, 2H), 10.84 (s, 1H). Anal. (C$_{16}$H$_{21}$ClN$_4$O$_5$•0.15H$_2$O) C, H, N, Cl. LCMS (APCI, M + H$^+$): 385.2/387.2.<br>Method of 1c: Made in 79% yield from intermediate 15b. |
| 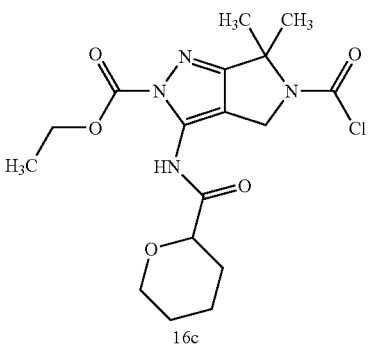<br>16c | ethyl 5-(chlorocarbonyl)-6,6-dimethyl-3-[(tetrahydro-2H-pyran-2-ylcarbonyl)amino]-5,6-dihydropyrrolo[3,4-c]pyrazole-2(4H)-carboxylate.<br>$^1$H NMR (dmso-d$_6$) δ: 1.35 (t, J = 7.1 Hz, 3H), 1.38 (m, 1H), 1.53 (m, 3H), 1.64 (s, 6H), 1.81 (m, 1H), 1.98 (m, 1H), 3.55 (m, 1H), 4.04 (m, 2H), 4.43 (q, J = 7.1 Hz, 2H), 4.87 (s, 2H), 10.76 (s, 1H). Anal. (C$_{17}$H$_{23}$ClN$_4$O$_5$) C, H, N, Cl. LCMS (APCI, M + H$^+$): 399.2/401.2.<br>Method of 1c: Made in 77% yield from intermediate 16b. |

| Structure and Example # | Chemical name, Analytical data and comments |
|---|---|
| 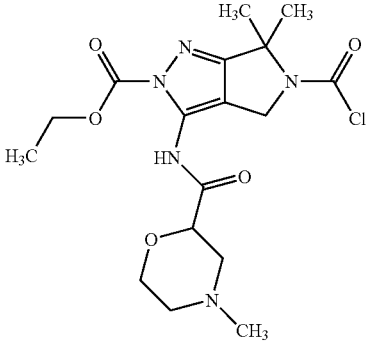<br>17c | ethyl 5-(chlorocarbonyl)-6,6-dimethyl-3-{[(4-methylmorpholin-2-yl)carbonyl]amino}-5,6-dihydropyrrolo[3,4-c]pyrazole-2(4H)-carboxylate.<br>$^1$H NMR (dmso-d$_6$) δ: 1.35 (t, J = 7.1 Hz, 3H), 1.64 (s, 6H), 2.04 (m, 2H), 2.22 (s, 3H), 2.63 (d, J = 11.4 Hz, 1H), 2.97 (d, J = 10.9 Hz, 1H), 3.68 (t, J = 10.2 Hz, 1H), 3.96 (d, J = 11.1 Hz, 1H), 4.22 (dd, J = 2.3, 9.3 Hz, 1H), 4.44 (q, J = 7.1 Hz, 2H), 4.87 (s, 2H), 10.78 (s, 1H). Anal. (C$_{17}$H$_{24}$ClN$_5$O$_5$) C, H, N, Cl. LCMS (APCI, M + H$^+$): 414.2/416.2.<br>Method of 1c: Made in 60% yield from intermediate 17b. |
| 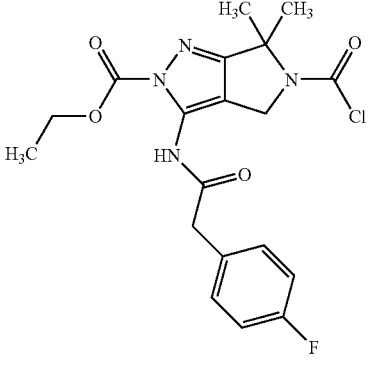<br>18c | ethyl 5-(chlorocarbonyl)-3-{[(4-fluorophenyl)acetyl]amino}-6,6-dimethyl-5,6-dihydropyrrolo[3,4-c]pyrazole-2(4H)-carboxylate.<br>$^1$H NMR (dmso-d$_6$) δ: 1.33 (t, J = 7.1 Hz, 3H), 1.63 (s, 6H), 3.83 (s, 2H), 4.41 (q, J = 7.3 Hz, 2H), 4.76 (s, 2H), 7.17 (t, J = 8.8 Hz, 2H), 7.35 (dd, J = 5.6, 8.6 Hz, 2H), 10.33 (s, 1H). Anal. (C$_{19}$H$_{20}$ClFN$_4$O$_4$) C, H, N, Cl, F. LCMS (APCI, M + H$^+$): 423.2/425.2.<br>Method of 1c: Made in 77% yield from intermediate 18b. |
| 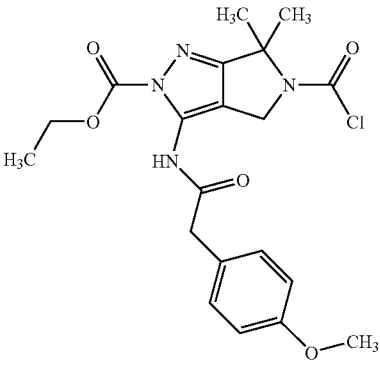<br>19c | ethyl 5-(chlorocarbonyl)-3-{[(4-methoxyphenyl)acetyl]amino}-6,6-dimethyl-5,6-dihydropyrrolo[3,4-c]pyrazole-2(4H)-carboxylate.<br>$^1$H NMR (dmso-d$_6$) δ: 1.32 (t, J = 7.1 Hz, 3H), 1.62 (s, 6H), 3.73 (s, 3H), 3.74 (s, 2H), 4.40 (q, J = 7.1 Hz, 2H), 4.77 (s, 2H), 6.90 (d, J = 8.6 Hz, 2H), 7.23 (d, J = 8.6 Hz, 2H), 10.25 (s, 1H). Anal. (C$_{20}$H$_{23}$ClN$_4$O$_5$) C, H, N, Cl. LCMS (API-ES, M + H$^+$): 435.1/437.1.<br>Method of 1c: Made in 79% yield from intermediate 19b. |
| 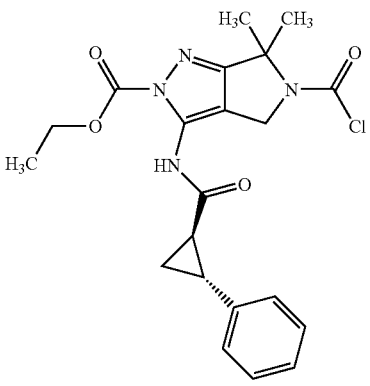<br>20c | ethyl 5-(chlorocarbonyl)-6,6-dimethyl-3-({[trans-2-phenyl cyclopropyl]carbonyl}amino)-5,6-dihydro pyrrolo[3,4-c]pyrazole-2(4H)-carboxylate.<br>$^1$H NMR (dmso-d$_6$) δ: 1.33 (t, J = 7.1 Hz, 3H), 1.40 (m, 1H), 1.52 (quint, J = 4.6 Hz, 1H), 1.64 (s, 6H), 2.44 (m, 1H), 2.51 (m, 1H), 4.41 (q, J = 7.1 Hz, 2H), 4.79 (s, 2H), 7.19 (m, 3H), 7.29 (t, J = 7.3 Hz, 2H), 10.59 (s, 1H). Anal. (C$_{21}$H$_{23}$ClN$_4$O$_4$) C, H, N, Cl. LCMS (APCI, M + H$^+$): 431.2/433.2.<br>Method of 1c: Made in 70% yield from intermediate 20b. |

-continued

| Structure and Example # | Chemical name, Analytical data and comments |
|---|---|
| 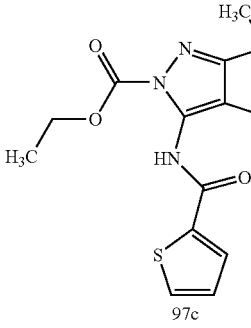 97c | Ethyl 5-(chlorocarbonyl)-6,6-dimethyl-3-[(2-thienylcarbonyl)amino]-5,6-dihydropyrrolo[3,4-c]pyrazole-2(4H)-carboxylate<br>$^1$H NMR (400 MHz, CHLOROFORM-d) δ ppm: 1.51 (t, J = 7.07 Hz, 3H) 1.56 (s, 6H) 4.60 (q, J = 7.24 Hz, 2H) 5.03 (s, 2H) 7.17 (dd, J = 4.93, 3.92 Hz, 1H) 7.65 (dd, J = 4.93, 1.14 Hz, 1H) 7.69 (dd, J = 3.79, 1.26 Hz, 1H) 10.98 (br. s., 1H)<br>Method of 1c. |
| 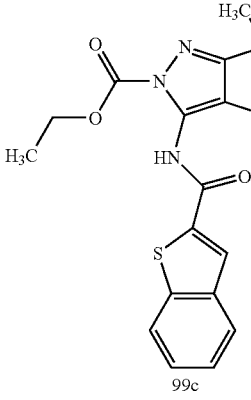 99c | Ethyl 3-[(1-benzothien-2-ylcarbonyl)amino]-5-(chlorocarbonyl)-6,6-dimethyl-5,6-dihydropyrrolo[3,4-c]pyrazole-2(4H)-carboxylate<br>$^1$H NMR (400 MHz, MeOD) δ ppm: 1.64 (d, J = 24.76 Hz, 6H) 3.65-3.75 (m, 2H) 4.64 (d, J = 3.03 Hz, 2H) 4.81-4.87 (m, 1H) 7.10-7.18 (m, 1H) 7.20-7.33 (m, 4H) 7.33-7.43 (m, 2H) 7.78-7.90 (m, 2H) 8.07 (s, 1H). Anal. ($C_{25}H_{25}N_5O_3S$•1.1HOAc•0.1$H_2O$) C, H, N, S.<br>Method of 1c. |

Preparation of Compound 1d: (1S)-2-(dimethylamino)-1-phenylethanol

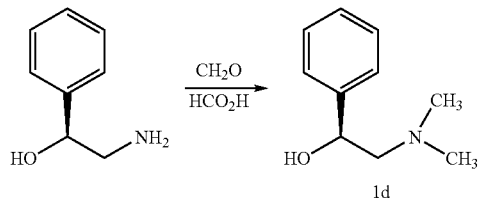

To a solution of (S)-(+)-2-amino-1-phenyl-ethanol (100.0 g, 729.0 mmol) in formic acid (400 mL) was added formaldehyde (800 mL, 37% wt in water) at room temperature. The solution was stirred at 95° C. overnight. After it was cooled to room temperature, conc. HCl was used to adjust the solution to pH=2. It was extracted with ether (3×500 mL) and then adjusted to pH=10 with solid NaOH. The resulting aqueous layer was extracted with $CH_2Cl_2$ (3×500 mL). The combined organic layers were dried over $Na_2SO_4$. Filtration and evaporation followed by flash chromatography (5% MeOH in $CH_2Cl_2$ to 4.5% MeOH/0.5% $NEt_3$ in $CH_2Cl_2$) gave (S)-2-dimethylamino-1-phenyl-ethanol (1d) as a light-yellow oil (68.0 g, 56%). $^1$H NMR (dmso-$d_6$) δ: 2.19 (s, 6H), 2.31 (dd, J=4.8, 12.4 Hz, 1H), 2.41 (dd, J=8.1, 12.4 Hz, 1H), 4.63 (dd, J=4.8, 7.8 Hz, 1H), 4.97 (br s, 1H), 7.21 (m, 1H), 7.31 (m, 4H). LCMS (APCI, M+H$^+$): 166.4.

Preparation of Compound 1: (1S)-2-(dimethylamino)-1-phenylethyl 3-(benzoylamino)-6,6-dimethyl-4,6-dihydropyrrolo[3,4-c]pyrazole-5(1H)-carboxylate A solution of potassium carbonate (861 mg, 6.23 mmol), intermediate 1c (1.218 g, 3.12 mmol), and alcohol 1d (772 mg, 4.67 mmol) in 1,2-dimethoxyethane (DME, 31 mL) was stirred in an 80° C. oil bath for 7.5 hours. After cooling to room temperature, the solvent was evaporated and the residue partitioned between ethyl acetate (25 mL) and deionized water (20 mL). The aqueous layer was back-extracted with ethyl acetate (2×15 mL), and the combined organic extracts dried over magnesium sulfate, filtered, and concentrated to dryness. The residue was dissolved in methanol (10 mL) and triethylamine (10 mL), stirred at room temperature for 19 hours, and again concentrated to dryness. The crude product was purified by silica gel chromatography, eluting with a gradient of 5-20% (ethanol+5% $NH_4OH$) in ethyl acetate, affording compound 1 (561.1 mg, 39%) as a white foam. $^1$H NMR (dmso-$d_6$) [some peaks are doubled due to the presence of tautomeric isomers] δ: [1.54 (s), 1.63 (s), 1.72 (s) 6H together], [2.20 (s), 2.22 (s) 6H together], [2.46 (d, J=4.8 Hz) 2.52 (d, J=4.8 Hz), 1H together], [2.73 (dd, J=8.3, 13.1 Hz), 2.82 (dd, J=8.3, 12.9 Hz) 1H together], [4.46 (m), 4.65 (br s) 2H together], 5.80 (dd, J=4.6, 8.3 Hz, 1H), 7.28 (m, 1H), 7.35 (m, 4H), 7.50 (m, 3H), 7.99 (t, J=7.4 Hz, 2H), 10.93 (br m, 1H), [12.25 (br s), 12.48 (br s) 1H together]. Anal. ($C_{25}H_{29}N_5O_3$.0.03EtOAc.0.35$H_2O$) C, H, N. HRMS: [M+H]$^+$ calc. 448.2343; found 448.2341; error −0.39 ppm.

| Structure and Example # | Chemical name, Analytical data and comments |
|---|---|
| 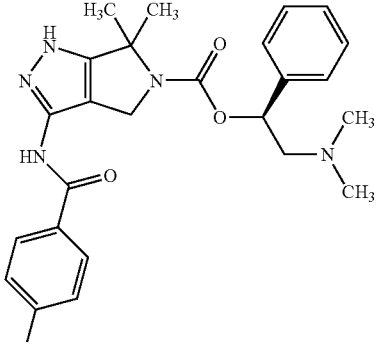<br>2 | (1S)-2-(dimethylamino)-1-phenylethyl 3-[(4-fluorobenzoyl)amino]-6,6-dimethyl-4,6-dihydropyrrolo[3,4-c]pyrazole-5(1H)-carboxylate.<br>$^1$H NMR (dmso-d$_6$) δ: [1.54 (s), 1.63 (s), 1.65 (s), 1.73 (s) 6H together], [2.20 (s), 2.22 (s) 6H together], [2.45 (d, J = 5.1 Hz), 2.52 (d, J = 4.6 Hz) 1H together], [2.73 (dd, J = 8.3, 12.9 Hz), 2.82 (dd, J = 8.6, 12.9 Hz) 1H together], [4.45 (m), 4.65 (s) 2H together], 5.80 (dd, J = 4.6, 8.1 Hz, 1H), 7.35 (m, 7H), 8.07 (br q, J = 5.0 Hz, 2H), [10.93 (br s), 10.97 (br s) 1H together], [12.25 (br s), 12.47 (br s), 12.50 (br s) 1H together]. Anal. (C$_{25}$H$_{28}$FN$_5$O$_3$•0.35H$_2$O) C, H, N, F. HRMS: [M +H]$^+$ calc. 466.22489; found 466.22468; error –0.46 ppm.<br>Method of Example 1: Made in 44% yield from intermediate 2c using alcohol 1d. |
| 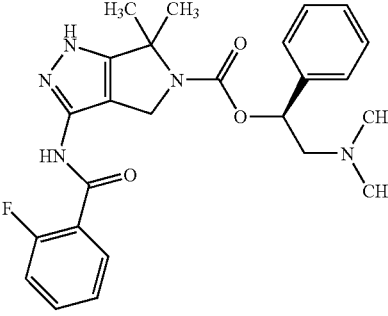<br>3 | (1S)-2-(dimethylamino)-1-phenylethyl 3-[(2-fluorobenzoyl)amino]-6,6-dimethyl-4,6-dihydropyrrolo[3,4-c]pyrazole-5(1H)-carboxylate.<br>$^1$H NMR (400 MHz, MeOD) δ ppm: 1.61 (s, 3H), 1.72 (s, 3H), 2.43 (s, 6H), 2.61 (dd, J = 13.60, 3.02 Hz, 1H), 2.98-3.10 (m, 1H), 4.73-4.85 (m, 2H), 5.92 (dd, J = 9.57, 3.02 Hz, 1H), 7.23-7.47 (m, 7H), 7.54-7.67 (m, 1H), 7.75-7.87 (m, 1H). Anal. (C$_{25}$H$_{28}$N$_5$O$_3$F•0.2HOAc•0.1H$_2$O) C, H, N. HPLC: >95% purity.<br>Method of Example 1: Made in 33% yield from intermediate 3c using alcohol 1d. |
| 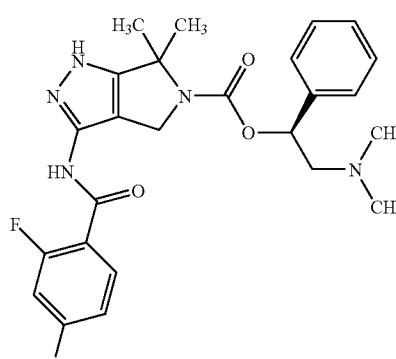<br>4 | (1S)-2-(dimethylamino)-1-phenylethyl 3-[(2,4-difluorobenzoyl) amino]-6,6-dimethyl-4,6-dihydropyrrolo[3,4-c]pyrazole-5(1H)-carboxylate.<br>$^1$H NMR (400 MHz, MeOD) δ ppm: 1.63 (s, 3H) 1.74 (s, 3H) 2.57 (s, 6H) 2.81 (dd, J = 13.39, 3.03 Hz, 1H) 3.15-3.26 (m, 1H) 4.75-4.85 (m, 2H) 5.99 (dd, J = 9.85, 3.03 Hz, 1H) 7.11-7.21 (m, 2H) 7.33-7.45 (m, 5H) 7.84-7.96 (m, 1H). Anal. (C$_{25}$H$_{27}$N$_5$O$_3$F$_2$•0.4HOAc) C, H, N. HPLC: >95% purity.<br>Method of Example 1: Made in 7% yield from intermediate 4c using alcohol 1d. |
| 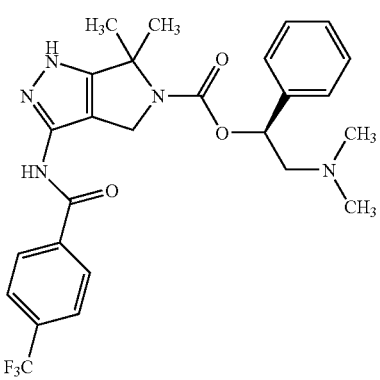<br>5 | 1S)-2-(dimethylamino)-1-phenylethyl 6,6-dimethyl-3-{[4-(trifluoro methyl)benzoyl]amino}-4,6-dihydropyrrolo[3,4-c]pyrazole-5(1H)-carboxylate.<br>$^1$H NMR (400 MHz, MeOD) δ ppm: 1.64 (s, 3H) 1.75 (s, 3H) 2.42 (none, 1H) 2.53 (s, 6H) 2.75 (dd, J = 13.47, 3.49 Hz, 1H) 3.07-3.21 (m, 1H) 4.75-4.82 (m, 2H) 5.91-6.03 (m, 1H) 7.29-7.50 (m, 5H) 7.86 (t, J = 8.01 Hz, 2H) 8.14 (t, J = 8.95 Hz, 2H). Anal. (C$_{26}$H$_{28}$N$_5$O$_3$F$_3$•0.5HOAc•0.3H$_2$O) C, H, N. HPLC: >95% purity.<br>Method of Example 1: Made in 15% yield from intermediate 5c using alcohol 1d. |

| Structure and Example # | Chemical name, Analytical data and comments |
|---|---|
| 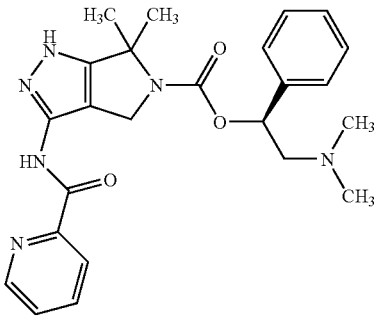<br>6 | (1S)-2-(dimethylamino)-1-phenylethyl 6,6-dimethyl-3-[(pyridin-2-ylcarbonyl)amino]-4,6-dihydropyrrolo[3,4-c]pyrazole-5(1H)-carboxylate.<br>$^1$H NMR (400 MHz, MeOD) δ ppm: 1.61 (s, 3H), 1.72 (s, 3H), 2.54 (s, 6H), 2.77 (d, J = 13.60 Hz, 1H), 3.08-3.24 (m, 1H) 4.56-4.79 (m, 1H), 4.91-5.03 (m, 1H), 5.90-6.05 (m, 1H), 7.29-7.36 (m, 1H), 7.36-7.49 (m, 4H), 7.58-7.69 (m, 1H), 7.99-8.09 (m, 1H), 8.21 (d, J = 7.81 Hz, 1H), 8.71 (d, J = 4.78 Hz, 1H). Anal. ($C_{24}H_{28}N_6O_3$•0.2HOAc) C, H, N. HPLC: >95% purity.<br>Method of Example 1: Made in 39% yield from intermediate 6c using alcohol 1d. |
| 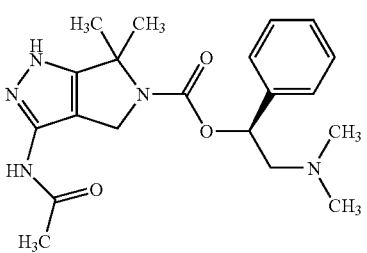<br>7 | (1S)-2-(dimethylamino)-1-phenylethyl 3-(acetylamino)-6,6-dimethyl-4,6-dihydropyrrolo[3,4-c]pyrazole-5(1H)-carboxylate.<br>$^1$H NMR (dmso-$d_6$) δ 1.34 (t, J = 8.0 Hz, 3H), 1.42-1.45 (m, 9H), 1.56 (s, 3H), 1.57 (s, 3H), 2.12-2.13 (d, J = 4.0 Hz, 3H), 4.36-4.43 (m, 4H), 10.15 (s, 1H); LCMS [M + H]$^+$ 367.<br>Method of Example 1: Made in 60% yield from intermediate 7c using alcohol 1d. |
| 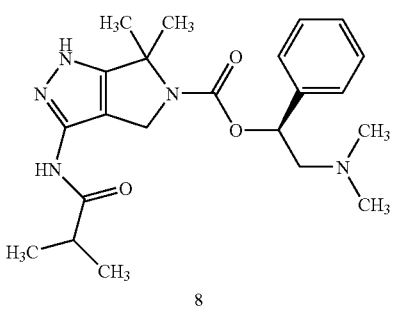<br>8 | (1S)-2-(dimethylamino)-1-phenylethyl 3-(isobutyrylamino)-6,6-dimethyl-4,6-dihydropyrrolo[3,4-c]pyrazole-5(1H)-carboxylate.<br>$^1$H NMR (dmso-$d_6$) δ: 1.05 (d, J = 6.8 Hz, 6H), [1.50 (s), 1.59 (s), 1.61 (s), 169 (s) 6H together], [219 (s) 221 (s) 6H together], [246 (dd, J = 4.6, 12.9 Hz), 2.52 (d, J = 4.8 Hz) 1H together], 2.59 (septet, J = 6.3 Hz, 1H), [2.73 (dd, J = 8.3, 12.6 Hz), 2.80 (dd, J = 8.3, 12.6 Hz) 1H together], [4.32 (d, J = 13.4 Hz), 4.39 (d, J = 13.4 Hz), 4.49 (br s), 4.57 (s) 2H together], 7.57 (dd, J = 4.8, 8.3 Hz, 1H), 7.29 (m, 1H), 7.34 (m, 4H), [10.29 (s), 10.35 (s), 10.46 (br s), 10.51 (br s) 1H together], [12.14 (br s), 12.27 (s), 12.30 (s) 1H together]. Anal. ($C_{22}H_{31}N_5O_3$•0.2cyclohexane•0.6H$_2$O) C, H, N. HRMS: [M + H]$^+$ calc. 414.2500; found 414.2492; error −1.87 ppm.<br>Method of Example 1: Made in 36% yield from intermediate 8c using alcohol 1d. |
| 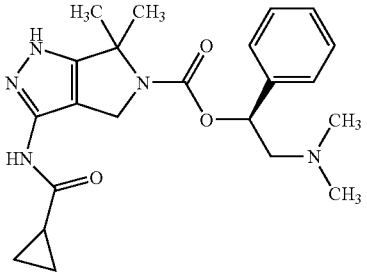<br>9 | (1S)-2-(dimethylamino)-1-phenylethyl 3-[(cyclopropylcarbonyl) amino]-6,6-dimethyl-4,6-dihydropyrrolo[3,4-c]pyrazole-5(1H)-carboxylate.<br>$^1$H NMR (dmso-$d_6$) δ: 0.77 (m, 4H), [1.49 (s), 1.59 (s), 1.68 (s) 6H together], 1.80 (m, 1H), [2.19 (s), 2.22 (s), 6H together], 2.50 (m, 1H), 2.74 (m, 1H), [4.27 (d, J = 13.4 Hz), 4.34 (d, J = 13.6 Hz), 4.48 (s), 4.52 (s) 2H together], 5.79 (m, 1H), 7.34 (m, 5H), [10.65 (s), 10.70 (s), 10.74 (s), 10.79 (s) 1H together], [12.16 (br s), 12.27 (s), 12.30 (s) 1H together]. Anal. ($C_{22}H_{31}N_5O_3$•0.1cyclohexane•0.6H$_2$O) C, H, N. HRMS: [M + H]$^+$ calc. 412.2343; found 412.2345; error 0.54 ppm.<br>Method of Example 1: Made in 41% yield from intermediate 9c using alcohol 1d. |
| 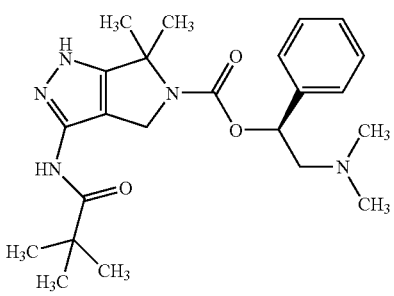<br>10 | (1S)-2-(dimethylamino)-1-phenylethyl 3-[(2,2-dimethylpropanoyl) amino]-6,6-dimethyl-4,6-dihydropyrrolo[3,4-c]pyrazole-5(1H)-carboxylate.<br>$^1$H NMR (dmso-$d_6$) δ: [1.16 (s), 1.18 (s) 9H together], 1.59 (m, 6H), [2.19 (s), 2.21 (s) 6H together], 2.52 (m, 1H), 2.74 (m, 1H), [4.31 (d, J = 14.6 Hz), 4.38 (d, J = 12.9 Hz), 4.50 (s), 4.56 (s) 2H together], 5.79 (m, 1H), 7.29 (m, 1H), 7.34 (m, 1H), [9.87 (s), 9.92 (s), 9.96 (br s), 10.02 (br s) 1H together], [11.94 (br s), 11.97 (br s), 12.31 (s), 12.34 (s) 1H together]. Anal. ($C_{23}H_{33}N_5O_3$•0.06cyclohexane•0.7H$_2$O) C, H, N. HRMS: [M + H]$^+$ calc. 428.2656; found 428.2649; error −1.58 ppm.<br>Method of Example 1: Made in 43% yield from intermediate 10c using alcohol 1d. |

| Structure and Example # | Chemical name, Analytical data and comments |
|---|---|
| 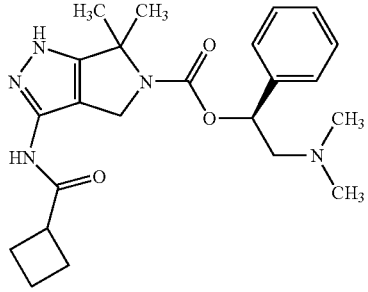<br>11 | (1S)-2-(dimethylamino)-1-phenylethyl 3-[(cyclobutylcarbonyl) amino]-6,6-dimethyl-4,6-dihydropyrrolo[3,4-c]pyrazole-5(1H)-carboxylate.<br>$^1$H NMR (dmso-d$_6$) δ 1H NMR (DMSO-d$_6$) 1.47-1.61 (m, 4H), 1.69-1.81 (m, 2H), 1.87-1.94 (m, 1H), 2.02-2.06 (m, 1H), 2.15-2.22 (m, 7H), 2.28-2.32 (m, 1H), 2.39-2.54 (m, 2H), 2.71-2.83 (m, 1H), 3.17-3.24 (m, 1H), 3.29-3.31 (m, 1H), 4.32-4.49 (m, 1H), 4.59-4.64 (m, 1H), 5.78-5.80 (m, 1H), 7.27-7.40 (m, 5H), 10.19-10.25 (m, 1H), 12.25-12.29 (m, 1H); Anal. (C$_{23}$H$_{31}$N$_5$O$_3$ 0.3 hexanes•0.5H$_2$O) C, H, N. HRMS: [M + H]$^+$ calc. 426.2500; found 426.2485.<br>Method of Example 1: Made from intermediate 11c using alcohol 1d. |
| 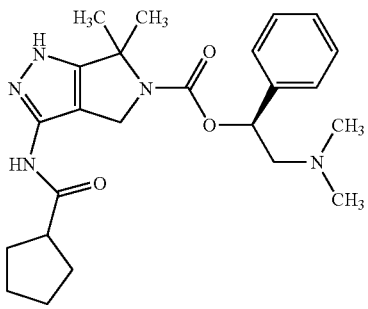<br>12 | (1S)-2-(dimethylamino)-1-phenylethyl 3-[(cyclopentylcarbonyl) amino]-6,6-dimethyl-4,6-dihydropyrrolo[3,4-c]pyrazole-5(1H)-carboxylate.<br>$^1$H NMR (dmso-d$_6$) δ: 1.59 (m, 12H), 1.80 (m, 2H), [2.19 (s), 2.21 (s), 6H together], 2.53 (m, 1H), 2.77 (m, 2H), [4.31 (d, J = 13.9 Hz), 4.39 (d, J = 14.6 Hz), 4.50 (br s), 4.56 (s) 2H together], 5.79 (m, 1H), 7.29 (m, 1H), 7.34 (m, 4H), [10.31 (br s), 10.37 (s), 10.48 (br s) 1H together], [12.11 (br s), 12.26 (s), 12.29 (s) 1H together]. Anal. (C$_{24}$H$_{33}$N$_5$O$_3$•0.2cyclohexane•0.8H$_2$O) C, H, N. HRMS: [M + H]$^+$ calc. 440.2656; found 440.2649; error −1.54 ppm.<br>Method of Example 1: Made in 48% yield from intermediate 12c using alcohol 1d. |
| 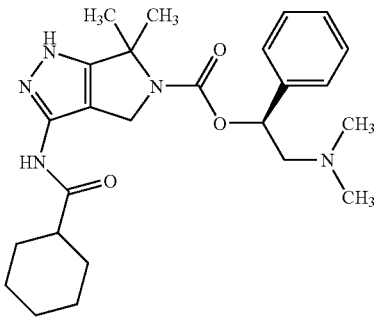<br>13 | (1S)-2-(dimethylamino)-1-phenylethyl 3-[(cyclohexylcarbonyl) amino]-6,6-dimethyl-4,6-dihydropyrrolo[3,4-c]pyrazole-5(1H)-carboxylate.<br>$^1$H NMR (dmso-d$_6$) δ: 1.18 (m, 4H), 1.35 (m, 2H), [1.49 (s), 1.58 (s) 6H together], 1.73 (m, 5H), [2.23 (s), 2.33 (br s) 6H together], 2.58-3.08 (m, 2H), [4.33 (m), 4.56 (m) 2H together], 5.85 (m, 1H), 7.30 (m, 1H), 7.36 (m, 4H), [10.26 (br s), 10.32 (br s) 1H together], [12.10 (br s), 12.29 (br s) 1H together]. Anal. (C$_{25}$H$_{35}$N$_5$O$_3$•1.3H$_2$O) C, H, N. HRMS: [M + H]$^+$ calc. 454.28127; found 454.28232; error 2.31 ppm.<br>Method of Example 1: Made in 26% yield from intermediate 13c using alcohol 1d. |
| 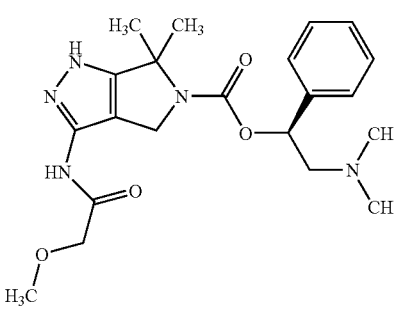<br>14 | (1S)-2-(dimethylamino)-1-phenylethyl 3-[(methoxyacetyl)amino]-6,6-dimethyl-4,6-dihydropyrrolo[3,4-c]pyrazole-5(1H)-carboxylate.<br>$^1$H NMR (dmso-d$_6$ + D$_2$O) δ: [1.43 (s), 1.53 (s), 1.64 (s) 6H together], [2.13 (s), 2.16 (s) 6H together], 2.41 (dd, J = 3.3, 13.6 Hz, 1H), [2.74 (dd, J = 9.4, 13.7 Hz), 2.83 (dd, J = 8.1, 12.9 Hz) 1H together], [3.28 (s), 3.31 (s) 3H together], [3.93 (s), 3.96 (s) 2H together], [4.26 (d, J = 14.4 Hz), 4.34 (d, J = 13.9 Hz), 4.51 (d, J = 13.4 Hz), 4.58 (d, J = 13.4 Hz) 2H together], 5.72 (m, 1H), 7.32 (m, 5H). Anal. (C$_{21}$H$_{29}$N$_5$O$_4$•0.3cyclohexane•0.8H$_2$O) C, H, N. HRMS: [M + H]$^+$ calc. 416.22923; found 416.22917; error −0.14 ppm.<br>Method of Example 1: Made in 43% yield from intermediate 14c using alcohol 1d. |

| Structure and Example # | Chemical name, Analytical data and comments |
|---|---|
| 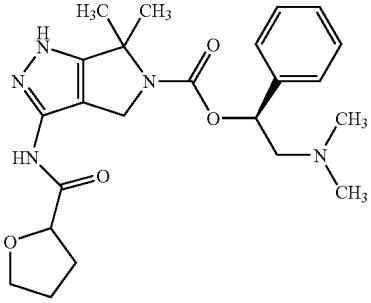<br>15 | (1S)-2-(dimethylamino)-1-phenylethyl 6,6-dimethyl-3-[(tetrahydrofuran-2-ylcarbonyl)amino]-4,6-dihydropyrrolo[3,4-c]pyrazole-5(1H)-carboxylate.<br>$^1$H NMR (dmso-d$_6$) δ: 1.60 (m, 6H), 1.85 (m, 3H), 2.18 (m, 1H), [2.19 (s), 2.22 (s) 6H together], 2.50 (m, 1H), 2.74 (m, 1H), 3.78 (m, 1H), 3.93 (quint, J = 6.8 Hz, 1H), [4.37 (m), 4.57 (m) 3H together], 5.79 (m, 1H), 7.34 (m, 5H), [10.02 (m), 10.33 (m) 1H together], [11.91 (s), 12.39 (s), 12.41 (s) 1H together]. Anal. (C$_{23}$H$_{31}$N$_5$O$_4$•0.15cyclohexane•0.6H$_2$O) C, H, N. HRMS: [M + H]$^+$ calc. 442.2449; found 442.2446; error −0.62 ppm.<br>Method of Example 1: Made in 45% yield from intermediate 15c using alcohol 1d. |
| 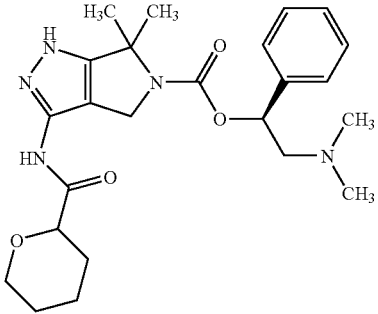<br>16 | (1S)-2-(dimethylamino)-1-phenylethyl 6,6-dimethyl-3-[(tetrahydro-2H-pyran-2-ylcarbonyl)amino]-4,6-dihydropyrrolo[3,4-c]pyrazole-5(1H)-carboxylate.<br>$^1$H NMR (dmso-d$_6$) δ: 1.46-1.69 (m, 10H), 1.82 (m, 2H), [2.19 (s), 2.21 (s) 6H together], 2.51 (m, 1H), [2.71 (dd, J = 8.6, 12.4 Hz), 2.80 (dd, J = 8.3, 12.6 Hz) 1H together], 3.47 (m, 1H), 3.94 (m, 2H), [4.35 (m), 4.54 (s), 4.57 (s) 2H together], 5.78 (m, 1H), 7.29 (m, 1H), 7.34 (m, 4H), [9.59 (s), 9.70 (s), 10.13 (s), 10.20 (s) 1H together], [11.85 (s), 11.88 (s), 12.38 (s), 12.41 (s) 1H together]. Anal. (C$_{24}$H$_{33}$N$_5$O$_4$•0.1cyclohexane•0.5H$_2$O) C, H, N. HRMS: [M + H]$^+$ calc. 456.2606; found 456.2597; error −1.92 ppm.<br>Method of Example 1: Made in 60% yield from intermediate 16c using alcohol 1d. |
| 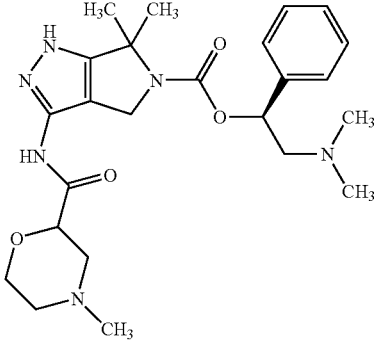<br>17 | (1S)-2-(dimethylamino)-1-phenylethyl 6,6-dimethyl-3-{[(4-methylmorpholin-2-yl)carbonyl]amino}-4,6-dihydropyrrolo[3,4-c]pyrazole-5(1H)-carboxylate.<br>$^1$H NMR (dmso-d$_6$) δ: 1.60 (m, 6H), 2.02 (m, 2H), [2.19 (s), 2.21 (s) 6H together], 2.23 (m, 3H), 2.59-2.91 (m, 4H), 3.59 (m, 1H), 3.90 (m, 1H), 4.11 (m, 1H), [4.33 (m), 4.64 (m), 4.55 (s) 2H together], 5.78 (m, 1H), 7.34 (m, 5H), [9.79 (br s), 9.88 (br s), 10.27 (br s), 10.33 (br s) 1H together], [11.88 (br s), 11.90 (br s), 12.40 (br s), 12.43 (br s) 1H together]. Anal. (C$_{24}$H$_{34}$N$_6$O$_4$•0.3Ethyl Acetate•0.4H$_2$O) C, H, N. HRMS: [M + H]$^+$ calc. 471.27143; found 471.27140; error −0.07 ppm.<br>Method of Example 1: Made in 58% yield from intermediate 17c using alcohol 1d. |
| 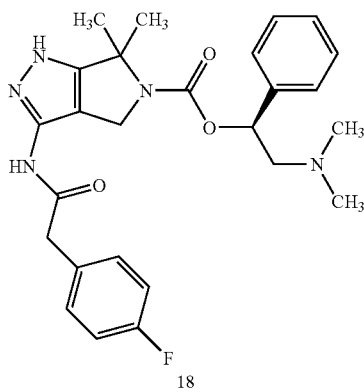<br>18 | (1S)-2-(dimethylamino)-1-phenylethyl 3-{[(4-fluorophenyl) acetyl]amino}-6,6-dimethyl-4,6-dihydropyrrolo[3,4-c]pyrazole-5(1H)-carboxylate.<br>$^1$H NMR (dmso-d$_6$) δ: [1.49 (s), 1.58 (s), 1.59 (s), 1.67 (s) 6H together], 2.19 (s, 6H), 2.50 (m, 1H), [2.71 (dd, J = 8.8, 13.1 Hz), 2.79 (dd, J = 8.6, 12.6 Hz) 1H together], [3.56 (br s), 3.59 (br s) 2H together], [4.32 (m), 4.52 (s) 2H together], 5.77 (m, 1H), 7.14 (m, 2H), 7.32 (m, 7H), 10.70 (m, 1H), 12.36 (m, 1H). Anal. (C$_{26}$H$_{30}$FN$_5$O$_3$•0.1ethyl acetate•0.2H$_2$O) C, H, N, F. HRMS: [M + H]$^+$ calc. 480.2406; found 480.2395; error −2.24 ppm.<br>Method of Example 1: Made in 53% yield from intermediate 18c using alcohol 1d. |

-continued

| Structure and Example # | Chemical name, Analytical data and comments |
|---|---|
| 19 | (1S)-2-(dimethylamino)-1-phenylethyl 3-{[(4-methoxyphenyl) acetyl] amino}-6,6-dimethyl-4,6-dihydropyrrolo [3,4-c]pyrazole-5(1H)-carboxylate.<br>$^1$H NMR (dmso-d$_6$) δ: [1.48 (s), 1.57 (s), 1.59 (s), 1.67 (s) 6H together], [2.18 (s), 2.19 (s) 6H together], 2.47 (m, 1H), [2.70 (dd, J = 8.1, 12.9 Hz), 2.79 (dd, J = 8.3, 12.6 Hz) 1H together], [3.49 (s), 3.52 (s) 2H together], [3.72 (s), 3.70 (s) 3H together], [4.30 (m), 4.51 (s) 2H together], 5.77 (dd, J = 4.5, 8.9 Hz, 1H), 6.86 (t, J = 8.9 Hz, 2H), 7.20 (m, 2H), 7.32 (m, 5H), 10.63 (br m, 1H), 12.34 (br m, 1H). Anal. (C$_{27}$H$_{33}$N$_5$O$_4$•0.1H$_2$O) C, H, N. HRMS: [M + H]$^+$ calc. 492.2605; found 492.2598; error −1.42 ppm.<br>Method of Example 1: Made in 39% yield from intermediate 19c using alcohol 1d. |
| 20 | (1S)-2-(dimethylamino)-1-phenylethyl 6,6-dimethyl-3-({[trans-2-phenylcyclopropyl]carbonyl}amino)-4,6-dihydropyrrolo[3,4-c]pyrazole-5(1H)-carboxylate.<br>$^1$H NMR (dmso-d$_6$) δ: 1.48-1.69 (m, 8H), [2.19 (s), 2.22 (s) 6H together], 2.36 (m, 1H), 2.53 (m, 1H), [2.72 (dd, J = 8.3, 11.9 Hz), 2.80 (dd, J = 8.3, 12.4 Hz) 1H together], [4.37 (m), 4.58 (s) 2H together], 5.79 (br s, 1H), 7.17 (m, 3H), 7.28 (m, 3H), 7.35 (m, 4H), 10.74 (m, 1H), 12.32 (m, 1H). Anal. (C$_{28}$H$_{33}$N$_5$O$_3$•0.6H$_2$O) C, H, N. HRMS: [M + H]$^+$ calc. 488.2656; found 488.2660; error 0.87 ppm.<br>Method of Example 1: Made in 22% yield from intermediate 20c using alcohol 1d. |

Example 21

2-(dimethylamino)-1-phenylethyl 3-(benzoylamino)-6,6-dimethyl-4,6-dihydropyrrolo[3,4-c]pyrazole-5(1H)-carboxylate

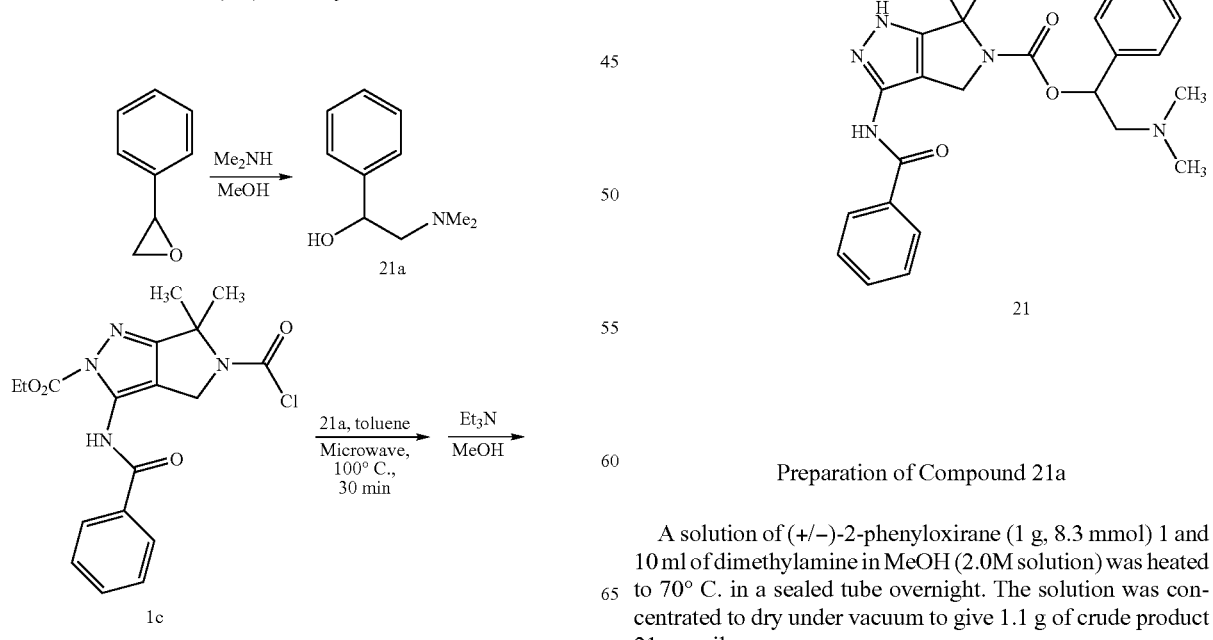

Preparation of Compound 21a

A solution of (+/−)-2-phenyloxirane (1 g, 8.3 mmol) 1 and 10 ml of dimethylamine in MeOH (2.0M solution) was heated to 70° C. in a sealed tube overnight. The solution was concentrated to dry under vacuum to give 1.1 g of crude product 21a as oil.

A solution of compound 1c (100 mg, 0.25 mmol) and 21a (60 mg, 0.37 mmol) in 5 ml of toluene was heated in microwave to 100° C. for 30 minutes. The solution was concentrated to dry by evaporation under reduced pressure. The residue was dissolved in MeOH (2 ml) and to the solution was added Et$_3$N (1 ml). The solution was stirred at r.t for 2 h, concentrated and purified by HPLC [10-40% CH$_3$CN/H$_2$O (0.1% TFA)] to give a TFA salt form of 21 in 29% yield. The salt exchange of TFA to HCl was performed by treating the TFA salt in 1N HCl-MeOH solution. Compound 21 (32 mg) was prepared as an HCl salt. $^1$H NMR (400 MHz, DMSO-d$_6$) δ ppm 1.54 (s, 3H) 1.66 (s, 3H) 2.86 (d, J=4.55 Hz, 3H) 2.89 (d, J=4.55 Hz, 3H) 3.01-3.10 (m, 2H) 4.66 (d, J=13.14 Hz, 1H) 4.96 (d, J=13.14 Hz, 1H) 6.18 (d, J=9.09 Hz, 1H) 7.33-7.40 (m, 1H) 7.45 (d, J=4.29 Hz, 4H) 7.52 (t, J=7.45 Hz, 3H) 7.60 (t, J=7.33 Hz, 1H) 8.02 (d, J=7.33 Hz, 1H) 10.27 (s, 1H) 11.04 (s, 1H) MS, m/z: 428.2 (M+1).

Example 24

(1R)-2-(dimethylamino)-1-pyridin-2-ylethyl 3-(benzoylamino)-6,6-dimethyl-4,6-dihydropyrrolo[3,4-c]pyrazole-5(1H)-carboxylate

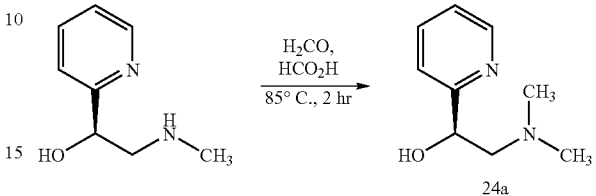

| Structure and Example # | Chemical name, Analytical data and comments |
| --- | --- |
| 22 | (2-(dimethylamino)-1-phenylethyl 3-[(4-fluorobenzoyl)amino]-6,6-dimethyl-4,6-dihydropyrrolo[3,4-c]pyrazole-5(1H)-carboxylate. <br> $^1$H NMR (400 MHz, MeOD) δ ppm: 1.62 (s, 3H), 1.73 (s, 3H), 2.45 (s, 6H), 2.60-2.72 (m, 1H), 3.01-3.11 (m, 1H), 4.72-4.87 (m, 2H), 5.90-5.99 (m, 1H), 7.20-7.48 (m, 7H), 7.95-8.10 (m, 2H). Anal. (C$_{25}$H$_{28}$FN$_5$O$_3$•0.6 H$_2$O•0.35 HOAc) C, H, N. LCMS (M + H$^+$): 466.2. <br> Method of Example 21: The title compound was made in 35% yield. |
| 23 | 2-(dimethylamino)-1-phenylethyl 3-[(2,4-difluorobenzoyl)amino]-6,6-dimethyl-4,6-dihydropyrrolo[3,4-c]pyrazole-5(1H)-carboxylate. <br> $^1$H NMR (400 MHz, MeOD) δ ppm: 1.61 (s, 3H), 1.73 (s, 3H), 2.40 (s, 6H), 2.56-2.68 (m, 1H), 2.95-3.08 (m, 1H), 4.75-4.92 (m, 2H), 5.89-5.98 (m, 1H), 7.06-7.51 (m, 7H), 7.83-7.95 (m, 1H). Anal. (C$_{25}$H$_{27}$F$_2$N$_5$O$_3$•0.3H$_2$O•0.4 HOAc) C, H, N. LCMS (APCI, M + H$^+$): 484.2. <br> Method of Example 21: The title compound was made in 20% yield. |

-continued

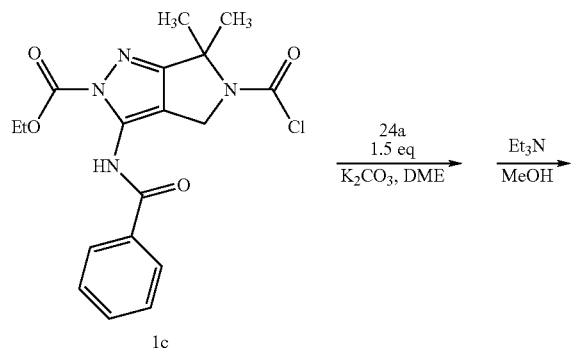

1c

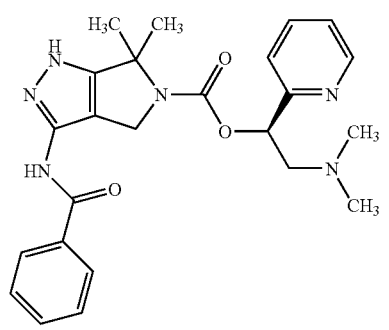

24

Preparation of Compound 24a:
(1R)-2-(dimethylamino)-1-pyridin-2-ylethanol

A mixture of (1R)-2-(methylamino)-1-pyridin-2-ylethanol (2.25 g, 10.0 mmol, prepared by the method of Tanis, et. al.*, see WO2004/085414, WO2004/085058 and WO2004/022567) 5.0 mL of 88% aqueous formic acid, and 10.0 mL of 37% aqueous formaldehyde solution was heated with stirring in a 95° C. oilbath for 2 hours, attaining a maximum internal temperature of 85° C. After cooling to room temperature, the solution was extracted with 20 mL diethyl ether, then the remaining aqueous layer was basified with aqueous NaOH (5N, 15 mL) to bring the pH=10. The basic solution was extracted with dichloromethane (2×50 mL). The combined dichloromethane extracts were dried over magnesium sulfate, filtered, concentrated, and purified by silica gel chromatography (eluting with 1:4:20 conc. aq. NH4OH:EtOH:EtOAc), to give 24a (1.09 g, 66%) as a pale yellow oil. $^1$H NMR (DMSO-$d_6$) δ: 2.19 (s, 6H), 2.43 (dd, J=8.3, 12.4 Hz, 1H), 2.53 (dd, J=4.3, 12.4 Hz, 1H), 4.67 (quint, J=4.0 Hz, 1H), 5.18 (d, J=4.0 Hz, 1H), 7.22 (ddd, J=1.3, 4.8, 7.6 Hz, 1H), 7.47 (d, J=8.1 Hz, 1H), 7.75 (d of t, $J_d$=1.8 Hz, $J_t$=7.7 Hz, 1H), 8.46 (d of q, $J_d$=4.8 Hz, $J_q$=0.8 Hz, 1H). Anal. ($C_9H_{14}N_2O$) C, H, N. LCMS (APCI, M+H$^+$): 167.4.

A solution of intermediate 1c (441 mg, 1.13 mmol), alcohol 24a (281.5 1.69 mmol) and potassium carbonate (312 mg, 2.26 mmol) in 1,2-dimethoxyethane (DME, 11.3 mL) was stirred under argon in an 85° C. oilbath for 4 hours. The still-warm solution was then filtered to remove solids, and the filtrate was concentrated to dryness. The remaining residue was dissolved in methanol (10.0 mL), triethylamine (10.0 mL) was added, and the mixture stirred at room temperature for 24 hours. After evaporation of solvents, the crude product was purified by silica gel chromatography (eluting with 1:4:20 conc. aq. NH$_4$OH:EtOH:EtOAc), to give 24 (163.5 mg, 32%) as an orange foam. $^1$H NMR (DMSO-$d_6$) δ: [1.56, (s), 1.64 (s), 1.67 (s), 1.72 (s) 6H together], [2.21 (s), 2.22 (s) 6H together], 2.74 (m, 2H), [4.44 (m), 4.69 (m) 2H together], 5.82 (m, 1H), 7.30 (t of d, $J_t$=7.6 Hz, $J_d$=4.9 Hz, 1H), 7.41 (t, J=7.7 Hz, 1H), 7.49-7.56 (m, 3H), 7.80 (q of d, $J_q$=7.8 Hz, $J_d$=1.5 Hz, 1H), 7.99 (t, J=6.8 Hz, 2H), 8.55 (t, J=4.9 Hz, 1H), 10.93 (m, 1H), [12.23 (br s), 12.46 (br s), 12.49 (br s) 1H together]. Anal. ($C_{24}H_{28}N_6O_3 \cdot 0.6H_2O$) C, H, N. LCMS (APCI, M+H$^+$): 449.4. HRMS: [M+H]$^+$ calc. 449.2296; found 449.2287; error −1.95 ppm.

| Structure and Example # | Chemical name, Analytical data and comments |
|---|---|
| ![structure 25] 25 | (1R)-2-(dimethylamino)-1-pyridin-2-ylethyl 3-[(4-fluorobenzoyl)amino]-6,6-dimethyl-4,6-dihydropyrrolo[3,4-c]pyrazole-5(1H)-carboxylate. $^1$H NMR (dmso-$d_6$) δ: [1.56 (s), 1.64 (s), 1.67 (s), 1.72 (s) 6H together], [2.21 (s), 2.22 (s) 6H together], 2.76 (m, 2H), [4.48 (m), 4.67 (m) 2H together], 5.82 (m, 1H), 7.31 (m, 3H), 7.41 (t, J = 8.1 Hz, 1H), 7.80 (q of d, $J_q$ = 7.8 Hz, $J_d$ = 1.5 Hz, 1H), 8.07 (br q, J = 5.8 Hz, 2H), 8.55 (t, J = 5.2 Hz, 1H), 10.97 (m, 1H), [12.23 (m), 12.47 (s), 12.50 (m) 1H together]. Anal. ($C_{24}H_{27}FN_6O_3 \cdot 0.5H_2O \cdot 0.11EtOAc$) C, H, N, F. HRMS: [M + H]$^+$ calc. 467.2202; found 467.2194; error −1.66 ppm. Method of Example 24. Obtained in 33% yield from intermediate 2c using alcohol 24a, DMF was used as the solvent instead of DME, and the reaction was stirred at 60° C. for 3.5 hours. |

-continued

| Structure and Example # | Chemical name, Analytical data and comments |
|---|---|
| 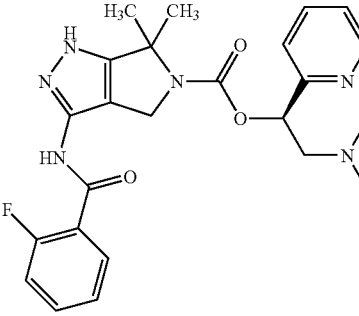<br>26 | (1R)-2-(dimethylamino)-1-pyridin-2-ylethyl 3-[(2-fluorobenzoyl)amino]-6,6-dimethyl-4,6-dihydropyrrolo[3,4-c]pyrazole-5(1H)-carboxylate. $^1$H NMR (dmso-$d_6$) δ: [1.56 (s), 1.64 (s), 1.67 (s), 1.72 (s) 6H together], [2.21 (s), 2.22 (s) 6H together], 2.75 (m, 2H), [4.47 (m), 4.69 (m) 2H together], 5.81 (m, 1H), 7.29 (m, 3H), 7.41 (t, J = 8.5 Hz, 1H), 7.54-7.65 (m, 2H), 7.80 (q of d, $J_q$ = 7.6 Hz, $J_d$ = 1.3 Hz, 1H), 8.54 (t, J = 5.6 Hz, 1H) [10.80 (br s), 10.88 (br s), 11.04 (v br s) 1H together], [12.31 (br s), 12.46 (br s), 12.49 (br s), 1H together]. Anal. ($C_{24}H_{27}FN_6O_3$•0.5$H_2O$•0.1cyclohexane) C, H, N, F. HRMS: [M + H]$^+$ calc. 467.2202; found 467.2202; error 0.05 ppm. Method of Example 24. Obtained in 15% yield from intermediate 3c using alcohol 24a. |
| 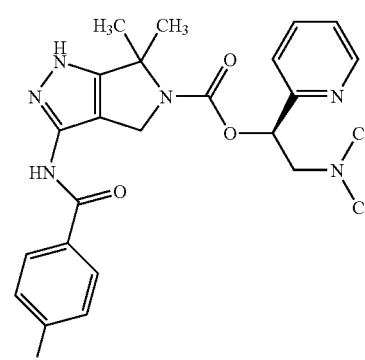<br>27 | (1R)-2-(dimethylamino)-1-pyridin-2-ylethyl 6,6-dimethyl-3-{[4-(trifluoromethyl)benzoyl]amino}-4,6-dihydropyrrolo[3,4-c]pyrazole-5(1H)-carboxylate. $^1$H NMR (dmso-$d_6$) δ: [1.56 (s), 1.63 (s), 1.67 (s), 1.72 (s) 6H together], [2.21 (s), 2.22 (s) 6H together], 2.75 (m, 2H), [4.45 (m), 4.70 (m) 2H together], 5.82 (quint, J = 3.8 Hz 1H), 7.30 (m, 1H), 7.41 (t, J = 8.1 Hz, 1H), 7.79 (m, 1H), 7.88 (br s, 2H), 8.17 (t, J = 8.1 Hz, 2H), 8.55 (t, J = 5.6 Hz, 1H), 11.22 (br s, 1H), 12.55 (br s, 1H). Anal. ($C_{25}H_{27}F_3N_6O_3$•0.55 $H_2O$) C, H, N, F. HRMS: [M + H]$^+$ calc. 517.2170; found 517.2169; error −01.5 ppm. Method of Example 24. Obtained in 42% yield from intermediate 5c using alcohol 24a. |
| 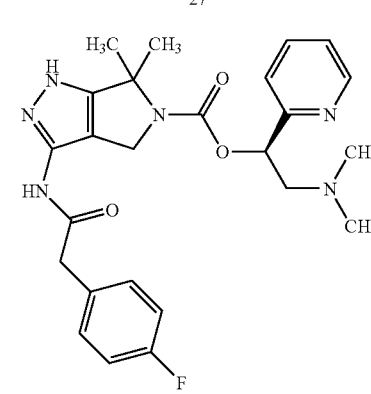<br>28 | (1R)-2-(dimethylamino)-1-pyridin-2-ylethyl 3-{[(4-fluorophenyl)acetyl]amino}-6,6-dimethyl-4,6-dihydropyrrolo[3,4-c]pyrazole-5(1H)-carboxylate. $^1$H NMR (dmso-$d_6$) δ: [1.51 (s), 1.59 (s), 1.62 (s), 1.67 (s) 6H together], 2.19 (s, 6H), 2.72 (m, 2H), 3.59 (m, 2H), [4.30 (d, J = 13.9 Hz) 4.34 (d, J = 12.9 Hz), 4.53 (d, J = 12.9 Hz), 4.57 (d, J = 13.4 Hz) 2H together], 5.79 (dd, J = 4.3, 7.8 Hz, 1H), 7.13 (t, J = 8.3 Hz, 2H), 7.33 (m, 4H), 7.78 (q, J = 7.1 Hz, 1H), 8.53 (t, J = 5.2 Hz, 1H), [10.65, (br s), 10.71 (br s) 1H together], [12.33 (br s), 12.37 (br s) 1H together]. HRMS: [M + H]$^+$ calc. 481.2358; found 481.2354; error −0.78 ppm. Method of Example 24. Obtained in 26% yield from intermediate 18c using alcohol 24a. |
| 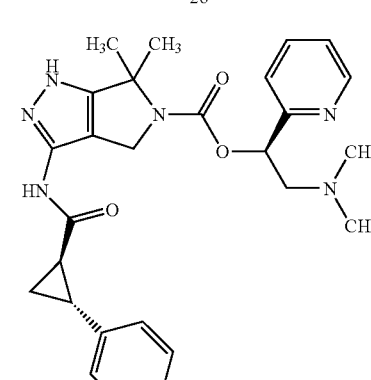<br>29 | (1R)-2-(dimethylamino)-1-pyridin-2-ylethyl 6,6-dimethyl-3-({[trans-2-phenylcyclopropyl]carbonyl}-amino)-4,6-dihydropyrrolo[3,4-c]pyrazole-5(1H)-carboxylate. $^1$H NMR (dmso-$d_6$) δ: 1.19-1.74 (m, 8H), 2.12 (br s, 1H), [2.20 (s), 2.22 (s) 6H together], 2.36 (br s, 1H), 2.75 (m, 2H), [4.38 (m), 4.60 (br s) 2H together], 5.82 (br s, 1H), 7.16 (br s, 3H), 7.28 (br s, 3H), 7.39 (t, J = 8.6 Hz, 1H), 7.80 (s, 1H), 8.54 (s, 1H). 10.74 (m, 1H). 12.33 (m, 1H), Anal. ($C_{27}H_{32}N_6O_3$•0.1 EtOAc•5$H_2O$) C, H, N. HRMS: [M + H]$^+$ calc. 489.2609; found 489.2611; error 0.46 ppm. Method of Example 24. Obtained in 18% yield from intermediate 20c using alcohol 24a. |

Example 30

(1S)-1-benzyl-2-(dimethylamino)ethyl 3-(benzoylamino)-6,6-dimethyl-4,6-dihydropyrrolo[3,4-c]pyrazole-5(1H)-carboxylate

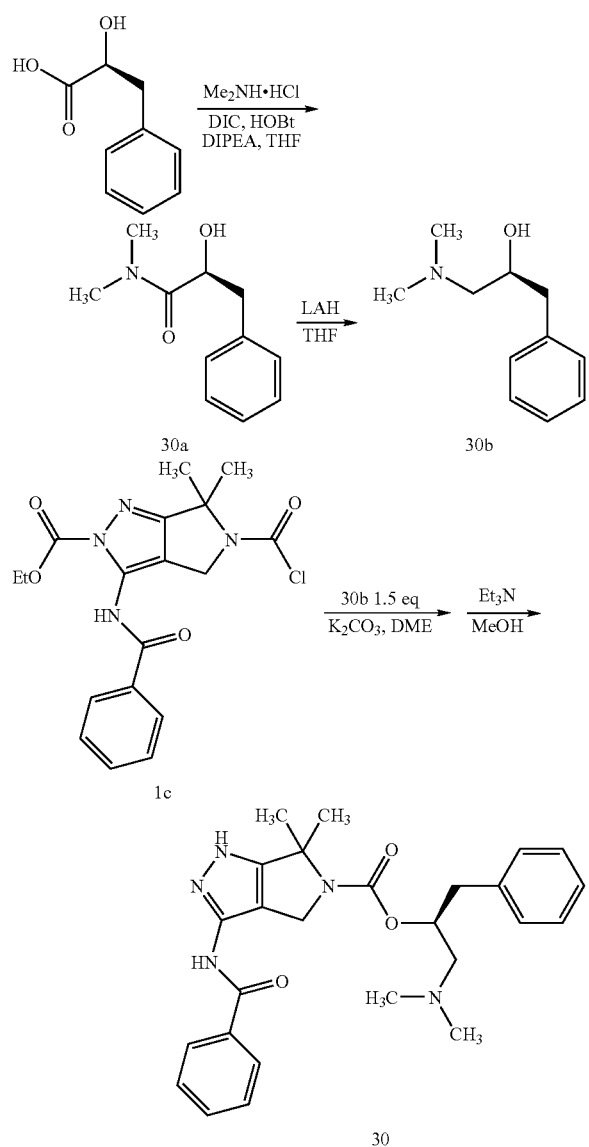

phy to give 30a (2.36 g, 62%) as a white solid. $^1$H NMR (400 MHz, MeOD) δ ppm: 2.83-2.92 (m, 7H), 2.93-3.01 (m, 1H), 4.66 (t, J=6.67 Hz, 1H), 7.15-7.33 (m, 5H).

Preparation of Compound 30b:
(S)-1-dimethylamino-3-phenylpropan-2-ol

To a stirred suspension of lithium aluminum hydride (1.99 g, 52.4 mmol) in THF (20 ml) was added a solution of intermediate 30a (2.35 g, 13.1 mmol) in THF (10 ml) at 0° C. The reaction mixture was stirred at room temperature overnight and then quenched with saturated $Na_2CO_3$ until effervescence ceased. The resulting mixture was filtered through celite and the filter cake was washed with dichloromethane. The filtrate was concentrated to dryness. The remaining residue was dissolved in ether. The solution was extracted with 2N HCl twice. The combined aqueous layer was washed ether and basified with solid NaOH to PH=10. The basic solution was extracted with ether twice. The combined ether extracts were dried over anhydrous $K_2CO_3$, filtered, concentrated to give the title compound as colorless oil (1.6 g, 74%). $^1$H NMR (400 MHz, MeOD) δ ppm: 2.24 (s, 6H), 2.28-2.39 (m, 2H), 2.63-2.79 (m, 2H), 3.87-3.99 (m, 1H), 7.12-7.31 (m, 5H).

A solution of intermediate 1c (165 mg, 0.42 mmol), alcohol 30b (104 mg 1.5 eq) and potassium carbonate (117 mg, 2 eq) in 1,2-dimethoxyethane (DME, 2 mL) was heated to 130° C. for 40 minutes in microwave reactor. The still-warm solution was then filtered to remove solids, and the filtrate was concentrated to dryness. The remaining residue was dissolved in methanol (1.0 mL), triethylamine (1.0 mL) was added, and the mixture was stirred at room temperature for 2 hours. After evaporation of solvents, the crude product was purified by prep-HPLC and lyophilized to give the title compound 30 (90 mg) as white solid in 46% yield. $^1$H NMR (400 MHz, MeOD) δ ppm: 1.51 (s, 3H), 1.66 (s, 3H), 2.37 (s, 6H), 2.58 (dd, J=13.60, 3.02 Hz, 1H), 2.76 (dd, J=13.22, 8.69 Hz, 1H), 2.82-2.90 (m, 1H), 2.92-3.01 (m, 1H), 4.49-4.73 (m, 2H), 5.18-5.28 (m, 1H), 7.14-7.23 (m, 1H), 7.23-7.31 (m, 4H), 7.53 (t, J=7.43 Hz, 2H), 7.61 (t, J=7.30 Hz, 1H), 7.95 (t, J=6.42 Hz, 2H). Anal. ($C_{26}H_{31}N_5O_3 \cdot 0.2HOAc \cdot 0.2H_2O$) C, H, N. HPLC: >95% purity.

Example 31

(1S)-1-benzyl-2-(dimethylamino)ethyl 3-[(2-fluorobenzoyl)amino]-6,6-dimethyl-4,6-dihydropyrrolo[3,4-c]pyrazole-5(1H)-carboxylate

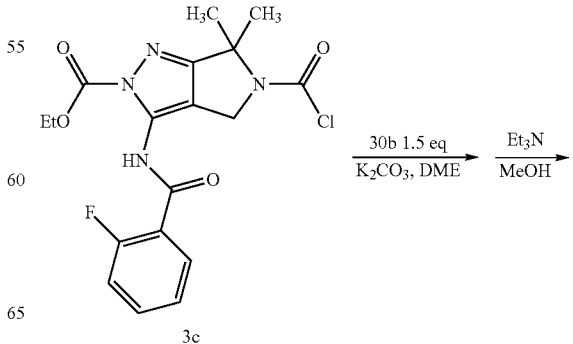

Preparation of Compound 30a:
(S)-2-hydroxy-N,N-dimethyl-3-phenylpropanamide

To a solution of (S)-2-hydroxy-3-phenylpropanoic acid (3.53 g, 21.2 mmol), dimethylamine hydrochloride (2.07 g, 1.2 eq), 1-hydroxybenzotriazole hydrate (HOBt, 3.25 g, 1 eq) and diisopropylethylamine (DIEPA, 4.43 ml, 1.2 eq) in THF (60 ml) was added diisopropylcarbodiimide (DIC, 3.65 ml, 1.1 eq) at 0° C. The reaction mixture was stirred at room temperature overnight and then concentrated to dryness under reduced pressure. The residue was partitioned between ethyl acetate and 1N HCl. The ethyl acetate extracts was washed with 1N NaOH, dried over magnesium sulfate, filtered, concentrated, and purified by silica gel chromatogra-

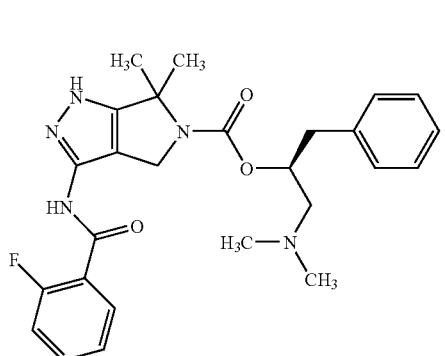

31

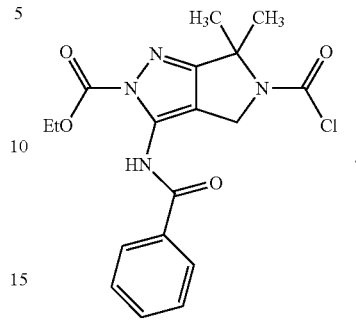

1c

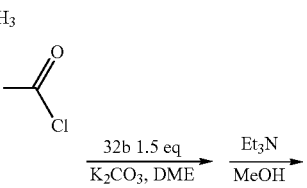

The title compound 31 was made in 56% yield by the method of Example 30. $^1$H NMR (400 MHz, MeOD) δ ppm: 1.50 (s, 3H), 1.66 (s, 3H), 2.43 (s, 6H), 2.63-2.71 (m, 1H), 2.79-2.91 (m, 2H), 2.97 (dd, J=13.72, 5.41 Hz, 1H), 4.53-4.74 (m, 2H), 5.21-5.31 (m, 1H), 7.13-7.22 (m, 1H), 7.24-7.31 (m, 5H), 7.33 (t, J=7.55 Hz, 1H), 7.54-7.65 (m, 1H), 7.74-7.88 (m, 1H). Anal. ($C_{26}H_{30}N_5O_3F$.0.2HOAc) C, H, N. HPLC: >95% purity.

Example 32

(1S)-1-cyclohexyl-2-(dimethylamino)ethyl 3-(benzoylamino)-6,6-dimethyl-4,6-dihydropyrrolo[3,4-c]pyrazole-5(1H)-carboxylate

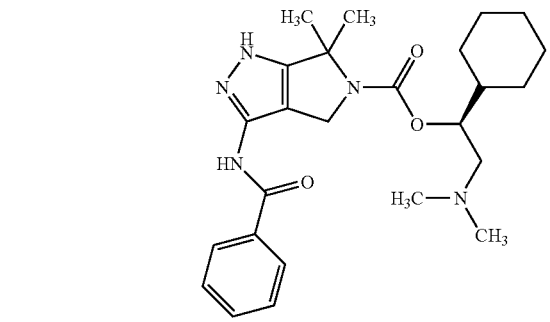

32

Preparation of Compound 32a: (S)-2-cyclohexyl-2-hydroxy-N,N-dimethylacetamide

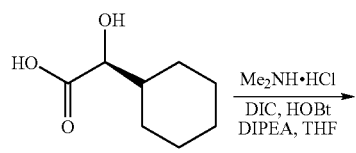

The title compound 32a was made in 75% yield by the method of Example 30a. $^1$H NMR (400 MHz, CHLOROFORM-d) δ ppm: 1.09-1.30 (m, 4H), 1.38-1.55 (m, 3H), 1.64 (d, J=11.08 Hz, 2H), 1.71-1.87 (m, 2H), 3.01 (d, J=6.04 Hz, 6H), 4.23 (d, J=2.77 Hz, 1H).

Preparation of Compound 32b: (S)-1-cyclohexyl-2-(dimethylamino)ethanol

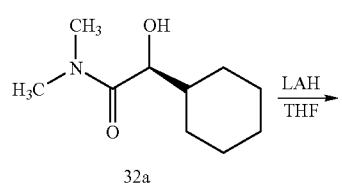

32a

The title compound 32b was made in 47% yield by the method of Example 30b. $^1$H NMR (400 MHz, CHLOROFORM-d) δ ppm: 1.04-1.26 (m, 6H), 1.58-1.82 (m, 5H), 2.90 (d, J=5.04 Hz, 3H), 2.96 (d, J=5.04 Hz, 3H), 2.98-3.03 (m, 1H), 3.15-3.26 (m, 1H), 3.85-3.94 (m, 1H), 11.34 (br. s., 1H).

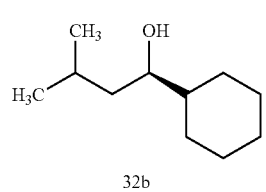

32b

The title compound 32 was made in 34% yield by the method of Example 30. $^1$H NMR (400 MHz, MeOD) δ ppm: 1.06-1.36 (m, 5H), 1.61-1.84 (m, 12H), 2.46 (s, 6H), 2.62-2.75 (m, 1H), 2.88 (dd, J=13.35, 9.06 Hz, 1H), 4.58-4.77 (m, 2H), 4.89-4.97 (m, 1H), 7.52 (t, J=7.43 Hz, 2H), 7.60 (t, J=7.30 Hz, 1H), 7.95 (d, J=7.30 Hz, 2H). Anal. ($C_{25}H_{35}N_5O_3$.0.2HOAc.0.7H$_2$O) C, H, N. HPLC: >95% purity.

| Structure and Example # | Chemical name, Analytical data and comments |
|---|---|
| 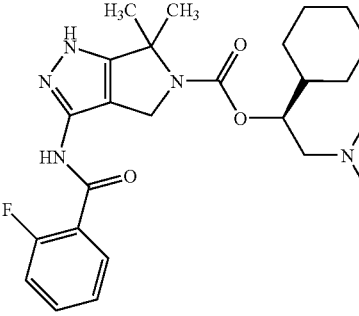<br>33 | (1S)-1-cyclohexyl-2-(dimethylamino)ethyl 3-[(2-fluorobenzoyl)amino]-6,6-dimethyl-4,6-dihydropyrrolo[3,4-c]pyrazole-5(1H)-carboxylate. $^1$H NMR (400 MHz, MeOD) δ ppm: 1.07-1.35 (m, 5H), 1.62-1.84 (m, 12H), 2.52 (s, 6H), 2.72-2.84 (m, 1H), 2.95 (dd, J = 13.47, 9.19 Hz, 1H), 4.60-4.79 (m, 2H), 4.90-4.96 (m, 1H), 7.22-7.37 (m, 2H), 7.53-7.66 (m, 1H), 7.75-7.86 (m, 1H). Anal. ($C_{25}H_{34}N_5O_3F$•0.4 HOAc•0.3 $H_2O$) C, H, N. HPLC: >95% purity. Method of Example 32 |
| 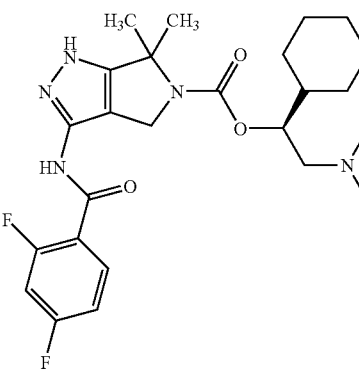<br>34 | (1S)-1-cyclohexyl-2-(dimethylamino)ethyl 3-[(2,4-difluorobenzoyl)amino]-6,6-dimethyl-4,6-dihydropyrrolo[3,4-c]pyrazole-5(1H)-carboxylate. $^1$H NMR (400 MHz, MeOD) δ ppm: 1.08-1.37 (m, 5H), 1.64-1.87 (m, 12H), 2.45 (s, 6H), 2.62-2.74 (m, 1H), 2.87 (dd, J = 13.35, 9.06 Hz, 1H), 4.57-4.79 (m, 2H), 4.89-4.96 (m, 1H), 7.05-7.22 (m, 2H), 7.81-7.95 (m, 1H). Anal. ($C_{25}H_{33}N_5O_3F_2$•0.3 HOAc•0.4 $H_2O$) C, H, N. HPLC: >95% purity. Method of Example 32 |

Example 35

(1S)-1-[(dimethylamino)methyl]-3-methylbutyl 3-(benzoylamino)-6,6-dimethyl-4,6-dihydropyrrolo[3,4-c]pyrazole-5(1H)-carboxylate

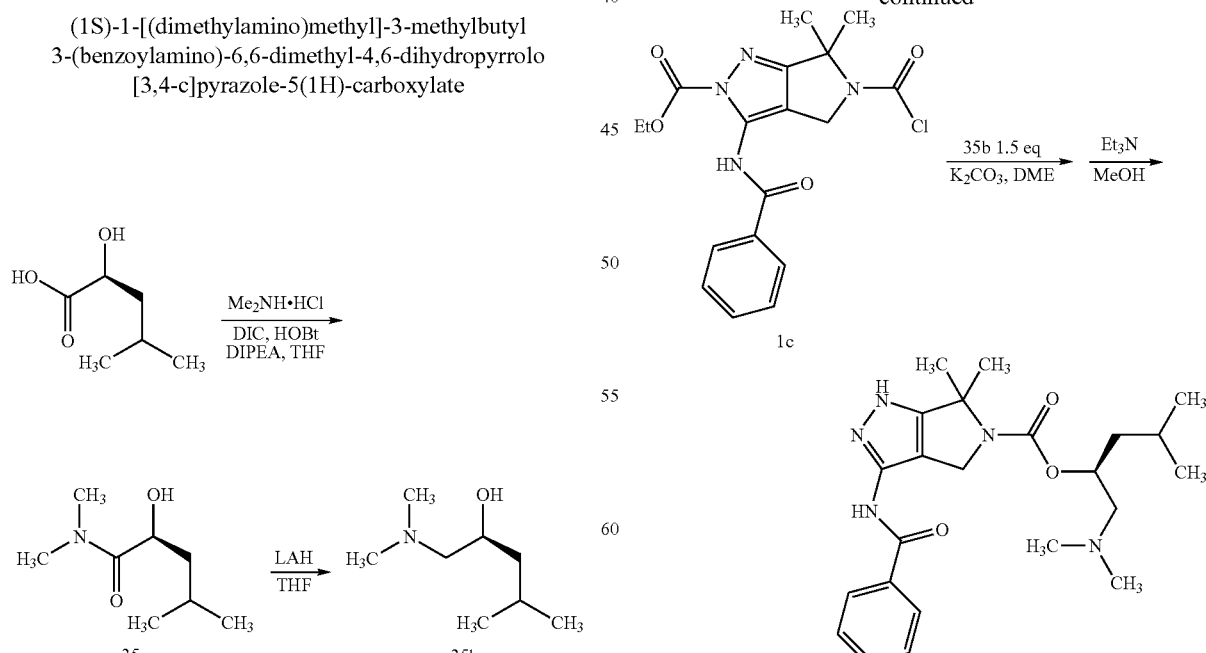

Preparation of Compound 35a:
(S)-2-hydroxy-N,N,4-trimethylpentanamide

The title compound 35a was made in 61% yield by the method of Example 30a. $^1$H NMR (400 MHz, CHLOROFORM-d) δ ppm: 0.94-1.01 (m, 6H), 1.27-1.36 (m, 1H), 1.38-1.48 (m, 1H), 1.95-2.04 (m, 1H), 2.70 (br. s., 1H), 2.99 (d, J=13.35 Hz, 6H), 4.40 (dd, J=10.07, 2.01 Hz, 1H).

Preparation of Compound 35b:
(S)-1-(dimethylamino)-4-methylpenta-2-ol

The title compound 35b was made in 63% yield by the method of Example 30b. $^1$H NMR (400 MHz, CHLOROFORM-d) δ ppm: 0.93 (dd, J=6.55, 3.78 Hz, 6H), 1.05-1.17 (m, 1H), 1.32-1.47 (m, 1H), 1.75-1.92 (m, 1H), 2.16-2.56 (m, 8H), 3.73-3.90 (m, 1H), 4.39 (br. s., 1H).

The title compound 35 was made in 54% yield by the method of Example 30. $^1$H NMR (400 MHz, MeOD) δ ppm: 0.92-1.00 (m, 6H), 1.36-1.48 (m, 1H), 1.53-1.63 (m, 1H), 1.67-1.80 (m, 7H), 2.37 (s, 6H), 2.48 (dd, J=12.84, 3.27 Hz, 1H), 2.56-2.74 (m, 1H), 4.54-4.78 (m, 2H), 5.05-5.16 (m, 1H), 7.52 (t, J=7.55 Hz, 2H), 7.60 (t, J=7.18 Hz, 1H), 7.94 (d, J=7.30 Hz, 2H). Anal. ($C_{23}H_{33}N_5O_3$.0.1HOAc.0.1$H_2O$) C, H, N. HPLC: >95% purity.

Example 36

(1S)-1-[(dimethylamino)methyl]-3-methylbutyl 3-[(4-fluorobenzoyl)amino]-6,6-dimethyl-4,6-dihydropyrrolo[3,4-c]pyrazole-5(H)-carboxylate

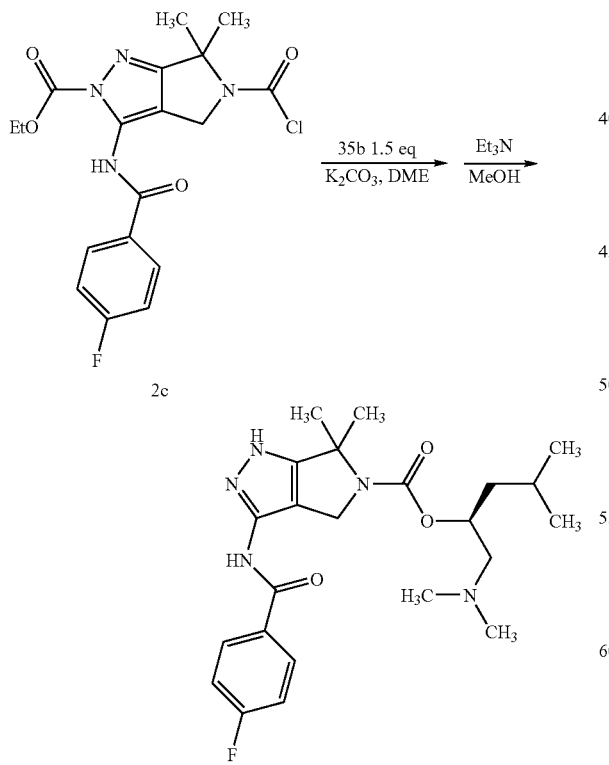

The title compound 36 was made in 22% yield from 2c by the method of Example 35. $^1$H NMR (400 MHz, MeOD) δ ppm: 0.97 (d, J=6.55 Hz, 6H), 1.37-1.51 (m, 1H), 1.54-1.61 (m, 1H), 1.64-1.77 (m, 7H), 2.40 (s, 6H), 2.44-2.57 (m, 1H), 2.59-2.79 (m, 1H), 4.52-4.74 (m, 2H), 5.05-5.18 (m, 1H), 7.25 (t, J=8.69 Hz, 2H), 7.93-8.09 (m, 2H). Anal. ($C_{23}H_{32}N_5O_3F$.0.2HOAc) C, H, N. HPLC: >95% purity.

Example 37

(1S)-2-(dimethylamino)-1-methylethyl 3-[(2,4-difluorobenzoyl)amino]-6,6-dimethyl-4,6-dihydropyrrolo[3,4-c]pyrazole-5(1H)-carboxylate

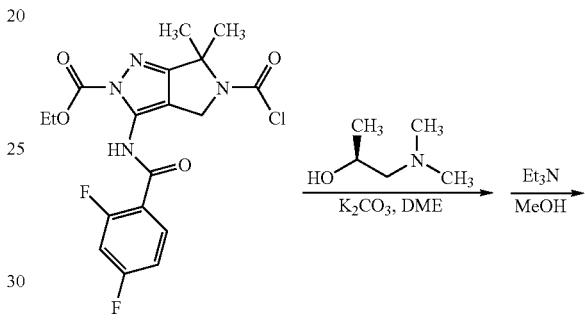

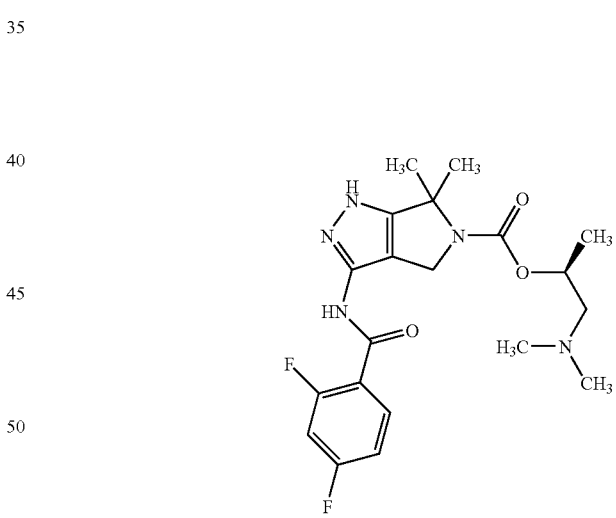

The title compound 37 was made in 25% yield by a similar procedure to example 1 using (S)-(+)-1-Dimethylamino-2-propanol. $^1$H NMR (400 MHz, MeOD) δ ppm: 1.26-1.35 (m, 3H), 1.73 (s, 6H), 2.47 (s, 6H), 2.55-2.66 (m, 1H), 2.74-2.91 (m, 1H), 4.60-4.75 (m, 2H), 5.02-5.17 (m, 1H), 7.09-7.18 (m, 2H), 7.82-7.92 (m, 1H). Anal. ($C_{20}H_{25}F_2N_5O_3$.0.4$H_2O$.0.3HOAc) C, H, N. LCMS (M+H$^+$): 422.3.

Example 38

2-(dimethylamino)-1-(2-fluorophenyl)ethyl 3-[(4-fluorobenzoyl)amino]-6,6-dimethyl-4,6-dihydropyrrolo[3,4-c]pyrazole-5(1H)-carboxylate

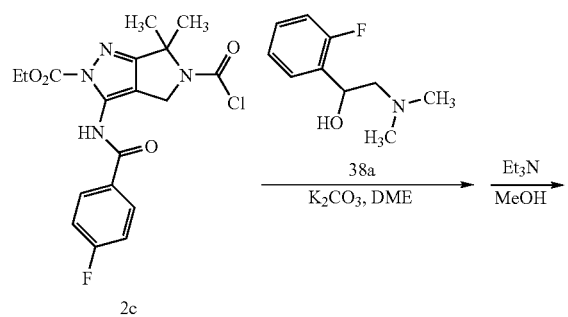

Example 39

2-(dimethylamino)-1-(4-fluorophenyl)ethyl 3-[(4-fluorobenzoyl)amino]-6,6-dimethyl-4,6-dihydropyrrolo[3,4-c]pyrazole-5(1H)-carboxylate

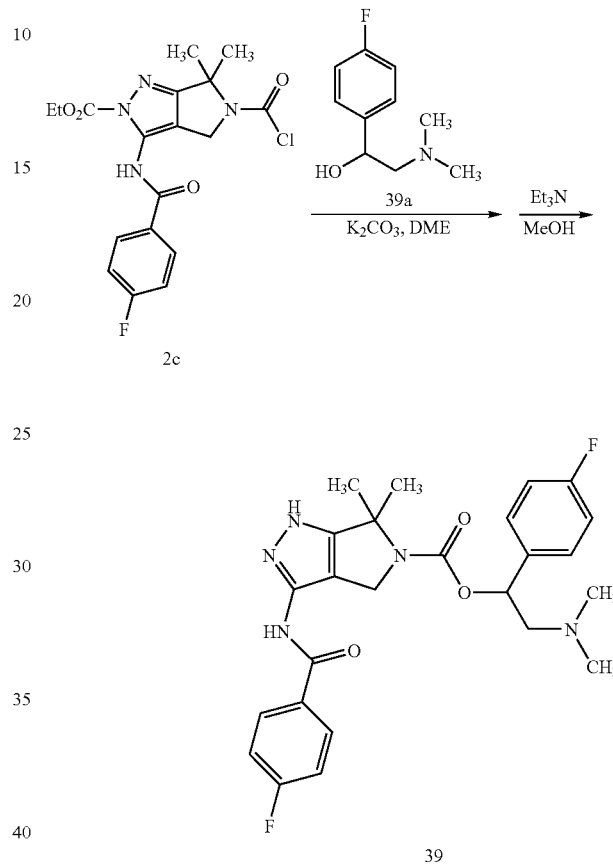

Preparation of Compound 38a: 2-Dimethylamino-1-(2-fluoro-phenyl)-ethanol

2-Amino-1-(2-fluoro-phenyl)-ethanol (2.18 g, 14.1 mmol) was methylated by the procedure used to make intermediate 1d, affording 38a (2.26 g, 12.3 mmol) as an crude oil (88% yield). $^1$H NMR (MeOD) δ: 2.54 (s, 6H), 2.66 (dd, J=9.09, 12.88 Hz, 1H), 2.81 (dd, J=9.09, 12.88 Hz, 1H), 5.33 (dd, J=3.28, 9.09 Hz, 1H), 7.19-7.28 (m, 1H), 7.33-7.40 (m, 1H), 7.43-7.51 (m, 1H), 7.69-7.76 (m, 1H). LCMS (APCI, M+H$^+$): 184.2.

Intermediate 2c (298 mg, 0.729 mmol) and alcohol 38a (200 mg, 1.09 mmol) were coupled by the method of Example 1, affording 38 (10 mg, 3%) as a white solid. $^1$H NMR (MeOD, a mixture of rotamers, only the chemical shifts of the major form is reported) δ: 1.53 (s, 3H), 1.65 (s, 3H), 2.96 (s, 6H), 3.37-3.47 (m, 1H), 3.71-3.81 (m, 1H), 4.75-4.86 (m, 2H), 6.29-6.36 (m, 1H), 7.07-7.24 (m, 4H), 7.30-7.40 (m, 1H), 7.43-7.53 (m, 1H), 7.87-7.97 (m, 1H). Anal. ($C_{25}H_{27}F_2N_5O_3$·1.88TFA·0.88 ethanol) C, H, N, F. LCMS (APCI, M+H$^+$): 484.2.

Preparation of Compound 39a: 2-Dimethylamino-1-(4-fluoro-phenyl)-ethanol

2-Amino-1-(4-fluoro-phenyl)-ethanol (2.10 g, 13.5 mmol) was methylated by the procedure used to make intermediate 1d, affording 39a (1.24 g, 6.78 mmol) as an oil (50% yield). $^1$H NMR (MeOD) δ: 2.55 (s, 6H), 2.62 (dd, J=3.79, 12.88 Hz, 1H), 2.83 (dd, J=9.09, 12.88 Hz, 1H), 5.01 (dd, J=3.54, 9.09 Hz, 1H), 7.28 (t, J=8.84 Hz, 2H), 7.61 (dd, J=5.31, 8.59 Hz, 2H). LCMS (APCI, M+H$^+$): 184.2.

Intermediate 2c (290 mg, 0.710 mmol) and alcohol 39a (260 mg, 1.42 mmol) were coupled by the method of Example 1, affording compound 39 (27 mg, 7%) as a white solid. $^1$H NMR (MeOD, a mixture of rotamers, only the chemical shifts of the major form is reported) δ: 1.52 (s, 3H), 1.64 (s, 3H), 2.94 (s, 3H), 2.97 (s, 3H), 3.32-3.40 (m, 1H), 3.66-3.77 (m, 1H), 4.77-4.86 (m, 2H), 6.04-6.11 (m, 1H), 7.04-7.23 (m, 4H), 7.40-7.49 (m, 2H), 7.87-7.98 (m, 2H). Anal. ($C_{25}H_{27}F_2N_5O_3$·2.03TFA·0.89 water) C, H, N, F. LCMS (APCI, M+H$^+$): 484.2.

Example 40

(1S)-2-[isopropyl(methyl)amino]-1-phenylethyl 3-[(4-fluorobenzoyl)amino]-6,6-dimethyl-4,6-dihydropyrrolo[3,4-c]pyrazole-5(H)-carboxylate

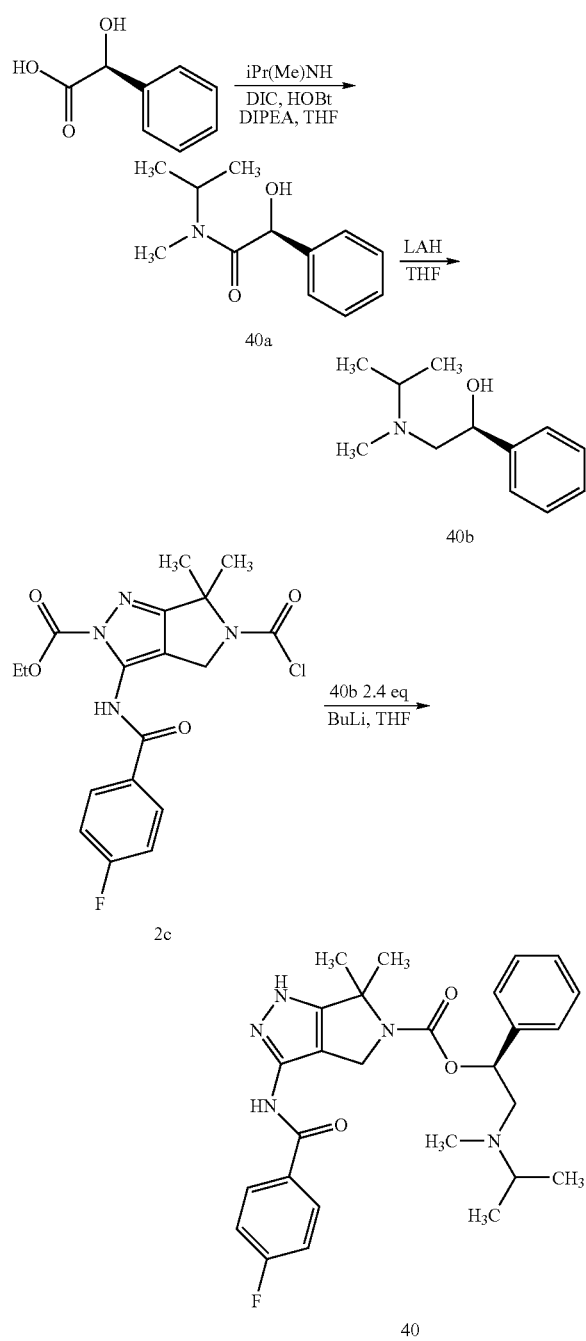

Preparation of Compound 40a: (S)-2-hydroxy-N-isopropyl-n-methyl-2-phenylacetamide The title compound 40a was made in 44% yield as an oil by the method of Example 30a using isopropylmethylamine. $^1$H NMR (400 MHz, CHLOROFORM-d) δ ppm: 0.55 (d, J=6.55 Hz, 1.5H), 1.03 (d, J=6.80 Hz, 1.5H), 1.16 (t, J=6.67 Hz, 3H), 2.56 (s, 1.5H), 2.86 (s, 1.5H), 3.80-3.96 (m, 0.5H), 4.87-4.95 (m, 0.5H), 5.19 (d, J=31.98 Hz, 1H), 7.28-7.41 (m, 5H).

Preparation of Compound 40b: (S)-2-(isopropyl(methyl)amino)-1-phenylethyanol The title compound 40b was made in 84% yield by the method of Example 30b. $^1$H NMR (400 MHz, MeOD) δ ppm: 1.02 (dd, J=11.46, 6.67 Hz, 6H), 2.32 (s, 3H), 2.46-2.63 (m, 2H), 2.86-2.95 (m, 1H), 4.70 (dd, J=9.06, 3.78 Hz, 1H), 7.20-7.28 (m, 1H), 7.29-7.39 (m, 4H).

To a solution of (S)-2-(isopropyl(methyl)amino)-1-phenylethyanol 40b (227 mg, 1.18 mmol) in THF (2 ml) was added 1.6M butyllithium solution in hexane (0.73 ml) at room temperature. The reaction mixture was stirred at room temperature for 20 minutes and then added ethyl 5-(chlorocarbonyl)-3-[(4-fluorobenzoyl)amino]-6,6-dimethyl-5,6-dihydropyrrolo[3,4-c]pyrazole-2(4H)-carboxylate 2c (200 mg, 0.49 mmol). The resulting mixture was heated at reflux for one hour and then concentrated to dryness under reduced pressure. The crude product was purified by prep-HPLC and lyophilized to give the title compound 40 in 4% yield (10 mg) as white solid. $^1$H NMR (400 MHz, MeOD) δ ppm: 1.06 (dd, J=21.65, 6.55 Hz, 6H), 1.62 (s, 3H), 1.72 (s, 3H), 2.42 (s, 3H), 2.62-2.72 (m, 1H), 2.88-3.04 (m, 2H), 4.82 (br. s., 2H), 5.81 (dd, J=9.19, 3.40 Hz, 1H), 7.21-7.33 (m, 3H), 7.34-7.44 (m, 4H), 7.97-8.06 (m, 2H). Anal. ($C_{27}H_{32}N_5O_3F.0.2HOAc.0.4H_2O$) C, H, N. HPLC: >95% purity.

Example 41

(R)-2-(dimethylamino)-2-phenylethyl 3-[(4-fluorobenzoyl)amino]-6,6-dimethyl-4,6-dihydropyrrolo[3,4-c]pyrazole-5(1H)-carboxylate

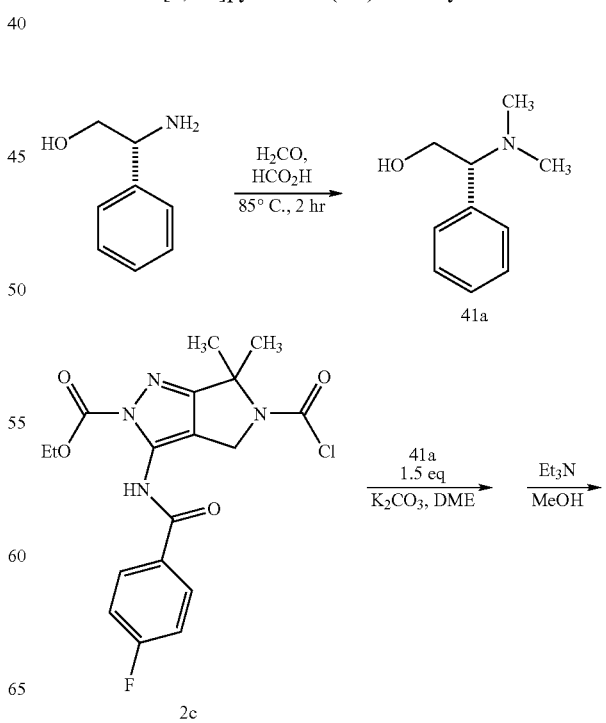

-continued

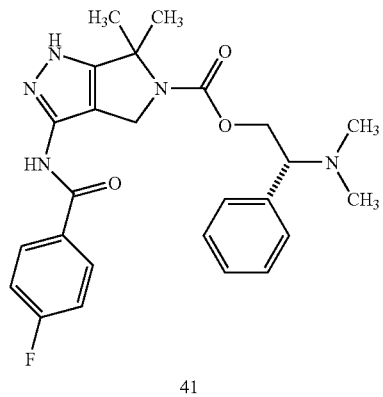

41

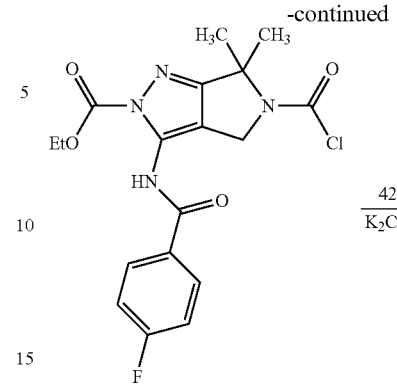

2c

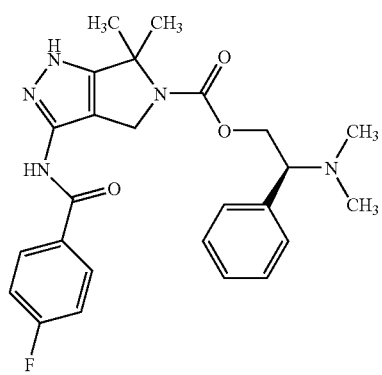

42

Preparation of Compound 41a:
(R)-2-(dimethylamino)-2-phenylethanol

The title compound 41a was made in 90% yield by the method of Example 1d using (R)-2-amino-2-phenylethanol. $^1$H NMR (400 MHz, MeOD) δ ppm: 2.21 (d, J=1.26 Hz, 6H), 3.32-3.39 (m, 1H), 3.75-3.84 (m, 1H), 3.90-4.00 (m, 1H), 7.24-7.39 (m, 5H).

The title compound 41 was made in 18% yield by the method of Example 30 from compound 2c. $^1$H NMR (400 MHz, MeOD) δ ppm: 1.65 (d, J=11.08 Hz, 6H), 2.33 (s, 6H), 3.63-3.75 (m, 1H), 4.38-4.56 (m, 4H), 7.20-7.34 (m, 3H), 7.38 (t, J=4.53 Hz, 4H), 7.93-8.07 (m, 2H). Anal. ($C_{25}H_{28}N_5O_3F.0.2HOAc.0.3H_2O$) C, H, N. HPLC: >95% purity.

Example 42

(S)-2-(dimethylamino)-2-phenylethyl 3-[(4-fluorobenzoyl)amino]-6,6-dimethyl-4,6-dihydropyrrolo[3,4-c]pyrazole-5(1H)-carboxylate Preparation of Compound 42a:
(S)-2-(dimethylamino)-2-phenylethanol The title compound 42a was made in 97% yield by the method of Example 1d using (S)-2-amino-2-phenylethanol. $^1$H NMR (400 MHz, MeOD) δ ppm: 2.20 (s, 6H), 3.35 (t, J=6.17 Hz, 1H), 3.79 (dd, J=11.33, 6.29 Hz, 1H), 3.94 (dd, J=11.33, 6.04 Hz, 1H), 7.23-7.37 (m, 5H).

The title compound 42 was made in 12% yield by the method of Example 30. $^1$H NMR (400 MHz, MeOD) δ ppm: 1.65 (d, J=11.33 Hz, 6H), 2.33 (s, 6H), 3.61-3.76 (m, 1H), 4.37-4.58 (m, 4H), 7.25 (q, J=8.64 Hz, 2H), 7.29-7.34 (m, 1H), 7.38 (t, J=4.66 Hz, 4H), 7.93-8.07 (m, 2H). Anal. ($C_{25}H_{28}N_5O_3F.0.4HOAc.$) C, H, N. HPLC: >95% purity.

Example 43

1-phenyl-2-pyrrolidin-1-ylethyl 3-[(4-fluorobenzoyl)amino]-6,6-dimethyl-4,6-dihydropyrrolo[3,4-c]pyrazole-5(1H)-carboxylate

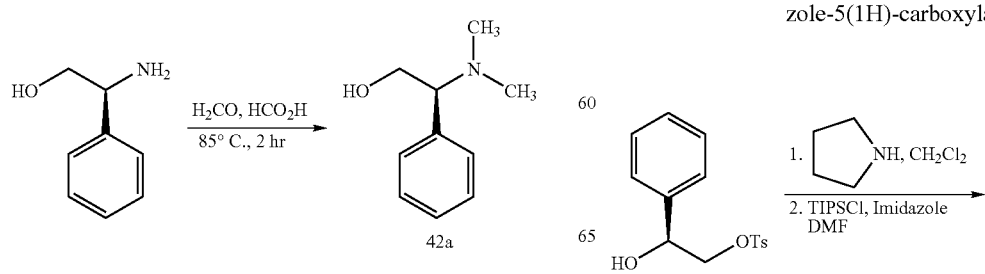

-continued

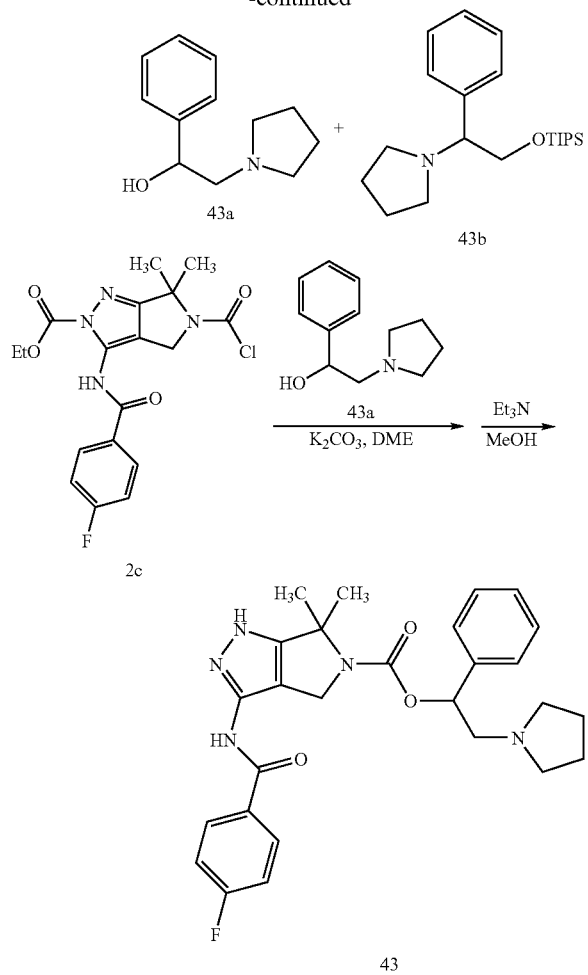

silica gel chromatography (eluting with Jan. 19, 1980 conc. aq. NH$_4$OH/EtOH/EtOAc), affording alcohol 43a (155.9 mg, 32%) as a white solid and silyl ether 43b (135.8 mg, 15%) as a yellow oil. 43a: $^1$H NMR (DMSO-d$_6$) δ: 1.64 (m, 4H), 2.53 (m, 5H, partially obscured by solvent), 2.60 (dd, J=7.8, 12.1 Hz, 1H), 4.62 (br s, 1H), 5.05 (br s, 1H), 7.21 (m, 1H), 7.32 (m, 4H). Anal. (C$_{12}$H$_{17}$NO.0.15H$_2$O) C, H, N. LCMS (APCI, M+H$^+$): 192.4.

Intermediate 2c (210 mg, 0.514 mmol) and alcohol 43a (147.5 mg, 0.771 mmol) were coupled by the method of Example 1, affording 43 (57.3 mg, 22%) as an off-white powder. $^1$H NMR (DMSO-d$_6$) δ: 1.53 (br s, 2H), 1.63 (m, 8H), 2.52 (m, 4H, partially obscured by solvent), 2.74 (m, 1H), [2.85 (m), 3.00 (m) 1H together], [4.43 (m), 4.64 (br s) 2H together], 5.78 (dd, J=5.8, 8.1 Hz, 1H), 7.35 (m, 7H), 8.07 (br s, 2H), 10.97 (m, 1H), [12.24 (br s), 12.49 (br s) 1H together]. Anal. (C$_{27}$H$_{30}$FN$_5$O$_3$.0.7H$_2$O) C, H, N, F. LCMS (APCI, M+H$^+$): 492.4. HRMS: [M+H]$^+$ calc. 492.24054; found 492.24017; error −0.76 ppm.

Example 44

1-methyl-3-phenylpyrrolidin-3-yl 3-[(4-fluorobenzoyl)amino]-6,6-dimethyl-4,6-dihydropyrrolo[3,4-c]pyrazole-5(1H)-carboxylate

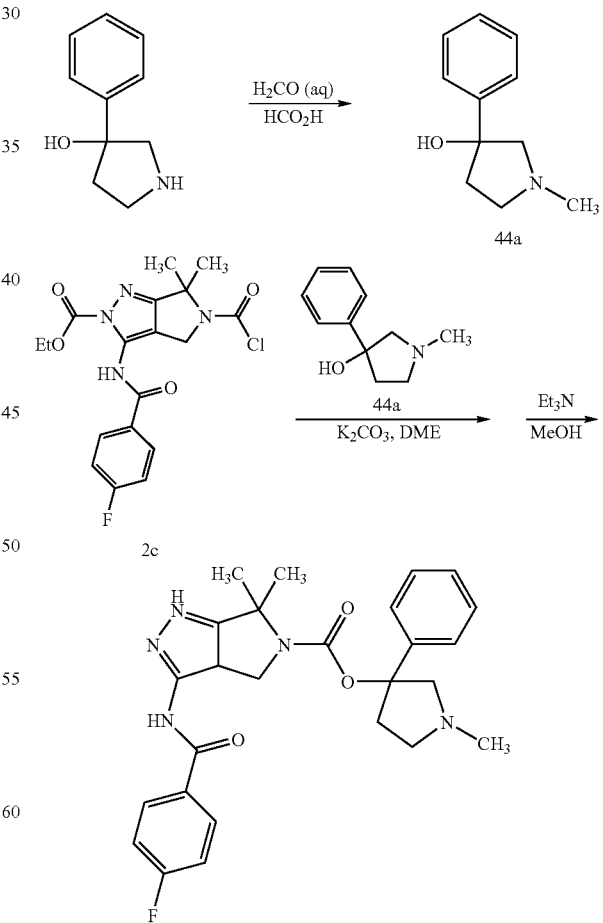

Preparation of Compound 43a:
1-Phenyl-2-pyrrolidin-1-yl-ethanol

Pyrrolidine (1.06 mL, 12.8 mmol) was added to a solution of (S)-(+)-1-phenyl-1,2-ethanediol-2-tosylate (745.8 mg, 2.55 mmol) in dichloromethane (2.55 mL). The mixture was stirred in a 40° C. oilbath for 28 hours. The solvents were evaporated, and the residue dissolved in ethyl acetate (30 mL). Saturated aqueous sodium bicarbonate solution (5 mL) and brine (5 mL) were added, and the layers separated. The aqueous layer was back-extracted with ethyl acetate (2×20 mL). The combined organic extracts were dried over magnesium sulfate, filtered, and concentrated, affording a mixture of 1-Phenyl-2-pyrrolidin-1-yl-ethanol and 2-Phenyl-2-pyrrolidin-1-yl-ethanol as a yellow oil (541.2 mg). Because the presence of isomeric products suggests the formation of an expoxide intermediate, racemization may have occurred in this reaction. The mixture of alcohols was dissolved in DMF (1.45 mL), triisopropylsilyl chloride (154 μL, 0.72 mmol) and imidazole (99 mg, 1.45 mmol) were added, and the solution stirred at room temperature for 42 hours. After evaporation of solvent, the residue was partitioned between ethyl acetate (20 mL) and saturated aqueous sodium bicarbonate solution (10 mL). The aqueous layer was back-extracted with ethyl acetate (2×10 mL). The combined organic extracts were dried over magnesium sulfate, filtered, concentrated, and purified by Preparation of compound 44a:
1-Methyl-3-phenyl-pyrrolidin-3-ol A mixture of 3-Phenyl-pyrrolidin-3-ol (2.01 g, 11.67 mmol), 5.8 mL of 88% aqueous formic acid, and 11.7 mL of 37% aqueous formaldehyde solution was stirred in a 100° C. oilbath for 1.5 hours, attaining a maximum internal temperature of 86° C. After cooling to room temperature, the solution was extracted with 20 mL diethyl ether, then the remaining aqueous layer was basified with 50% aqueous sodium hydroxide to bring the pH=8. The basic solution was extracted with ethyl acetate (3×25 mL). The combined ethyl acetate extracts were dried over magnesium sulfate, filtered, concentrated, and purified by silica gel chromatography (eluting with Jan. 19, 1980 conc. aq. NH$_4$OH/EtOH/EtOAc) to give 44a (260.4 mg, 12%) as a yellow liquid. $^1$H NMR (DMSO-d$_6$) δ: 2.02 (m, 1H), 2.08 (m, 1H), 2.29 (s, 3H), 2.63 (d, J=9.6 Hz, 1H), 2.71 (m, 2H), 2.79 (d, J=9.6 Hz, 1H), 5.21 (s, 1H), 7.17 (t, J=7.2 Hz, 1H), 7.29 (t, J=7.6 Hz, 1H), 7.47 (t, J=7.3 Hz, 1H). Anal. (C$_{11}$H$_{15}$NO.0.16H$_2$O) C, H, N. LCMS (APCI, M+H$^+$): 178.4.

Intermediate 2c (201.1 mg, 0.49 mmol) and alcohol 44a (131 mg, 0.74 mmol) were coupled by the method of Example 1, affording 44 (72.1 mg, 30%) as a pale yellow solid. $^1$H NMR (DMSO-d$_6$) δ: [1.52 (d, J=9.3 Hz), 1.76 (J=14.4 Hz) 6H together], 2.24 (septet, J=7.3 Hz, 1H), [2.30 (s), 2.31 (s) 3H together], 2.39 (m, 1H), 2.57 (quint, J=8.1 Hz, 1H), 2.76 (m, 1H), 2.85 (t, J=11.1 Hz, 1H), 3.22 (t, J=10.0 Hz, 1H), [4.37 (br s), 4.69 (br s) 2H together], 7.21 (m, 1H), 7.32 (m, 6H), 8.08 (m, 2H), 10.97 (br m, 1H), 12.48 (br m, 1H). Anal. (C$_{26}$H$_{28}$FN$_5$O$_3$.0.45H$_2$O) C, H, N, F. LCMS (APCI, M+H$^+$): 478.4. HRMS: [M+H]$^+$ calc. 478.2249; found 478.2240; error −1.83 ppm.

Example 45

(1S,2S)-2-(dimethylamino)-1-phenylpropyl 3-[(4-fluorobenzoyl)amino]-6,6-dimethyl-4,6-dihydropyrrolo[3,4-c]pyrazole-5(1H)-carboxylate

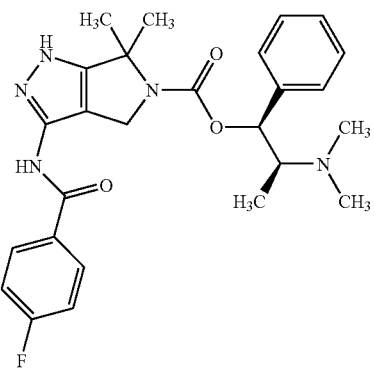

45

To a solution of (1S,2S)-2-dimethylamino-1-phenylpropan-1-ol (210 mg, 1.18 mmol) in THF (2 ml) was added 1M lithium bis(trimethylsilyl)amide solution in hexane (1.17 ml) at room temperature. The reaction mixture was stirred at room temperature for 20 minutes and then added ethyl 5-(chlorocarbonyl)-3-[(4-fluorobenzoyl)amino]-6,6-dimethyl-5,6-dihydropyrrolo[3,4-c]pyrazole-2(4H)-carboxylate 2c (200 mg, 0.49 mmol). The resulting mixture was stirred at room temperature for one hour and then concentrated to dryness under reduced pressure. The crude product was purified by prep-HPLC and lyophilized to give the title compound 45 (20 mg) in 0.4% yield as white solid. $^1$H NMR (400 MHz, MeOD) δ ppm: 0.81 (d, J=7.05 Hz, 3H), 1.58 (s, 2H), 1.71 (s, 3H), 1.88 (d, J=23.42 Hz, 1H), 2.48 (s, 6H) 3.17-3.29 (m, 1H), 4.70 (br. s., J=13.09 Hz, 2H), 5.69 (d, J=9.32 Hz, 1H), 7.20-7.34 (m, 3H), 7.35-7.46 (m, 4H), 8.03 (dd, J=8.81, 5.29 Hz, 2H). Anal. (C$_{26}$H$_{30}$N$_5$O$_3$F.0.2HOAc.0.5H$_2$O) C, H, N. HPLC: >95% purity.

Example 46

3-(benzoylamino)-N-[(1S)-2-(dimethylamino)-1-phenylethyl]-6,6-dimethyl-4,6-dihydro pyrrolo[3,4-c]pyrazole-5(1H)-carboxamide

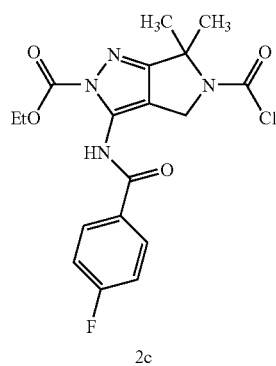
2c

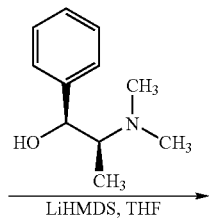

LiHMDS, THF

HBTU, Me$_2$NH$_2$Cl
K$_2$CO$_3$, CH$_2$Cl$_2$

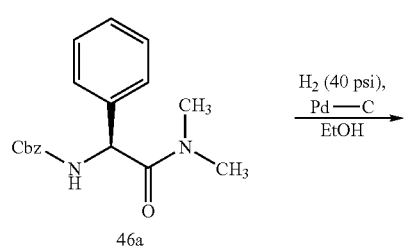
46a

H$_2$ (40 psi),
Pd—C
EtOH

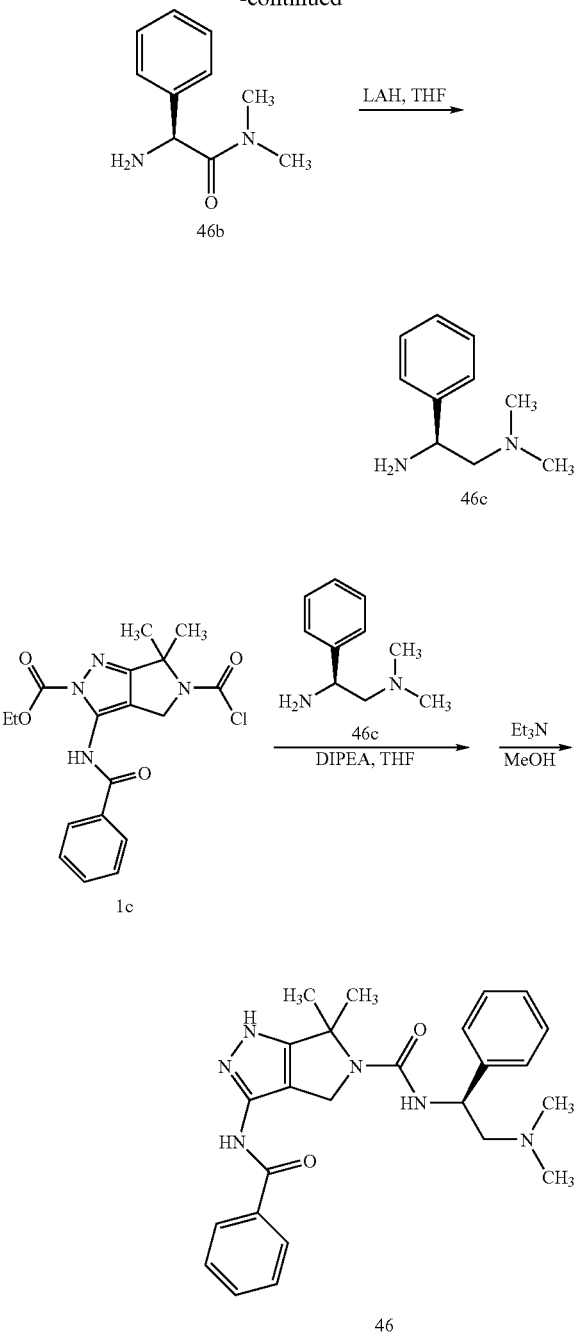

Preparation of Compound 46a: benzyl [(1S)-2-(dimethylamino)-2-oxo-1-phenylethyl]-carbamate To a mixture of (2S)-{[(benzyloxy)carbonyl]amino}(phenyl)acetic acid (196 g, 688 mmol), HBTU (261 g, 688 mmol), and dichloromethane (2.8 L) were added sequentially potassium carbonate (285 g, 2.06 mol) and dimethylamine hydrochloride (84.1 g, 1031 mmol). The reaction mixture was heated at 40° C. overnight. After cooling to room temperature, the solids were filtered, washed with ethyl acetate (2×500 mL) and the filtrate concentrated to a residue. Water (1 L) was added to the residue and the solution kept in an ultrasonic cleanser for 2 hours. The precipitated solids were collected and washed with water (4×300 mL), hexane (2×500 mL), and dried under vacuum for 24 hours. The solid crude product was dissolved in chloroform (300 mL) and un-dissolved solids were filtered off. The filtrate was concentrated to dryness and the residue dissolved in hexane/ethyl acetate (2:1) (250 mL) and allowed to stand at room temperature overnight. The resulting crystals were collected by filtration, washed with hexane/ethyl acetate (3:1) (100 mL) and dried in high vacuum at 40° C. for 24 hours to give 46a (100.0 g, 47%) as a white crystalline solid. $^1$H NMR (CDCl$_3$) δ: 2.88 (s, 3H), 2.98 (s, 3H), 5.01 (d, J=12.2 Hz, 1H), 5.11 (d, J=12.2 Hz, 1H), 5.58 (d, J=7.5 Hz, 1H), 6.37 (d, J=7.2 Hz, 1H), 7.32 (m, 10H).

Preparation of Compound 46b:
(2S)-2-amino-N,N-dimethyl-2-phenylacetamide

To a solution of 46a (80.0 g, 256 mmol) in ethanol (1.2 L) was added a slurry of Pd/C (10%, 9.0 g) in ethyl acetate (50 mL). The reaction mixture was shaken in Parr-apparatus under hydrogen (40 psi) overnight. The catalyst was removed by filtration through celite. The filter pad was washed with ethanol (2×200 mL) and the combined filtrate was concentrated to give 46b (40.2 g, 88%) as a white solid. $^1$H NMR (CDCl$_3$) δ: 2.85 (s, 3H), 2.99 (s, 3H), 4.72 (s, 1H), 7.33 (m, 5H).

Preparation of Compound 46c:
N-[(2S)-2-amino-2-phenylethyl]-N,N-dimethylamine

A flask containing dry THF (2300 mL) under a nitrogen atmosphere was chilled by an ice-water bath. Lithium aluminum hydride pellets (59.0 g, 1555 mmol) were added. To this LAH suspension, a solution of amide 46b (123.0 g, 691 mmol) in dry THF (800 mL) was slowly added over approximately 1 hour. The resulting reaction mixture was heated at reflux for 5 hours, then cooled to 10° C. The cooled reaction mixture was slowly quenched with saturated sodium sulfate solution (380 mL) and stirred overnight. The precipitated solids were filtered off and washed with ethyl acetate (4×500 mL). The filtrate was concentrated to a residue that was purified on silica gel column (10% methanol, 5% triethylamine in chloroform) to afford 46c (66.7 g, 59%) as a light yellow liquid. $^1$H NMR (CDCl$_3$) δ: 2.24 (dd, J=3.6, 12.1 Hz, 1H), 2.29 (s, 6H), 2.47 (dd, J=10.6, 12.1 Hz, 1H), 4.07 (dd, J=3.6, 10.4 Hz, 1H), 7.24 (m, 1H), 7.37 (m, 4H).

To a solution of ethyl 3-(benzoylamino)-5-(chlorocarbonyl)-6,6-dimethyl-5,6-dihydropyrrolo[3,4-c]pyrazole-2(4H)-carboxylate 1c (120 mg, 0.31 mmol) and N-[(2S)-2-amino-2-phenylethyl]-N,N-dimethylamine (76 mg, 1.5 eq) in THF (3 ml) was added diisopropylethylamine (54 ul, 1.0 eq) at room temperature. The reaction mixture was stirred at reflux for 2 hours and then evaporated to dryness. The residue was dissolved in methanol (1 ml) and triethylamine (1 ml), stirred at room temperature for 2 hours, and again evaporated to dryness. The crude product was purified by prep-HPLC and lyophilized to give the title compound 46 in 20% yield (27 mg) as white foam. $^1$H NMR (400 MHz, MeOD) δ ppm: 1.60 (s, 3H), 1.67 (s, 3H), 2.42 (s, 6H), 2.56-2.70 (m, 1H), 2.84-3.02 (m, 1H), 4.55-4.71 (m, 2H), 5.01 (dd, J=10.36, 4.04 Hz, 1H), 7.16 (t, J=7.20 Hz, 1H), 7.21-7.34 (m, 4H), 7.37-7.54 (m, 3H), 7.82-7.92 (m, 2H). Anal. (C$_{25}$H$_{30}$N$_6$O$_2$.1.0HOAc.0.6H$_2$O) C, H, N. HPLC: >95% purity.

| Structure and Example # | Chemical name, Analytical data and comments |
|---|---|
| 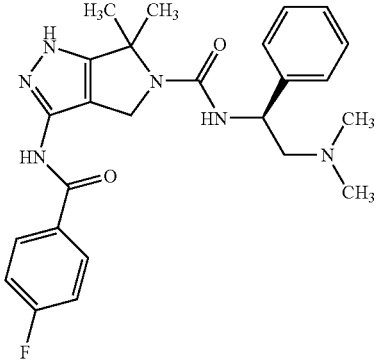<br>47 | N-[(1S)-2-(dimethylamino)-1-phenylethyl]-3-[(4-fluorobenzoyl)amino]-6,6-dimethyl-4,6-dihydropyrrolo[3,4-c]pyrazole-5(1H)-carboxamide. $^1$H NMR (400 MHz, CDCl$_3$) δ ppm: 163 (s, 3H), 1.71 (s, 3H), 2.36 (s, 6H), 2.42-2.50 (m, 1H), 2.79-2.94 (m, 1H), 4.57-4.70 (m, 2H), 4.81-4.96 (m, 1H), 5.85-5.95 (m, 1H), 6.99-7.30 (m, 7H), 7.86-7.95 (m, 2H), 10.27 (s, 1H). Anal. (C$_{25}$H$_{29}$FN$_6$O$_2$•0.81 HOAc) C, H, N. LCMS (APCI, M + H$^+$): 465.1. Method of Example 46: Made in 45% yield from intermediate 2c using amine 46c. |
| 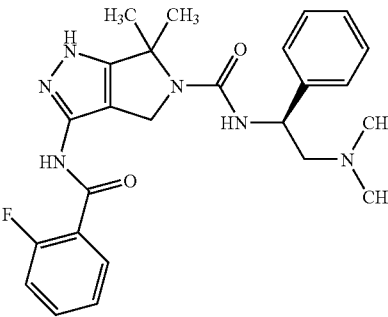<br>48 | N-[(1S)-2-(dimethylamino)-1-phenylethyl]-3-[(2-fluorobenzoyl)amino]-6,6-dimethyl-4,6-dihydropyrrolo[3,4-c]pyrazole-5(1H)-carboxamide. $^1$H NMR (400 MHz, MeOD) δ ppm: 1.68 (s, 3H), 1.75 (s, 3H), 2.45 (s, 6H), 2.62 (dd, J = 12.72, 4.41 Hz, 1H), 2.91-3.03 (m, 1H), 4.67-4.82 (m, 2H), 5.07 (dd, J = 10.70, 4.41 Hz, 1H), 7.21-7.43 (m, 7H), 7.52-7.66 (m, 1H), 7.78-7.89 (m, 1H), Anal. (C$_{25}$H$_{29}$N$_6$O$_2$F•0.2 HOAc•0.4 H$_2$O) C, H, N. HPLC: >95% purity. Method of Example 46: Made in 37% yield from intermediate 3c using amine 46c. |
| 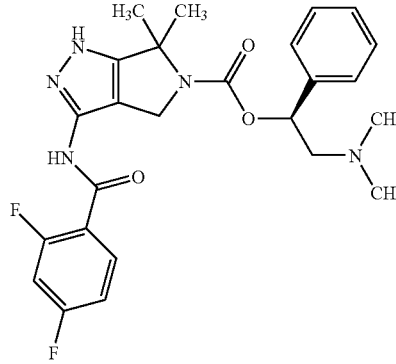<br>49 | 3-[(2,4-difluorobenzoyl)amino]-N-[(1S)-2-(dimethylamino)-1-phenylethyl]-6,6-dimethyl-4,6-dihydropyrrolo[3,4-c]pyrazole-5(1H)-carboxamide. $^1$H NMR (400 MHz, MeOD) δ ppm: 1.68 (s, 3H), 1.75 (s, 3H), 2.44 (s, 6H), 2.61 (dd, J = 12.84, 4.28 Hz, 1H), 2.93-3.01 (m, 1H), 4.74 (m, 2H), 5.07 (dd, J = 10.58, 4.53 Hz, 1H), 7.10-7.43 (m, 7H), 7.85-7.93 (m, 1H). Anal. (C$_{26}$H$_{28}$F$_2$N$_6$O$_2$•0.2 H$_2$O•0.2 HOAc) C, H, N. LCMS (APCI, M + H$^+$): 483.3. Method of Example 46: Made in 35% yield from intermediate 4c using amine 46c. |
| 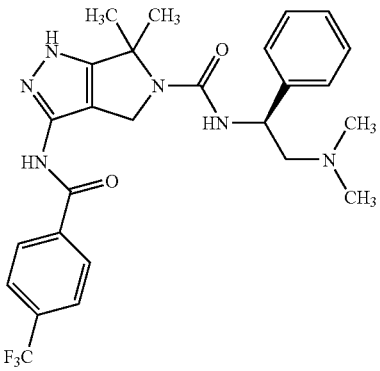<br>50 | N-[(1S)-2-(dimethylamino)-1-phenylethyl]-6,6-dimethyl-3-{[4-(trifluoromethyl)benzoyl]amino}-4,6-dihydropyrrolo[3,4-c]pyrazole-5(1H)-carboxamide. $^1$H NMR (400 MHz, MeOD) δ ppm: 1.72 (s, 3H), 1.79 (s, 3H), 2.61 (s, 6H), 2.86 (dd, J = 12.81, 4.33 Hz, 1H), 3.16 (dd, J = 12.81, 11.11 Hz, 1H), 4.68-4.81 (m, 2H), 5.17 (dd, J = 10.83, 4.24 Hz, 1H), 7.26-7.48 (m, 5H), 7.86 (d, J = 8.10 Hz, 2H), 8.15 (d, J = 8.10 Hz, 2H). Anal. (C$_{26}$H$_{29}$N$_6$O$_2$F$_3$•0.7 HOAc•0.3 H$_2$O) C, H, N. HPLC: >95% purity. Method of Example 46: The title compound was made in 24% yield. |

-continued

| Structure and Example # | Chemical name, Analytical data and comments |
|---|---|
| 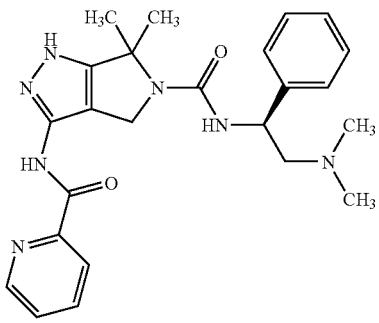<br>51 | N-[(1S)-2-(dimethylamino)-1-phenylethyl]-6,6-dimethyl-3-[(pyridin-2-ylcarbonyl)amino]-4,6-dihydropyrrolo[3,4-c]pyrazole-5(1H)-carboxamide. $^1$H NMR (400 MHz, MeOD) δ ppm: 1.69 (s, 3H), 1.76 (s, 3H), 2.52 (s, 6H), 2.72 (dd, J = 12.97, 4.15 Hz, 1H), 3.06 (t, J = 11.83 Hz, 1H), 4.72-4.85 (m, 2H), 5.11 (dd, J = 10.83, 4.28 Hz, 1H), 7.23-7.30 (m, J = 7.18, 7.18 Hz, 1H), 7.31-7.44 (m, 4H), 7.62 (dd, J = 6.67, 5.67 Hz, 1H), 8.03 (t, J = 7.68 Hz, 1H), 8.20 (d, J = 7.81 Hz, 1H), 8.71 (d, J = 4.53 Hz, 1H). Anal. ($C_{24}H_{29}N_7O_2$•0.3 HOAc•0.3 $H_2O$) C, H, N. HPLC: >95% purity. Method of Example 46: Made in 54% yield from intermediate 6c using amine 46c. |
| 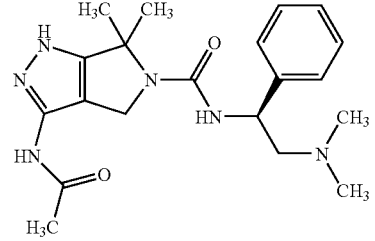<br>52 | 3-(acetylamino)-N-[(1S)-2-(dimethylamino)-1-phenylethyl]-6,6-dimethyl-4,6-dihydropyrrolo[3,4-c]pyrazole-5(1H)-carboxamide. $^1$H NMR (DMSO-$d_6$) δ 1.52 (s, 3H), 1.59 (s, 3H), 1.98 (s, 3H), 2.20 (s, 6H), 2.37-2.45 (m, 1H), 2.62-2.69 (m, 1H), 4.43 (s, 2H), 4.85 (s, 1H), 6.17 (s, 1H), 7.18 (t, J = 8.0 Hz, 1H), 7.28 (t, J = 8.0 Hz, 2H), 7.34 (d, J = 4.0 Hz, 2H), 10.37 (s, 1H), 12.24 (s, 1H); Anal. ($C_{20}H_{28}N_6O_2$•0.75 $H_2O$•0.2 EtOAc) C, H, N. HRMS [M + H]$^+$ calcd. 385.2347; found 385.2345. Method of Example 46: Made in 67% yield from intermediate 7c using amine 46a. |
| 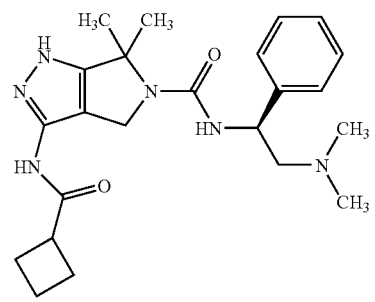<br>53 | 3-[(cyclobutylcarbonyl)amino]-N-[(1S)-2-(dimethylamino)-1-phenylethyl]-6,6-dimethyl-4,6-dihydropyrrolo[3,4-c]pyrazole-5(1H)-carboxamide. $^1$H NMR (dmso-$d_6$) δ 1.52 (s, 3H), 1.60 (s, 3H), 1.76-1.81 (m, 1H), 1.88-1.97 (m, 1H), 2.03-2.07 (m, 2H), 2.14-2.23 (m, 4H), 2.26-2.45 (m, 4H), 3.19-3.27 (m, 2H), 4.48-4.55 (m, 2H), 4.98 (s, 1H), 6.38 (s, 1H), 7.21 (t, J = 8.0 Hz, 1H), 7.31 (t, J = 8.0 Hz, 2H), 7.38 (d, J = 8.0 Hz, 2H), 10.23 (s, 1H), 12.25 (s, 1H), Anal. ($C_{23}H_{32}N_6O_2$•1.5 $H_2O$•0.1 EtOAc) C, H, N. HRMS [M + H]$^+$ calcd. 425.2660; found 425.2668. Method of Example 46: Made in 84% yield from intermediate 11c using amine 46a. |
| 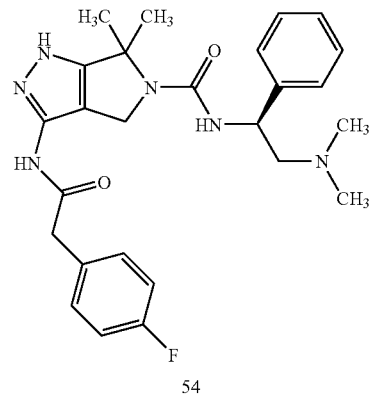<br>54 | N-[(1S)-2-(dimethylamino)-1-phenylethyl]-3-{[(4-fluorophenyl)acetyl]amino}-6,6-dimethyl-4,6-dihydropyrrolo[3,4-c]pyrazole-5(1H)-carboxamide. $^1$H NMR (dmso-$d_6$) δ: 1.50 (s, 3H), 1.58 (s, 3H), 2.15 (s, 6H), 2.34 (dd, J = 6.3, 12.6 Hz, 1H), 2.61 (dd, J = 9.1, 11.9 Hz, 1H), 3.61 (s, 2H), 4.42 (m, 2H), 4.82 (q, J = 8.3 Hz, 1H), 6.18 (br d, J = 6.8 Hz, 1H), 7.15 (q, J = 9.1 Hz, 3H), 7.26 (q, J = 7.6 Hz, 2H), 7.32 (m, 4H), 10.67 (br s, 1H), 12.29 (br s, 1H); Anal. ($C_{26}H_{31}FN_6O_2$•0.6 $H_2O$) C, H, N. HRMS: [M + H]$^+$ calc. 479.2566; found 479.2550; error −3.29 ppm. Method of Example 46: Made in 45% yield from intermediate 18c using amine 46a. |

| Structure and Example # | Chemical name, Analytical data and comments |
|---|---|
| 55 | N-[(1S)-2-(dimethylamino)-1-phenylethyl]-3-{[(4-methoxyphenyl)acetyl]amino}-6,6-dimethyl-4,6-dihydropyrrolo[3,4-c]pyrazole-5(1H)-carboxamide. $^1$H NMR (dmso-d$_6$) δ: 1.50 (s, 3H), 1.58 (s, 3H), 2.15 (s, 6H), 2.34 (dd, J = 6.1, 12.1 Hz, 1H), 2.60 (dd, J = 9.4, 12.1 Hz, 1H), 3.52 (s, 2H), 3.72 (s, 3H), 4.41 (m, 2H), 4.82 (d of t, J$_d$ = 8.3 Hz, J$_t$ = 7.1 Hz, 1H), 6.18 (br d, J = 7.6 Hz, 1H), 6.87 (d, J = 8.6 Hz, 2H), 7.16 (t, J = 7.2 Hz, 1H), 7.21 (d, J = 8.6 Hz, 2H), 7.26 (t, J = 7.6 Hz, 2H), 7.34 (d, J = 7.1 Hz, 2H), 10.60 (br s, 1H), 12.27 (br s, 1H). Anal. (C$_{27}$H$_{34}$N$_6$O$_3$•0.7 H$_2$O) C, H, N. HRMS: [M + H]$^+$ calc. 491.2765; found 491.2758; error −1.42 ppm. Method of Example 46: Made in 60% yield from intermediate 19c using amine 46a. |
| 56 | N-[(1S)-2-(dimethylamino)-1-phenylethyl]-6,6-dimethyl-3-({[trans-2-phenylcyclopropyl]carbonyl}amino)-4,6-dihydropyrrolo[3,4-c]pyrazole-5(1H)-carboxamide. $^1$H NMR (dmso-d$_6$) δ: 1.34 (br s, 1H), 1.44 (br s, 1H), 1.52 (s, 3H), 1.59 (s, 3H), 2.15 (m, 1H), 2.18 (s, 6H), 2.34 (m, 2H), 2.65 (br t, J = 10.0 Hz, 1H), 4.47 (br s, 2H), 4.85 (q, J = 7.3 Hz, 1H), 6.21 (br s, 1H), 7.16 (m, 4H), 7.28 (t, J = 6.6 Hz, 4H), 7.36 (d, J = 7.6 Hz, 2H), 10.72 (br s, 1H), 12.27 (br s, 1H). Anal. (C$_{28}$H$_{34}$N$_6$O$_2$•0.5 H$_2$O) C, H, N. HRMS: [M + H]$^+$ calc. 487.2816; found 487.2813; error −0.62 ppm. Method of Example 46: Made in 46% yield from intermediate 20c using amine 46a. |

Example 57

N-[(1S)-2-(dimethylamino)-1-phenylethyl]-6,6-dimethyl-3-[(2-thienylcarbonyl)amino]-4,6-dihydropyrrolo[3,4-c]pyrazole-5(1H)-carboxamide

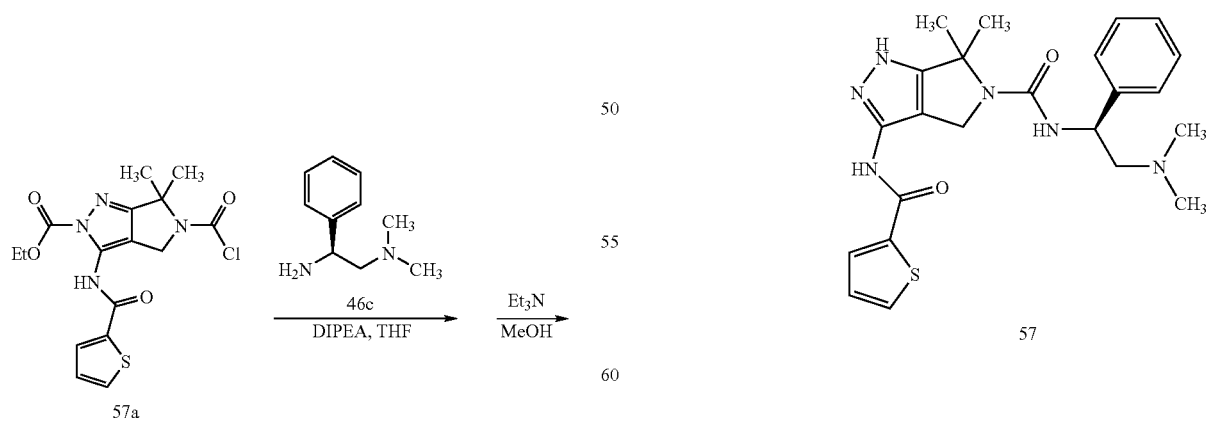

Preparation of Compound 57a: ethyl 5-(chlorocarbonyl)-3-(thiophene-2-carboxamido)-6,6-dimethyl-5,6-dihydropyrrolo[3,4-c]pyrazole-2(4H)-carboxylate The title compound was made in 71% overall yield from intermediate I(g) using thiophene-2-carbonyl chloride by the method of example 1c. $^1$H NMR (400 MHz, CHLOROFORM-d) δ ppm: 1.51 (t, J=7.07 Hz, 3H), 1.56 (s, 6H), 4.60 (q, J=7.24 Hz, 2H), 5.03 (s, 2H), 7.17 (dd, J=4.93, 3.92 Hz, 1H), 7.65 (dd, J=4.93, 1.14 Hz, 1H), 7.69 (dd, J=3.79, 1.26 Hz, 1H), 10.98 (br. s., 1H).

The title compound was made in 53% yield from 57a by the procedure similar to example 46: $^1$H NMR (400 MHz, MeOD) δ ppm: 1.70 (s, 3H), 1.77 (s, 3H), 2.89 (s, 6H), 3.27 (dd, J=13.01, 4.17 Hz, 1H), 3.44-3.53 (m, 1H), 4.67 (d, J=12 Hz, 1H), 4.76 (d, J=12 Hz, 1H), 5.33 (dd, J=11.62, 4.04 Hz, 1H), 7.17-7.22 (m, 1H), 7.28-7.47 (m, 5H), 7.73-7.78 (m, 1H), 7.87-7.93 (m, 1H). Anal. ($C_{23}H_{28}N_6O_2S·1HCl·1.25HOAc$) C, H, N. LCMS (APCI, M+H$^+$): 453.3.

Example 58

3-(benzoylamino)-6,6-dimethyl-N-[trans-2-phenyl-cyclopropyl]-4,6-dihydropyrrolo[3,4-c]pyrazole-5(1H)-carboxamide To a solution of ethyl 3-(benzoylamino)-6,6-dimethyl-5,6-dihydropyrrolo[3,4-c]pyrazole-2(4H)-carboxylate 1b (85 mg, 0.26 mmol) and triethylamine (109 ul, 3 eq.) in dichloromethane (3 ml) was added trans-2-phenylcyclopropyl isocyanate (54 ul, 1.4 eq). The resulting mixture was stirred at room temperature for 2 hours and then evaporated to dryness. The residue was dissolved in methanol (1 ml) and triethylamine (1 ml), stirred at room temperature for 19 hours, and again evaporated to dryness. The crude product was purified by prep-HPLC and lyophilized to give the title compound 58 in 58% yield (63 mg) as white foam. $^1$H NMR (400 MHz, MeOD) δ ppm: 1.01-1.16 (m, 2H), 1.66 (d, J=3.54 Hz, 6H), 1.92-2.02 (m, 1H), 2.64-2.75 (m, 1H), 4.45 (s, 2H), 6.99-7.09 (m, 3H), 7.09-7.19 (m, 2H), 7.37-7.55 (m, 3H), 7.80-7.89 (m, 2H). Anal. ($C_{24}H_{25}N_5O_2·0.1HOAc·0.6H_2O$) C, H, N, S. HPLC: >95% purity.

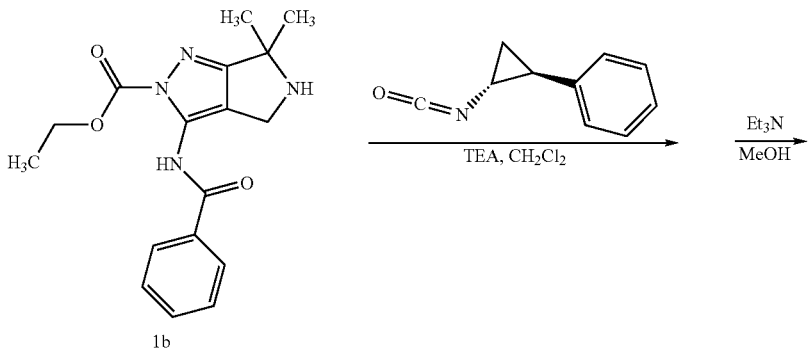

1b

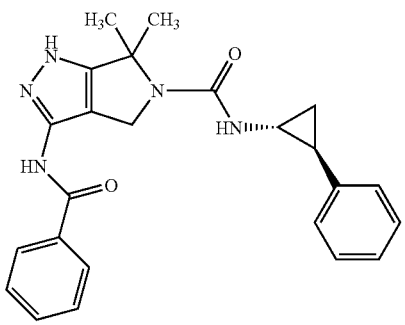

58

Example 59

3-(benzoylamino)-N-(1-benzylpyrrolidin-3-yl)-6,6-dimethyl-4,6-dihydropyrrolo[3,4-c]pyrazole-5(1H)-carboxamide

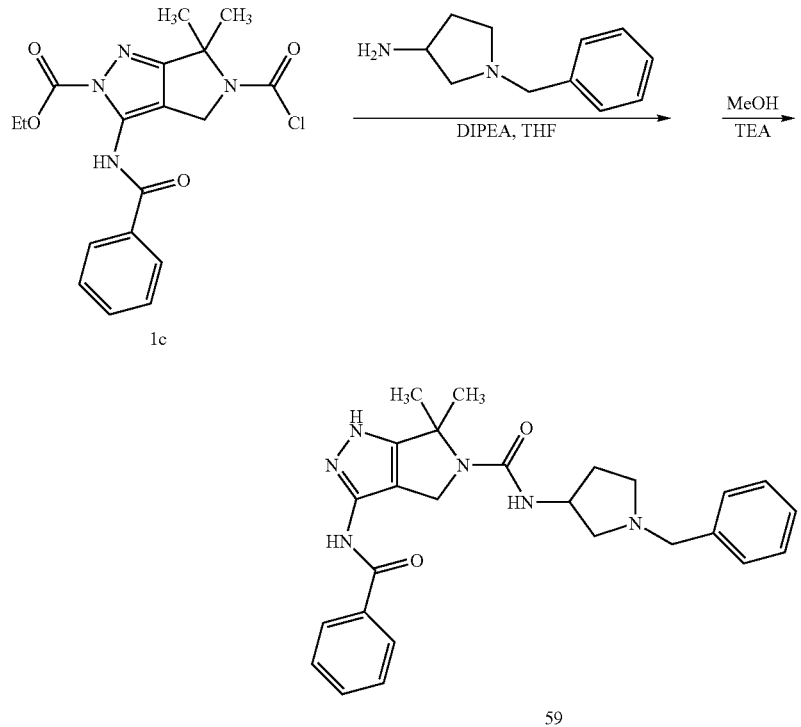

Examples 59-63 were generated in a library format using a general procedure:

To a 10×95 mm test tube were added one 3×6 mm stir bar, the appropriate carbamyl chloride solution 1c (0.1 M in THF, 80 μmol, 1.0 eq.) the appropriate amine solution, (0.1 M in THF, 80 μmol, 1.0 eq) and DIPEA solution (1 M in THF, 80 μmol, 1.0 equiv). The reaction was stirred at 80° C. for 16 h. MeOH (500 μL) and TEA (500 μL) were added, and the reaction mixture was allowed to stir at RT overnight. The solvents were evaporated, and the residue containing product and DIPEA-HCl was reconstituted in DMSO. Purification using super critical fluid chromatography (SFC) gave the desired product. 59 in 30% yield. $^1$H NMR (500 MHz, DMSO) δ ppm 1.59 (s, 11H) 1.92 (s, 1H) 2.48 (d, J=2.47 Hz, 1H) 2.50 (s, 1H) 4.34 (s, 3H) 4.45 (s, 4H) 7.43 (s, 6H) 7.96 (s, 3H) 10.84 (s, 1H) 12.41 (s, 1H). LCMS (APCI, M+H$^+$); 459.

| Structure and Example # | Chemical name, Analytical data and comments |
|---|---|
| ![Example 60 structure] 60 | 3-(benzoylamino)-6,6-dimethyl-N-(1-phenyl-2-pyrrolidin-1-ylethyl)-4,6-dihydropyrrolo[3,4-c]pyrazole-5(1H)-carboxamide. 1H NMR (500 MHz, DMSO-d6) d ppm 1.55 (s, 3H) 1.64 (s, 3H) 1.87 (s, 2H) 1.98 (s, 2H) 3.44-3.53 (m, 2H) 3.55-3.65 (m, 2H) 4.53 (d, J = 12.09 Hz, 1H) 4.74 (d, J = 12.91 Hz, 1H) 5.24-5.28 (m, 1H) 6.72-6.74 (m, 1H) 7.19-7.27 (m, 1H) 7.30-7.36 (m, 2H) 7.39 (d, J = 8.24 Hz, 2H) 7.46 (t, J = 7.83 Hz, 2H) 7.53 (d, J = 7.14 Hz, 1H) 7.98 (d, J = 7.42 Hz, 2H) 10.86 (s, 1H) 12.42 (s, 1H). LCMS (APCI, M + H$^+$); 473. Method of Example 59: Made in 12% yield starting from 1c. |

| Structure and Example # | Chemical name, Analytical data and comments |
|---|---|
| 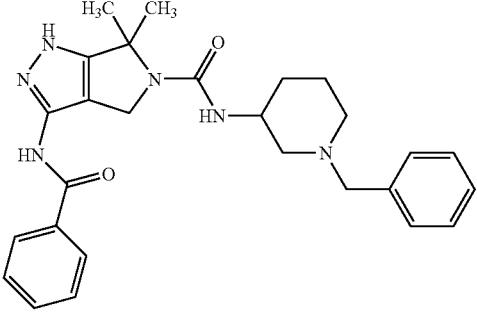<br>61 | 3-(benzoylamino)-N-(1-benzylpiperidin-3-yl)-6,6-dimethyl-4,6-dihydropyrrolo[3,4-c]pyrazole-5(1H)-carboxamide. 1H NMR (500 MHz, DMSO-d6) d ppm 1.20-1.36 (m, 1H) 1.36-1.48 (m, 1H) 1.57 (s, 3H) 1.58 (s, 3H) 1.88-2.02 (m, 2H) 2.27-2.42 (m, 1H) 2.58-2.68 (m, 1H) 3.45 (s, 1H) 3.56-3.67 (m, 1H) 4.33-4.47(m, 3H) 5.60-5.68 (m, 2H) 7.14-7.21 (m, 1H) 7.27 (d, J = 3.02 Hz, 3H) 7.45 (t, J = 7.55 Hz, 2H) 7.53 (t, J = 7.42, 6.32 Hz, 1H) 7.97 (d, J = 7.42 Hz, 1H) 10.80 (s, 1H) 11.95 (s, 1H) 12.35 (s, 1H). LCMS (APCI, M + H$^+$); 473. Method of Example 59: Made in 27% yield starting from 1c. |
| 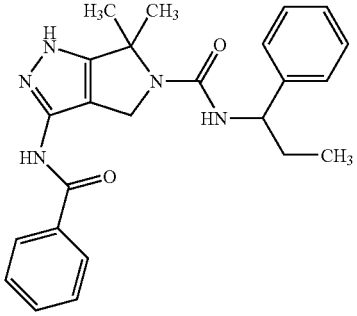<br>62 | 3-(benzoylamino)-6,6-dimethyl-N-(1-phenylpropyl)-4,6-dihydropyrrolo[3,4-c]pyrazole-5(1H)-carboxamide. 1H NMR (500 MHz, DMSO-d6) d ppm 0.81 (t, J = 7.42 Hz, 3H) 1.48-1.56 (m, 3H) 1.60 (s, 3H) 1.62-1.67 (m, J = 7.14, 7.14, 7.14 Hz, 1H) 1.71-1.79 (m, 1H) 4.52 (s, 2H) 4.57 (dd, J = 8.24, 7.69 Hz, 1H) 6.28 (d, J = 8.52 Hz, 1H) 7.13 (t, J = 6.87 Hz, 1H) 7.24 (t, J = 7.55 Hz, 2H) 7.31 (d, J = 7.69 Hz, 2H) 7.45 (t, J = 7.55 Hz, 2H) 7.53 (t, J = 7.14 Hz, 1H) 7.98 (d, J = 7.42 Hz, 2H) 10.79 (s, 1H) 12.35 (s, 1H). LCMS (APCI, M + H$^+$); 418. Method of Example 59: Made in 34% yield starting from 1c. |
| 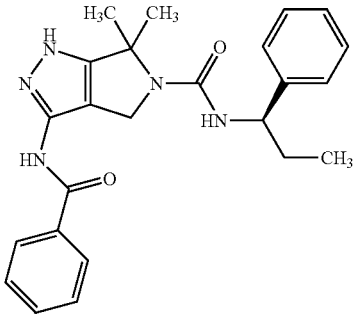<br>63 | 3-(benzoylamino)-6,6-dimethyl-N-[(1R)-1-phenylpropyl]-4,6-dihydropyrrolo[3,4-c]pyrazole-5(1H)-carboxamide. 1H NMR (500 MHz, DMSO-d6) d ppm 0.81 (t, J = 7.42 Hz, 3H) 1.52 (s, 3H) 1.60 (s, 3H) 1.65 (dd, J = 14.01, 6.59 Hz, 1H) 1.70-1.80 (m, 1H) 4.52 (s, 2H) 4.57 (q, J = 7.14 Hz, 1H) 6.28 (d, J = 7.97 Hz, 1H) 7.13 (t, J = 7.14 Hz, 1H) 7.24 (t, J = 7.55 Hz, 2H) 7.31 (d, J = 7.69 Hz, 2H) 7.45 (t, J = 7.55 Hz, 2H) 7.53 (t, J = 6.73 Hz, 1H) 7.98 (d, J = 7.42 Hz, 2H) 10.79 (s, 1H) 12.35 (s, 1H). LCMS (APCI, M + H$^+$); 418. Method of Example 59: Made in 25% yield starting from 1c. |

Example 64

N-[(1S)-2-amino-1-phenylethyl]-3-(benzoylamino)-6,6-dimethyl-4,6-dihydropyrrolo[3,4-c]pyrazole-5(1H)-carboxamide

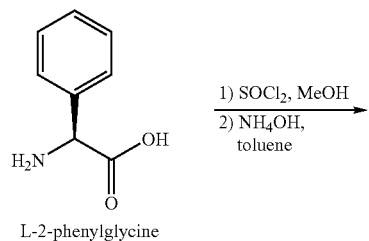

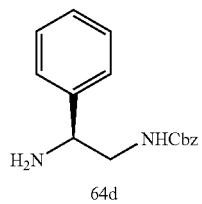

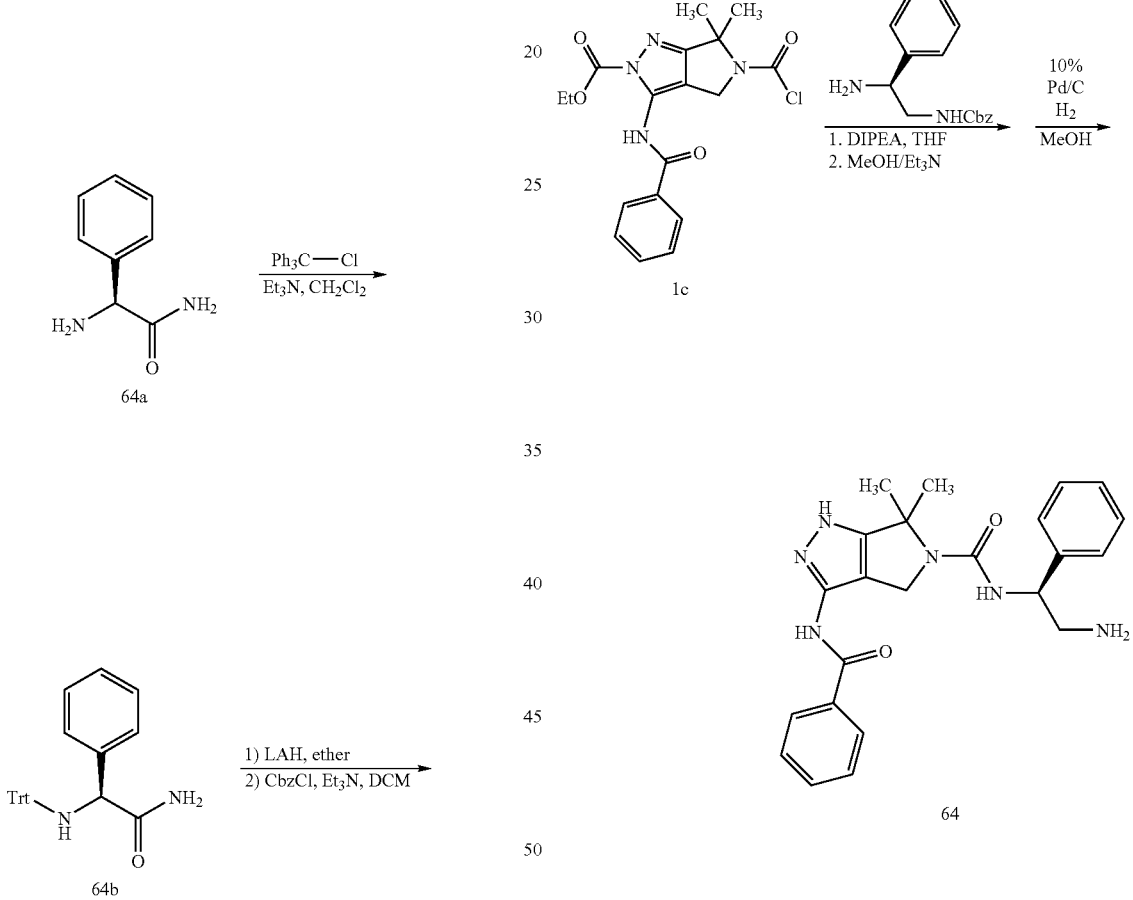

Preparation of compound 64d: (S)-benzyl 2-amino-2-phenylethylcarbamate

SOCl$_2$ (785 g, 6.6 mol) was added dropwise to CH$_3$OH (1.5 L) at 0□, then the reaction mixture was warmed to room temperature and stirred for 2 h. After addition of L-amino-phenyl-acetic acid (250 g, 1.66 mol) portionwise, the mixture was stirred at room temperature overnight. The mixture was evaporated to dryness to give compound a white powder. This white solid was then dissolved in 1.5 liter of toluene.

NH$_3$H$_2$O (875 mL, 28%) was then added dropwise. The resulting mixture was stirred at room temperature for 30 h. The mixture was evaporated to a small volume, and the precipitate was filtered and washed with anhydrous ether to provide compound 64a (120 g, 46%) as a white solid. Compound 64a (120 g, 0.81 mol) and trimethyl amine (78 g, 0.77 mol) in anhydrous CH$_2$Cl$_2$ (1.5 L) was added dropwise a solution of triphenylmethyl chloride (214 g, 0.77 mol) in anhydrous CH$_2$Cl$_2$ (200 mL). The mixture was stirred at room temperature overnight, and TLC (CH$_2$Cl$_2$/MeOH 10:1) indicated that the reaction was complete. The mixture was quenched with water and extracted with CH$_2$Cl$_2$ (500 mL×3). The combined organic layers were washed with brine, dried over Na$_2$SO$_4$ and evaporated to give a pale yellow solid which was washed with ether to afford compound 64b as a white solid (300 g, 95%). Compound 64b (300 g, 0.76 mol) in anhydrous ethyl ether (1.5 L) was added LiAlH$_4$ (300 g, 7.89 mol) at 0□ in portions, then the reaction mixture was warmed to room temperature and stirred for 60 h. TLC (pentane/ethyl acetate 1:1) showed the reaction was complete. To the reaction mixture was added H$_2$O slowly (100 mL) at −10□, and the resulting mixture was then filtered and evaporated to give a pale yellow oil. This yellow pale oil and triethylamine (63.32 g, 0.58 mol) in CH$_2$Cl$_2$ (1.5 L) was added dropwise CbzCl (98 g, 0.58 mol) at 0□. The reaction mixture was stirred at room temperature overnight. The mixture was washed with water and brine. The organic layer was evaporated to dryness and the residue was purified by column chromatography to give compound 64c (150 g, 56%). Compound 64c (150 g, 0.29 mol) in CH$_3$OH (200 L) was added dropwise HCl/CH$_3$OH (200 mL, 7 mol/L) at 0□, and the mixture was stirred overnight. TLC (CH$_2$Cl$_2$/CH$_3$OH 20:1) showed the reaction was complete. The reaction mixture was evaporated until solid precipitated. The solid was filtered and washed with ethyl ether to afford compound 64d (58.6 g, 74%) as a HCl salt. H$^1$ NMR in dmso-d$^6$ δ ppm: 8.8-8.6 (m, 3H, b), 7.55-7.15 (m, 10H), 4.97 (s, 2H), 4.45-4.25 (m, 1H), 3.60-3.40 (m, 2H).

The title compound 64 was prepared in 19% yield by the procedure similar to example 46 except the last step using 10% Pd—C in MeOH to cleave Cbz group. $^1$H NMR (400 MHz, MeOD) δ ppm: 1.70 (s, 3H), 1.77 (s, 3H), 1.91 (s, 2H), 3.21-3.27 (m, 2H), 4.68-4.81 (m, 2H), 5.10 (dd, J=9.35, 5.31 Hz, 1H), 7.28-7.64 (m, 8H) 7.93-7.99 (m, 2H). Anal. (C$_{23}$H$_{26}$N$_6$O$_2$.1.5H$_2$O.1.0HOAc) C, H, N. LCMS (M+H$^+$): 419.2.

Example 65

N-[(3R)-1-benzylpyrrolidin-3-yl]-3-[(cyclobutylcarbonyl)amino]-6,6-dimethyl-4,6-dihydropyrrolo[3,4-c]pyrazole-5(1H)-carboxamide

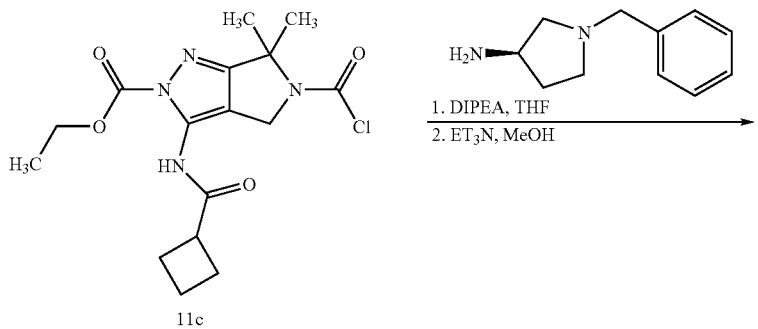

11c

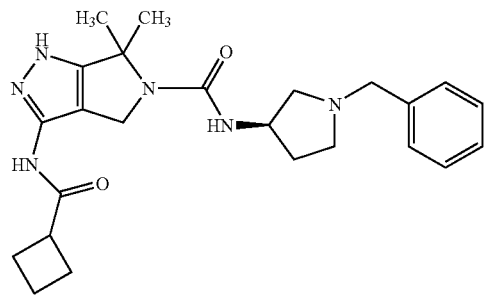

65

The title compound 65 was prepared in 98% yield by the procedure similar to example 46 using (R)-1-benzylpyrrolidin-3-amine. $^1$H NMR (dmso-d$_6$) δ: 1.52 (s, 3H), 1.60 (s, 3H), 1.76-1.81 (m, 1H), 1.88-1.97 (m, 1H), 2.03-2.07 (m, 2H), 2.14-2.23 (m, 4H), 2.26-2.45 (m, 4H), 3.19-3.27 (m, 2H), 4.48-4.55 (m, 2H), 4.98 (s, 1H), 6.38 (s, 1H), 7.21 (t, J=8.0 Hz, 1H), 7.31 (t, J=8.0 Hz, 2H), 7.38 (d, J=8.0 Hz, 2H), 10.23 (s, 1H), 12.25 (s, 1H); Anal. (C$_{23}$H$_{32}$N$_6$O$_2$. 1.5H$_2$O.0.1 EtOAc) C, H, N. HRMS [M+H]$^+$ calcd. 425.2660; found 425.2668.

Example 66

N-{5-[4-(dimethylamino)-3-phenylbutanoyl]-6,6-dimethyl-1,4,5,6-tetrahydropyrrolo[3,4-c]pyrazol-3-yl}-4-fluorobenzamide

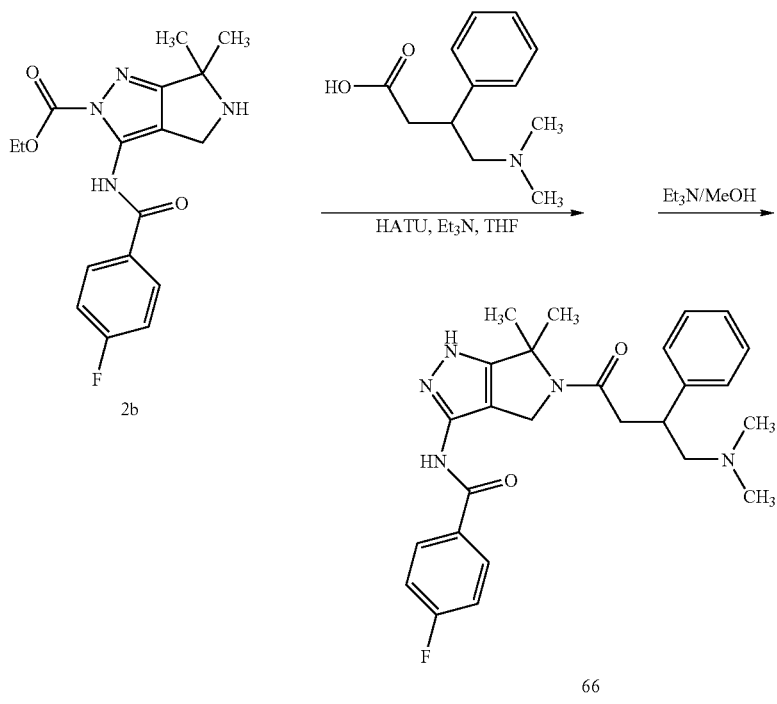

To the mixture of 4-(dimethylamino)-3-phenylbutanoic acid (257.1 mg, 1.24 mmol) (prepared according to Iwao, Junichi, Jpn. Tokkyo Koho (1969), JP44027218) and HATU (542.2 mg, 1.43 mmol) in THF (4 mL), was added the solution of 2b (373.7 mg, 1.08 mmol) and Et$_3$N (0.53 mL, 3.8 mmol) in THF (4 mL). The resulting mixture was stirred for 6 hours at room temperature. Then, the solvents were removed under the reduced pressure. The resulting residue was dissolved in MeOH (5 mL) and Et$_3$N (5 mL), and stirred for 4 hours at room temperature. After removing the solvents, the residue was subjected to prep HPLC to give 66 (100 mg, 20%).

$^1$H NMR (400 MHz, MeOD) δ ppm: 1.59 (s, 3H), 1.75 (s, 3H), 2.50 (m, 6H), 2.68-2.85 (m, 2H), 2.93-3.06 (m, 2H), 3.49-3.59 (m, 1H), 4.57 (d, J=12 Hz, 1H), 4.75 (d, J=12 Hz, 1H), 7.21-7.39 (m, 7H), 7.98-8.04 (m, 2H). Anal. (C$_{26}$H$_{30}$FN$_5$O$_2$.0.8H$_2$O.0.8HOAc) C, H, N. LCMS (M+H$^+$): 464.2.

Example 67

N-{5-[3-(4-chlorophenyl)-4-(dimethylamino)butanoyl]-6,6-dimethyl-1,4,5,6-tetrahydropyrrolo[3,4-c]pyrazol-3-yl}benzamide

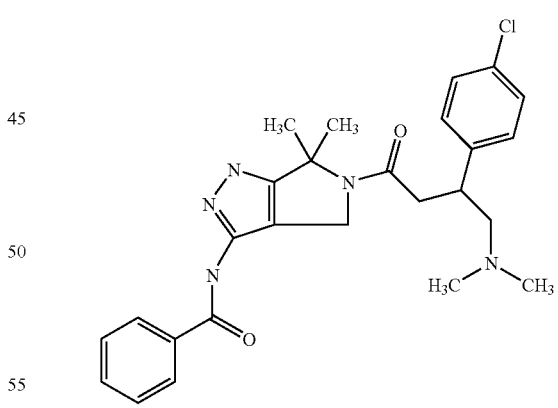

The title compound 67 was prepared in 21% yield according to the same procedure as example 66. The 4-(dimethylamino)-3-(4-chlorophenyl) butanoic acid is prepared according to Iwao, Junichi, Jpn. Tokkyo Koho (1969), JP44027218). 67; $^1$H NMR (400 MHz, MeOD) δ ppm: 1.51 (s, 3H), 1.66 (s, 3H), 2.41 (s, 6H), 2.58-2.65 (m, 1H), 2.69-2.77 (m, 1H), 2.81-2.94 (m, 2H), 3.41-3.49 (m, 1H), 4.54 (d, J=12.38 Hz, 1H), 4.68 (d, J=12.38 Hz, 1H), 7.22-7.28 (m, 4H), 7.40-7.54 (m, 3H), 7.82-7.87 (m, 2H). Anal. (C$_{26}$H$_{30}$ClN$_5$O$_2$.0.95H$_2$O.0.7HOAc) C, H, N. LCMS (M+H$^+$): 482.2.

Example 68
(1S)-2-(dimethylamino)-1-phenylethyl 6,6-dimethyl-3-[(1,3-thiazol-4-ylcarbonyl)amino]-4,6-dihydropyrrolo[3,4-c]pyrazole-5(1H)-carboxylate
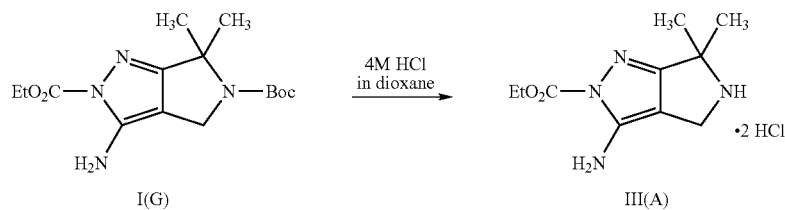
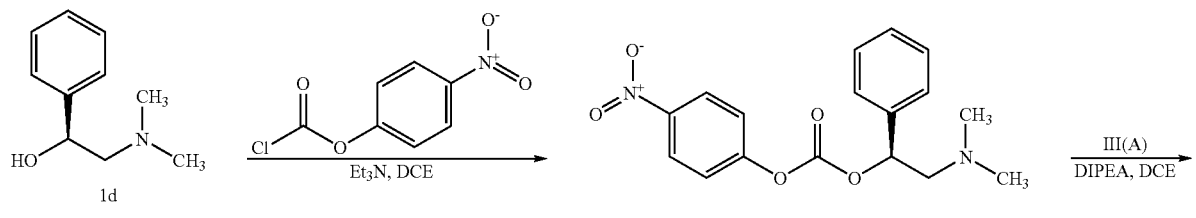
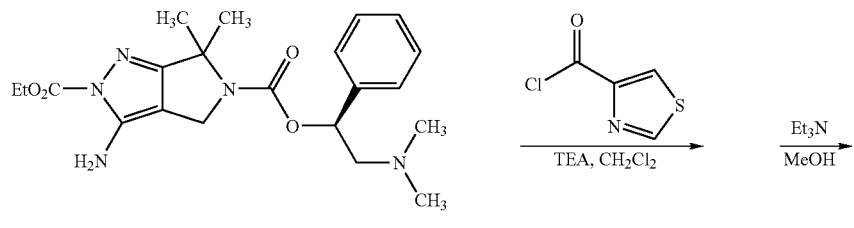
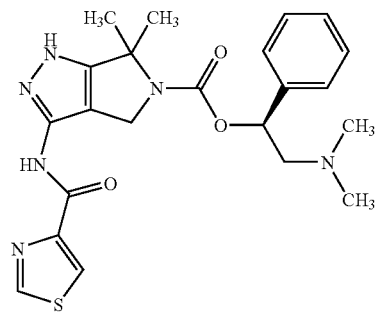
68

Preparation of Compound I(l): ethyl 3-amino-6,6-dimethyl-5,6-dihydropyrrolo[3,4-c]pyrazole-2(4H)-carboxylate dihydrochloride To a stirred slurry of I(g) (40.00 g, 123.3 mmol) in ethanol (270 mL) was added 4 M HCl solution in dioxane (155 mL) dropwise. The resulting clear solution was stirred at room temperature overnight. The reaction mixture was concentrated under vacuum and the residue was stirred with hexanes (300 mL) for 30 min. The solid product was collected by filtration, washed with hexanes (2×100 mL) and dried under vacuum at 40° C. to afford dihydrochloride salt I(L) (35.80 g, 98%) as white solid. $^1$H NMR (300 MHz, dmso-$d_6$) δ: 1.31 (t, J=7.2 Hz, 3H), 1.59 (s, 6H), 4.09 (t, J=4.7 Hz, 2H), 4.36 (q, J=7.1 Hz, 2H), 10.14 (s, 2H).

Preparation of Compound 68a: 5-[(1S)-2-(dimethylamino)-1-phenylethyl] 2-ethyl 3-amino-6,6-dimethylpyrrolo[3,4-c]pyrazole-2,5(4H,6H)-dicarboxylate. To a stirred solution of (S)-2-dimethylamino-1-phenyl-ethanol (1d, 21.50 g, 130.0 mmol) in 1,2-dichloroethane (500 mL) was added triethylamine (26.30 g, 260.0 mmol) and 4-nitrophenyl chloroformate (27.00 g, 130.0 mmol) at room temperature under nitrogen. The solution was stirred at 50° C. overnight. A total of 16.8 g (130.0 mmol) of diisopropylethylamine was To a solution of (S)-5-(2-(dimethylamino)-1-phenylethyl) 2-ethyl 3-amino-6,6-dimethylpyrrolo[3,4-c]pyrazole-2,5 (4H,6H)-dicarboxylate 68a (150 mg, 0.36 mmol) and triethylamine (100 ul, 2 eq) in dichloromethane (2 ml) was added thiazole-4-carbonyl chloride (1.5 eq) at room temperature. The reaction mixture was stirred at room temperature for 2 hours and then evaporated to dryness. The residue was dissolved in methanol (1 ml) and triethylamine (1 ml), stirred at room temperature for 19 hours, and again evaporated to dryness. The crude product was purified by prep-HPLC and lyophilized to give the title compound 68 in 12% yield (20 mg) as white foam. $^1$H NMR (400 MHz, MeOD) δ ppm: 1.61 (s, 3H), 1.72 (s, 3H), 2.43 (s, 6H), 2.62 (dd, J=13.72, 3.15 Hz, 1H), 3.03 (dd, J=13.60, 9.82 Hz, 1H), 4.77-4.84 (m, 1H), 4.87-4.94 (m, 1H), 5.92 (dd, J=9.57, 3.02 Hz, 1H), 7.27-7.34 (m, 1H), 7.35-7.48 (m, 4H), 8.43 (d, J=1.26 Hz, 1H), 9.08 (d, J=2.01 Hz, 1H). Anal. ($C_{22}H_{26}N_6O_3S.0.1HOAc.0.5H_2O$) C, H, N, S. HPLC: >95% purity.

Example 69

(1S)-2-(dimethylamino)-1-phenylethyl 6,6-dimethyl-3-{[(1-methyl-1H-imidazol-4-yl)carbonyl]amino}-4,6-dihydropyrrolo[3,4-c]pyrazole-5(1H)-carboxylate

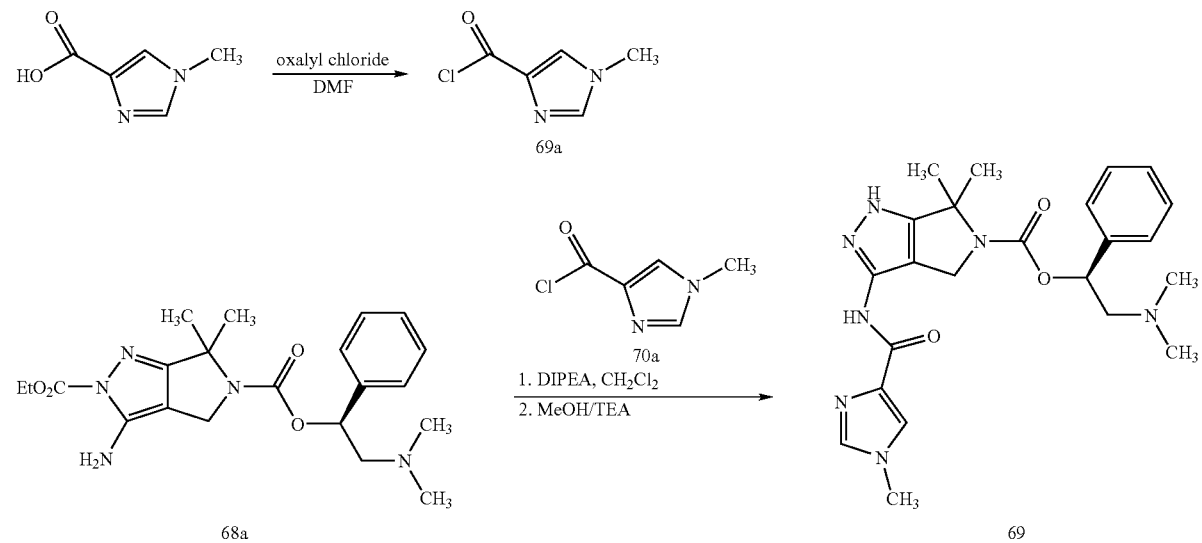

then added, followed by I(L) (17.90 g, 60.25 mmol). Stirring was continued at 50° C. for another 12 h. After cooling to room temperature, the solution was diluted with dichloromethane (1.5 L), washed with water (2×1.0 L), then brine (1.0 L), then dried over sodium sulfate. Another batch with the exact scale was also carried out. These two batches were combined during workup. Filtration and evaporation followed by flash chromatography (4.75% MeOH/0.25% $NEt_3$/95% DCM) afforded 68a (5.00 g, 10%) as a light yellow gummy oil. $^1$H NMR ($CDCl_3$, a mixture of rotamers, only the chemical shifts of the major form is reported) δ: 1.45 (t, J=7.1 Hz, 3H), 1.63 (s, 3H), 1.72 (s, 3H), 2.29 (s, 3H), 2.36 (s, 3H), 2.55-2.63 (m, 1H), 2.88 (dd, J=13, 8.3 Hz, 1H), 4.29 (q, J=13 Hz, 1H), 4.51 (q, J=7.1 Hz, 2H0, 5.44 (d, J=10.7 Hz, 1H), 5.8-5.95 (m, 1H), 7.25-7.42 (m, 5H). LCMS (APCI, M+H$^+$) 416.

Preparation of Compound 69a

At 0° C., a suspension of 1-methyl-1H-imidazole-4-carboxylic acid (100.9 mg, 0.8 mmol) in $CH_2Cl_2$ (8 mL) was added oxalylchloride (305 mg, 0.21 mL, 2.4 mmol) followed by addition of 1 drop of DMF. The mixture was stirred for 2 days at 25° C. All solvent was removed in vacuo to give a crude 69a.

A $CH_2Cl_2$ solution of (S)-5-(2-(dimethylamino)-1-phenylethyl) 2-ethyl 3-amino-6,6-dimethylpyrrolo[3,4-c]pyrazole-2,5(4H,6H)-dicarboxylate 68a (100 mg, 0.24 mmol) and diisoproplyethylamine (0.42 mL) was added to the crude 69a. The mixture was stirred at 25° C. for 18 h. All solvent was removed in vacuo. The residue was re-dissolved in MeOH-triethylamine co-solvent (2 mL, 1:1 v/v). The solution was stirred at 25° C. for 16 h. All solvent was evaporated. The residue was purified by Prep HPLC to afford the title compound 69 as a white solid (40 mg, 37% overall yield). $^1$H NMR (dmso-d$_6$) δ: 1.44 (s, 3H), 1.57 (s, 3H), 2.83-2.86 (m, 6H), 3.03 (m, 2H), 3.68 (s, 3H), 4.60 (d, J=13.3 Hz, 1H), 4.84 (d, J=13.4 Hz, 1H), 6.08 (d, J=7.3 Hz, 1H), 7.3-7.4 (m, 5H), 7.75 (s, 1H), 7.78 (s, 1H). LCMS [M+H]$^+$: 452. Anal. (C$_{23}$H$_{29}$N$_7$O$_3$.1.75H$_2$O.1.7TFA) C, H, N.

Example 70

3-{[(4-fluorophenyl)acetyl]amino}-6,6-dimethyl-N-[trans-2-phenylcyclopropyl]-4,6-dihydropyrrolo[3,4-c]pyrazole-5(1H)-carboxamide

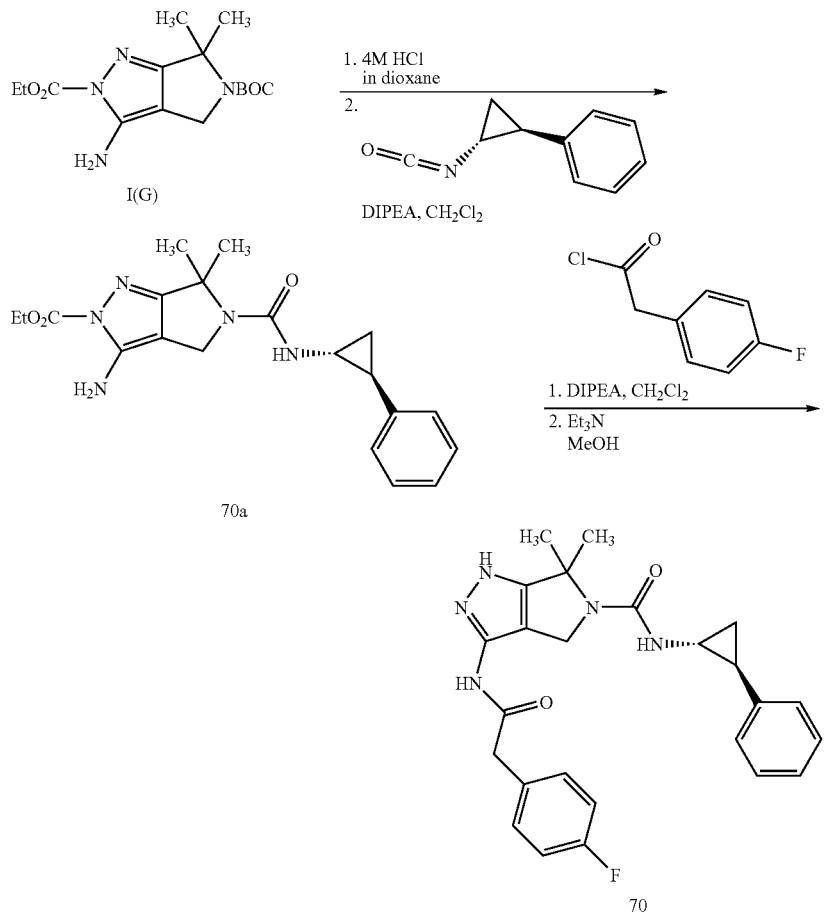

Preparation of Compound 70a: ethyl 3-amino-6,6-dimethyl-5-({[trans-2-phenyl-cyclopropyl]amino}carbonyl)-5,6-dihydropyrrolo[3,4-c]pyrazole-2(4H)-carboxylate Compound I(g) (5.30 g, 16.3 mmol) was dissolved in 20.4 mL of 4.0 M HCl/dioxane solution (81.7 mmol) and stirred at room temperature for 2.5 hours. The solution was then evaporated to dryness, and the crude amine hydrochloride I(l) residue suspended in 50 mL dichloromethane. The suspension was cooled in an ice/salt bath (−13° C. bath temperature). Diisopropylethylamine (9.95 mL, 57.1 mmol) was added, followed by dropwise addition of trans-2-phenylcyclopropyl isocyanate (2.60 g, 16.3 mmol). The resulting mixture was stirred at −10° C. for 1 hour. After evaporation of dichloromethane, the residue was partitioned between ethyl acetate (50 mL) and a mixture of saturated aqueous sodium bicarbonate (30 mL) and deionized water (20 mL). The aqueous layer was back-extracted with ethyl acetate (20 mL), and the combined organic extracts dried over magnesium sulfate, filtered, and concentrated to give 6.67 g of crude product as an off-white foam. Trituration from acetonitrile afforded pure 70a (5.82 g, 86%) as a white powder. $^1$H NMR (dmso-d$_6$) δ: 1.03 (m, 1H), 1.19 (m, 1H), 1.31 (t, J=7.2 Hz, 3H), 1.55 (d, J=2.8 Hz, 6H), 1.91 (m, 1H), 2.74 (m, 1H), 4.09 (d, J=11.6 Hz, 1H), 4.13 (d, J=11.9 Hz, 1H), 4.34 (q, J=7.1 Hz, 2H), 6.32 (d, J=2.8 Hz, 1H), 6.52 (s, 2H), 7.10 (d, J=7.1 Hz, 2H), 7.14 (d, J=7.3 Hz, 1H), 7.24 (t, J=7.4 Hz, 2H). Anal. (C$_{20}$H$_{25}$N$_5$O$_3$.0.6 CH$_3$CN.0.3H$_2$O) C, H, N. LCMS (APCI, M+H$^+$): 384.2.

Diisopropylethylamine (98.2 μL, 0.56 mmol) was added to a room temperature solution of 70a (108.1 mg, 0.282 mmol) in dichloromethane (0.9 mL), followed by (4-Fluorophenyl)-acetyl chloride (54.5 mg, 0.310 mmol). The mixture was stirred at room temperature for 23 hours. Triethylamine (2.5 mL) and methanol (2.5 mL) were added, and stirring continued for 3 days. After evaporation to dryness, the crude product was purified by silica gel chromatography (eluting with 70% ethyl acetate in hexanes) to give 70 (38.9 mg, 30%) as a white solid. $^1$H NMR (dmso-d$_6$) δ: 0.99 (q, J=7.3 Hz, 1H), 1.21

(quint, J=4.7 Hz, 1H), 1.58 (s, 6H), 1.90 (m, 1H), 2.72 (m, 1H), 3.59 (s, 2H), 4.32 (s, 2H), 6.38 (d, J=3.0 Hz, 1H), 7.11 (m, 5H), 7.23 (t, J=7.5 Hz, 2H), 7.31 (dd, J=5.7, 8.3 Hz, 2H), 10.65 (s, 1H), 12.29 (s, 1H). Anal. (C$_{25}$H$_{26}$FN$_5$O$_2$.0.55H$_2$O) C, H, N, F. HRMS: [M+H]$^+$ calc. 448.2143; found 448.2138; error 1.12 ppm.
Example 71
N-[(1S)-2-(dimethylamino)-1-phenylethyl]-6,6-dimethyl-3-[(1,3-thiazol-2-ylcarbonyl)amino]-4,6-dihydropyrrolo[3,4-c]pyrazole-5(1H)-carboxamide
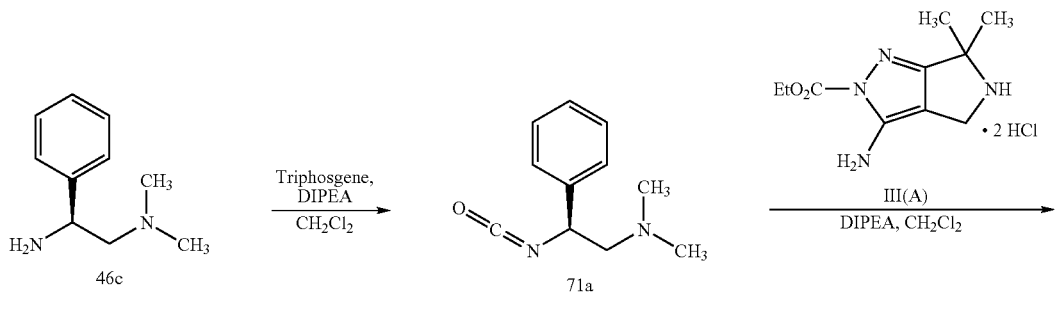
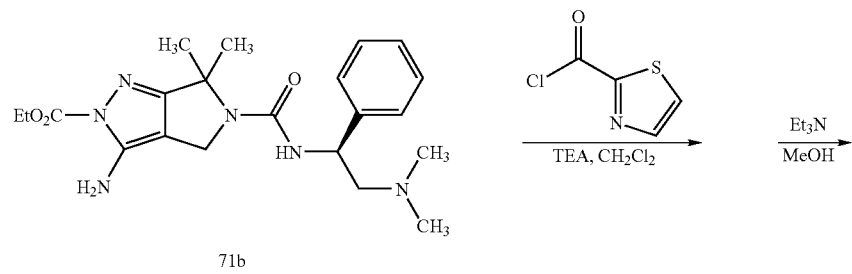
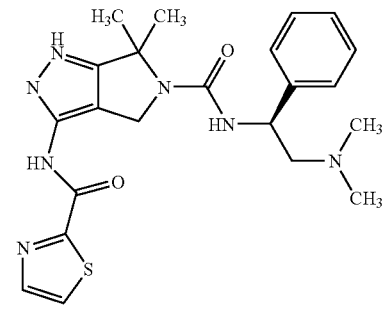

Preparation of Compound 71a: (2-Isocyanato-2-phenyl-ethyl)-dimethyl-amine

To a cooled (0° C.) and stirred solution of triphosgene (27.1 g, 91.32 mmol) in dichloromethane (250 mL) was added a solution of diisopropylethyl amine (23.6 g, 182.26 mmol) in dichloromethane (50 mL) dropwise over a period of 20 min. A solution of amine 46c (15.0 g, 91.32 mmol) in dichloromethane (100 mL) was then added dropwise to the brown reaction mixture while maintaining the temperature below 10° C. The resulting mixture was removed from cooling and stirred for 2 h at room temperature. The reaction solution was concentrated under vacuum to a residue, stirred with 10% DCM in hexane (50 mL), then the solid precipitate 71a was separated by filtration and used for the next reaction without further purification. (Note: The obtained solid product was stored under nitrogen). $^1$H NMR (300 MHz, dmso-$d_6$): δ 3.29 (s, 3H), 3.38 (s, 3H), 3.68 (t, J=10.1 Hz, 1H), 4.42 (dd, J=11.5, 6.5 Hz, 1H), 5.35 (dd, J=9.6, 6.2 Hz, 1H), 7.4-7.6 (m, 5H).

Preparation of Compound 71b: ethyl 3-amino-5-({[(1S)-2-(dimethylamino)-1-phenylethyl-]amino}carbonyl)-6,6-dimethyl-5,6-dihydropyrrolo[3,4-c]pyrazole-2(4H)-carboxylate To a cooled (0° C.) and stirred slurry of I(L) (25.0 g, 84.12 mmol) were sequentially added diisopropylethylamine (74 mL, 420.1 mmol) and 71a (17.1 g, 75.71 mmol). After stirring at room temperature for 10 h under nitrogen, the mixture was diluted with dichloromethane (100 mL) and washed with water (2×100 mL). The organic solution was dried ($Na_2SO_4$), filtered, and concentrated under vacuum. The obtained crude product was purified on silica gel column (10% MeOH/DCM) to give 71b (23.0 g, 73.7%) as light yellow solid. M.p: 96-97° C. $^1$H NMR (300 MHz, dmso-$d_6$): δ 1.32 (t, J=7.1 Hz, 3H), 1.51 (s, 3H), 1.57 (s, 3H), 2.19 (s, 6H), 2.40 (m, 1H), 2.60 (m, 1H), 4.23 (m, 2H), 4.35 (q, J=6.7 Hz, 2H), 4.78 (m, 1H), 6.00 (d, J=6 Hz, 1H), 6.55 (s, 2H), 7.18-7.40 (m, 5H). LCMS (APCI, M+H$^+$): 415.

To a solution of ethyl 3-amino-5-({[(1S)-2-(dimethylamino)-1-phenylethyl-]amino}carbonyl)-6,6-dimethyl-5,6-dihydropyrrolo[3,4-c]pyrazole-2(4H)-carboxylate 71b (150 mg, 0.36 mmol) and triethylamine (100 ul, 2 eq) in dichloromethane (2 ml) was added thiazole-2-carbonyl chloride (1.5 eq) at room temperature. The reaction mixture was stirred at room temperature for 2 hours and then evaporated to dryness. The residue was dissolved in methanol (1 ml) and triethylamine (1 ml), stirred at room temperature for 19 hours, and again evaporated to dryness. The crude product was purified by prep-HPLC and lyophilized to give the title compound 71 in 43% yield (70 mg) as white foam. $^1$H NMR (400 MHz, MeOD) δ ppm: 1.68 (s, 3H), 1.75 (s, 3H), 2.41 (s, 6H), 2.55 (dd, J=12.84, 4.28 Hz, 1H), 2.94 (dd, J=12.59, 10.83 Hz, 1H), 4.69-4.82 (m, 2H), 5.05 (dd, J=10.70, 4.41 Hz, 1H), 7.20-7.28 (m, 1H), 7.30-7.42 (m, 4H), 7.94 (d, J=3.02 Hz, 1H), 8.04 (d, J=3.02 Hz, 1H). Anal. ($C_{22}H_{27}N_7O_2S.0.2HOAc.1.2H_2O$) C, H, N, S. HPLC: >95% purity.

Example 72

N-[(1S)-2-(dimethylamino)-1-phenylethyl]-6,6-dimethyl-3-[(1,3-thiazol-4-ylcarbonyl)amino]-4,6-dihydropyrrolo[3,4-c]pyrazole-5(1H)-carboxamide

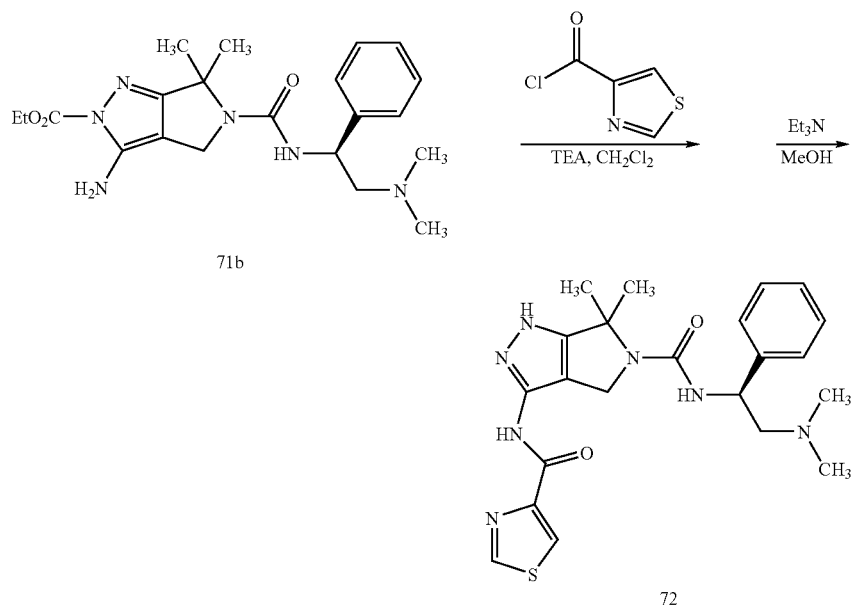

To a solution of ethyl 3-amino-5-({[(1S)-2-(dimethylamino)-1-phenylethyl-]amino}carbonyl)-6,6-dimethyl-5,6-dihydropyrrolo[3,4-c]pyrazole-2(4H)-carboxylate 71b (150 mg, 0.36 mmol) and triethylamine (100 ul, 2 eq) in dichloromethane (2 ml) was added thiazole-4-carbonyl chloride (1.5 eq) at room temperature. The reaction mixture was stirred at room temperature for 2 hours and then evaporated to dryness. The residue was dissolved in methanol (1 ml) and triethylamine (1 ml), stirred at room temperature for 19 hours, and again evaporated to dryness. The crude product was purified by prep-HPLC and lyophilized to give the title compound 72 in 34% yield (55 mg) as white foam. $^1$H NMR (400 MHz, MeOD) δ ppm: 1.68 (s, 3H), 1.75 (s, 3H), 2.49 (s, 6H), 2.68 (dd, J=12.97, 4.66 Hz, 1H), 3.01 (dd, J=12.59, 10.83 Hz, 1H), 4.69-4.81 (m, 2H), 5.09 (dd, J=10.70, 4.41 Hz, 1H), 7.25 (t, J=7.05 Hz, 1H), 7.30-7.44 (m, 4H), 8.41 (d, J=1.51 Hz, 1H), 9.08 (d, J=2.01 Hz, 1H). Anal. ($C_{22}H_{27}N_7O_2S \cdot 0.5HOAc \cdot 0.5H_2O$) C, H, N, S. HPLC: >95% purity.

The following Examples 73-95 were made using similar methods.

| Structure and Example # | Chemical name, Analytical data and comments |
|---|---|
| 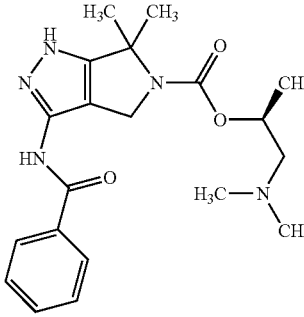 73 | (1S)-2-(dimethylamino)-1-methylethyl 3-(benzoylamino)-6,6-dimethyl-4,6-dihydropyrrolo[3,4-c]pyrazole-5(1H)-carboxylate. $^1$H NMR (400 MHz, MeOD) δ ppm: 1.24-1.38 (m, 3H), 1.66-1.80 (m, 6H), 2.44 (s, 1.5H), 2.53 (s, 4.5), 2.57-2.75 (m, 1H), 2.79-2.98 (m, 1H), 4.57-4.76 (m, 2H), 5.03-5.20 (m, 1H), 7.47-7.63 (m, 3H), 7.90-7.99 (m, 2H). Anal. ($C_{20}H_{27}N_5O_3 \cdot 0.5 H_2O \cdot 0.5 HOAc$) C, H, N. LCMS (APCI, M + H$^+$): 386.2. Method of Example 1 using (S)-(+)-1-Dimethylamino-2-propanol in place of 1d. |
| 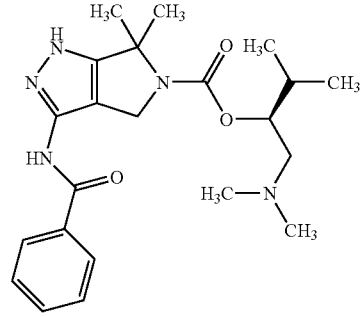 74 | (1S)-1-[(dimethylamino)methyl]-2-methylpropyl 3-(benzoylamino)-6,6-dimethyl-4,6-dihydropyrrolo[3,4-c]pyrazole-5(1H)-carboxylate. $^1$H NMR (400 MHz, MeOD) δ ppm: 0.95-1.06 (m, 6H) 1.73 (d, J = 6.29 Hz, 6H) 1.89-1.98 (m, 3H) 2.41-2.65 (m, 6H) 2.71-3.09 (m, 2H) 4.60-4.80 (m, 2H) 4.93-5.05 (m, 1H) 7.52 (t, J = 7.43 Hz, 2H) 7.56-7.64 (m, 1H) 7.89-7.99 (m, 2H). Anal. ($C_{22}H_{31}N_5O_3 \cdot 0.2 HOAc \cdot 0.3 H_2O$) C, H, N. HPLC: >95% purity. Method of Example 30. |
| 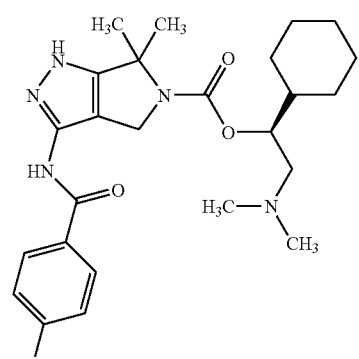 75 | (1S)-1-cyclohexyl-2-(dimethylamino)ethyl 3-[(4-fluorobenzoyl)amino]-6,6-dimethyl-4,6-dihydropyrrolo[3,4-c]pyrazole-5(1H)-carboxylate $^1$H NMR (400 MHz, MeOD) δ ppm: 1.08-1.39 (m, 5H) 1.63-1.88 (m, 12H) 2.89-3.00 (m, 6H) 3.37 (dd, J = 13.72, 1.89 Hz, 1H) 3.45-3.56 (m, 1H) 4.62-4.82 (m, 2H) 4.98-5.11 (m, 1H) 7.26 (t, J = 8.81 Hz, 2H) 7.92-8.08 (m, 2H). Anal. ($C_{25}H_{34}N_5O_3F \cdot 0.7 HOAc \cdot 2.5 H_2O$) C, H, N. HPLC: >95% purity Method of Example 30. |

| Structure and Example # | Chemical name, Analytical data and comments |
|---|---|
| 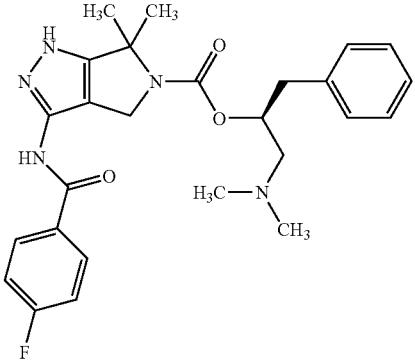<br>76 | (1S)-1-benzyl-2-(dimethylamino)ethyl 3-[(4-fluorobenzoyl)amino]-6,6-dimethyl-4,6-dihydropyrrolo[3,4-c]pyrazole-5(1H)-carboxylate<br>$^1$H NMR (400 MHz, MeOD) δ ppm: 1.48-1.58 (m, 3H)<br>1.61-1.71 (m, 3H) 2.27-2.39 (m, 6H) 2.57 (dd, J = 13.22, 3.15 Hz, 1H) 2.64-2.79 (m, 1H) 2.81-3.05 (m, 2H) 4.48-4.72 (m, 2H) 5.18-5.29 (m, 1H) 7.15-7.22 (m, 1H) 7.22-7.32 (m, 6H) 7.93-8.07 (m, 2H).<br>Anal. ($C_{26}H_{30}N_5O_3F$•0.3 HOAc•0.2 $H_2O$) C, H, N. HPLC: >95% purity Method of Example 30. |
| 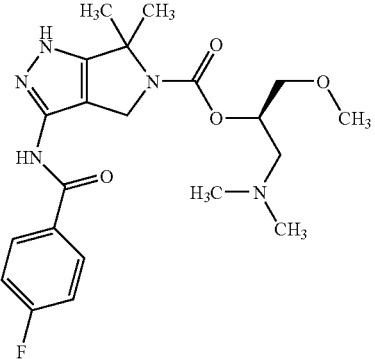<br>77 | (1R)-2-(dimethylamino)-1-(methoxymethyl)ethyl 3-[(4-fluorobenzoyl)amino]-6,6-dimethyl-4,6-dihydropyrrolo[3,4-c]pyrazole-5(1H)-carboxylate $^1$H NMR (400 MHz, MeOD) δ ppm: 1.68-1.76 (m, 6H) 2.42-2.56 (m, 6H) 2.77-3.00 (m, 2H) 3.37-3.41 (m, 3H) 3.50-3.61 (m, 2H) 4.59-4.75 (m, 2H) 5.09-5.24 (m, 1H) 7.25 (t, J = 8.44 Hz, 2H) 7.93-8.07 (m, 2H). Anal. ($C_{21}H_{28}N_5O_4F$•0.5 HOAc•0.4 $H_2O$) C, H, N. HPLC: >95% purity Method of Example 30 using (R)-1-(dimethylamino)-3-methoxypropan-2-ol in place of 30b and using 2c in place of 1c. |
| 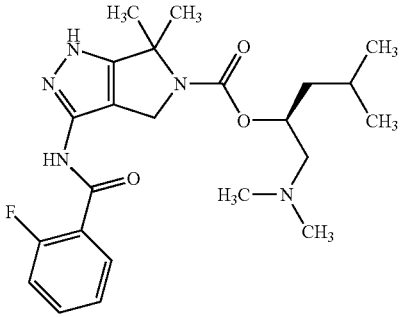<br>78 | (1S)-1-[(dimethylamino)methyl]-3-methylbutyl 3-[(2-fluorobenzoyl)amino]-6,6-dimethyl-4,6-dihydropyrrolo[3,4-c]pyrazole-5(1H)-carboxylate<br>$^1$H NMR (400 MHz, MeOD) δ ppm 0.91-1.05 (m, 6H) 1.33-1.48 (m, 1H) 1.53-1.63 (m, 1H) 1.65-1.80 (m, 7H) 2.34-2.50 (m, 6H) 2.57-2.89 (m, 2H) 4.54-4.80 (m, 2H) 5.07-5.27 (m, 1H) 7.15-7.38 (m, 2H) 7.52-7.65 (m, 1H) 7.75-7.89 (m, 1H). Anal. ($C_{23}H_{32}N_5O_3F$•0.2 HOAc•0.1 $H_2O$) C, H, N. HPLC: >95% purity Method of Example 35. |
| 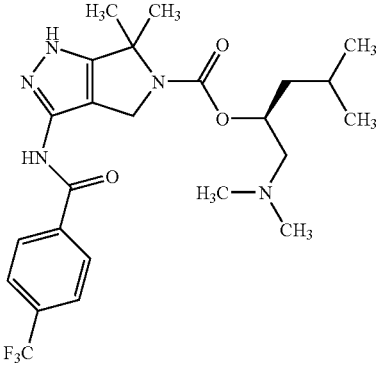<br>79 | (1S)-1-[(dimethylamino)methyl]-3-methylbutyl 6,6-dimethyl-3-{[4-(trifluoromethyl)benzoyl]amino}-4,6-dihydropyrrolo[3,4-c]pyrazole-5(1H)-carboxylate $^1$H NMR (400 MHz, MeOD) δ ppm 0.97 (d, J = 6.55 Hz, 6H) 1.38-1.49 (m, 1H) 1.53-1.63 (m, 1H) 1.66-1.77 (m, 7H) 2.29-2.39 (m, 6H) 2.40-2.52 (m, 1H) 2.57-2.73 (m, 1H) 4.55-4.75 (m, 2H) 5.05-5.23 (m, 1H) 7.84 (d, J = 8.31 Hz, 2H) 8.12 (d, J = 8.06 Hz, 2H). Anal. ($C_{24}H_{32}N_5O_3F_3$•0.1 HOAc•0.2 $H_2O$) C, H, N. HPLC: >95% purity Method of Example 35. |

| Structure and Example # | Chemical name, Analytical data and comments |
|---|---|
| 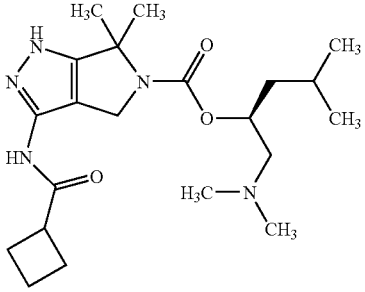<br>80 | (S)-1-[(dimethylamino)methyl]-3-methylbutyl 3-[(cyclobutylcarbonyl)amino]-6,6-dimethyl-4,6-dihydropyrrolo[3,4-c]pyrazole-5(1H)-carboxylate $^1$H NMR (400 MHz, MeOD) δ ppm 1.36-1.49 (m, 1H) 1.51-1.61 (m, 1H) 1.64-1.74 (m, 7H) 1.86-1.95 (m, 1H) 1.98-2.10 (m, 1H) 2.12-2.25 (m, 2H) 2.26-2.36 (m, 8H) 2.36-2.46 (m, 1H) 2.52-2.67 (m, 1H) 3.22-3.28 (m, 1H) 4.58 (br. s., 2H) 5.04-5.21 (m, 1H). Anal. ($C_{21}H_{35}N_5O_3$•0.2 HOAc•0.1 $H_2O$) C, H, N. HPLC: >95% purity Method of Example 35. |
| 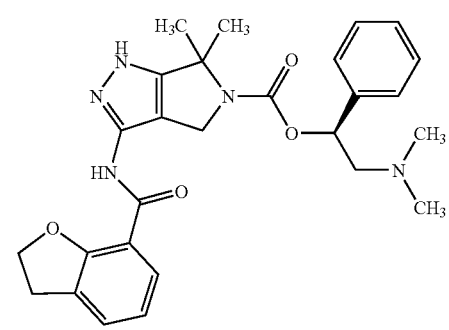<br>81 | (1S)-2-(dimethylamino)-1-phenylethyl 3-[(2,3-dihydro-1-benzofuran-7-ylcarbonyl)amino]-6,6-dimethyl-4,6-dihydropyrrolo[3,4-c]pyrazole-5(1H)-carboxylate $^1$H NMR (400 MHz, MeOD) δ ppm 1.58-1.84 (m, 6H) 2.35-2.52 (m, 6H) 2.64-2.73 (m, 1H) 3.03-3.18 (m, 1H) 3.32-3.39 (m, 2H) 4.80-4.86 (m, 3H) 4.90-4.97 (m, 1H) 5.90-6.01 (m, 1H) 6.96-7.08 (m, 1H) 7.32 (q, J = 6.80 Hz, 1H) 7.36-7.51 (m, 5H) 7.75-7.87 (m, 1H). Anal. ($C_{27}H_{31}N_5O_4$•0.2 HOAc•0.4 $H_2O$) C, H, N. HPLC: >95% purity Method of Example 1. |
| 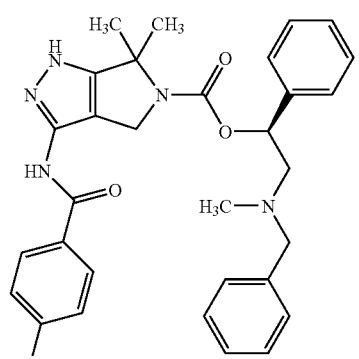<br>82 | (1S)-2-[benzyl(methyl)amino]-1-phenylethyl 3-[(4-fluorobenzoyl)amino]-6,6-dimethyl-4,6-dihydropyrrolo[3,4-c]pyrazole-5(1H)-carboxylate $^1$H NMR (400 MHz, MeOD) δ ppm: 1.61-1.72 (m, 3H) 1.72-1.84 (m, 3H) 2.25-2.41 (m, 3H) 2.55-2.71 (m, 1H) 2.91-3.10 (m, 1H) 3.49-3.60 (m, 1H) 3.62-3.75 (m, 1H) 4.61-4.85 (m, 2H) 5.89-6.03 (m, 1H) 7.14-7.21 (m, 1H) 7.21-7.31 (m, 7H) 7.31-7.35 (m, 3H) 7.35-7.41 (m, 1H) 7.96-8.07 (m, 2H). Anal. ($C_{31}H_{32}N_5O_3F$•0.4 $H_2O$) C, H, N. HPLC: >95% purity Method of Example 40. |

| Structure and Example # | Chemical name, Analytical data and comments |
|---|---|
| 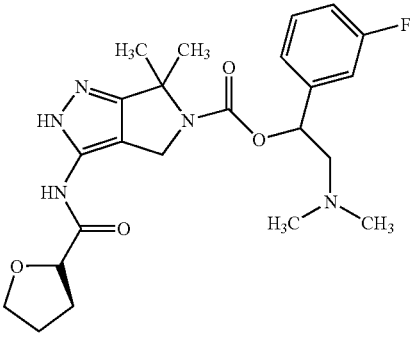<br>83<br>Diastereomer A and diastereomer B | 2-(dimethylamino)-1-(3-fluorophenyl)ethyl 6,6-dimethyl-3-((R)-tetrahydrofuran-2-carboxamido)pyrrolo[3,4-c]pyrazole-5(2H,4H,6H)-carboxylate Diastereomer A: white solid; retention time: 2.530 min LCMS: M + H: 460; $^1$H NMR (300 MHz, DMSO-d$_6$) d ppm 1.50-1.67 (m, 6H), 1.83-1.94 (m, 3H), 2.20-2.32 (m, 7H), 2.49-2.61 (m, 1H), 2.72-2.85 (m, 1H), 3.74-3.84 (m, 1H), 3.89-3.96 (m, 1H), 4.29-4.40 (m, 2H), 4.57 (s, 1H), 5.79 (t, 1H, J = 4 Hz), 7.09-7.25 (m, 3H), 7.37-7.44 (m, 1H), 10.04 (s, 1/2H), 10.31 (s, 1/2H), 11.92 (s, 1/2H), 12.41 (s, 1/2H); ); HRMS: calcd. M + H: 460.23546; observed M + H: 460.23486; Anal.: (C$_{23}$H$_{30}$N$_5$O$_4$F•1 H$_2$O) C, H, N Diastereomer B: white solid; retention time: 2.552 min LCMS: M + H: 460; $^1$H NMR (300 MHz, DMS0-d$_6$) d ppm 1.50-1.67 (m, 6H), 1.83-1.94 (m, 3H), 2.20-2.32 (m, 7H), 2.49-2.61 (m, 1H), 2.72-2.85 (m, 1H), 3.74-3.84 (m, 1H), 3.89-3.96 (m, 1H), 4.29-4.40 (m, 2H), 4.57 (s, 1H), 5.79 (t, 1H, J = 4 Hz), 7.09-7.25 (m, 3H), 7.37-7.44 (m, 1H), 10.04 (s, 1/2H), 10.31 (s, 1/2H), 11.92 (s, 1/2H), 12.41 (s, 1/2H); ); HRMS: calcd. M + H: 460.23546; observed M + H: 460.23547; Anal.: (C$_{23}$H$_{30}$N$_5$O$_4$F•1.25 H$_2$O) C, H, N. Method of Example 89. |
| 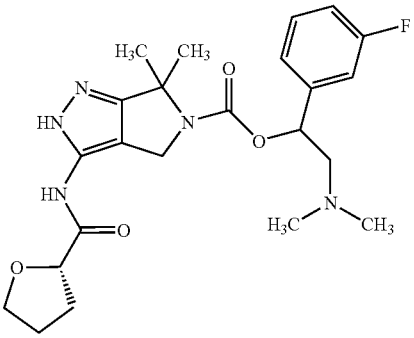<br>84<br>Diastereomer A and diastereomer B | 2-(dimethylamino)-1-(3-fluorophenyl)ethyl 6,6-dimethyl-3-((S)-tetrahydrofuran-2-carboxamido)pyrrolo[3,4-c]pyrazole-5(2H,4H,6H)-carboxylate Diastereomer A: white solid; retention time: 2.518 min, LCMS: M + H: 460; $^1$H NMR (300 MHz, DMS0-d$_6$) d ppm 1.50-1.67 (m, 6H), 1.83-1.90 (m, 3H), 2.20-2.32 (m, 7H), 2.49-2.60 (m, 1H), 2.66-2.83 (m, 1H), 3.74-3.85 (m, 1H), 3.89-3.96 (m, 1H), 4.30-4.38 (m, 2H), 4.57 (s, 1H), 5.79 (t, 1H, J = 4 Hz), 7.09-7.25 (m, 3H), 7.37-7.44 (m, 1H), 10.04 (s, 1/2H), 10.32 (s, 1/2H), 11.91 (s, 1/2H), 12.41 (s, 1/2H); ); HRMS: 460; calcd. M + H: 460.23546; obervered M + H: 460.23522; Anal.: (C$_{23}$H$_{30}$N$_5$O$_4$F•1 H$_2$O) C, H, N<br>Diastereomer B: white solid; retention time: 2.550 min,<br>LCMS: M + H: 460; $^1$H NMR (300 MHz, DMSO-d$_6$) d ppm 1.50-1.67 (m, 6H), 1.83-1.90 (m, 3H), 2.20-2.32 (m, 7H), 2.49-2.60 (m, 1H), 2.66-2.83 (m, 1H), 3.74-3.85 (m, 1H), 3.89-3.96 (m, 1H), 4.30-4.38 (m, 2H), 4.57 (s, 1H), 5.79 (t, 1H, J = 4 Hz), 7.09-7.25 (m, 3H), 7.37-7.44 (m, 1H), 10.04 (s, 1/2H), 10.32 (s, 1/2H), 11.91 (s, 1/2H), 12.41 (s, 1/2H); ); HRMS: calcd. M + H: 460.23546; observed M + H: 460.23427; Anal.: (C$_{23}$H$_{30}$N$_5$O$_4$F•1 H$_2$O) C, H, N Method of Example 89. |
| 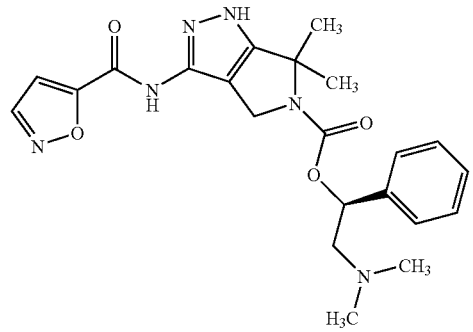<br>85 | (S)-2-(dimethylamino)-1-phenylethyl 3-(isoxazole-5-carboxamido)-6,6-dimethylpyrrolo[3,4-c]pyrazole-5(1H,4H,6H)-carboxylate. $^1$H NMR (400 MHz, DMSO) δ ppm: 1.54 (s, 3H), 1.65 (s, 3H), 2.51 (s, 6H), 4.36 (m, 2H), 5.91 (m, 1H), 7.25-7.46 (m, 5H). Anal. (C$_{22}$H$_{26}$N$_6$O$_4$•1.12 HOAc•1.52 H$_2$O) C, H, N. HPLC: >95% purity. Method of Example 69. |

| Structure and Example # | Chemical name, Analytical data and comments |
|---|---|
| 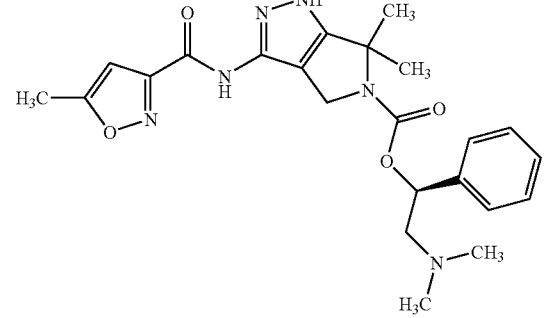<br>86 | (S)-2-(dimethylamino)-1-phenylethyl 6,6-dimethyl-3-(5-methylisoxazole-3-carboxamido)pyrrolo[3,4-c]pyrazole-5(1H,4H,6H)-carboxylate. $^1$H NMR (400 MHz, DMSO) δ ppm: 1.53 (s, 3H), 1.62 (s, 3H), 2.22 (m, 6H), 2.50 (s, 3H), 4.63 (s, 2H), 5.81 (m, 1H), 6.73 (s, 1H), 7.30-7.46 (m, 5H). Anal. ($C_{23}H_{28}N_6O_4 \cdot 0.33$ HOAc•1.0 $H_2O$) C, H, N. HPLC: >95% purity. Method of Example 69. |
| 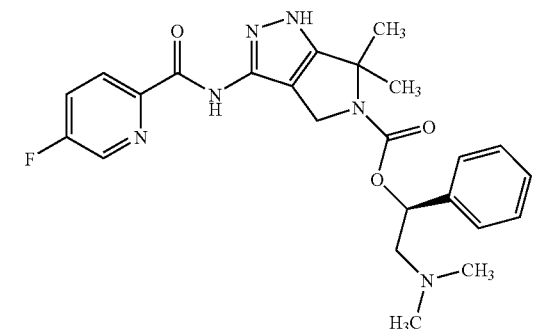<br>87 | (S)-2-(dimethylamino)-1-phenylethyl 3-(3-fluoropicolinamido)-6,6-dimethylpyrrolo[3,4-c]pyrazole-5(1H,4H,6H)-carboxylate. $^1$H NMR (400 MHz, DMSO) δ ppm: 1.53 (s, 3H), 1.62 (s, 3H), 2.21 (m, 6H), 2.75 (m, 2H), 4.50 (m, 2H), 5.81 (m, 1H), 7.25-7.38 (m, 5H), 8.00 (m, 1H), 8.25 (m, 1H), 8.73 (m, 1H). Anal. ($C_{24}H_{27}N_6O_3 \cdot 0.15$ HOAc•1.30 $H_2O$) C, H, N. HPLC: >95% purity. Method of Example 69 |
| 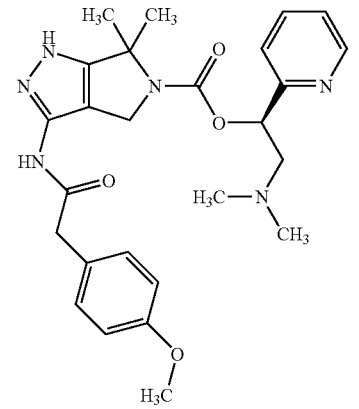<br>88 | (1R)-2-(dimethylamino)-1-pyridin-2-ylethyl 3-{[(4-methoxyphenyl)-acetyl]amino}-6,6-dimethyl-4,6-dihydropyrrolo[3,4-c]pyrazole-5(1H)-carboxylate $^1$H NMR (dmso-$d_6$) δ: [1.51 (s), 1.58 (s), 1.62 (s), 1.67 (s) 6H together], [2.19 (s), 2.20 (s) 6H together], 2.75 (m, 2H), 3.51 (m 2H), [3.70 (s), 3.71 (s) 3H together], [4.32 (m), 4.55 (m) 2H together], 5.79 (dd, J = 4.3, 7.8 Hz, 1H), 6.86 (t, J = 7.5 Hz, 2H), 7.20 (t, J = 8.2 Hz, 2H), 7.29 (t of d, $J_t$ = 8.0 Hz, $J_d$ = 4.9 Hz, 1H), 7.36 (m, 1H), 7.79 (q, J = 6.6 Hz, 1H), 8.53 (t, J = 5.3 Hz, 1H), 10.64 (br s, 1H). 12.35 (br s, 1H). Anal. ($C_{26}H_{32}N_6O_4 \cdot 0.3$ $H_2O$) C, H, N. HRMS: [M + H]$^+$ calc. 493.2558; found 493.2551; error −1.37 ppm. Method of Example 24. |
| 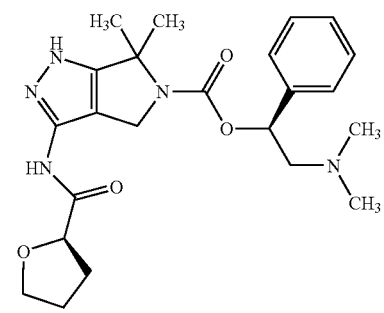<br>89 | (S)-2-(dimethylamino)-1-phenylethyl 6,6-dimethyl-3-((R)-tetrahydrofuran-2-carboxamido)pyrrolo[3,4-c]pyrazole-5(1H,4H,6H)-carboxylate $^1$HNMR (300 MHz, dmso-$d_6$) δ: 1.35 (t, J = 7.1 Hz, 3H), [1.42 (s), 1.45 (s), 9H together], 1.57 (dd, J = 2.8, 6.6 Hz, 6H), 1.86 (m, 2H), 1.96 (m, 1H), 2.23 (m, 1H), 3.91 (m, 2H), 4.47 (m, 5H), 10.80 (s, 1H). LCMS (APCI, M + H$^+$): 423. Anal. ($C_{20}H_{30}N_4O_6 \cdot 0.15$ EtOAc) C, H, N Method of Example 1 using 89a in place of 1a. Preparation of 89a is shown following this table. |

-continued

| Structure and Example # | Chemical name, Analytical data and comments |
|---|---|
| 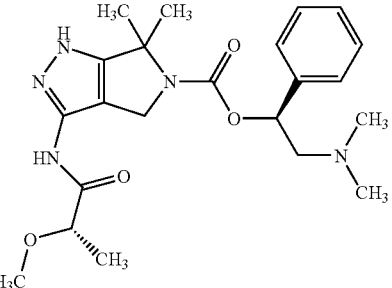<br>90 | (S)-2-(dimethylamino)-1-phenylethyl 3-((S)-2-methoxypropanamido)-6,6-dimethylpyrrolo[3,4-c]pyrazole-5(1H,4H,6H)-carboxylate. $^1$HNMR (300 MHz, MeOD) δ: [1.38 (d, J = 6.8 Hz), 1.42 (d, J = 6.8 Hz), 3H together], [1.59 (s), 1.66 (s), 1.70 (s), 1.80 (s), 6H together], [2.32 (s), 2.37 (s), 6H together], [2.53 (dd, J = 3.0, 13.4 Hz), 2.63 (dd, J = 4.6, 13.4 Hz), 1H together], [2.95 (dd, J = 9.6, 13.4 Hz), 3.01 (dd, J = 8.3, 13.4 Hz)], [3.42 (s), 3.45 (s), 3H together], 3.92 (m, 1H), 4.46-4.83 (m, 2H), [5.89 (dd, J = 3.0, 9.6 Hz), 5.94 (dd, J = 4.6, 8.6 Hz), 1H together], 7.31 (m, 1H), 7.38 (m, 4H). LCMS (APCI, M + H$^+$): 430. HRMS: M + H$^+$calc. 430.24488, found 430.24489, error 0.02 ppm. Anal. (C$_{22}$H$_{31}$N$_5$O$_4$•0.5 H$_2$0.2 Cyclohexane) C, H, N.<br>Method of Example 89. |
| 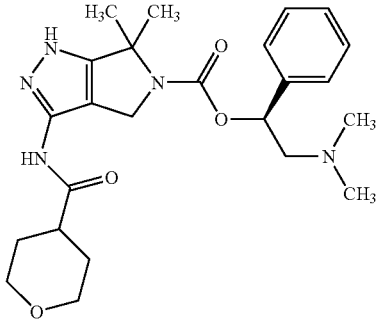<br>91 | (S)-2-(dimethylamino)-1-phenylethyl 6,6-dimethyl-3-(tetrahydro-2H-pyran-4-carboxamido)pyrrolo[3,4-c]pyrazole-5(1H,4H,6H)-carboxylate $^1$HNMR (300 MHz, MeOD) δ: [1.59 (s), 1.64 (s), 1.69 (s), 1.79 (s), 6H together], 1.76-1.90 (m, 4H), [2.38 (s), 2.49 (s), 6H together], 2.68 (m, 2H), 3.10 (dd, J = 9.9, 13.6 Hz, 1H), 3.49 (t of d, J$_t$ = 11.5 Hz, J$_d$ = 2.8 Hz, 2H), 4.00 (m, 2H), [4.46 (d, J = 13.4 Hz), 4.52 (d, J = 13.4 Hz), 4.70 (d, J = 13.4 Hz), 4.78 (d, J = 13.4 Hz), 2H together], 5.94 (dd, J = 3.0, 9.6 Hz, 1H), 7.31 (m, 1H), 7.38 (m, 4H).. LCMS (APCI, M + H$^+$): 456. HRMS: M + H$^+$ calc. 456.26053, found 456.26051, error −0.05 ppm. Anal. (C$_{24}$H$_{33}$N$_5$O$_4$•1.4 H$_2$O•0.4 HOAc) C, H, N. Method of Example 89. |
| 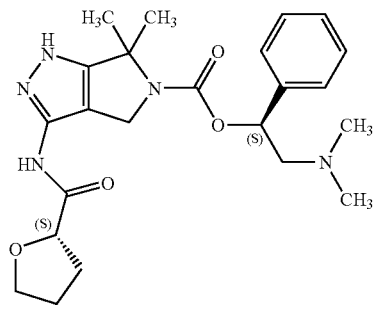<br>92 | (S)-2-(dimethylamino)-1-phenylethyl 6,6-dimethyl-3-((S)-tetrahydrofuran-2-carboxamido)pyrrolo[3,4-c]pyrazole-5(1H,4H,6H)-carboxylate. $^1$HNMR (300 MHz, MeOD, some peaks doubled due to tautomeric isomerization) δ: [1.59 (s), 1.65 (s), 1.69 (s), 1.79 (s), 6H together], 1.96 (m, 2H), 2.07 (m, 1H), 2.31-2.40 (m, 1H), [2.32 (s), 2.37 (s), 6H together], [2.53 (dd, J = 3.0, 13.4 Hz), 2.63 (dd, J = 4.6, 13.4 Hz), 1H together], [2.94 (dd, J = 9.4, 13.4 Hz), 3.01 (dd, J = 8.3, 13.4 Hz), 1H together], 3.92 (m, 1H), 4.07 (m, 1H), [4.43 (dd, J = 5.8, 8.3 Hz), 4.46 (dd, J = 5.8, 8.3 Hz), 1H together], 4.50-4.83 (m, 2H), [5.89 (dd, J = 3.3, 9.6 Hz), 5.94 (dd, J = 4.6, 8.3 Hz), 1H together], 7.31 (m, 1H), 7.38 (m, 4H).. LCMS (APCI, M + H$^+$): 442. HRMS: M + H$^+$ calc. 442.24488, found 442.24444, error −0.99 ppm. Anal. (C$_{23}$H$_{31}$N$_5$O$_4$•0.6 H$_2$O•0.4 cyclohexane) C, H, N. Method of Example 89. |
| 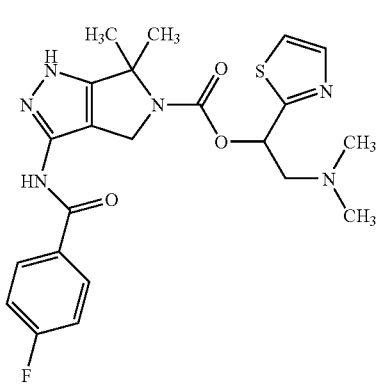<br>93 | 2-(dimethylamino)-1-(thiazol-2-yl)ethyl 3-(4-fluorobenzamido)-6,6-dimethylpyrrolo[3,4-c]pyrazole-5(1H,4H,6H)-carboxylate $^1$H NMR (MeOD) δ: 1.64 (s, 3H), 1.68 (s, 3H), 2.94 (s, 6H), 3.96-4.10 (m, 2H), 4.60-4.80 (m, 2H), 6.42 (dd, J = 3.54, 8.08 Hz, 1H), 7.16 (t, J = 8.84 Hz, 2H), 7.70 (dd, J = 3.28, 63.66 Hz, 2H), 7.88-7.97 (m, 2H). LCMS (APCI, M + H$^+$): 473.2. Anal. (C$_{22}$H$_{25}$FN$_6$O$_3$S•1.85 TFA•0.44 water) C, H, N. Method of Example 1. |

| Structure and Example # | Chemical name, Analytical data and comments |
|---|---|
| 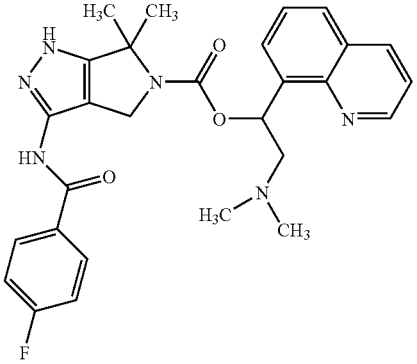<br>94 | 2-(dimethylamino)-1-(quinolin-8-yl)ethyl 3-(4-fluorobenzamido)-6,6-dimethylpyrrolo[3,4-c]pyrazole-5(1H,4H,6H)-carboxylate $^1$H NMR (MeOD) δ: 1.54 (s, 3H), 1.67 (s, 3H), 2.98 (s, 3H), 3.13 (s, 3H), 3.60-3.75 (m, 2H), 4.87-4.98 (m, 2H), 7.14-7.28 (m, 3H), 7.51 (q, J = 4.28 Hz, 1H), 7.59 (t, J = 7.58 Hz, 1H), 7.83 (d, J = 7.07 Hz, 1H), 7.89 (d, J = 8.34, 1H). 7.95 (dd, J = 5.31, 8.84 Hz, 2H), 8.29 (dd, J = 1.77, 8.34 Hz, 1H), 8.88-8.94 (m, 1H). LCMS (APCI, M + H$^+$): 517.2. Anal. ($C_{28}H_{29}FN_6O_3$•2.12 TFA•0.26 water) C, H, N. Method of Example 1. |
| 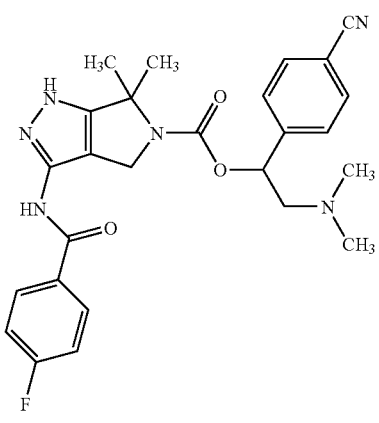<br>95 | 1-(4-cyanophenyl)-2-(dimethylamino)ethyl 3-(4-fluorobenzamido)-6,6-dimethylpyrrolo[3,4-c]pyrazole-5(1H,4H,6H)-carboxylate $^1$H NMR (MeOD) δ: 1.5 5 (s, 3H), 1.65 (s, 3H), 2.26 (s, 6H), 2.52 (dd, J = 4.42, 13.38 Hz, 1H), 2.88 (dd, J = 9.35, 13.39 Hz, 1H). 4.71-4.87 (m, 2H), 5.87 (dd, J = 3.28, 9.09 Hz, 1H), 7.20 (t, J = 8.34 Hz, 2H), 7.54 (t, J = 8.34 Hz, 2H), 7.59 (t, J = 8.34 Hz, 2H), 7.97 (t, J = 8.59 Hz, 2H). LCMS (APCI, M + H$^+$): 491.2. Anal. ($C_{26}H_{27}FN_6O_3$•0.92 water) C, H, N. Method of Example 1. |

Preparation of compound 89a: (R)-5-tert-butyl 2-ethyl 6,6-dimethyl-3-(tetrahydrofuran-2-carboxamido)pyrrolo[3,4-c]pyrazole-2,5(4H,6H)-dicarboxylate

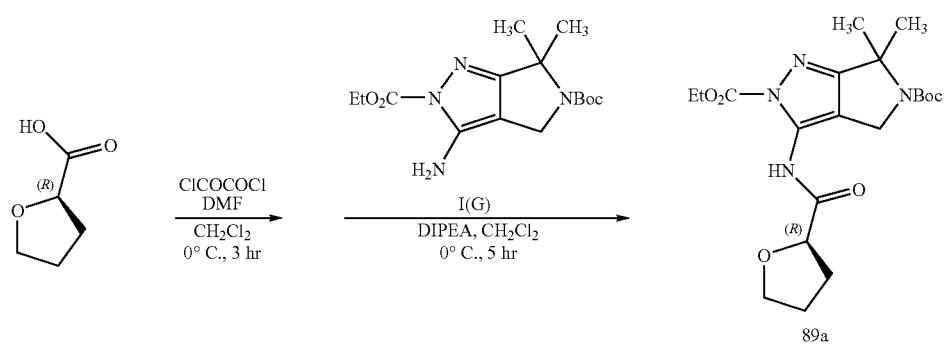

(R)-tetrahydrofuran-2-carboxylic acid (1.39 g, 12.0 mmol) was dissolved in dichloromethane (24 mL) and cooled to 0° C. Oxalyl chloride (4.57 g, 36.0 mmol) was added dropwise, followed by DMF (25 uL). After stirring for 3 hours at 0° C., the solution was concentrated to dryness then rotavop over DME (2×5 mL) to remove residual oxalyl chloride, then redissolved in DME (8.0 mL). In another flask, 5-tert-butyl 2-ethyl 3-amino-6,6-dimethylpyrrolo[3,4-c]pyrazole-2,5(4H,6H)-dicarboxylate I(G) (1.95 g, 6.0 mmol) and diisopropyl ethyl amine (2.09 mL, 12.0 mmol) were dissolved in dichloromethane (8.0 mL) and cooled to 0° C. The acid chloride solution was added dropwise, causing fuming and raising the internal temperature to 15° C. Reaction was at 0° C. for 5 hours. Aqueous workup using NaHCO$_3$ and DME followed by silica gel column provided 89a (2.2572 g, 86%) as a white foam. ¹HNMR (300 MHz, dmso-d₆) δ: 1.35 (t, J=7.1 Hz, 3H), [1.42 (s), 1.45 (s), 9H together], 1.57 (dd, J=2.8, 6.6 Hz, 6H), 1.86 (m, 2H), 1.96 (m, 1H), 2.23 (m, 1H), 3.91 (m, 2H), 4.47 (m, 5H), 10.80 (s, 1H). LCMS (APCI, M+H⁺): 423. Anal. (C₂₀H₃₀N₄O₆·0.15 EtOAc) C, H, N.

The following Examples were also prepared.

| Structure and Example # | Chemical name, Analytical data and comments |
|---|---|
| 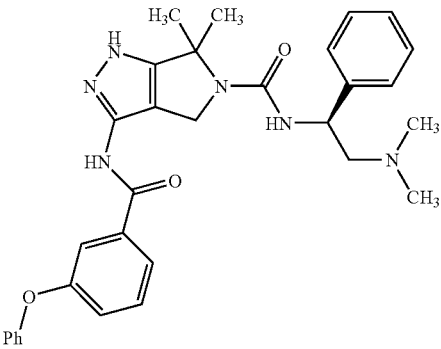 96 | N-[(1S)-2-(dimethylamino)-1-phenylethyl]-6,6-dimethyl-3-[(3-phenoxybenzoyl)amino]-4,6-dihydropyrrolo[3,4-c]pyrazole-5(1H)-carboxamide ¹H NMR (400 MHz, CDCl₃) δ ppm: 1.63 (s, 3H), 1.72 (s, 3H), 2.10-2.55 (m, 7H), 2.60-2.90 (m, 1H), 4.50-4.97 (m, 3H), 5.55-4.90 (m, 1H), 5.55-5.95 (m, 1H), 6.92-7.67 (m, 14H), 10.17 (bs, 1H). Anal. (C₃₁H₃₄N₆O₃·0.5 H₂O·0.2 EtOAc) C, H. N. LCMS (APCI, M + H⁺): 539.2. Method of Example 46. |
| 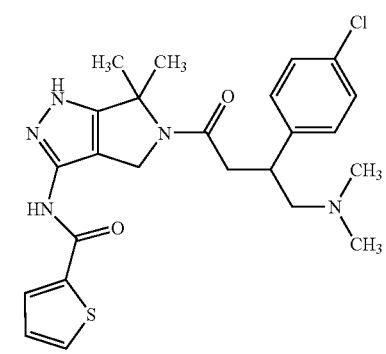 97 | N-{5-[3-(4-chlorophenyl)-4-(dimethylamino)butanoyl]-6,6-dimethyl-1,4,5,6-tetrahydropyrrolo[3,4-c]pyrazol-3-yl}thiophene-2-carboxamide ¹H NMR (400 MHz, MeOD) δ ppm: 1.58 (s, 3H), 1.73 (s, 3H), 2.61-2.72 (m, 1H), 2.74-2.97 (m, 3H), 3.46-3.58 (m, 1H), 4.59 (d, J = 12.38 Hz, 1H), 4.73 (d, J= 12.38 Hz, 1H), 7.12-7.22 (m, 1H), 7.26-7.40 (m, 4H), 7.70-7.79 (m, 1H), 7.85-7.93 (m, 1H). Anal. (C₂₄H₂₈ClN₅O₂S·0.9HOAc) C, H, N. LCMS (APCI, M + H⁺): 487.2. Method of Example 66 using 97b in place of 2b. 97b was made following the same method of making compound 1b. |
| 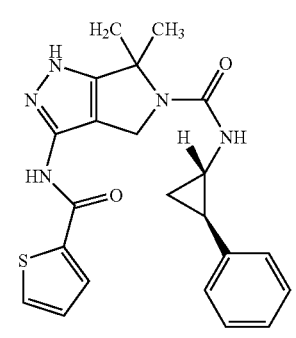 98 | 6,6-dimethyl-N-[trans-2-phenylcyclopropyl]-3-[(2-thienylcarbonyl)amino]-4,6-dihydropyrrolo[3,4-c]pyrazole-5(1H)-carboxamide ¹H NMR (400 MHz, MeOD) δ ppm 1.01-1.15 (m, 2H) 1.64 (d, J = 3.28 Hz, 6H) 1.92-2.00 (m, 1H) 2.63-2.72 (m, 1H) 4.41 (s, 2H) 6.98-7.06 (m, 3H) 7.06-7.17 (m, 3H) 7.65 (dd, J = 5.05, 1.26 Hz, 1H) 7.78 (dd, J = 3.79, 1.01 Hz, 1H). Anal. (C₂₂H₂₃N₅O₂S·0.8 HOAc·0.8 H₂O) C, H, N, S. Method of Example 58 using compound 97b in place of 1b. Compound 97b was made following the same method of making compound 1b. |

| Structure and Example # | Chemical name, Analytical data and comments |
|---|---|
| 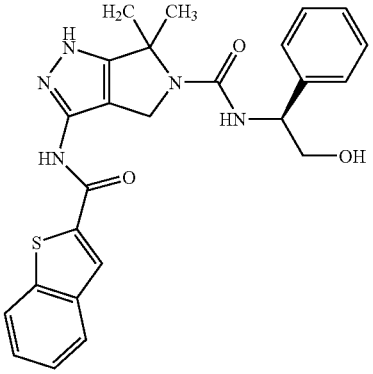<br>99 | 3-[(1-benzothien-2-ylcarbonyl)amino]-N-[(1S)-2-hydroxy-1-phenylethyl]-6,6-dimethyl-4,6-dihydropyrrolo[3,4-c]pyrazole-5(1H)-carboxamide $^1$H NMR (400 MHz, MeOD) δ ppm: 1.64 (d, J = 24.76 Hz, 6H) 3.65-3.75 (m, 2H) 4.64 (d, J = 3.03 Hz, 2H) 4.81-4.87 (m, 1H) 7.10-7.18 (m, 1H) 7.20-7.33 (m, 4H) 7.33-7.43 (m, 2H) 7.78-7.90 (m, 2H) 8.07 (s, 1H). Anal. ($C_{25}H_{25}N_5O_3S$•1.1 HOAc•0.1 $H_2O$) C, H, N, S. Method of Example 46 using 99c in place of 1c. 99c was made using the method of 1c. |
| 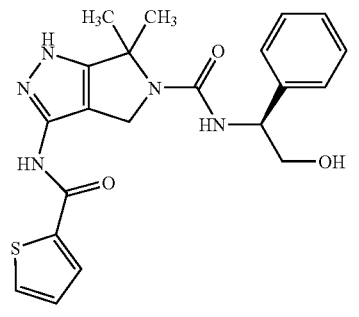<br>100 | N-[(1S)-2-hydroxy-1-phenylethyl]-6,6-dimethyl-3-[(2-thienylcarbonyl)amino]-4,6-dihydropyrrolo[3,4-c]pyrazole-5(1H)-carboxamide 1H NMR (400 MHz, MeOD) δ ppm: 1.62 (s, 3H) 1.68 (s, 3H) 3.65-3.76 (m, 2H) 4.62 (d, J = 2.27 Hz, 2H) 4.82-4.90 (m, 1H) 7.08-7.19 (m, 2H) 7.22-7.36 (m, 4H) 7.68 (dd, J = 4.93, 0.88 Hz, 1H) 7.83 (dd, J = 3.79, 1.01 Hz, 1H). Anal. ($C_{21}H_{23}N_5O_3S$•0.5 HOAc•0.1 $H_2O$)<br>C, H, N, S. Method of Example 46 using 97c in place of 1c. 97c was made using the method of 1c. |
| 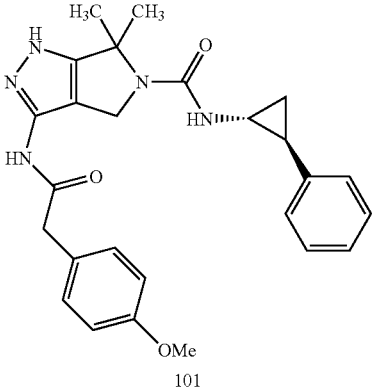<br>101 | 3-{[(4-methoxyphenyl)acetyl]amino}-6,6-dimethyl-N-[trans-2-phenylcyclopropyl]-4,6-dihydropyrrolo[3,4-c]pyrazole-5(1H)-carboxamide 1H NMR (400 MHz, MeOD) δ ppm: 0.99-1.12 (m, 2H) 1.62 (d, J = 3.28 Hz, 6H) 1.89-1.98 (m, J = 9.35, 9.35 Hz, 1H) 2.62-2.71 (m, 1H) 3.52 (s, 2H) 3.68 (s, 3H) 4.31 (s, 2H) 6.79 (d, J = 8.59 Hz, 2H) 6.99-7.06 (m, 3H) 7.10-7.19 (m, 4H). Anal. ($C_{26}H_{29}N_5O_3$•0.3 HOAc•0.2 $H_2O$) C, H, N. Method of Example 70. |
| 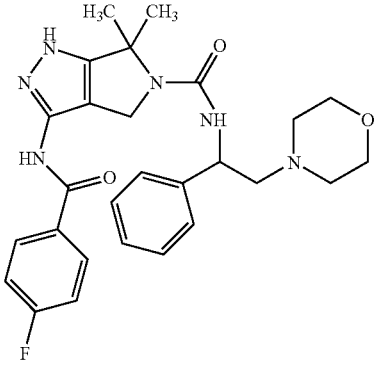<br>102 | 3-[(4-fluorobenzoyl)amino]-6,6-dimethyl-N-(2-morpholin-4-yl-1-phenylethyl)-4,6-dihydropyrrolo[3,4-c]pyrazole-5(1H)-carboxamide 1H NMR (400 MHz, MeOD) δ ppm: 1.63 (d, J = 22.48 Hz, 6H) 2.36-2.45 (m, 2H) 2.46-2.60 (m, 3H) 2.69 (dd, J = 12.88, 10.11 Hz, 1H) 3.55-3.68 (m, 4H) 4.63 (s, 2H) 4.89 (dd, J = 9.85, 4.80 Hz, 1H) 7.10-7.20 (m, 3H) 7.23 (t, J = 7.58 Hz, 2H) 7.26-7.31 (m, 2H) 7.90-7.98 (m, 2H). Anal. ($C_{27}H_{31}N_6O_3F$•0.5 HOAc) C, H, N. Method of Example 59 using 2c in place of 1c. |

| Structure and Example # | Chemical name, Analytical data and comments |
|---|---|
| 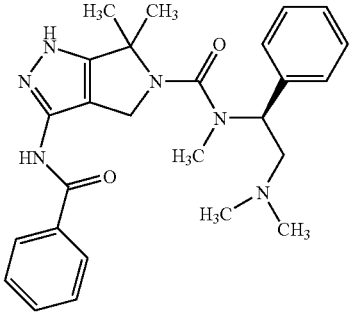 103 | 3-(benzoylamino)-N-[(1S)-2-(dimethylamino)-1-phenyl-ethyl]-N,6,6-trimethyl-4,6-dihydropyrrolo[3,4-c]pyrazole-5(1H)-carboxamide $^1$H NMR (400 MHz, MeOD) δ ppm: 1.76 (d, J = 9.32 Hz, 6H) 2.45 (s, 6H) 2.66 (s, 3H) 3.08 (d, J = 6.04 Hz, 2H) 4.73 (br. s., 2H) 5.13 (t, J = 7.30 Hz, 1H) 7.29 (t, J = 7.30 Hz, 1H) 7.38 (t, J = 7.55 Hz, 2H) 7.41-7.46 (m, 2H) 7.51 (t, J = 7.55 Hz, 2H) 7.59 (t, J = 7.18 Hz, 1H) 7.92 (d, J = 7.81 Hz, 2H). Anal. ($C_{26}H_{32}N_6O_2F$•0.3 HOAc•0.2 $H_2O$) C, H, N. Method of Example 59. |
| 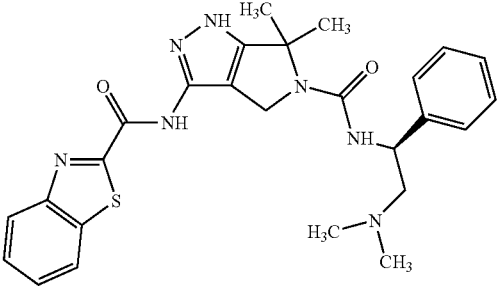 104 | (S)-N-(5-((2-(dimethylamino)-1-phenylethyl)carbamoyl)-6,6-dimethyl-1,4,5,6-tetrahydropyrrolo[3,4-c]pyrazol-3-yl)benzo[d]thiazole-2-carboxamide $^1$H NMR (400 MHz, DMSO) δ ppm: 1.59 (s, 3H), 1.67 (s, 3H), 2.85 (d, J = 3 Hz, 1H), 2.89 (d, 3H, J = 3 Hz), 4.67(dd, J = 9, 6 Hz, 2H), 5.35 (m, 1H), 6.78 (m, 1H), 7.30-7.45 (m, 5H), 7.60-8.40 (m, 5H). Anal. ($C_{26}H_{29}N_7O_2S_1$•2.1 TFA•1 $H_2O$) C, H, N. Method of Example 72. |
| 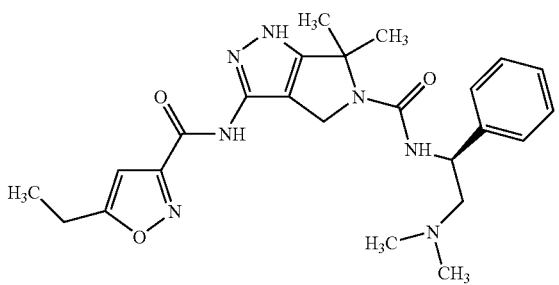 105 | (S)-N-(2-(dimethylamino)-1-phenyl)-3-(5-ethylisoxazole-3-carboxamido)-6,6-dimethylpyrrolo[3,4-c]pyrazole-5(1H,4H,6H)-carboxamide. $^1$H NMR (400 MHz, DMSO) δ ppm: 1.25 (t, J = 6 Hz, 3H), 1.55 (s, 3H), 1.62 (s, 3H), 2.22 (s, 6H), 2.67-2.87 (m, 4H), 4.52 (s, 2H), 4.87 (d, J = 6 Hz, 1H), 6.26 (d, J = 6 Hz, 1H), 6.73 (s, 1H), 7.30-7.46 (m, 5H). Anal. ($C_{24}H_{31}N_7O_3$•0.60 HOAc•1.8 $H_2O$) C, H, N. Method of Example 72. |
| 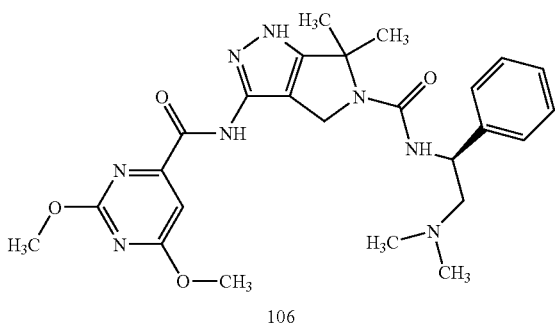 106 | (S)-3-(2,4-dimethoxypyrimidine-6-carboxamido)-N-(2-(dimethylamino)-1-phenylethyl)-6,6-dimethylpyrrolo[3,4-c]pyrazole-5(1H,4H,6H)-carboxamide. $^1$H NMR (400 MHz, DMSO) δ ppm: 1.59 (s, 3H), 1.67 (s, 3H), 2.85 (d, J = 3 Hz, 1H), 2.89 (d, 3H, J = 3 Hz), 3.33-3.59 (m, 2H), 3.97 (s, 3H), 4.06 (s, 3H), 4.79 (m, 1H), 5.36 (m, 1H), 6.82 (d, J = 6 Hz, 1H), 7.04 (s, 1H), 7.30-7.46 (m, 5H). Anal. ($C_{25}H_{32}N_8O_4$•1.3 TFA•2.28 $H_2O$) C, H, N. Method of Example 72. |

| Structure and Example # | Chemical name, Analytical data and comments |
|---|---|
| 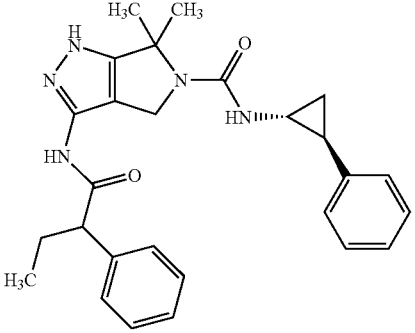 107 | 6,6-dimethyl-3-[(2-phenylbutanoyl)amino]-N-[trans-2-phenylcyclopropyl]-4,6-dihydropyrrolo[3,4-c]pyrazole-5(1H)-carboxamide $^1$H NMR (dmso-d$_6$) δ: 0.83 (t, J = 7.2 Hz, 3H), 1.01 (m, 1H), 1.24 (m, 1H), 1.55 (s, 3H), 1.59 (s, 3H), 1.66 (m, 1H), 1.93 (m, 1H), 2.02 (m, 1H), 2.74 (m, 1H), 3.62 (dd, J = 7.0, 8.1 Hz, 1H), 4.35 (dd, J = 5.3, 12.1 Hz, 1H), 4.40 (dd, J = 6.1, 12.1 Hz, 1H), 6.43 (d, J = 2.5 Hz, 1H), 7.09(d, J = 8.1 Hz, 2H), 7.13(d, J = 6.8 Hz, 1H), 7.24 (m, 3H), 7.35 (m, 4H), 10.61 (s, 1H), 12.27 (s, 1H). Anal. (C$_{27}$H$_{31}$N$_5$O$_2$) C, H, N. HRMS: [M + H]$^+$calc. 458.2251; found 458.2540 Method of Example 70. |
| 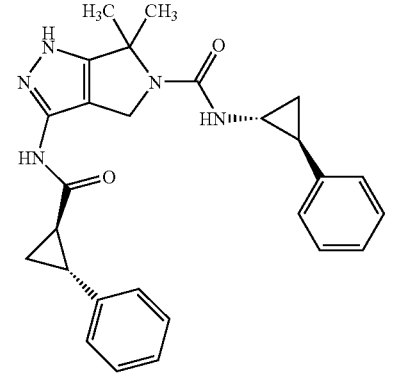 108 | 6,6-dimethyl-N-[trans-2-phenylcyclopropyl]-3-({[trans-2-phenylcyclopropyl]-carbonyl}amino)-4,6-dihydropyrrolo[3,4-c]pyrazole-5(1H)-carboxamide $^1$H NMR (dmso-d$_6$) δ: 1.03 (m, 1H), 1.24 (m, 1H), 1.33 (m, 1H), 1.42 (m, 1H), 1.59 (s, 6H), 1.94 (m, 1H), 2.13 (m, 1H), 2.31 (m, 1H), 2.75 (m, 1H), 4.37 (s, 2H), 6.41 (s, 1H), 7.20 (m, 10H), 10.71 (s, 1H), 12.25 (s, 1H). Anal. (C$_{27}$H$_{29}$N$_5$O$_2$•0.6 H$_2$O) C, H, N. HRMS: [M + H]$^+$ calc. 456.2394; found 456.2390 Method of Example 70. |
| 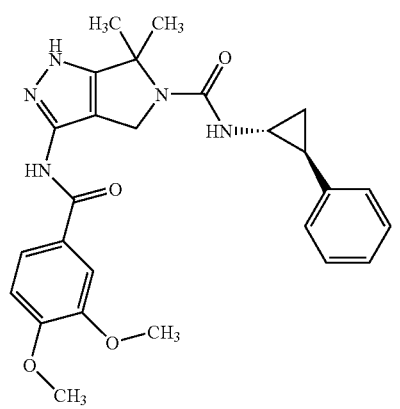 109 | 3-[(3,4-dimethoxybenzoyl)amino]-6,6-dimethyl-N-[trans-2-phenyl-cyclopropyl]-4,6-dihydropyrrolo[3,4-c]pyrazole-5 (1H)-carboxamide $^1$H NMR (dmso-d$_6$) δ: 0.98-1.07 (m, 1H) 1.21-1.29 (m, 1H) 1.63 (s, 6H) 1.91-2.00 (m, 1H) 2.71-2.81 (m, 1H) 3.82 (s, 6H) 4.45(s, 2H) 6.45 (d, J = 2.8 Hz, 1H) 7.04 (d, J = 8.3 Hz, 1H) 7.07-7.16 (m, 3H) 7.24 (t, J = 7.5 Hz, 2H) 7.63 (s, 1H) 7.67 (d, J = 8.6 Hz, 1H) 10.76 (s, 1H) 12.39 (s, 1H). Anal. (C$_{26}$H$_{29}$N$_5$O$_4$•0.8 H$_2$O•3 cyclo-hexane) C, H, N. HRMS: [M + H]$^+$ calc. 476.2292; found 476.2300 Method of Example 70. |

Example 110

(S)-3-(6-chloro-2-fluoro-3-methylbenzamido)-N-(2-(dimethylamino)-1-phenylethyl)-6,6-dimethylpyrrolo[3,4-c]pyrazole-5(1H,4H,6H)-carboxamide

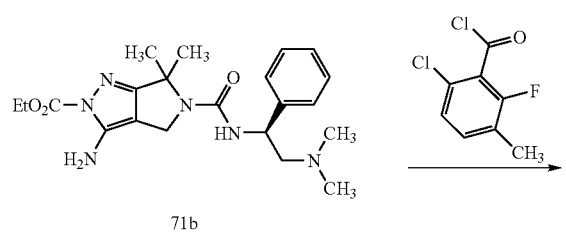

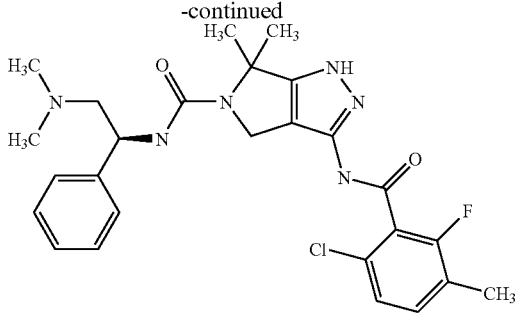

To a 13×100 mm test tube were added one 3×6 mm stir bar, compound 71b, (0.1 M in $CH_2Cl_2$, 80 μmol, 1.0 eq), DIPEA solution (2 M in $CH_2Cl_2$, 160 μmol, 2.0 equiv), and 6-chloro-2-fluoro-3-methylbenzoyl chloride (0.1 M in $CH_2Cl_2$, 160 μmol, 2.0 eq.). The reaction was covered and stirred at RT for 12 h. NaOH (1M, 1000 μmol, 12.5 equiv) was added, and the reaction mixture was agitated for 15 minutes. After centrifugation, the top layer was removed. The organic layer was evaporated. MeOH (500 μL) and TEA (500 μL) were added, and the reaction mixture was allowed to stir at RT overnight. The solvents were evaporated, and the residue was reconstituted in DMSO. $^1$H NMR (500 MHz, $D_2O$) d ppm 1.52 (s, 3H) 1.59 (s, 3H) 2.13 (s, 6H) 2.21 (s, 3H) 2.34 (dd, J=12.22, 5.63 Hz, 1H) 2.59 (dd, J=12.91, 10.16 Hz, 1H) 4.48 (d, J=11.81 Hz, 1H) 4.52 (d, J=12.09 Hz, 1H) 4.81 (q, J=5.77 Hz, 1H) 6.18 (br. s., 1H) 7.14 (t, J=7.55 Hz, 1H) 7.21-7.27 (m, 3H) 7.28-7.38 (m, 3H). LCMS: M+H$^+$: 513.2

| Structure and Example # | Chemical name, Analytical data and comments |
|---|---|
| 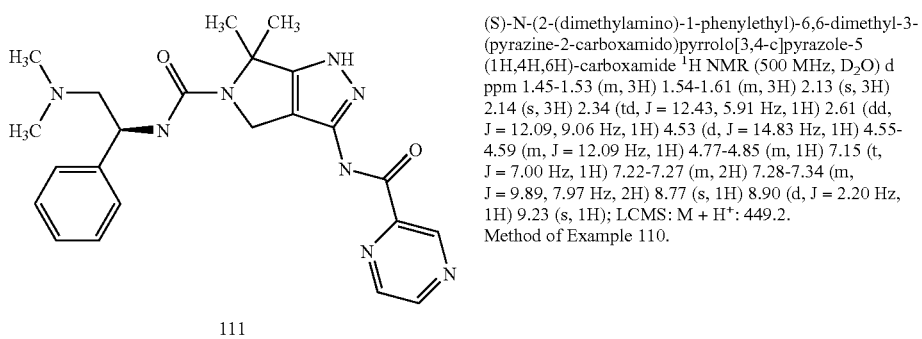<br>111 | (S)-N-(2-(dimethylamino)-1-phenylethyl)-6,6-dimethyl-3-(pyrazine-2-carboxamido)pyrrolo[3,4-c]pyrazole-5(1H,4H,6H)-carboxamide $^1$H NMR (500 MHz, $D_2O$) d ppm 1.45-1.53 (m, 3H) 1.54-1.61 (m, 3H) 2.13 (s, 3H) 2.14 (s, 3H) 2.34 (td, J = 12.43, 5.91 Hz, 1H) 2.61 (dd, J = 12.09, 9.06 Hz, 1H) 4.53 (d, J = 14.83 Hz, 1H) 4.55-4.59 (m, J = 12.09 Hz, 1H) 4.77-4.85 (m, 1H) 7.15 (t, J = 7.00 Hz, 1H) 7.22-7.27 (m, 2H) 7.28-7.34 (m, J = 9.89, 7.97 Hz, 2H) 8.77 (s, 1H) 8.90 (d, J = 2.20 Hz, 1H) 9.23 (s, 1H); LCMS: M + H$^+$: 449.2. Method of Example 110. |
| 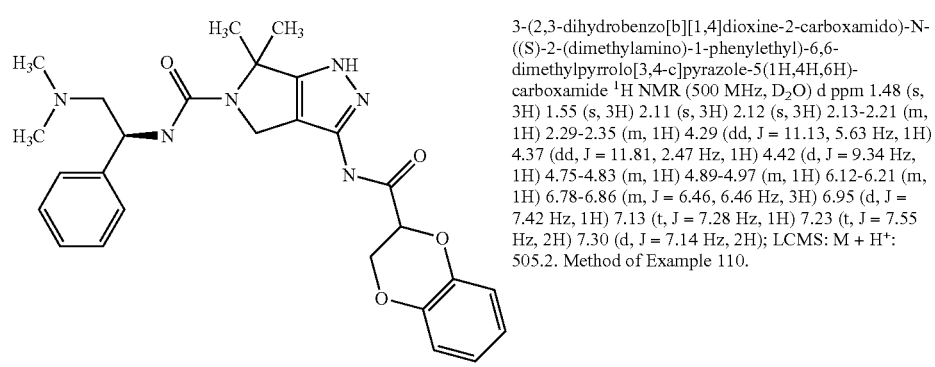<br>112 | 3-(2,3-dihydrobenzo[b][1,4]dioxine-2-carboxamido)-N-((S)-2-(dimethylamino)-1-phenylethyl)-6,6-dimethylpyrrolo[3,4-c]pyrazole-5(1H,4H,6H)-carboxamide $^1$H NMR (500 MHz, $D_2O$) d ppm 1.48 (s, 3H) 1.55 (s, 3H) 2.11 (s, 3H) 2.12 (s, 3H) 2.13-2.21 (m, 1H) 2.29-2.35 (m, 1H) 4.29 (dd, J = 11.13, 5.63 Hz, 1H) 4.37 (dd, J = 11.81, 2.47 Hz, 1H) 4.42 (d, J = 9.34 Hz, 1H) 4.75-4.83 (m, 1H) 4.89-4.97 (m, 1H) 6.12-6.21 (m, 1H) 6.78-6.86 (m, J = 6.46, 6.46 Hz, 3H) 6.95 (d, J = 7.42 Hz, 1H) 7.13 (t, J = 7.28 Hz, 1H) 7.23 (t, J = 7.55 Hz, 2H) 7.30 (d, J = 7.14 Hz, 2H); LCMS: M + H$^+$: 505.2. Method of Example 110. |

-continued

| Structure and Example # | Chemical name, Analytical data and comments |
|---|---|
| 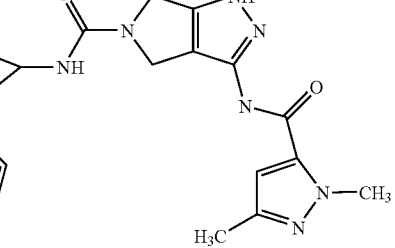 113 | 3-(1,3-dimethyl-1H-pyrazole-5-carboxamido)-6,6-dimethyl-N-[trans-(2-phenylcyclopropyl)]pyrrolo[3,4-c]pyrazole-5(1H,4H,6H)-carboxamide $^1$H NMR (500 MHz, D$_2$O) d ppm 0.96-1.01 (m, J = 12.91, 5.77 Hz, 1H) 1.14-1.23 (m, 1H) 1.58 (s, 6H) 1.91 (ddd, J = 9.06, 5.77, 3.30 Hz, 1H) 2.13 (s, 3H) 2.68-2.74 (m, 1H) 3.90 (d, J = 3.57 Hz, 1H) 3.97 (s, 3H) 4.37 (s, 2H) 6.36 (s, 1H) 6.86 (s, 1H) 7.04-7.11 (m, 3H) 7.20 (t, J = 7.55 Hz, 2H) 10.64-10.76 (m, 1H); LCMS: M + H$^+$: 434.2. Method of Example 110 using 70a in place of 71b. |
| 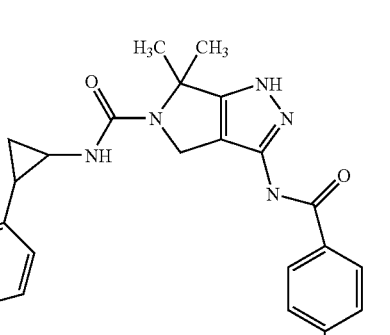 114 | 3-(4-ethylbenzamido)-6,6-dimethyl-N-[trans-(2-phenylcyclopropyl)]pyrrolo[3,4-c]pyrazole-5(1H,4H,6H)-carboxamide $^1$H NMR (500 MHz, D$_2$O) d ppm 0.99 (dd, J = 12.91, 5.77 Hz, 1H) 1.16 (t, J = 7.69 Hz, 3H) 1.19-1.23 (m, 1H) 1.59 (s, 6H) 1.86-1.93 (m, 1H) 2.63 (q, J = 7.51 Hz, 2H) 2.72 (dd, J = 7.14, 4.12 Hz, 1H) 4.39 (s, 2H) 6.37 (d, J = 1.65 Hz, 1H) 7.04-7.11 (m, 3H) 7.20 (t, J = 7.55 Hz, 2H) 7.29 (d, J = 7.69 Hz, 2H) 7.89 (d, J = 7.97 Hz, 2H) 10.71 (s, 1H); LCMS: M + H$^+$: 444.2. Method of Example 110 using 70a in place of 71b. |

The following compounds were also prepared following methods described previously.

| Structure and Example # | Chemical name, Analytical data and comments |
|---|---|
| 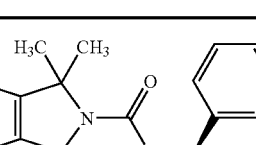 115 | N-[(1S)-2-amino-1-phenylethyl]-3-[(4-fluorobenzoyl)amino]-6,6-dimethyl-4,6-dihydropyrrolo[3,4-c]pyrazole-5(1H)-carboxamide $^1$H NMR (400 MHz, MeOD) ☐ ppm: 1.69 (s, 3H), 1.76 (s, 3H), 3.12-3.25 (m, 2H), 4.60-4.81 (m, 2H), 4.99-5.16 (m, 1H), 7.17-7.48 (m, 7H) 7.86-8.12 (m, 2H). Anal. (C$_{23}$H$_{25}$FN$_6$O$_2$•1.6 H$_2$O•1.0 HOAc) C, H, N. LCMS (APCI, M + H$^+$): 437.2. Method of Example 64 using 2c in place if 1c. |

| Structure and Example # | Chemical name, Analytical data and comments |
|---|---|
| 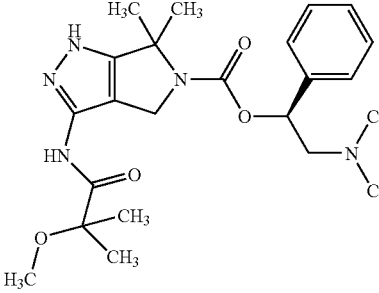<br>116 | (S)-2-(dimethylamino)-1-phenylethyl 3-(2-methoxy-2-methylpropanamido)-6,6-dimethylpyrrolo[3,4-c]pyrazole-5(1H,4H,6H)-carboxylate $^1$HNMR (300 MHz, CDCl$_3$, some peaks doubled due to tautomeric isomerization) δ [1.46 (s), 1.49 (s), 6H together], [1.63 (s), 1.70 (s), 1.73 (s), 1.79 (s), 6H together], [2.30 (s), 2.35 (s), 6H together], 2.60 (t of d, Jt = 13.4 Hz, Jd = 4.6 Hz, 1H), 2.89 (dd, J = 8.3, 13.1 Hz, 1H), [3.356 (s), 3.360 (s), 3H) together], [4.45 (d, J = 13.1 Hz), 4.51 (d, J = 13.1 Hz), 4.71 (d, J = 12.9 Hz), 4.76 (d, J = 13.1 Hz), 2H together], [5.93 (dd, J = 4.8, 8.3 Hz), 5.95 (dd, J = 5.3, 8.3 Hz), 1H together], 7.37 (m, 5H), [9.07 (br s), 9.40 (br s), 1H together]. LCMS (APCI, M + H$^+$): 444. HRMS: M + H$^+$ calc. 444.26053, found 444.26056, error 0.06 ppm. Anal. (C$_{23}$H$_{33}$N$_5$O$_4$•0.5 H$_2$O•0.4 Cyclohexane) C, H, N. Method of Example 1. |
| 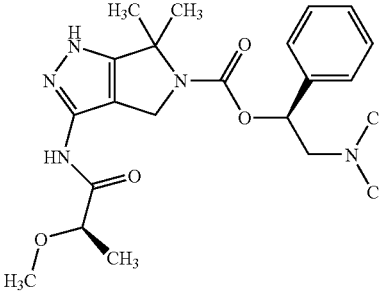<br>117 | (S)-2-(dimethylamino)-1-phenylethyl 3-((R)-2-methoxypropanamido)-6,6-dimethylpyrrolo[3,4-c]pyrazole-5(1H,4H,6H)-carboxylate. $^1$HNMR (300 MHz, MeOD) δ [1.39 (d, J = 6.8 Hz), 1.42 (d, J = 6.8 Hz), 3H together], [1.59 (s), 1.66 (s), 1.70 (s), 1.79 (s), 6H together ], [2.32 (s), 2.37 (s), 6H together], [2.53 (dd, J = 3.3, 13.6 Hz), 2.63 (dd, J = 4.6, 13.4 Hz), 1H together], [2.94 (dd, J = 9.6, 13.6 Hz), 3.01 (dd, J = 8.6, 13.1 Hz), 1H together], [3.42 (s), 3.45 (s), 3H together], 3.92 (m, 1H), 4.47-4.83 (m, 2H), [5.89 (dd, J = 3.0, 9.6 Hz), 5.94 (dd, J = 4.6, 8.6 Hz), 1H together], 7.31 (m, 1H), 7.38 (m, 4H). LCMS (APCI, M + H$^+$): 430. HRMS: M + H$^+$ calc. 430.24488, found 430.24609. Method of Example 89. |
| 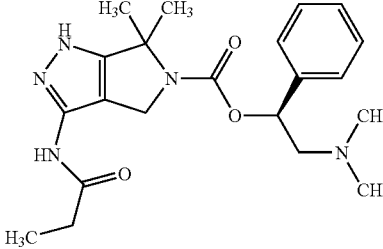<br>118 | (S)-2-(dimethylamino)-1-phenylethyl 6,6-dimethyl-3-propionamidopyrrolo[3,4-c]pyrazole-5(1H,4H,6H)-carboxylate $^1$HNMR (300 MHz, MeOD), δ[1.17 (t, J = 7.6 Hz), 1.21 (t, J = 7.6 Hz), 3H together], [1.59 (s), 1.63 (s), 1.70 (s), 1.79 (s), 6H together], [2.37 (q, J = 7.6 Hz), 2.41 (q, J = 7.6 Hz), 2H together], [2.43 (s), 2.57 (s), 6H together], [2.77 (dd, J = 4.3, 13.4 Hz), 2.82 (dd, J = 3.0, 13.4 Hz), 1H together], 3.19 (dd, J = 9.9, 13.6 Hz, 1H), [4.46 (d, J = 13.4 Hz), 4.52 (d, J = 13.4 Hz), 4.70 (d, J = 13.4 Hz), 4.79 (d, J = 13.4 Hz), 2H together], 5.97 (dd, J = 2.8, 9.9 Hz, 1H), 7.32 (m, 1H), 7.41 (m, 4H). LCMS (APCI, M + H$^+$): 400. HRMS: M + H$^+$ calc. 400.23432, found 400.23425,. Anal. (C$_{21}$H$_{29}$N$_5$O$_3$•1.8 H$_2$O•0.5 HOAc) C, H, N. Method of Example 1. |
| 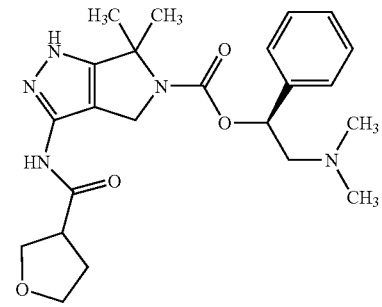<br>119 | (S)-2-(dimethylamino)-1-phenylethyl 6,6-dimethyl-3-(tetrahydrofuran-3-carboxamido)pyrrolo[3,4-c]pyrazole-5(1H,4H,6H)-carboxylate $^1$HNMR (300 MHz, MeOD) δ [1.59 (s), 1.65 (s), 1.69 (s), 1.79 (s), 6H together], 2.21 (q, J = 7.3 Hz, 2H), [2.32 (s), 2.37 (s), 6H together], 2.53 (dd, J = 3.0, 13.4 Hz, 1H), [2.96 (dd, J = 9.6, 13.4 Hz), 3.01 (dd, J = 8.6, 13.4 Hz), 1H together], 3.32 (m, 1H), 3.79-4.04 (m, 4H), 4.43-4.80 (m, 2H), [5.89 (dd, J = 3.0, 9.6 Hz), 5.93 (dd, J = 4.3, 8.3 Hz), 1H together], 7.38 (m, 5H). LCMS (APCI, M + H$^+$): 442. HRMS: M + H$^+$ calc. 442.24488, found 442.24397. Anal. (C$_{23}$H$_{31}$N$_5$O$_4$•0.9 H$_2$O•1.0 cyclohexane) C, H, N. Method of Example 89. |

| Structure and Example # | Chemical name, Analytical data and comments |
|---|---|
| 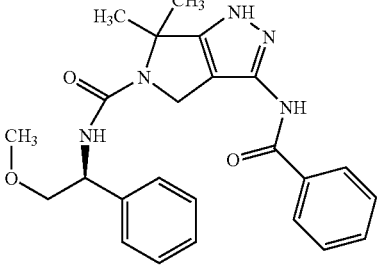<br>120 | (S)-3-benzamido-N-(2-methoxy-1-phenylethyl)-6,6-dimethylpyrrolo[3,4-c]pyrazole-5(1H,4H,6H)-carboxamide $^1$H NMR (500 MHz, DEUTERIUM OXIDE) d ppm 1.49-1.57 (m, 3H) 1.60 (s, 3H) 3.58 (t, J = 10.16, 8.24 Hz, 2H) 4.51 (d, J = 11.54 Hz, 1H) 4.54 (d, J = 11.54 Hz, 1H) 4.93 (dq, J = 7.28, 7.07, 1.10 Hz, 1H) 6.33 (d, J = 8.24 Hz, 1H) 7.16 (t, J = 7.14 Hz, 1H) 7.26 (t, J = 7.28 Hz, 2H) 7.33 (d, J = 7.97 Hz, 2H) 7.45 (t, J = 7.55 Hz, 2H) 7.53 (t, J = 7.00 Hz, 1H) 7.98 (d, J = 7.42 Hz, 2H) 10.81 (s, 1H) 12.37 (s, 1H). LCMS (APCI, M + H$^+$): 434.2. Method of Example 1. |

Example 121

(S)-2-(methylamino)-1-phenylethyl 3-(4-fluorobenzamido)-6,6-dimethylpyrrolo[3,4-c]pyrazole-5(1H,4H,6H)-carboxylate

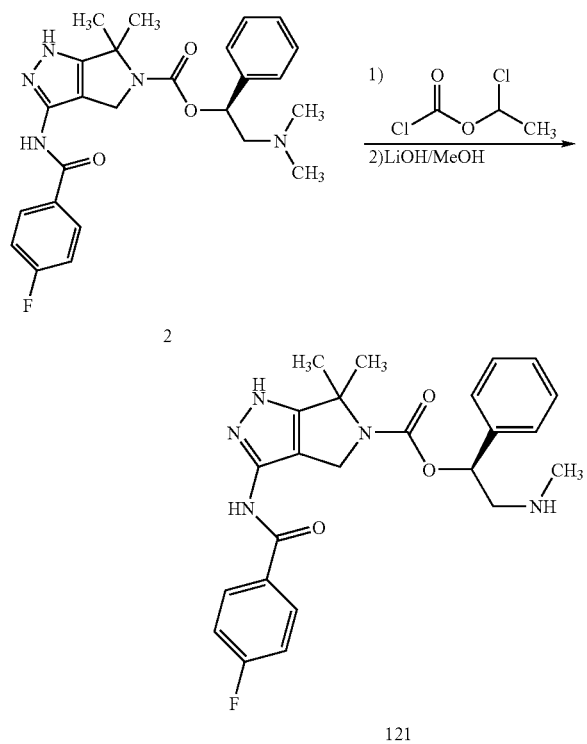

To a solution of compound 2 (194 mg, 0.406 mmol) and 1,8-bis(dimethylamino)naphthalene (34.8 mg, 0.4 eq) in 2 ml 1,2-dichloroethane was added 1-chloroethyl chloroformate (133 ul, 3 eq) at 0° C. The reaction mixture was stirred at reflux for 1 hour and then evaporated to dryness. The residue was dissolved in 1 ml methanol and 1 ml 2N LiOH, stirred at reflux for 1 hour, and again evaporated to dryness. The crude product was purified by prep-HPLC and lyophilized to give the title compound in 28% yield (51 mg) as white foam. $^1$H NMR (400 MHz, MeOD) d ppm 1.62 (s, 3H) 1.73 (s, 3H) 2.59 (s, 3H) 3.05 (dd, J=13.22, 3.40 Hz, 1H) 3.27 (dd, J=13.09, 9.57 Hz, 1H) 4.75-4.83 (m, 1H) 4.92 (m, 1H) 5.91 (dd, J=9.57, 3.53 Hz, 1H) 7.22-7.31 (m, 2H) 7.31-7.38 (m, 1H) 7.38-7.48 (m, 4H) 8.01-8.08 (m, 2H).). Anal. ($C_{24}H_{26}N_5O_3F$.0.4HOAc.0.7H$_2$O) C, H, N.

Biological Testing, Ki Data, Cellular Assay Data and In Vivo Efficacy Data

Cloning, expression, and purification of recombinant PAK4 Kinase domain (PAK4 KD): The cDNA coding for PAK4 was amplified from the EST clone (#12) (purchased from Research Genetics) by using PCR. P33 (ACATATG TCC CATGAGCAGT TCCGGGCTGC CCTGCAGCT) and P34 (CTCA TGGGTGCTTC AGCAGCTCGG CTGC-CGTGGC) were used as the 5' primer and 3' primer in PCR respectively. The PCR amplified product was cloned into Topo vector (Invitrogen Inc.), and verified by DNA sequencing. PAK4 KD was then subcloned into expression plasmid pET28a(+), pET24a(+), or pGST4.5. The recombinant plasmids containing PAK4 KD was transformed into BL21(DE3) cells for recombinant protein expression. The production of PAK4 KD was induced at 27° C. by the addition of IPTG into the cells. The cells were then harvested and lyzed for protein purification. Ni-NTA column (pET28a(+), pET24a(+)) and glutathione column (pGST4.5) were used for the purification. The purified protein was then subjected to thrombin to cleave the N-terminal tags that were inherited from the expression plasmids, and thus gave the PAK4 KD that were used for the Ki assay of this invention.

PAK4 kinase domain enzymatic assay conditions: the enzymatic activity of PAK4 KD was measured by its ability to catalyze the transfer of a phosphate residue from a nucleoside triphosphate to an amino acid side chain of a commercially available peptide (amino acid sequence EVPRRKSLVGT-PYWM). The conversion of ATP to ADP accompanies the catalytic reaction. The PAK4 KD catalyzed production of ADP from ATP was coupled to the oxidation of NADH through the activities of pyruvate kinase (PK) and lactate dehydrogenase (LDH). The conversion of NADH to NAD$^+$ is monitored by the decrease in absorbance at 340 nm (e340=6.22 cm$^{-1}$ mM$^{-1}$) using a Molecular Devices SPEC-TRAMAX 190 in conjunction with the Biomec FX. Typical reaction solutions contain 2 mM phosphoenolpyruvate, 0.35 mM NADH, 10 mM MgCl$_2$, 1 mM DTT, 0.4 mM peptide (EVPRRKSLVGTPYWM) 0.04 mM ATP, 1 units/mL PK, 1 units/mL LDH, 0.01% Tween 20 in 50 mM HEPES, pH 7.5. Assays are initiated with the addition of 25 nM PAK4 KD. The PAK KD Ki of each compound of the invention (the inhibitor) was calculated based on multiple of Percent Inhibition numbers of the inhibitor at different inhibitor concentrations. The peptide (amino sequence EVPRRKSLVGT-PYWM) was purchased from American Peptide Company. NADH, MgCl$_2$, HEPES, DTT, ATP and PK/LDH were purchased from Sigma. Tween 20 was purchased from Calbiochem.

A sandwich ELISA method was used to measure the PAK4 kinase activity in whole cells. The level of PAK4-dependent phosphorylation of GEF-H1b can be determined by monitoring the binding of a phosphospecific antibody to GEF-H1b. A modified HEK 293 cell line is used in the bioassay and it has been engineered to overexpress both GEF-H1b and the kinase domain (KD) of PAK4. The KD of PAK4 is inducible in this cell line by tetracycline (Trex system, Invitrogen). The name of this cell line has been designated TR-293-KDG. To establish a phosphorylation event on GEF-HL, cells are induced with doxycycline to express the PAK4 KD. Negative control wells do not receive induction. Candidate substance effect is measured as the ability to block this phosphorylation event.

ELISA plate was prepared by pre-coating the plates with a capture antibody (α-HA-tag mouse monoclonal antibody), blocked with BSA, and washed in 0.1% tween 20 in tris-buffered saline (TBST). Tissue culture plates (precoated with poly-D-lysine) were seeded with TR-293-KDG cells. The TR-293-KDG Cells were induced to express the PAK4 KD with doxycycline overnight and subsequently & concomitantly treated with candidate substances or diluent for an additional 3-hour, continuous exposure. Cells were then lysed with a modified RIPA buffer supplemented with protease inhibitors. The fresh whole cell lysates were then added to the ELISA plate for 2-hours. Between all subsequent steps plates were washed 4 times with TBST. Detection antibody (recognizing the phospho-specific eptitope on GEF-H1b) was added for 1 hour, followed by addition of an enzyme linked goat α-rabbit secondary antibody for 45 minutes. Color development of the enzyme-linked antibody was performed with a peroxidase substrate, ABTS (Moss, Inc.) with absorbance at 405 nM read with a spectrophotometer after 30 minute incubation. EC50 values were calculated by sigmoid curve fitting using a four-parameter analysis.

PAK4 Kinase Domain Ki data and PAK4 cellular assay EC50 data of the compounds of Examples 1-121:

| Ex. # | Ki data (nM) | EC50 (nM) |
| --- | --- | --- |
| 1 | 10.1 | 10.7 |
| 2 | 16.7 | 9.7 |
| 3 | 42.1 | 50.0 |
| 4 | 68.0 | 14.6 |
| 5 | 14.4 | 271 |
| 6 | 30.9 | 27.9 |
| 7 | 314 | 230 |
| 8 | 124 | 7.4 |
| 9 | 96.4 | 13.3 |
| 10 | 75 | 7.2 |
| 11 | 101 | 15.7 |
| 12 | 95.5 | 3.27 |
| 13 | 109 | 3.9 |
| 14 | 356 | |
| 15 | 145 | 16.1 |
| 16 | 118 | 17.9 |
| 17 | 259 | 110 |
| 18 | 23.3 | 28.3 |
| 19 | 7.87 | 67.8 |
| 20 | 8.13 | 80.2 |
| 21 | 24.8 | 37.6 |
| 22 | 17.4 | 14.8 |
| 23 | 122 | 3.90 |
| 24 | 63.7 | 140 |
| 25 | 78.6 | 153 |
| 26 | 278 | 244 |
| 27 | 82.1 | 79.9 |
| 28 | 73.2 | 280 |
| 29 | 27.1 | 419 |
| 30 | 106 | 2090 |
| 31 | 858 | 230 |
| 32 | 57.1 | 162 |
| 33 | 220 | |
| 34 | 510 | 60 |
| 35 | 92.3 | 216 |
| 36 | 103 | 315 |
| 37 | 564 | |
| 38 | 43.2 | 113 |
| 39 | 47.5 | 15.3 |
| 40 | 64.9 | 152 |
| 41 | 786 | |
| 42 | 955 | |
| 43 | 58.1 | 439 |
| 44 | 800 | |
| 45 | 318 | 21.1 |
| 46 | 33.6 | 32.1 |
| 47 | 54.2 | 34.7 |
| 48 | 98.3 | 36.4 |
| 49 | 193 | 90.8 |
| 50 | 33.8 | 335 |
| 51 | 118 | 20.3 |
| 52 | 354 | 242 |
| 53 | 210 | 28.0 |
| 54 | 41 | 353 |
| 55 | 13.6 | 148 |
| 56 | 6.9 | 37.1 |
| 57 | 11.3 | 16.0 |
| 58 | 96.0 | |
| 59 | 448 | |
| 60 | 267 | |
| 61 | 444 | |
| 62 | 308 | |
| 63 | 178 | |
| 64 | 19.3 | 4000 |
| 65 | 849 | |
| 66 | 556 | |
| 67 | 193 | |
| 68 | 48.2 | 34.1 |
| 69 | 149 | 226 |
| 70 | 223 | |
| 71 | 101 | 84.1 |
| 72 | 93.8 | 362 |
| 73 | 354 | 200 |
| 74 | 475 | |
| 75 | 73.1 | 115 |
| 76 | 468 | |
| 77 | 345 | 167 |
| 78 | 284 | |
| 79 | 96 | 2120 |
| 80 | 756 | 12 |
| 81 | 240 | 104 |
| 82 | 434 | 301 |
| 83A | | 560 |
| 83B | 36.2 | 5 |
| 84A | 70 | 16 |
| 84B | | 396 |
| 85 | 143 | 4 |
| 86 | 68.7 | 18 |
| 87 | 67.3 | |
| 88 | 35.6 | 88 |
| 89 | 156 | 10 |
| 90 | 251 | 4 |
| 91 | 286 | |
| 92 | 345 | 103 |
| 93 | 335 | 178 |
| 94 | 161 | 413 |
| 95 | 137 | 127 |
| 96 | 12.5 | 59 |
| 97 | 110 | 1510 |
| 98 | 19.5 | 1080 |

-continued

| Ex. # | Ki data (nM) | EC50 (nM) |
|---|---|---|
| 99 | 67.9 | 423 |
| 100 | 108 | 178 |
| 101 | 113 | 4000 |
| 102 | 621 | |
| 103 | 512 | |
| 104 | 89 | 9 |
| 105 | 121 | 4000 |
| 106 | 412 | |
| 107 | 260 | |
| 108 | 70 | 1150 |
| 109 | 176 | |
| 110 | 81.7 | |
| 111 | 42% inhibition at 1 μM | |
| 112 | 66% inhibition at 1 μM | |
| 113 | 65% inhibition at 1 μM | |
| 114 | 70% inhibition at 1 μM | |
| 115 | 20.8 | 4000 |
| 116 | 212 | 50 |
| 117 | 357 | 8.8 |
| 118 | 226 | |
| 119 | 260 | 52 |
| 120 | 463 | |
| 121 | 16.2 | 124 |

Compound of Example 2 (1S)-2-(dimethylamino)-1-phenylethyl 3-[(4-fluorobenzoyl)amino]-6,6-dimethyl-4,6-dihydropyrrolo[3,4-c]pyrazole-5(1H)-carboxylate showed in vivo tumor growth inhibition of HCT116 human colorectal carcinoma tumor xenografts in athymic mice. The details are provided in the following paragraphs.

Material and preparation: The HCT116 cell line was obtained from American Type Culture Collection (ATCC, Bethesda, Md.). Cells were grown as monolayers in McCoy's media each supplemented with 10% FBS (each from Life Technologies, Inc., Bethesda, Md.) and maintained at 37° C. in a humidified atmosphere at 5% $CO_2$. Tumor cells for implantation into athymic mice were harvested near confluence by incubation with 0.05% Trypsin-EDTA. Cells were pelleted at 450×g for 5-10 minutes and the cell pellets were re-suspended in serum-free McCoy's medium supplemented with 50% matrigel. Tumor cells ($1 \times 10^6$ cells/animal) were implanted s.c. into the hindflank region of each mouse on day 0 and allowed to grow to the designated size prior to the administration of compound for each experiment.

Tumor growth inhibition: Treatment was initiated when tumors were approximately 200 mm3 in size. Compound of Example 2 or vehicle (methyl cellulose, MC) was administered as an oral gavage daily or every other day at 10 mL/kg. Tumors were measured using Vernier calipers, and tumor volumes were calculated utilizing the formula length× width2×0.4. Tumor volume was measured on the indicated days, with the median tumor volume indicated for each group of 12 animals; median±SEM. At the end of the study, the maximum percent tumor growth inhibition was calculated as 100×(tumor volume$_{final}$–tumor volume$_{initial}$) for Compound 1f Example 2-treated group/(tumor volume$_{final}$–tumor volume$_{initial}$) for vehicle group on day 39 and tumor growth delay was calculated as median tumor volume$_{treated}$–median tumor volume$_{control}$ when median tumor volume reached 1250 mm$^3$.

Tumor growth delay: Treatment with Compound of Example 2 began on day 11 when tumors reached a volume of ~200 mm$^3$ and continued for 28 days until the control tumors reached evaluation size (1250 mm$^3$). Tumor measurement continued until treated tumors reached evaluation size (1250 mm$^3$) in order to assess tumor growth delay. Compound of Example 2 was administered to tumor-bearing mice by oral gavage as a solution in MC in 10 mL/kg volume and compared with vehicle alone administered in the same volume. Oral administration of Compound of Example 2 at 50 mg/kg/day or 75 mg/kg every other day was demonstrated to result in statistically significant tumor growth inhibition (p=0.05) of 50% or 37%, respectively compared with vehicle-treated controls (FIG. 1). In addition, a tumor growth delay of 12.2 or 9.8 days was observed at the 50 mg/kg/day or 75 mg/kg every other day dose levels, respectively (FIG. 1). Mice administered Compound of Example 2 throughout the 28 day treatment cycle generally appeared healthy and continued to gain weight.

The tumor growth inhibition and tumor growth delay results of compound of Example 2, (1S)-2-(dimethylamino)-1-phenylethyl 3-[(4-fluorobenzoyl)amino]-6,6-dimethyl-4,6-dihydropyrrolo[3,4-c]pyrazole-5(1H)-carboxylate, are summarized in the following table and FIG. 1.

| Endpoint | Parameter | 50 mg/kg QD | 75 mg/Kg/QOD |
|---|---|---|---|
| Tumor growth inhibition (TGI) | % TGI$_{max}$ d39 | 50.0 | 36.6 |
| Tumor growth delay | T-C$_{1250\ mm3}$ (Days) | 12.2 | 9.8 |

As shown in FIG. 1, Compound of Example 2 inhibited/delayed growth of HCT116 human colorectal carcinoma tumor xenografts in athymic mice. Oral administration of compound of Example 2 at 50 mg/kg/day (QD) or 75 mg/kg/every other day (QOD) was initiated when the tumors reached an average size of 200 mm$^3$ on Day 11 and continued until Day 39 at which time treatment was ceased. Tumor volume was measured on the indicated days, with the mean tumor volume indicated for groups of 10 animals; median±SEM. *ANOVA p<0.01 for both 50 & 75 mg/kg vs. vehicle groups at indicated timepoints.

We claim:

1. A compound of formula I,

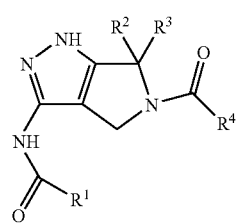

wherein:
R$^1$ is ethyl, t-butyl, R, -L-(C$_3$-C$_{12}$ cycloalkyl), -L-phenyl, -L-(5-12 member heteroaryl), -L-(3-12 member heterocyclyl) and -L-(C$_3$-C$_{12}$ unsaturated nonaromatic carbocyclyl);

each $R^2$ and $R^3$ is independently H, $C_1$-$C_8$ alkyl, $C_2$-$C_8$ alkenyl, $C_2$-$C_8$ alkynyl, —($C_1$-$C_3$ alkylene)$_m$-($C_3$-$C_{12}$ cycloalkyl) or —($C_1$-$C_6$ perfluoroalkyl), and each $R^2$ and $R^3$ is optionally further substituted by 1-3 groups selected from halide, —CN, oxo, —OH, —NH$_2$, $C_1$-$C_6$ monoalkylamino and $C_2$-$C_8$ dialkylamino; or $R^2$ and $R^3$ together with the carbon atom that $R^2$ and $R^3$ attach to, form a ring selected from 3-5 member nonaromatic carbocyclylene and 3-5 member heterocyclylene, and the said ring is optionally further substituted by 1-3 groups selected from $C_1$-$C_3$ alkyl, $C_1$-$C_3$ perfluoroalkyl, oxo, —($C_1$-$C_3$ alkylene)$_m$-halide, —($C_1$-$C_3$ alkylene)$_m$-CN, —($C_1$-$C_3$ alkylene)$_m$-OH, —($C_1$-$C_3$ alkylene)$_m$-NH$_2$, —($C_1$-$C_3$ alkylene)$_m$-($C_1$-$C_6$ monoalkylamino) and —($C_1$-$C_3$ alkylene)$_m$-($C_2$-$C_8$ dialkylamino);

$R^4$ is selected from —OR$^5$, —O—R$^6$—R$^7$, —O—CH(R$^8$)R$^9$, —N(R$^t$)—R$^6$—R$^7$, —N(R$^t$)CH(R$^8$)R$^9$, —CH(R$^t$)—R$^6$—R$^7$, —CH(R$^t$)—CH(R$^8$)—R$^9$, —B—(C$_1$-C$_3$ alkylene)-CH(R$^8$)R$^9$ and —B—(C$_1$-C$_3$ alkylene)$_m$-CH(R$^{10}$)R$^9$, and B is —O—, —N(R$^t$)— or —CH(R$^t$)—;

$R^5$ is R;

$R^6$ is a divalent radical selected from —(C$_3$-C$_7$ cycloalkylene)-, -(3 to 7 member heterocyclylene)- and -(5 to 7 member heteroarylene)-, provided when $R^4$ is —CH$_2$—R$^6$—R$^7$ and R$^7$ is unsubstituted phenyl, R$^6$ is not unsubstituted thiazolylene; R$^6$ is optionally further substituted by 1-4 groups selected from C$_1$-C$_3$ alkyl, oxo, C$_1$-C$_3$ perfluoroalkyl, —(C$_1$-C$_3$ alkylene)$_m$-halide, —(C$_1$-C$_3$ alkylene)$_m$-(C$_1$-C$_3$ alkylamino), —(C$_1$-C$_3$ alkylene)$_m$-NH$_2$, —(C$_1$-C$_3$ alkylene)$_m$-OH and —(C$_1$-C$_3$ alkylene)$_m$-(C$_1$-C$_3$ alkoxy);

$R^7$ is selected from phenyl, C$_{10}$-C$_{12}$ aryl, C$_3$-C$_{12}$ cycloalkyl, C$_4$-C$_{12}$ unsaturated nonaromatic carbocyclyl, 3-12 member heterocyclyl and 5-12 member heteroaryl;

$R^8$ is —(C$_1$-C$_6$ alkylene)$_n$-NR$^p$R$^q$, wherein each R$^p$ and R$^q$ is independently H or C$_1$-C$_6$ alkyl, or R$^p$ and R$^q$, together with the nitrogen atom which R$^p$ and R$^q$ attach to, form a ring selected from 3-7 member heterocyclyl and 5-7 member heteroaryl, and the said ring is optionally further substituted by 1-6 groups selected from halide, C$_1$-C$_3$ alkyl, oxo and C$_1$-C$_3$ perfluoroalkyl;

$R^9$ is selected from C$_1$-C$_6$ alkyl, C$_2$-C$_6$ alkenyl, C$_2$-C$_6$ alkynyl, C$_1$-C$_6$ alkoxyl, C$_1$-C$_6$ perfluoroalkyl, phenyl, -(L$^1$)-phenyl, C$_{10}$-C$_{12}$ aryl, -(L$^1$)-(C$_{10}$-C$_{12}$ aryl), C$_3$-C$_{12}$ cycloalkyl, -(L$^1$)—(C$_3$-C$_{12}$ cycloalkyl), C$_4$-C$_{12}$ unsaturated nonaromatic carbocyclyl, -(L$^1$)-(C$_4$-C$_{12}$ unsaturated nonaromatic carbocyclyl), 3-12 member heterocyclyl, -(L$^1$)-(3-12 member heterocyclyl), 5-12 member heteroaryl and -(L$^1$)-(5-12 member heteroaryl);

$R^{10}$ is selected from C$_1$-C$_6$ alkyl, C$_1$-C$_6$ perfluoroalkyl, —(C$_1$-C$_6$ alkylene)$_m$-(C$_1$-C$_6$ alkoxyl), —(C$_1$-C$_6$ alkylene)$_m$-(CONR$^j$R$^k$) wherein each R$^j$ and R$^k$ is independently H or C$_1$-C$_3$ alkyl, —(C$_1$-C$_3$ alkylene)$_m$-(C$_3$-C$_6$ cycloalkyl) and —(C$_1$-C$_3$ alkylene)$_m$-(3 to 6 member heterocyclyl), and R$^{10}$ is optionally further substituted by 1-3 groups selected from halide, —OH, oxo and C$_1$-C$_3$ alkyl, provided that when R$^4$ is —B—CH(R$^{10}$)R$^9$, B is NH or CH$_2$ and R$^9$ is unsubstituted —CH$_3$ or unsubstituted phenyl, R$^{10}$ is not unsubstituted CH$_3$;

each R is independently selected from the group consisting of methyl, n-propyl, isopropyl, n-butyl, sec-butyl, isobutyl, C$_5$-C$_8$ alkyl, C$_2$-C$_8$ alkenyl, C$_2$-C$_8$ alkynyl, —(C$_1$-C$_3$ alkylene)$_m$-(C$_3$-C$_{12}$ cycloalkyl), —(C$_1$-C$_3$ alkylene)$_m$-phenyl, —(C$_1$-C$_3$ alkylene)$_m$-(5-12 member heteroaryl), —(C$_1$-C$_3$ alkylene)$_m$-(3-12 member heterocyclyl), —(C$_1$-C$_3$ alkylene)$_m$—(C$_3$-C$_{12}$ unsaturated non-aromatic carbocyclyl), —(C$_1$-C$_6$ perfluoroalkyl), —(C$_1$-C$_3$ alkylene)$_m$-halide, —(C$_1$-C$_3$ alkylene)$_m$-CN, —(C$_1$-C$_3$ alkylene)$_m$-C(O)R$^a$, —(C$_1$-C$_3$ alkylene)$_m$-C(O)OR$^a$, —(C$_1$-C$_3$ alkylene)$_m$-C(O)NR$^a$R$^b$, —(C$_1$-C$_3$ alkylene)$_m$-OR$^a$, —(C$_1$-C$_3$ alkylene)$_m$-OC(O)R$^a$, —(C$_1$-C$_3$ alkylene)$_m$-OC(O)NR$^a$R$^b$, —(C$_1$-C$_3$ alkylene)$_m$-O—S(O)R$^a$, —(C$_1$-C$_3$ alkylene)$_m$-OS(O)$_2$R$^a$, —(C$_1$-C$_3$ alkylene)$_m$-OS(O)$_2$NR$^a$R$^b$, —(C$_1$-C$_3$ alkylene)-(C$_1$-C$_3$ alkylene)$_m$-N$_2$, —(C$_1$-C$_3$ alkylene)$_m$-NR$^a$R$^b$, —(C$_1$-C$_3$ alkylene)$_m$-N(R$^a$)C(O)R$^b$, —(C$_1$-C$_3$ alkylene)$_m$-N(R$^a$)C(O)OR$^b$, —(C$_1$-C$_3$ alkylene)$_m$-N(R$^c$)C(O)NR$^a$R$^b$, —(C$_1$-C$_3$ alkylene)$_m$-N(R$^a$)S(O)$_2$R$^b$, (C$_1$-C$_3$ alkylene)$_m$-N(R$^a$)S(O)R$^b$, —(C$_1$-C$_3$ alkylene)$_m$-SR$^a$, —(C$_1$-C$_3$ alkylene)$_m$-S(O)R$^a$, —(C$_1$-C$_3$ alkylene)$_m$-S(O)$_2$R$^a$, —(C$_1$-C$_3$ alkylene)$_m$-S(O)NR$^a$R$^b$, —(C$_1$-C$_3$ alkylene)$_m$-S(O)$_2$NR$^a$R$^b$, —(C$_1$-C$_3$ alkylene)$_m$-O—(C$_1$-C$_3$ alkylene)$_m$-NR$^a$R$^b$ and —(C$_1$-C$_3$ alkylene)$_m$-NR$^a$-(C$_1$-C$_3$ alkylene)-OR$^b$; the said C$_3$-C$_{12}$ cycloalkyl, the said phenyl, the said 3-12 member heterocyclyl and the said 5-12 member heteroaryl are independently optionally further substituted by 1-3 groups selected from —F, C$_1$-C$_3$ alkyl, C$_1$-C$_3$ perfluoroalkyl and oxo;

each R$^a$, R$^b$ and R$^c$ is independently H, C$_1$-C$_8$ alkyl, C$_2$-C$_8$ alkenyl, —(C$_1$-C$_3$ alkylene)$_m$-(C$_3$-C$_8$ cycloalkyl), —(C$_1$-C$_3$ alkylene)$_m$-(C$_3$-C$_8$ cycloalkenyl), C$_2$-C$_8$ alkynyl, —(C$_1$-C$_3$ alkylene)$_m$-phenyl, —(C$_1$-C$_3$ alkylene)$_m$-(5-7 member heteroaryl) or —(C$_1$-C$_3$ alkylene)$_m$-(3-8 member heterocyclyl), and each R$^a$, R$^b$ and R$^c$ is independently optionally further substituted by 1-3 groups selected from halide, hydroxyl, —CN, C$_1$-C$_6$ alkyl, C$_1$-C$_6$ perfluoroalkyl, C$_1$-C$_6$ alkoxyl and C$_1$-C$_6$ alkylamino; or, when connected to the same nitrogen, R$^a$ and R$^b$ may optionally form a ring selected from -(5-7 member heteroaryl) and -(3-8 member heterocyclyl), and the said ring is optionally further substituted by 1-3 groups selected from halide, hydroxyl, —CN, C$_1$-C$_6$ alkyl, C$_1$-C$_6$ perfluoroalkyl, C$_1$-C$_6$ alkoxyl and C$_1$-C$_6$ alkylamino;

each R$^t$ is independently H or C$_1$-C$_3$ alkyl;

each R$^1$, R$^5$, R$^7$ and R$^9$ is independently optionally further substituted by 1-6 groups selected from oxo and R$^x$;

each R$^x$ is independently ethyl, t-butyl or R;

each L is independently a bivalent radical selected from —(C$_1$-C$_3$ alkylene)$_m$-(C$_3$-C$_7$ cycloalkylene)-, —(C$_2$-C$_8$ alkenylene)-, —(C$_2$-C$_8$ alkynylene)-, —O—(C$_1$-C$_3$ alkylene)$_m$- and —NH—(C$_1$-C$_3$ alkylene)$_m$-;

each L$^1$ is independently a bivalent radical selected from —(C$_1$-C$_3$ alkylene)-, —O—, —(C$_1$-C$_3$ alkylene)-O—, —N(R$^t$)— and —(C$_1$-C$_3$ alkylene)-N(R$^t$)—; and each m is independently 0 or 1;

or a pharmaceutically acceptable salt thereof.

2. The compound of claim 1 or a pharmaceutically acceptable salt thereof, wherein R$^2$ is unsubstituted methyl and R$^3$ is unsubstituted methyl.

3. The compound of claim 2, or a pharmaceutically acceptable thereof, wherein R$^1$ is selected from the group consisting of C$_1$-C$_8$ alkyl, —(C$_1$-C$_3$ alkylene)$_m$-phenyl, —(C$_3$-C$_7$ cycloalkylene)-phenyl, —(C$_1$-C$_3$ alkylene)$_m$-(C$_3$-C$_{12}$ cycloalkyl), —(C$_3$-C$_7$ cycloalkylene)-(C$_3$-C$_{12}$ cycloalkyl), —(C$_1$-C$_3$ alkylene)$_m$-(C$_3$-C$_{12}$ unsaturated nonaromatic carbocyclyl), —(C$_3$-C$_7$ cycloalkylene)-(C$_3$-C$_{12}$ unsaturated nonaromatic carbocyclyl)-(C$_1$-C$_3$ alkylene)$_m$-(5-10 member heteroaryl), —(C$_3$-C$_7$ cycloalkylene)-(5-10 member heteroaryl), —(C$_1$-C$_3$ alkylene)$_m$-(3-10 member heterocyclyl) and —(C$_3$-C$_7$ cycloalkylene)-(3-10 member heterocyclyl), and R$^1$ is optionally further substituted by 1-6 groups selected from the group consisting of $C_1$-$C_3$ alkyl, —($C_1$-$C_3$ alkylene)$_m$-($C_3$-$C_5$ cycloalkyl), —($C_1$-$C_3$ alkylene)$_m$-(3-6 member heterocyclyl optionally further substituted by 1-2 methyl), F, Cl, —CN, $C_1$-$C_3$ perfluoroalkyl, —($C_1$-$C_3$ alkylene)$_m$-NH$_2$, —($C_1$-$C_3$ alkylene)$_m$-NH($C_1$-$C_4$ alkyl), —($C_1$-$C_3$ alkylene)$_m$-N($C_1$-$C_4$ alkyl)($C_1$-$C_4$ alkyl), —($C_1$-$C_3$ alkylene)$_m$-NH—($C_3$-$C_5$ cycloalkyl)-($C_1$-$C_3$ alkylene)$_m$-OH, —($C_1$-$C_3$ alkylene)$_m$-O—($C_1$-$C_4$ alkyl), —($C_1$-$C_3$ alkylene)$_m$-O—($C_3$-$C_5$ cycloalkyl), —($C_1$-$C_3$ alkylene)$_m$-C(O)—NH$_2$, —($C_1$-$C_3$ alkylene)$_m$-C(O)—NH—($C_1$-$C_4$ alkyl) and —($C_1$-$C_3$ alkylene)$_m$-C(O)—N($C_1$-$C_4$ alkyl)($C_1$-$C_4$ alkyl).

4. The compound of claim 2, or a pharmaceutically acceptable thereof, wherein $R^1$ is selected from the group consisting of $C_1$-$C_8$ alkyl, $C_3$-$C_8$ cycloalkyl, phenyl, —($C_1$-$C_3$ alkylene)-phenyl, -(cyclopropylene)-phenyl, -pyridinyl, —($C_1$-$C_3$ alkylene)-pyridinyl, —(cyclopropylene)-pyridinyl, -pyrimidinyl, —($C_1$-$C_3$ alkylene)-pyrimidinyl, -(cyclopropylene)-pyrimidinyl, thiophenyl, —($C_1$-$C_3$ alkylene)-thiophenyl, -(cyclopropylene)-thiophenyl, pyrazolyl, —($C_1$-$C_3$ alkylene)-pyrazolyl, -(cyclopropylene)-pyrazolyl, tetrahydrofuranyl, —($C_1$-$C_3$ alkylene)-tetrahydrofuranyl, —($C_1$-$C_3$ cyclopropylene)-tetrahydrofuranyl, tetrahydropyranyl, —($C_1$-$C_3$ alkylene)-tetrahydropyranyl, —($C_1$-$C_3$ cyclopropylene)-tetrahydropyranyl, morpholinyl, —($C_1$-$C_3$ alkylene)-morpholinyl, -(cyclopropylene)-morpholinyl, imidazolyl, —($C_1$-$C_3$ alkylene)-imidazolyl, -(cyclopropylene)-imidazolyl, thiazolyl, —($C_1$-$C_3$ alkylene)-thiazolyl, -(cyclopropylene)-thiazolyl, isothiazolyl, —($C_1$-$C_3$ alkylene)-isothiazolyl, -(cyclopropylene)-isothiazolyl, oxazolyl, —($C_1$-$C_3$ alkylene)-oxazolyl, -(cyclopropylene)-oxazolyl, isoxazolyl, —($C_1$-$C_3$ alkylene)-isoxazolyl, -(cyclopropylene)-isoxazolyl, benzothiophenyl, —($C_1$-$C_3$ alkylene)-benzothiophenyl, -(cyclopropylene)-benzothiophenyl, benzothiazolyl, —($C_1$-$C_3$ alkylene)-benzothiazolyl, -(cyclopropylene)-benzothiazolyl, dihydrobenzofuranyl, —($C_1$-$C_3$ alkylene)-dihydrobenzofuranyl, -(cyclopropylene)-dihydrobenzofuranyl, pyrazinyl, —($C_1$-$C_3$ alkylene)-pyrazinyl and -(cyclopropylene)-pyrazinyl, wherein $R^1$ is optionally further substituted by 1-3 groups selected from F, Cl, $C_1$-$C_3$ alkyl, $C_1$-$C_3$ perfluoroalkyl and $C_1$-$C_3$ alkoxyl.

5. A compound of formula II,

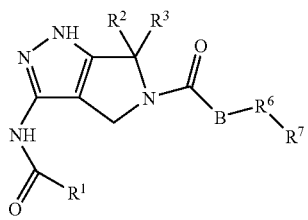

II wherein:
B is —O—, —NR$^t$— or —CHR$^t$—, wherein R$^t$ is H or $C_1$-$C_3$ alkyl;
$R^1$ is selected from the group consisting of $C_1$-$C_8$ alkyl, —($C_1$-$C_3$ alkylene)$_m$-phenyl, —($C_3$-$C_5$ cycloalkylene)-phenyl, —($C_1$-$C_3$ alkylene)$_m$-($C_3$-$C_{10}$ cycloalkyl), —($C_1$-$C_3$ alkylene)$_m$-($C_5$-$C_{10}$ cycloalkenyl), —($C_1$-$C_3$ alkylene)$_m$-(3-10 member heterocyclyl), —($C_3$-$C_5$ cycloalkylene)-(3-10 member heterocyclyl), —($C_1$-$C_3$ alkylene)$_m$-(5-12 member heteroaryl) and —($C_3$-$C_5$ cycloalkylene)-(5-12 member heteroaryl), and $R^1$ is optionally further substituted by 1-6 groups selected from —($C_1$-$C_3$ alkylene)$_m$-halide, —($C_1$-$C_3$ alkylene)$_m$-hydroxyl, —($C_1$-$C_3$ alkylene)$_m$-CN, $C_1$-$C_6$ alkyl, $C_1$-$C_6$ perfluoroalkyl, —($C_1$-$C_3$ alkylene)$_m$-($C_1$-$C_6$ alkoxyl), —($C_1$-$C_3$ alkylene)$_m$-NH$_2$, —($C_1$-$C_3$ alkylene)$_m$-($C_1$-$C_6$ alkylamino), —($C_1$-$C_3$ alkylene)$_m$-($C_3$-$C_5$ cycloalkyl) and —($C_1$-$C_3$ alkylene)$_m$-(3-5 member heterocyclyl), and the said $C_3$-$C_5$ cycloalkyl and the said 3-5 member heterocyclyl is optionally further substituted by 1-3 group selected from —F, $C_1$-$C_3$ alkyl, $C_1$-$C_3$ perfluoroalkyl and oxo;

each $R^2$ and $R^3$ is independently $C_1$-$C_3$ alkyl, or $R^2$ and $R^3$, together with the carbon atom that $R^2$ and $R^3$ attach to, form a $C_3$-$C_4$ cycloalkylene;

$R^6$ is a divalent radical selected from cyclopropylene, cyclobutylene, cyclopentylene and -(3-6 member heterocyclylene)-, $R^6$ is optionally further substituted by 1-6 groups selected from halide, $C_1$-$C_3$ alkyl, oxo and $C_1$-$C_3$ perfluoroalkyl;

$R^7$ is selected from phenyl, 5 member heteroaryl, pyridinyl, 6 member heteroaryl containing 2-3 heteroatoms selected from N, S and O, 7-10 member heteroaryl and 3-12 member heterocyclyl, $R^7$ is optionally further substituted by 1-6 groups selected from halide, —$C_1$-$C_3$ perfluoroalkyl, $C_1$-$C_3$ alkyl, $C_1$-$C_3$ alkoxy, $C_1$-$C_3$ alkylamino, —OH, —NH$_2$ and —CN;

each m is independently 0 or 1; or
a pharmaceutically acceptable salt thereof.

6. The compound of claim 5, or a pharmaceutically acceptable thereof, wherein $R^2$ is methyl; $R^3$ is methyl; B is —O—, —NH— or —CH$_2$—; $R^1$ is selected from the group consisting of $C_1$-$C_8$ alkyl, phenyl, —($C_1$-$C_3$ alkylene)-phenyl, -(cyclopropylene)-phenyl, $C_3$-$C_{10}$ cycloalkyl, —($C_1$-$C_3$ alkylene)-($C_3$-$C_{10}$ cycloalkyl), 3-10 member heterocyclyl, —($C_1$-$C_3$ alkylene)-(3-10 member heterocyclyl), -(cyclopropylene)-(3-10 member heterocyclyl), 5-12 member heteroaryl, —($C_1$-$C_3$ alkylene)-(5-12 member heteroaryl) and -(cyclopropylene)-(5-12 member heteroaryl), and $R^1$ is optionally further substituted by 1-6 groups selected from F, Cl, hydroxyl, CN, $C_1$-$C_6$ alkyl, $C_1$-$C_6$ perfluoroalkyl and —($C_1$-$C_3$ alkylene)$_m$-($C_1$-$C_6$ alkoxyl).

7. The compound of claim 6, or a pharmaceutically acceptable thereof, where $R^6$ is unsubstituted cyclopropylene.

8. The compound of claim 6, or a pharmaceutically acceptable thereof, wherein $R^6$ is cyclopropylene substituted by 1-3 groups selected from F, Cl, $C_1$-$C_3$ alkyl and $C_1$-$C_3$ perfluoalkyl.

9. The compound of claim 6, or a pharmaceutically acceptable thereof, wherein $R^7$ is selected from the group consisting of phenyl, 5-6 member heteroaryl and 4-7 member heterocyclyl, and $R^7$ is optionally further substituted by 1-3 groups selected from F, Cl, $C_1$-$C_3$ alkyl, $C_1$-$C_3$ perfluoalkyl and $C_1$-$C_3$ alkoxyl.

10. A compound of formula III,

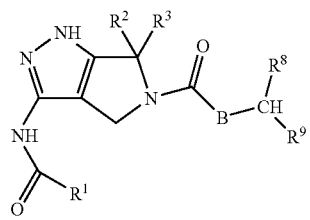

III wherein:
B is —O—, —NR'— or —CHR'—, wherein R$^t$ is H or C$_1$-C$_3$ alkyl;
R$^1$ is selected from C$_1$-C$_8$ alkyl, —(C$_1$-C$_3$ alkylene)$_m$-phenyl, —(C$_3$-C$_5$ cycloalkylene)-phenyl, —(C$_1$-C$_3$ alkylene)$_m$-(C$_3$-C$_{10}$ cycloalkyl), —(C$_1$-C$_3$ alkylene)$_m$-(C$_5$-C$_{10}$ cycloalkenyl), —(C$_1$-C$_3$ alkylene)$_m$-(3-10 member heterocyclyl), —(C$_3$-C$_5$ cycloalkylene)-(3-10 member heterocyclyl), —(C$_1$-C$_3$ alkylene)$_m$-(5-12 member heteroaryl) and —(C$_3$-C$_5$ cycloalkylene)-(5-12 member heteroaryl), and R$^1$ is optionally further substituted by 1-6 groups selected from —(C$_1$-C$_3$ alkylene)$_m$-halide, —(C$_1$-C$_3$ alkylene)$_m$-hydroxyl, —(C$_1$-C$_3$ alkylene)$_m$-CN, C$_1$-C$_6$ alkyl, C$_1$-C$_6$ perfluoroalkyl, —(C$_1$-C$_3$ alkylene)$_m$-(C$_1$-C$_6$ alkoxyl), —(C$_1$-C$_3$ alkylene)$_m$-NH$_2$, —(C$_1$-C$_3$ alkylene)$_m$-(C$_1$-C$_6$ alkylamino), —(C$_1$-C$_3$ alkylene)$_m$-(C$_3$-C$_5$ cycloalkyl) and —(C$_1$-C$_3$ alkylene)$_m$ -(3-5 member heterocyclyl), and the said C$_3$-C$_5$ cycloalkyl and the said 3-5 member heterocyclyl is optionally further substituted by 1-3 group selected from —F, C$_1$-C$_3$ alkyl, C$_1$-C$_3$ perfluoroalkyl and oxo;
each R$^2$ and R$^3$ is independently C$_1$-C$_3$ alkyl, or R$^2$ and R$^3$, together with the carbon atom that R$^2$ and R$^3$ attach to, form a C$_3$-C$_4$ cycloalkylene;
R$^8$ is —(C$_1$-C$_6$ alkylene)$_m$-NR$^p$R$^q$, wherein each R$^p$ and R$^q$ is independently H, C$_1$-C$_3$ alkyl, or R$^p$ and R$^q$, together with the nitrogen atom they attach to, form a ring selected from 3-7 member heterocyclyl and 5-7 member heteroaryl, the said ring is optionally further substituted by 1-6 groups selected from halide, C$_1$-C$_3$ alkyl and C$_1$-C$_3$ perfluoroalkyl;
R$^9$ is selected from C$_1$-C$_6$ alkyl, C$_1$-C$_6$ perfluoroalkyl, phenyl, —(C$_1$-C$_3$ alkylene)-phenyl, C$_{10}$-C$_{12}$ aryl, C$_3$-C$_{12}$ cycloalkyl, —(C$_1$-C$_3$ alkylene)-(C$_3$-C$_{12}$ cycloalkyl), C$_4$-C$_{12}$ unsaturated nonaromatic carbocyclyl, —(C$_1$-C$_3$ alkylene)-(C$_4$-C$_{12}$ unsaturated nonaromatic carbocyclyl), 3-12 member heterocyclyl, —(C$_1$-C$_3$ alkylene)-(3-12 member heterocyclyl), 5-12 member heteroaryl and —(C$_1$-C$_3$ alkylene)-(5 to 12 member heteroaryl), and each R$^9$ is independently optionally further substituted by 1-6 groups selected from halide, C$_1$-C$_6$ alkyl, C$_1$-C$_6$ perfluoroalkyl, —OH, C$_1$-C$_6$ alkoxy, —(C$_1$-C$_6$ alkylene)-(C$_1$-C$_6$ alkoxy)-NH$_2$, —(C$_1$-C$_6$ alkylene)-NH$_2$, —(C$_1$-C$_6$ alkylene)-(C$_1$-C$_6$ alkylamino), C$_1$-C$_6$ alkylamino and CN; and
each m is independently 0 or 1;
or a pharmaceutically acceptable salt thereof.

11. The compound of claim 10, or a pharmaceutically acceptable thereof, wherein R$^2$ is methyl; R$^3$ is methyl; B is —O—, —NH— or —CH$_2$—; R$^1$ is selected from the group consisting of C$_1$-C$_8$ alkyl, phenyl, —(C$_1$-C$_3$ alkylene)-phenyl, -(cyclopropylene)-phenyl, C$_3$-C$_{10}$ cycloalkyl, —(C$_1$-C$_3$ alkylene)-(C$_3$-C$_{10}$ cycloalkyl), 3-10 member heterocyclyl, —(C$_1$-C$_3$ alkylene)-(3-10 member heterocyclyl), -(cyclopropylene)-(3-10 member heterocyclyl), 5-12 member heteroaryl, —(C$_1$-C$_3$ alkylene)-(5-12 member heteroaryl) and -(cyclopropylene)-(5-12 member heteroaryl), and R$^1$ is optionally further substituted by 1-6 groups selected from F, Cl, hydroxyl, CN, C$_1$-C$_6$ alkyl, C$_1$-C$_6$ perfluoroalkyl and —(C$_1$-C$_3$ alkylene)$_m$-(C$_1$-C$_6$ alkoxyl).

12. The compound of claim 11, or a pharmaceutically acceptable thereof, wherein R$^8$ is —(C$_1$-C$_6$ alkylene)$_m$-NR$^p$R$^q$, wherein each R$^p$ and R$^q$ is independently H or C$_1$-C$_3$ alkyl.

13. The compound of claim 12, or a pharmaceutically acceptable thereof, wherein R$^8$ is selected from —CH$_2$—N—(CH$_3$)$_2$, —CH$_2$—NH—CH$_3$ and —CH$_2$—NH$_2$.

14. The compound of claim 11, or a pharmaceutically acceptable thereof, wherein R$^8$ is —(C$_1$-C$_6$ alkylene)$_m$-NR$^p$R$^q$, and R$^p$ and R$^q$, together with the nitrogen atom they attach to, form a 3-7 member heterocyclyl, the said 3-7 member heterocyclyl is optionally further substituted by 1-6 groups selected from halide, C$_1$-C$_3$ alkyl and C$_1$-C$_3$ perfluoroalkyl.

15. The compound of claim 11, or a pharmaceutically acceptable thereof, wherein R$^9$ is selected from the group consisting of C$_1$-C$_8$ alkyl, phenyl, —(C$_1$-C$_3$ alkylene)-phenyl, 5-6 member heteroaryl and 3-7 member cycloalkyl, and R$^9$ is optionally further substituted with 1-6 groups selected from F, Cl, C$_1$-C$_6$ alkyl, C$_1$-C$_6$ perfluoroalkyl, —OH, C$_1$-C$_6$ alkoxy, —(C$_1$-C$_6$ alkylene)-(C$_1$-C$_6$ alkoxy) and CN.

16. A compound selected from the group consisting of

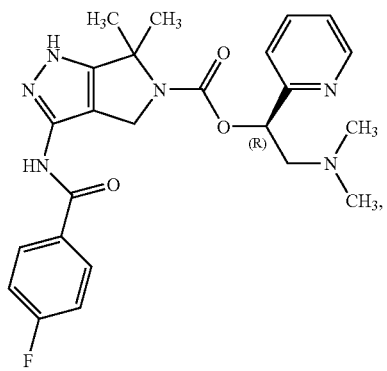

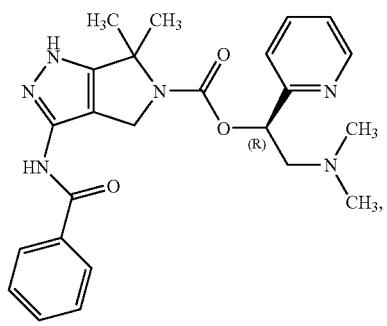

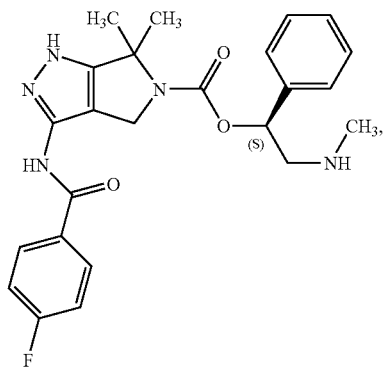

-continued
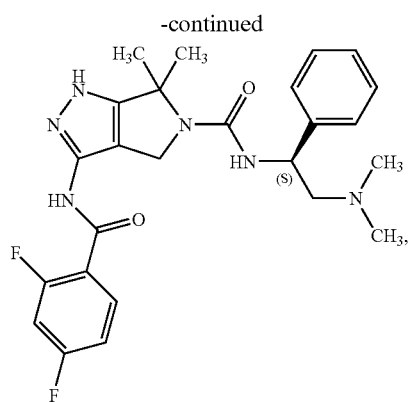
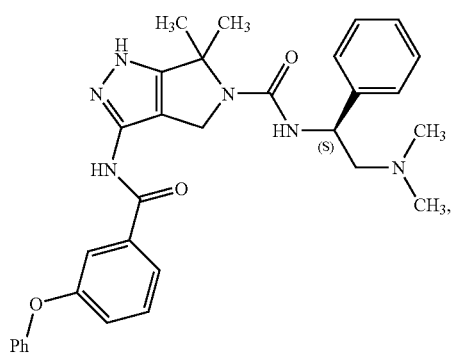
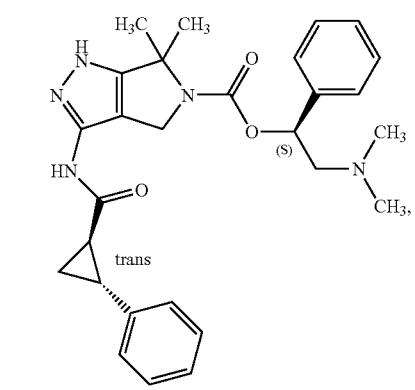
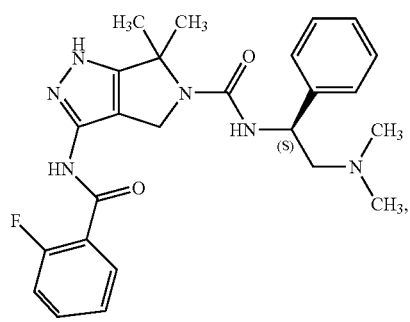
-continued
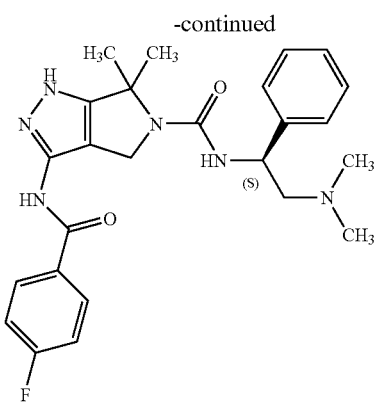
and
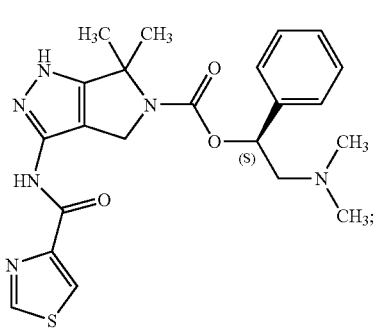
or a pharmaceutically acceptable salt thereof.
17. A compound selected from the group consisting of
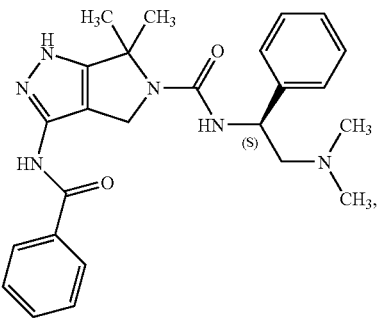
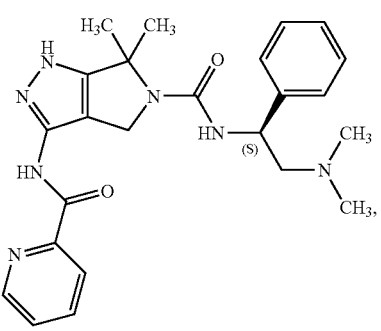

-continued
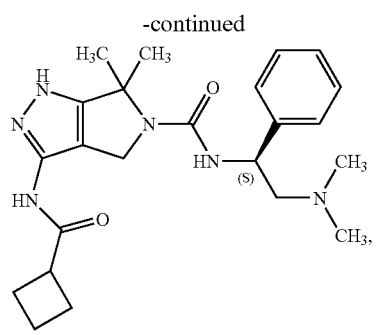
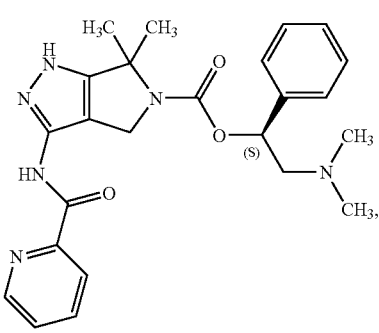
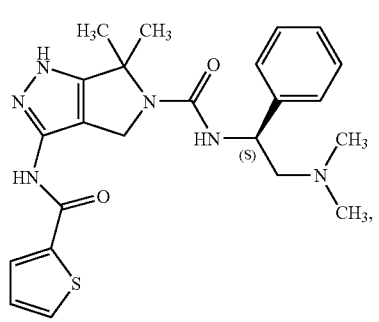
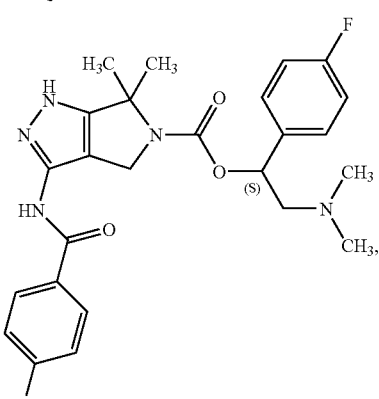
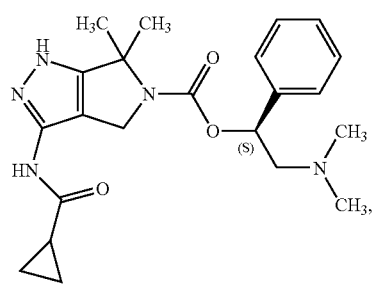
-continued
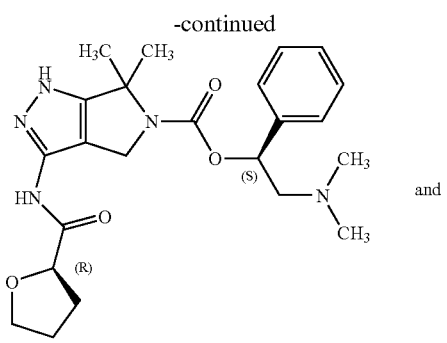
and
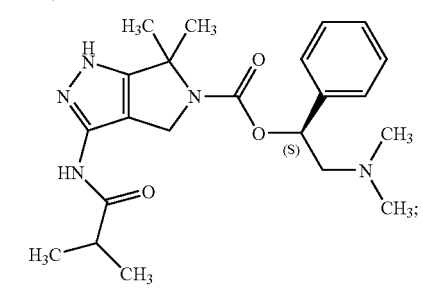
or a pharmaceutically acceptable salt thereof.
18. A compound selected from the group consisting of
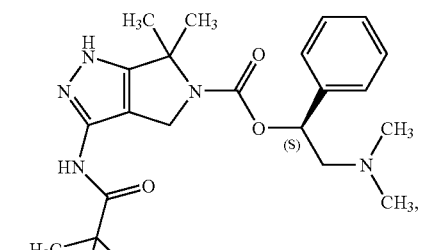
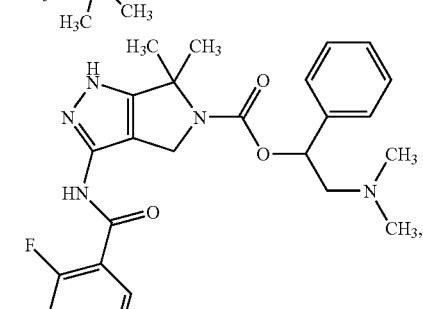
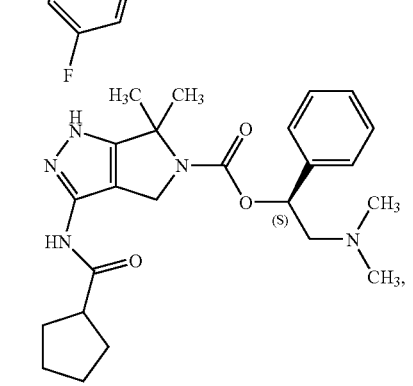

-continued

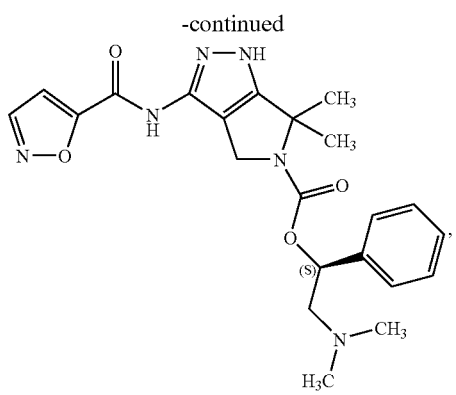

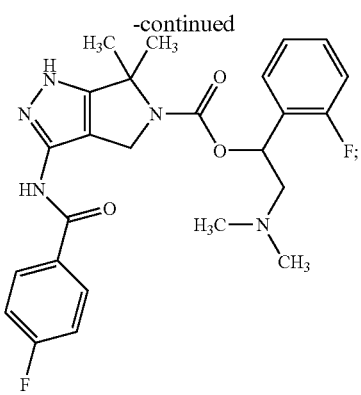

or a pharmaceutically acceptable salt thereof.

19. A pharmaceutical composition comprising the compound of claim 1, or a pharmaceutically acceptable salt thereof.

20. A method to treat abnormal cell growth in a mammal, comprising administering to the mammal the compound of claim 1, or a pharmaceutically acceptable salt thereof.

21. A method of inhibiting a PAK4 protein kinase comprising contacting the PAK4 kinase with the compound of claim 1 or with a pharmaceutically acceptable salt thereof.

22. A compound of the formula or a pharmaceutically acceptable salt thereof.

23. A pharmaceutical composition comprising the compound of claim 22, or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 7,884,117 B2 | Page 1 of 1 |
| APPLICATION NO. | : 12/158241 | |
| DATED | : February 8, 2011 | |
| INVENTOR(S) | : Junhun Zhang et al. | |

It is certified that error appears in the above-identified patent and that said Letters Patent is hereby corrected as shown below:

In column 185, claim 1, line 36, replace "–$(C_1-C_6$ alkylene$)_n$-$NR^qR^q$" with -- –$(C_1-C_6$ alkylene$)_m$-$NR^pR^q$ --.

In column 186, claim 1, lines 8-9, replace "$(C_1-C_3$ alkylene$)$-$(C_1-C_3$ alkylene$)_m$-$N_2$" with -- –$(C_1-C_3$ alkylene$)_m$-$OS(O)NR^aR^b$, –$(C_1-C_3$ alkylene$)_m$-$NO_2$ --.

In column 186, claim 3, lines 56-57, "acceptable thereof" should read --acceptable salt thereof--.

In column 187, claim 4, lines 13-14, "acceptable thereof" should read --acceptable salt thereof--.

In column 188, claim 6, lines 28-29, "acceptable thereof" should read --acceptable salt thereof--.

In column 188, claim 7, lines 42-43, "acceptable thereof" should read --acceptable salt thereof--.

In column 188, claim 8, lines 44-45, "acceptable thereof" should read --acceptable salt thereof--.

In column 188, claim 9, lines 48-49, "acceptable thereof" should read --acceptable salt thereof--.

In column 189, claim 11, line 49, "acceptable thereof" should read --acceptable salt thereof--.

In column 189, claim 12, line 62, "acceptable thereof" should read --acceptable salt thereof--.

In column 189, claim 13, line 66, "acceptable thereof" should read --acceptable salt thereof--.

In column 190, claim 14, line 2, "acceptable thereof" should read --acceptable salt thereof--.

In column 190, claim 15, line 9, "acceptable thereof" should read --acceptable salt thereof--.

Signed and Sealed this
Twenty-sixth Day of July, 2011

David J. Kappos
*Director of the United States Patent and Trademark Office*